US009691990B2

(12) United States Patent
Mun et al.

(10) Patent No.: US 9,691,990 B2
(45) Date of Patent: Jun. 27, 2017

(54) COMPOUND, ORGANIC ELECTRONIC ELEMENT USING SAME, AND ELECTRONIC DEVICE USING THE LATTER

(75) Inventors: Soungyun Mun, Yongin-si (KR); Bumsung Lee, Cheonan-si (KR); Jungcheol Park, Seongnam-si (KR); Kiwon Kim, Suwon-si (KR); Yongwook Park, Anyang-si (KR); Jeongkeun Park, Seongnam-si (KR); Heesun Ji, Seongnam-si (KR); Junghwan Park, Seoul (KR)

(73) Assignee: Duk San Neolux Co., Ltd. (KR)

( * ) Notice: Subject to any disclaimer, the term of this patent is extended or adjusted under 35 U.S.C. 154(b) by 826 days.

(21) Appl. No.: 14/008,340

(22) PCT Filed: Mar. 29, 2012

(86) PCT No.: PCT/KR2012/002343
§ 371 (c)(1),
(2), (4) Date: Sep. 27, 2013

(87) PCT Pub. No.: WO2012/134203
PCT Pub. Date: Oct. 4, 2012

(65) Prior Publication Data

US 2014/0027747 A1 Jan. 30, 2014

(30) Foreign Application Priority Data

Apr. 1, 2011 (KR) ........................ 10-2011-0030303

(51) Int. Cl.
*H01L 51/50* (2006.01)
*H01L 51/00* (2006.01)
(Continued)

(52) U.S. Cl.
CPC .......... *H01L 51/006* (2013.01); *C07C 211/54* (2013.01); *C07D 209/80* (2013.01);
(Continued)

(58) Field of Classification Search
None
See application file for complete search history.

(56) References Cited

U.S. PATENT DOCUMENTS 6,699,599 B2 3/2004 Li et al.
8,026,665 B2 9/2011 Kim et al.
(Continued)

FOREIGN PATENT DOCUMENTS

JP 2010-092940 A 4/2010
KR 10-2006-0115951 A 11/2006
(Continued)

OTHER PUBLICATIONS

Van Slyke, S. A. et al., "Organic electroluminescent devices with improved stability", Applied Physics Letters, vol. 69, No. 15, pp. 2160-2162, Oct. 7, 1996.
(Continued)

*Primary Examiner* — Gregory Clark
(74) *Attorney, Agent, or Firm* — Harness, Dickey & Pierce, P.L.C.

(57) ABSTRACT

The present invention relates to a compound, which is represented by one chemical formula among the chemical formulas (1) to (3), an organic electronic element comprising the compound, and an electronic device comprising the organic electronic element. The compound is characterized by comprising at least one phenyl group having at least one substitution with deuterium or tritium.

8 Claims, 6 Drawing Sheets

(51) Int. Cl.

| | |
|---|---|
| ***C07D 333/36*** | (2006.01) |
| ***C07D 333/76*** | (2006.01) |
| ***C07C 211/54*** | (2006.01) |
| ***C07D 409/04*** | (2006.01) |
| ***C07D 409/10*** | (2006.01) |
| ***C07D 209/80*** | (2006.01) |
| ***C07D 209/86*** | (2006.01) |
| ***C07D 307/91*** | (2006.01) |
| ***C09B 57/00*** | (2006.01) |

(52) U.S. Cl.

CPC ......... *C07D 209/86* (2013.01); *C07D 307/91* (2013.01); *C07D 333/36* (2013.01); *C07D 333/76* (2013.01); *C07D 409/04* (2013.01); *C07D 409/10* (2013.01); *C09B 57/008* (2013.01); *H01L 51/0068* (2013.01); *H01L 51/0072* (2013.01); *H01L 51/0073* (2013.01); *H01L 51/0074* (2013.01); *C07C 2103/18* (2013.01); *C07C 2103/94* (2013.01); *Y02E 10/549* (2013.01)

(56) References Cited

U.S. PATENT DOCUMENTS

| | | | |
|---|---|---|---|
| 8,507,904 B2 | 8/2013 | Kim et al. | |
| 2008/0191614 A1* | 8/2008 | Kim | C07B 59/001 313/504 |
| 2010/0033081 A1 | 2/2010 | Yamada et al. | |
| 2010/0244008 A1 | 9/2010 | Lee et al. | |
| 2011/0127495 A1 | 6/2011 | Hong et al. | |
| 2012/0018717 A1 | 1/2012 | Kim et al. | |
| 2012/0080670 A1 | 4/2012 | Park et al. | |
| 2012/0168734 A1 | 7/2012 | Park et al. | |
| 2012/0217492 A1 | 8/2012 | Kim et al. | |
| 2013/0001540 A1 | 1/2013 | Kim et al. | |
| 2013/0069049 A1 | 3/2013 | Park et al. | |

FOREIGN PATENT DOCUMENTS

| | | | | |
|---|---|---|---|---|
| KR | 10-2008-0077288 A | | 8/2008 | |
| KR | 10-2009-0051141 A | | 5/2009 | |
| KR | 10-1108519 B1 | | 1/2012 | |
| WO | WO-2010-114583 A1 | | 10/2010 | |
| WO | WO-2011-093056 A1 | | 8/2011 | |
| WO | WO 2012/177006 | * | 12/2012 | H01L 51/52 |

OTHER PUBLICATIONS

Kim, Youngkyoo et al., "Accelerated pre-oxidation method for healing progressive electrical short in organic light-emitting devices", Applied Physics Letters, vol. 82, No. 14, pp. 2200-2202, Apr. 7, 2003.

Poon, C.O. et al., "Improved performance and stability of organic light-emitting devices with silicon oxy-nitride buffer layer", Applied Physics Letters, vol. 83, No. 5, pp. 1038-1040, Aug. 4, 2003.

Tokito, Shizuo et al., "Thermal stability in oligomeric triphenylamine/tris(8-quinolinolato) aluminum electroluminescent devices", Applied Physics Letters, vol. 70, No. 15, pp. 1929- 1931, Apr. 14, 1997.

Buckingham, A.D. et al., "Partial Miscibility of Liquid Mixtures of Protonated and Deuterated High Polymers", Journal of Polymer Science: Polymer Physics Edition, vol. 18, pp. 853-861, 1980.

Shirota, Yasuhiko et. al., "Charge Carrier Transporting Molecular Materials and Their Applications in Devices", Chemical Reviews, vol. 107, No. 4, pp. 953-1010, 2007.

Yang, Yu et al., "Synthesis and Properties of Partially Fluorinated Amorphous Ring Containing Polymers: Poly[bis(2,2-difluorovinyl)formal], Poly[bis(2,2- difluorovinyl)difluoroformal], and Poly[bis(1-deuterio-2,2-difluorovinyl)difluoroformal]", Macromolecules, vol. 37, No. 21, pp. 7918-7923, 2004.

International Search Report (in Korean with English translation) and Written Opinion (in Korean) for PCT/KR2012/002343, mailed Oct. 29, 2012; ISA/KR.

* cited by examiner

COMPOUND, ORGANIC ELECTRONIC ELEMENT USING SAME, AND ELECTRONIC DEVICE USING THE LATTER

CROSS-REFERENCE TO RELATED APPLICATION

This application claims priority from and the benefit under 35 U.S.C. §119(a) of Korean Patent Application No. 10-2011-0030303, filed on Apr. 1, 2011, which is hereby incorporated by reference for all purposes as if fully set forth herein.

TECHNICAL FIELD

The present invention relates to a compound, an organic electronic element using the same, and an electronic device thereof.

BACKGROUND ART

A flat panel display element performs a very important role of supporting an advanced image information society that has recently quickly grown mainly in the internet field. Especially, an organic electro-luminescence element (organic EL element) that can be driven at a low voltage in a self-emission manner is excellent in a viewing angle and a contrast ratio, compared to a liquid crystal display (LCD) (the most widely used flat panel display element). Also, the organic electro-luminescence element does not require a backlight, and thus can be manufactured in such a manner that it can have a light weight and a thin thickness. Also, it is advantageous in view of power consumption. Furthermore, it has been spotlighted as a next generation display device due to a high response speed, and a wide color reproduction range. In general, an organic electro-luminescence element has an anode including a transparent electrode, an organic material layer including a light emitting area, and a metal electrode (cathode), which are sequentially formed on a glass substrate.

Herein, the organic material layer may include not only an emitting layer (EML) but also a hole injection layer (HIL), a hole transport layer (HTL), an electron transport layer (ETL) or an electron injection layer (EIL). For light emission of an emitting layer, it may further include an electron blocking layer (EBL) or a hole blocking layer (HBL). When an organic electro-luminescence element with such a structure is applied with an electric field, holes are injected from the anode, and electrons are injected from the cathode. The injected holes and electrons are transferred from the hole transport layer and the electron transport layer, respectively, and recombined in the emitting layer so as to form light emitting excitons. The formed light emitting excitons are transited to ground states while emitting light. Herein, in order to increase the efficiency and stability of a light emission state, a light emitting pigment (guest) may be doped in the emitting layer (host).

In order to utilize such an organic electro-luminescence element in various display media, the life span of a device is most important. At present, much research on improvement of the life span of an organic electro-luminescence element has been conducted.

DISCLOSURE OF INVENTION

Technical Problem

An object of the present invention is to achieve effects such as efficiency increase, driving voltage reduction, life span increase, stability increase, and manufacturing efficiency improvement in an organic electronic element.

Solution to Problem

In order to accomplish this object, there is provided a compound represented by Formula below.

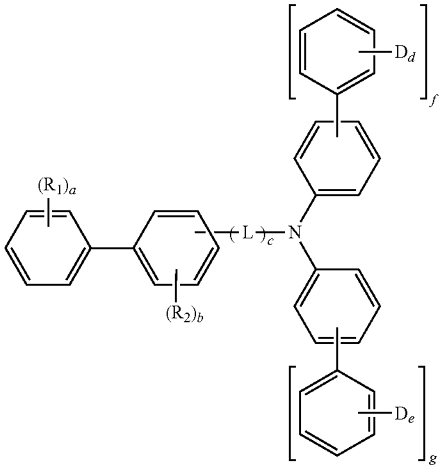

In accordance with another aspect of the present invention, there is provided an organic electronic element including the compound represented by Formula above, and an electronic device thereof.

Advantageous Effects

In a novel compound substituted with heavy hydrogen, and an organic electronic element including the same, according to the present invention, it is possible to achieve effects such as efficiency increase, driving voltage reduction, life span increase, stability increase, and manufacturing efficiency improvement.

MODE FOR INVENTION

Figure 1:
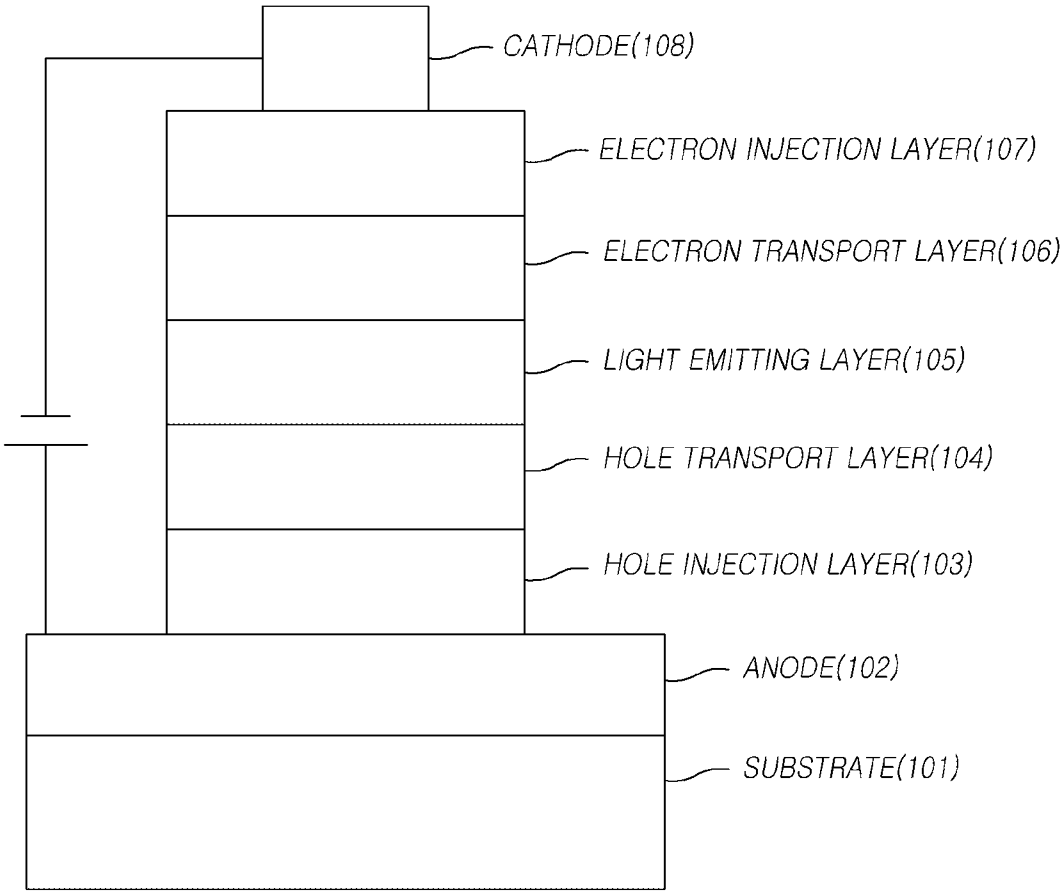
FIGS. 1 to 6 show examples of an organic electro-luminescence element which can employ a compound according to the present invention.

Hereinafter, exemplary embodiments of the present invention will be described with reference to the accompanying drawings. In the following description, the same elements will be designated by the same reference numerals although they are shown in different drawings. Further, in the following description of the present invention, a detailed description of known functions and configurations incorporated herein will be omitted when it may make the subject matter of the present invention rather unclear.

In addition, terms, such as first, second, A, B, (a), (b) or the like may be used herein when describing components of the present invention. Each of these terminologies is not used to define an essence, order or sequence of a corresponding component but used merely to distinguish the corresponding component from other component(s). It should be noted that if it is described in the specification that one component is "connected," "coupled" or "joined" to another component, a third component may be "connected," "coupled," and "joined" between the first and second components, although the first component may be directly connected, coupled or joined to the second component.

The present invention relates to a compound having a low driving voltage characteristic, a hole injection/hole transport layer material including the compound, and an organic electronic element including the material.

In order to improve a lifespan characteristic of an organic electronic element, e.g., an organic electro-luminescence element, much research on an organic material to be inserted into a hole transport layer or a buffer layer has been conducted (refer to: S. A. Van Slyke et al, Appl. Phys. Lett., 69, 2160, 1996), For this, it is required to develop a hole injection layer material capable of improving the hole mobility from the anode to the organic layer, which has high uniformity and low degree of crystallinity during formation of a thin film after its deposition (refer to: Youngkyoo Kim et al, Appl. Phys. Lett., 82, 2200, 2003).

Also, it is required to develop a hole injection layer material that can delay penetration/diffusion of metal oxide from an anode electrode (ITO) to an organic layer (one of causes of life span reduction of an organic electro-luminescence element) (refer to: C.O. Poon et al, Appl. Phys. Lett., 83, 1083, 2003), and has a stable property against Joule heating caused by driving of a device, that is, a high glass transition temperature (refer to: Shizuo Tokito, Appl. Phys. Lett., 70(15), 1929, 1997). Also, in the formation of an organic electro-luminescence element, a deposition method is mainly used. Thus, it is required to develop a highly heat-resistant material that can stand for a long time in such a deposition method.

Especially, in a currently used organic electro-luminescence element, in order to improve the manufacturing efficiency, it is required to use a material having both functions of a hole injection layer and a hole transport layer. In other words, it is required to use a material that can simplify a device structure, thereby increasing the manufacturing efficiency. Such a structure has to have a high hole mobility according to the increase in the layered thickness, and also requires a high deposition speed, that is, a high heat resistance, so as to improve the manufacturing efficiency of manufacturing time.

The inventors of the present invention have continuously researched and developed an organic material that can not only maintain excellent characteristics of organic material layers in an organic electronic element, e.g., an organic electro-luminescence element, but also achieve improved characteristics.

According to the research results obtained by the inventors, it was found that a compound substituted with heavy hydrogen showed better thermodynamic behavior compared to a non-substituted compound. In view of this thermodynamic characteristic, for example, in U.S. Pat. No. 6,699,599, it was found that when iridium compound is substituted with heavy hydrogen, a higher luminous efficiency can be achieved due to the difference in a bond length between carbon-hydrogen and carbon-heavy hydrogen. This is because in a compound including carbon and heavy hydrogen, with a smaller bond length, the intermolecular van der waals force is decreased by the smaller bond length.

Also, according to the research results obtained by the inventors of the present invention, it was found that when a compound is substituted with heavy hydrogen, Zero Point Energy, that is, ground state energy, is lowered, and the bond length of heavy hydrogen-carbon is shortened. Accordingly, the Molecular hardcore volume is reduced, thereby reducing Electronical polarizability. This weakens the Intermolecular interaction, thereby increasing the thin film volume (refer to: Buckingham, A. D.; Hentschel, H. G. E. J. Polym. Sci. 1980, 18, 853). Due to this characteristic, it is possible to reduce the degree of crystallinity of a thin film. In other words, an amorphous state of the thin film can be achieved. Thus, it was determined that the characteristic will be very effective in the achievement of an amorphous state generally required for improving a life span and a driving characteristic of an OLED (refer to: Chem. Rev. 2007, 107, 953-1010 953)

As a result, it was found that the material substituted with heavy hydrogen shows lower visible ray absorption than a material of a carbon-hydrogen bond. Then, it was determined that this characteristic can be advantageous in an increase of the efficiency in a luminous element such as an organic electro-luminescence element. Also, it was determined that the material substituted with heavy hydrogen can highly increase heat resistance (refer to: Macromolecules 2004, 37, 7918).

Based on the results of research and development of the inventors of the present invention, the present invention provides a compound including an amine group substituted with heavy hydrogen, in which the compound can maintain the above described excellent characteristics of organic material layers of an organic electro-luminescence element, but also satisfy the requirements of an organic material.

In other words, the present invention provides a compound represented by Formula 1 below.

[Formula 1]

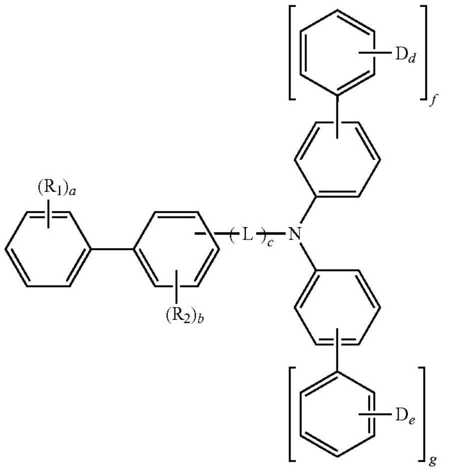

In Formula 1, $R_1$~$R_2$ each may be independently selected from the group consisting of an hydrogen atom; a $C_6$~$C_{60}$ aryl group substituted or unsubstituted with at least one substituent selected from the group including a halogen group, an amino group, a nitrile group, a nitro group, a $C_1$~$C_{20}$ alkyl group, a $C_1$~$C_{20}$ alkoxy group, a $C_1$~$C_{20}$ alkylamine group, a $C_1$~$C_{20}$ alkylthiophene group, a $C_6$~$C_{20}$ arylthiophene group, a $C_2$~$C_{20}$ alkenyl group, a $C_2$~$C_{20}$ alkynyl group, a $C_3$~$C_{20}$ cycloalkyl group, a $C_6$~$C_{60}$ aryl group, a $C_8$~$C_{20}$ arylalkenyl group, a silane group, a boron group, a germanium group, and a $C_2$~$C_{20}$ heterocyclic group; a substituted or unsubstituted $C_3$~$C_{60}$ heteroaryl group that is substituted or unsubstituted with at least one substituent selected from the group including a halogen group, a $C_1$~$C_{20}$ alkyl group, a $C_2$~$C_{20}$ alkenyl group, a $C_1$~$C_{20}$ alkoxy group, a $C_6$~$C_{20}$ arylamine group, a $C_6$~$C_{60}$ aryl group, a $C_7$~$C_{20}$ arylalkyl group, a $C_8$~$C_{20}$ arylalkenyl group, a $C_2$~$C_{20}$ heterocyclic group, a nitrile group, and an acetylenic group, and comprises at least one of O, N, and S; a $C_1$~$C_{30}$ alkoxy group substituted or unsubstituted with at least one substituent selected from the group including a halogen group, an amino group, a nitrile group, a nitro group, a $C_1$~$C_{20}$ alkyl group, a $C_2$~$C_{20}$ alkenyl group, a $C_1$~$C_{20}$ alkoxy group, a $C_1$~$C_{20}$ cycloalkyl group, a $C_2$~$C_{30}$ heterocycloalkyl group, a $C_6$~$C_{60}$ aryl group, and a $C_3$~$C_{60}$ heteroaryl group; a $C_6$~$C_{30}$ aryloxy group substituted or unsubstituted with at least one substituent selected from the group including a halogen group, an amino group, a nitrile group, a nitro group, a $C_1$~$C_{20}$ alkyl group, a $C_2$~$C_{20}$ alkenyl group, a $C_1$~$C_{20}$ alkoxy group, a $C_3$~$C_{30}$ cycloalkyl group, a $C_2$~$C_{30}$ heterocycloalkyl group, a $C_6$~$C_{60}$ aryl group, and a $C_3$~$C_{60}$ heteroaryl group; a $C_6$~$C_{60}$ arylamine group substituted or unsubstituted with at least one substituent selected from the group including a halogen group, an amino group, a nitrile group, a nitro group, a $C_1$~$C_{20}$ alkyl group, a $C_2$~$C_{20}$ alkenyl group, a $C_1$~$C_{20}$ alkoxy group, a $C_3$~$C_{30}$ cycloalkyl group, a $C_2$~$C_{30}$ heterocycloalkyl group, a $C_6$~$C_{60}$ aryl group, and a $C_3$~$C_{60}$ hetero aryl group; and a $C_1$~$C_{60}$ alkyl group substituted or unsubstituted with at least one substituent selected from the group including a $C_1$~$C_{20}$ alkyl group, a $C_2$~$C_{20}$ alkenyl group, a $C_1$~$C_{20}$ alkoxy group, a $C_6$~$C_{20}$ aryl group, a $C_7$~$C_{20}$ arylalkyl group, a $C_8$~$C_{20}$ arylalkenyl group, a $C_2$~$C_{20}$ heterocyclic group, a nitrile group, and an acetylenic group, but the present invention is not limited thereto.

Herein, in $R_1$~$R_2$, adjacent groups may be combined with each other to form an alicyclic, aromatic or heterocyclic ring. Meanwhile, a may represent an integer of 1 to 5, and b may represent an integer of 1 to 4, but the present invention is not limited thereto.

Meanwhile, L may be selected from the group consisting of a $C_6$~$C_{60}$ arylene group substituted or unsubstituted with at least one substituent selected from the group including a nitro group, a nitrile group, a halogen group, an alkyl group, an alkoxy group, and an amino group; and a $C_3$~$C_{60}$ hetero arylene group substituted or unsubstituted with at least one substituent selected from the group including a nitro group, a nitrile group, a halogen group, an alkyl group, an alkoxy group, and an amino group, but the present invention is not limited thereto. Herein, c may represent an integer of 0 to 2, but the present invention is not limited thereto.

Also, D represents deuterium or tritium, and d may represent an integer of 0 to 5, and e may represent an integer of 0 to 5, with the proviso that d+e≥1, but the present invention is not limited thereto.

Also, f and g each represent an integer of 0 to 3, with the proviso that f+g≥1.

According to another aspect of the present invention, there is provided a compound represented by Formula 2 or 3.

[Formula 2]

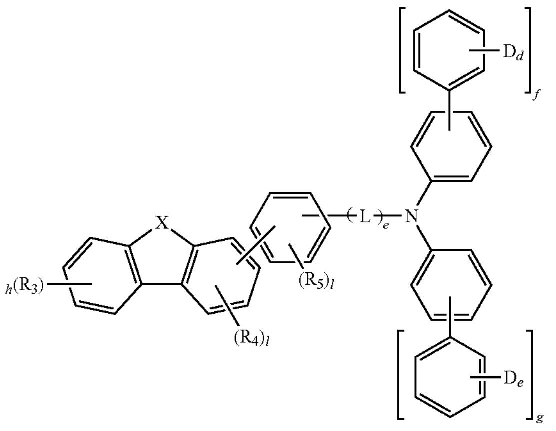

-continued

[Formula 3]

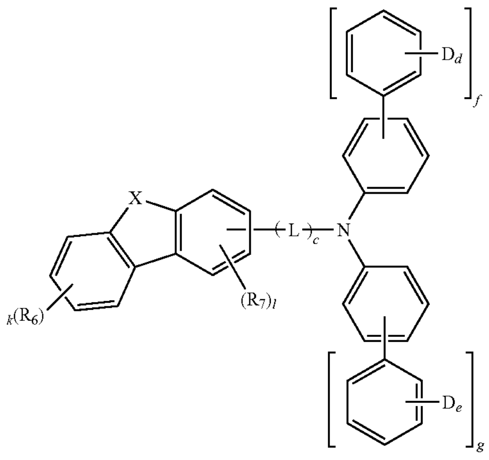

In Formulas 2 and 3, X represents CR'R", NR', O, or S, and R3 to R5 and R6 to R7 each may be independently selected from the group consisting of an hydrogen atom; a $C_6$~$C_{60}$ aryl group substituted or unsubstituted with at least one substituent selected from the group including a halogen group, an amino group, a nitrile group, a nitro group, a $C_1$~$C_{20}$ alkyl group, a $C_1$~$C_{20}$ alkoxy group, a $C_1$~$C_{20}$ alkylamine group, a $C_1$~$C_{20}$ alkylthiophene group, a $C_6$~$C_{20}$ arylthiophene group, a $C_2$~$C_{20}$ alkenyl group, a $C_2$~$C_{20}$ alkynyl group, a $C_3$~$C_{20}$ cycloalkyl group, a $C_6$~$C_{60}$ aryl group, a $C_8$~$C_{20}$ arylalkenyl group, a silane group, a boron group, a germanium group, and a $C_2$~$C_{20}$ heterocyclic group; a substituted or unsubstituted $C_3$~$C_{60}$ heteroaryl group that is substituted or unsubstituted with at least one substituent selected from the group including a halogen group, a $C_1$~$C_{20}$ alkyl group, a $C_2$~$C_{20}$ alkenyl group, a $C_1$~$C_{20}$ alkoxy group, a $C_6$~$C_{20}$ arylamine group, a $C_6$~$C_{60}$ aryl group, a $C_7$~$C_{20}$ arylalkyl group, a $C_8$~$C_{20}$ arylalkenyl group, a $C_2$~$C_{20}$ heterocyclic group, a nitrile group, and an acetylenic group, and comprises at least one of O, N, and S; a $C_1$~$C_{30}$ alkoxy group substituted or unsubstituted with at least one substituent selected from the group including a halogen group, an amino group, a nitrile group, a nitro group, a $C_1$~$C_{20}$ alkyl group, a $C_2$~$C_{20}$ alkenyl group, a $C_1$~$C_{20}$ alkoxy group, a $C_3$~$C_{30}$ cycloalkyl group, a $C_2$~$C_{30}$ heterocycloalkyl group, a $C_6$~$C_{60}$ aryl group, and a $C_3$~$C_{60}$ heteroaryl group; a $C_6$~$C_{30}$ aryloxy group substituted or unsubstituted with at least one substituent selected from the group including a halogen group, an amino group, a nitrile group, a nitro group, a $C_1$~$C_{20}$ alkyl group, a $C_2$~$C_{20}$ alkenyl group, a $C_1$~$C_{20}$ alkoxy group, a $C_3$~$C_{30}$ cycloalkyl group, a $C_3$~$C_{60}$ heterocycloalkyl group, a $C_6$~$C_{60}$ aryl group, and a $C_3$~$C_{60}$ heteroaryl group; a $C_6$~$C_{60}$ arylamine group substituted or unsubstituted with at least one substituent selected from the group including a halogen group, an amino group, a nitrile group, a nitro group, a $C_1$~$C_{20}$ alkyl group, a $C_2$~$C_{20}$ alkenyl group, a $C_1$~$C_{20}$ alkoxy group, a $C_3$~$C_{30}$ cycloalkyl group, a $C_2$~$C_{30}$ heterocycloalkyl group, a $C_6$~$C_{60}$ aryl group, and a $C_3$~$C_{60}$ hetero aryl group; and a $C_1$~$C_{50}$ alkyl group substituted or unsubstituted with at least one substituent selected from the group including a $C_1$~$C_{20}$ alkyl group, a $C_2$~$C_{20}$ alkenyl group, a $C_1$~$C_{20}$ alkoxy group, a $C_6$~$C_{20}$ aryl group, a $C_7$~$C_{20}$ arylalkyl group, a $C_8$~$C_{20}$ arylalkenyl group, a $C_2$~$C_{20}$ heterocyclic group, a nitrile group, and an acetylenic group, but the present invention is not limited thereto.

Herein, in $R_3$~$R_7$, adjacent groups may be combined with each other to form a saturated or unsaturated ring, that is, an alicyclic, aromatic or heterocyclic.

R' and R" each may be independently selected from the group consisting of an hydrogen atom; a C1~C50 alkyl group substituted or unsubstituted with at least one substituent selected from the group including a $C_1$~$C_{20}$ alkyl group, a $C_2$~$C_{20}$ alkenyl group, a $C_1$~$C_{20}$ alkoxy group, a $C_6$~$C_{20}$ aryl group, a $C_7$~$C_{20}$ arylalkyl group, a $C_8$~$C_{20}$ arylalkenyl group, a $C_2$~$C_{20}$ heterocyclic group, a nitrile group, and an acetylenic group; a C6~C60 aryl group substituted or unsubstituted with at least one substituent selected from the group including a halogen group, an amino group, a nitrile group, a nitro group, a $C_1$~$C_{20}$ alkyl group, a $C_1$~$C_{20}$ alkoxy group, a $C_1$~C20 alkylamine group, a $C_1$~$C_{20}$ alkylthiophene group, a $C_6$~$C_{20}$ arylthiophene group, a $C_2$~$C_{20}$ alkenyl group, a $C_2$~$C_{20}$ alkynyl group, a C3~$C_{20}$ cycloalkyl group, a $C_6$~$C_{60}$ aryl group, a $C_8$~$C_{20}$ arylalkenyl group, a silane group, a boron group, a germanium group, and a $C_2$~$C_{20}$ heterocyclic group; and a substituted or unsubstituted $C_2$~$C_{60}$ heterocyclic group that is substituted or unsubstituted with at least one substituent selected from the group including a halogen group, a $C_1$~$C_{20}$ alkyl group, a $C_2$~$C_{20}$ alkenyl group, a $C_1$~$C_{20}$ alkoxy group, a $C_6$~$C_{20}$ arylamine group, a $C_6$~$C_{60}$ aryl group, a $C_7$~$C_{20}$ arylalkyl group, a $C_3$~$C_{20}$ arylalkenyl group, a $C_2$~$C_{20}$ heterocyclic group, a nitrile group, and an acetylenic group, and comprises at least one of O, N, and S, but the present invention is not limited thereto.

Herein, h and k each may represent an integer of 1 to 4, i and l each may represent an integer of 1 to 3, and j may represent an integer of 1 to 4, but the present invention is not limited thereto.

Also, L may be selected from the group consisting of a $C_6$~$C_{60}$ arylene group substituted or unsubstituted with at least one substituent selected from the group including a nitro group, a nitrile group, a halogen group, an alkyl group, an alkoxy group, and an amino group; and a $C_3$~$C_{60}$ hetero arylene group substituted or unsubstituted with at least one substituent selected from the group including a nitro group, a nitrile group, a halogen group, an alkyl group, an alkoxy group and an amino group, but the present invention is not limited thereto. Meanwhile, c may represent an integer of 0 to 2, but the present invention is not limited thereto.

Also, D represents heavy hydrogen or tritium. Meanwhile, d may represent an integer of 0 to 5, and e may represent an integer of 0 to 5, with the proviso that d+e≥1, but the present invention is not limited thereto.

Also, f and g each represent an integer of 0 to 3, with the proviso that f+g≥1, but the present invention is not limited thereto.

In Formulas above, Examples of the heterocyclic group may include a thiophene group, a furan group, a pyrrole group, an imidazole group, a thiazole group, an oxazole group, an oxadiazole group, a triazole group, a pyridyl group, a bipyridyl group, a triazine group, an acridyl group, a pyridazine group, a quinolinyl group, an isoquinoline group, an indole group, a carbazole group, a benzoxazole group, a benzimidazole group, a benzthiazole group, a benzcarbazole group, a benzthiophene group, a dibenzothiophene group, a benzfuranyl group, a dibenzofuranyl group, and the like, but, the present invention is not limited thereto.

As described above, adjacent substituents may be combined with each other to form a substituted or unsubstituted saturated or unsaturated cycle (or ring), for example, an aliphatic, aromatic, or heteroaromatic cyclic or polycyclic ring.

According to another embodiment of the present invention, the present invention may include two or more structures of Formula 1.

Meanwhile, the compound having the structural formula may be used in a soluble process. In other words, through a soluble process of the compound, an organic material layer of an organic electronic element, that will be described later, can be formed. In other words, when the compound is used as an organic material layer, the organic material layer may be manufactured with a smaller number of layers by using various polymer materials by means of a soluble process or a solvent process (e.g., spin coating, dip coating, doctor blading, screen printing, inkjet printing or thermal transfer) instead of deposition.

Meanwhile, the compound represented by each of Formulas 1 to 3 may include one or more of compounds represented by Formula 4 below.

Formula 4]

2-1

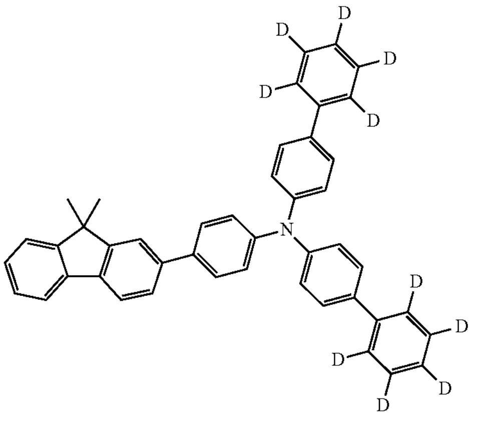

2-2

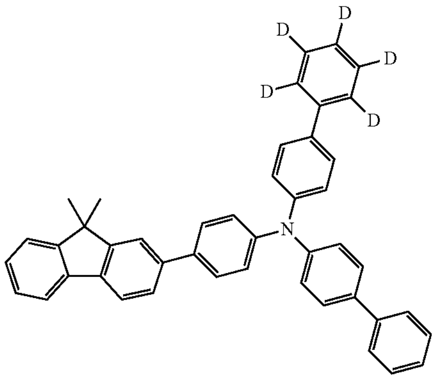

-continued
2-3
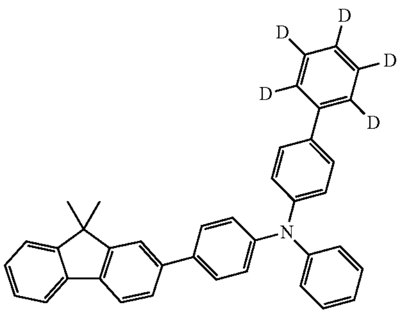
2-4
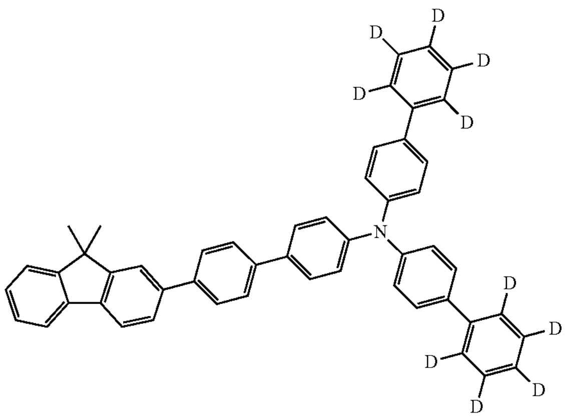
2-5
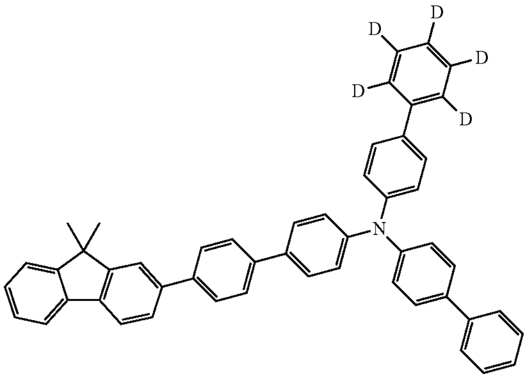
2-6
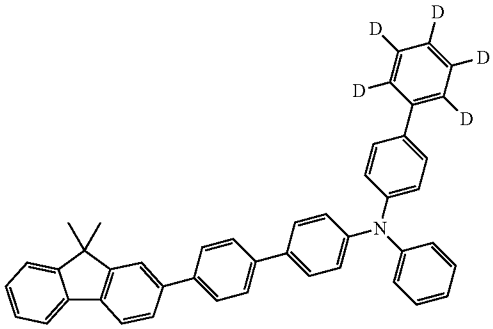
2-7
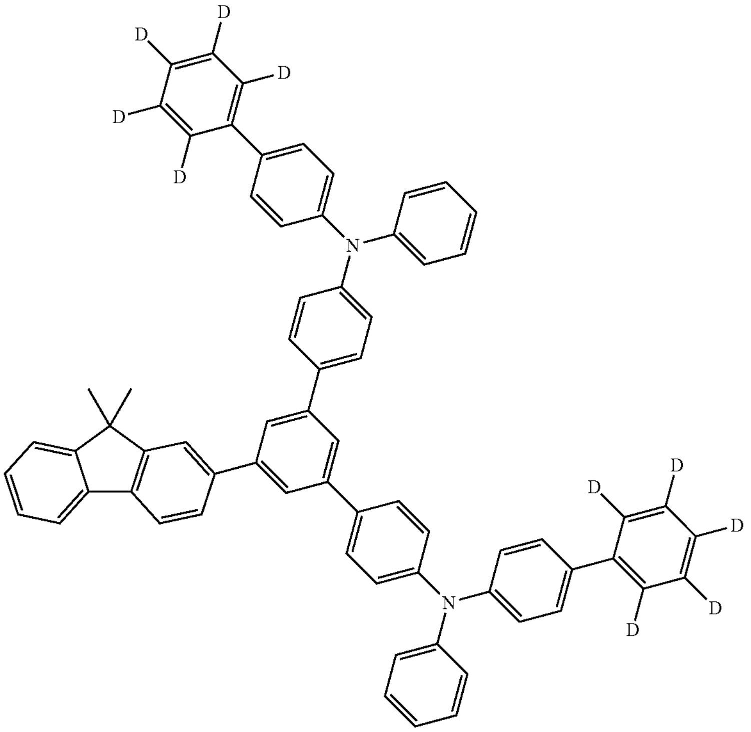

-continued
2-8
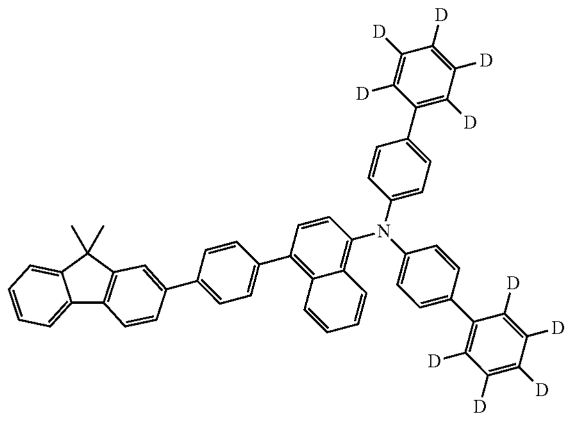
2-9
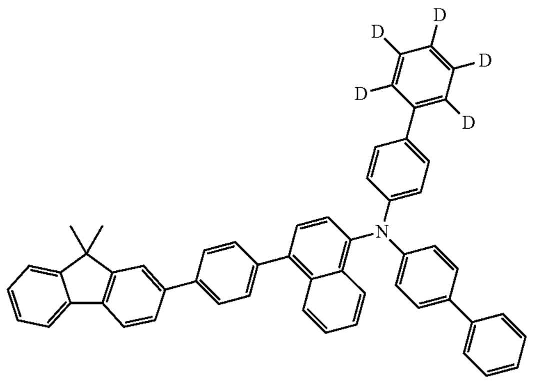
2-10
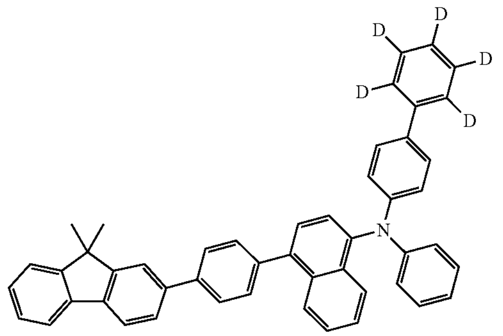
2-11
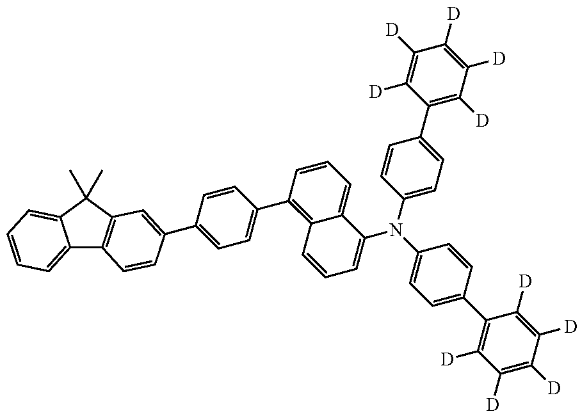
2-12
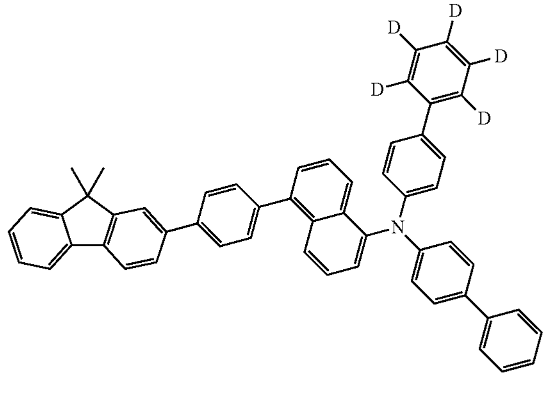
2-13
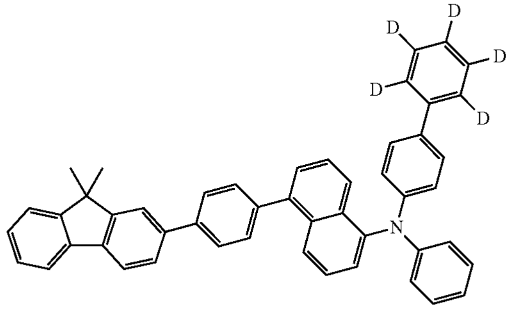

-continued
2-14
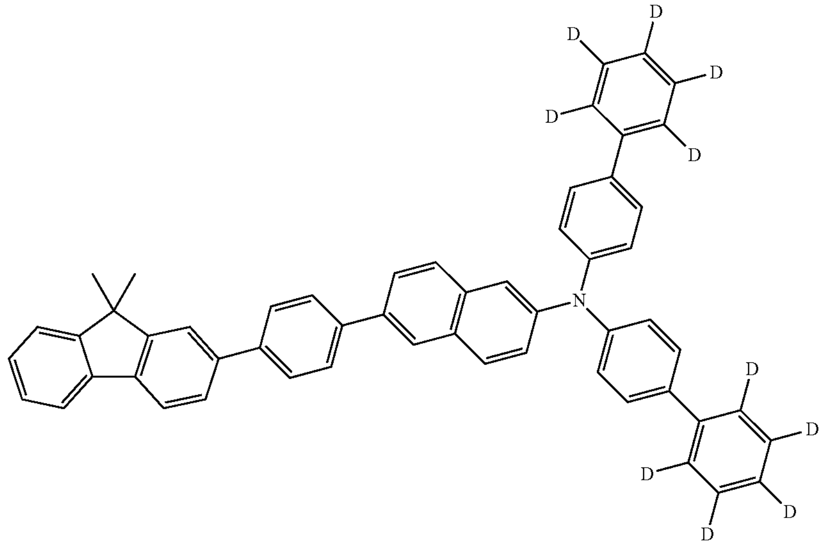
2-15
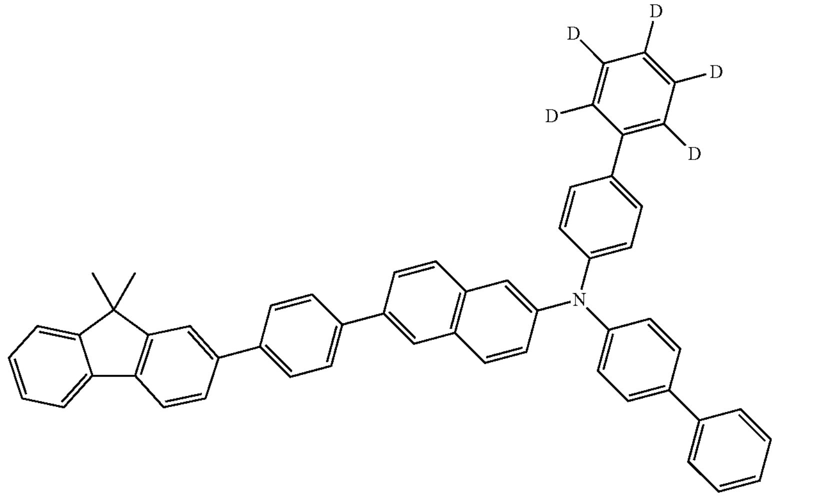
2-16
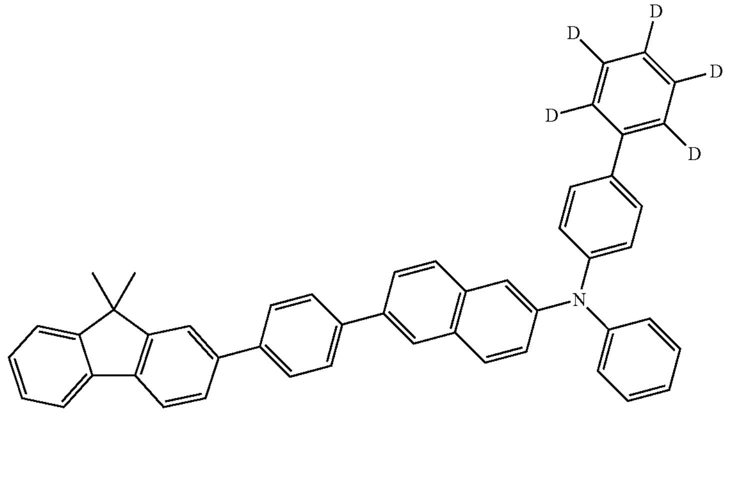

-continued
2-17
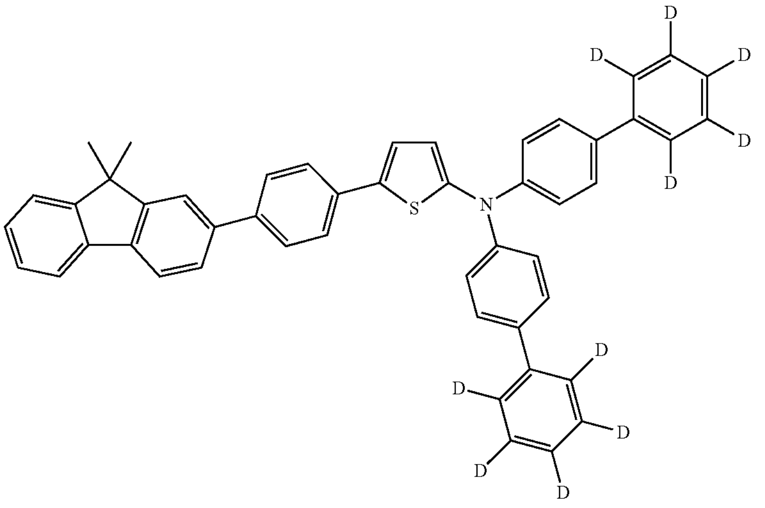
2-18
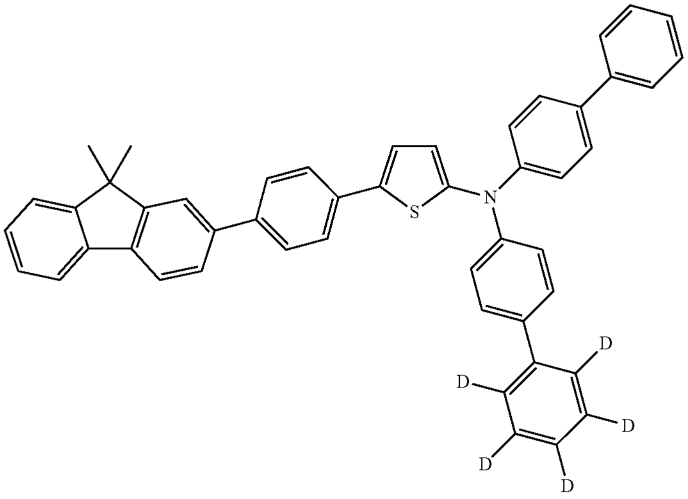
2-19
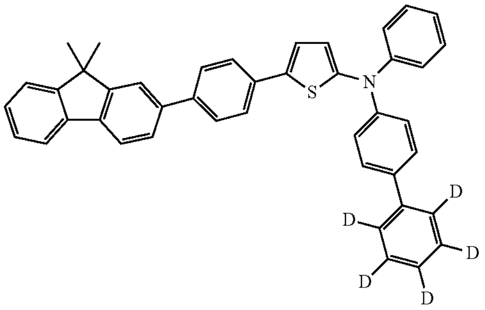
2-20
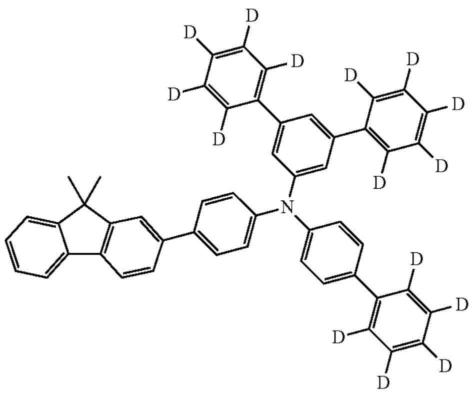

-continued
2-21
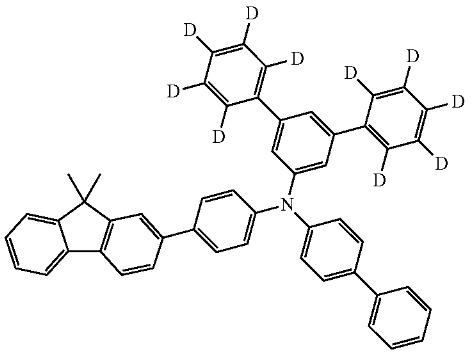
2-22
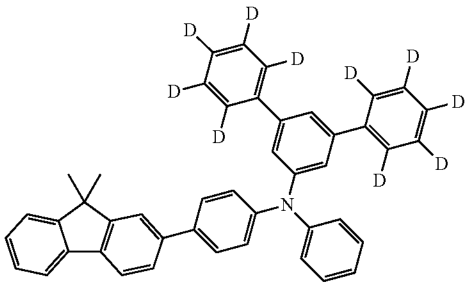
2-23
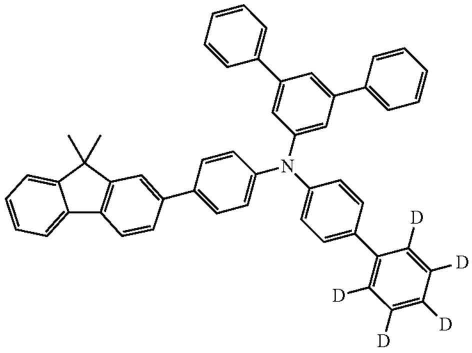
2-24
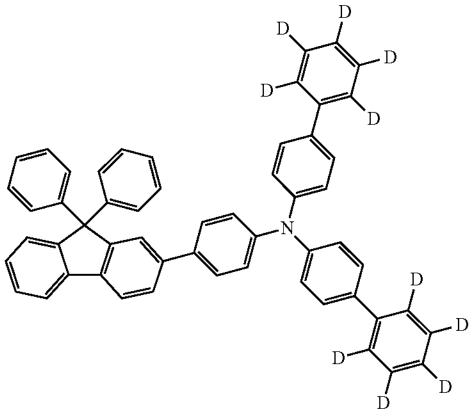
2-25
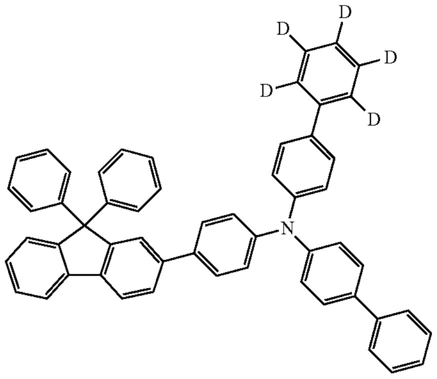
2-26
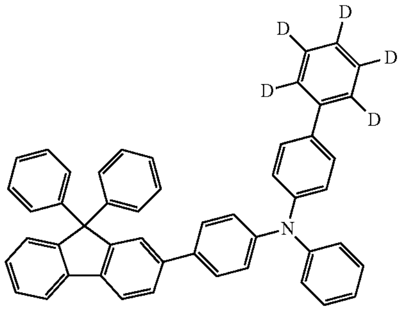

-continued
2-27
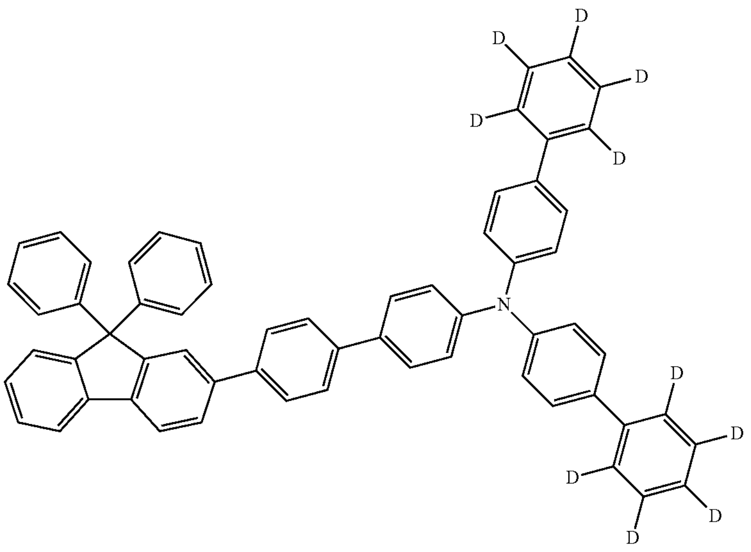
2-28
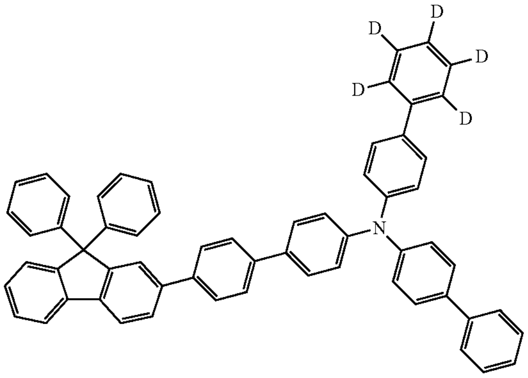
2-29
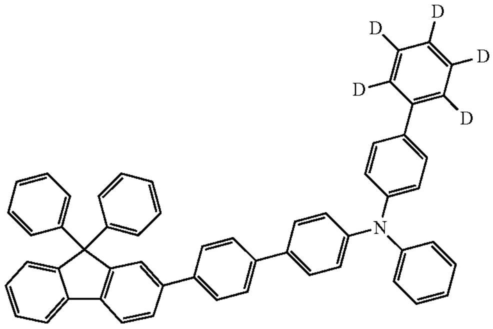

-continued
2-30
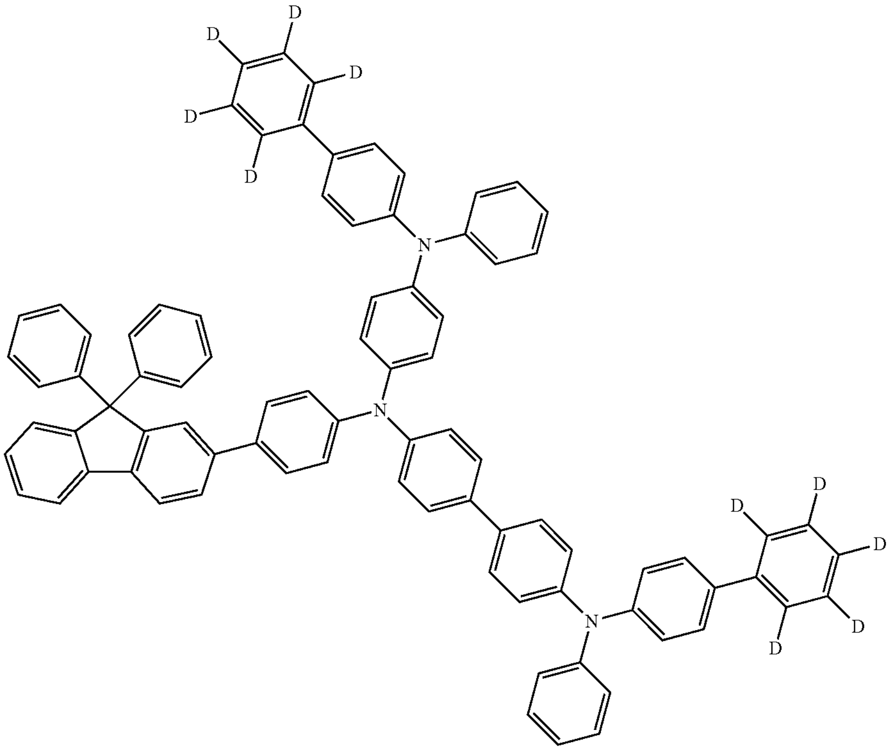
2-31
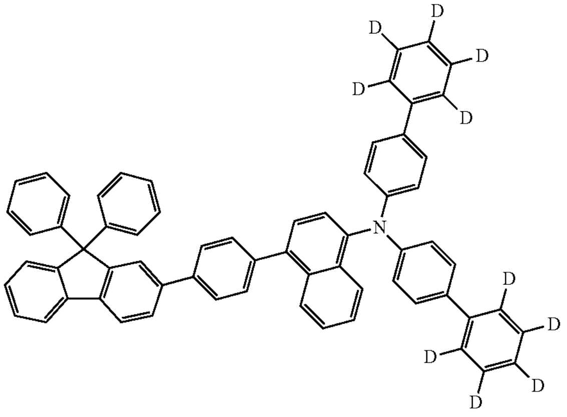
2-32
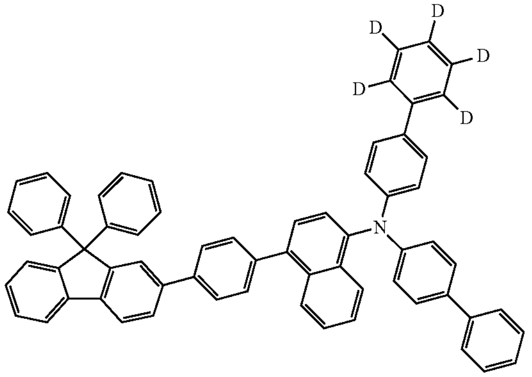
2-33
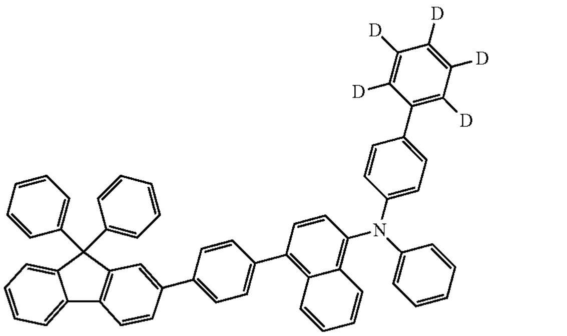
2-34
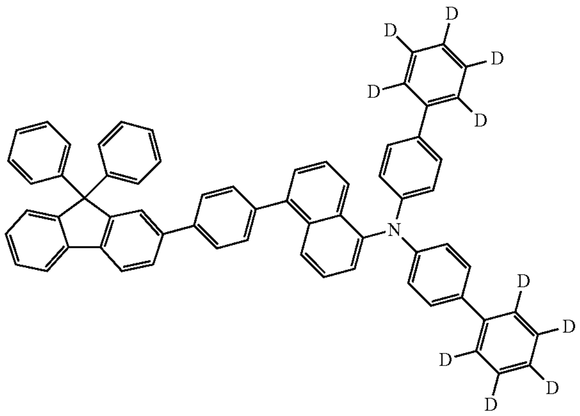

-continued
2-35
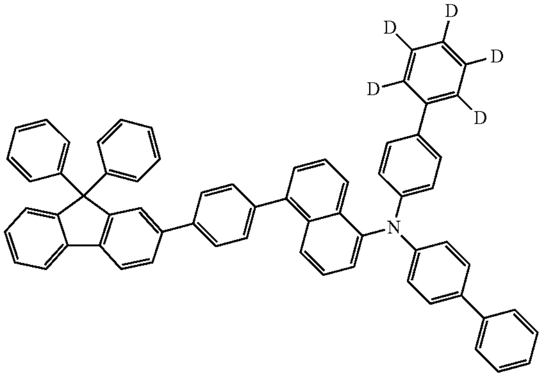
2-36
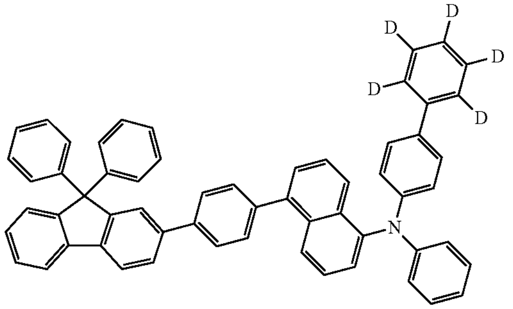
2-37
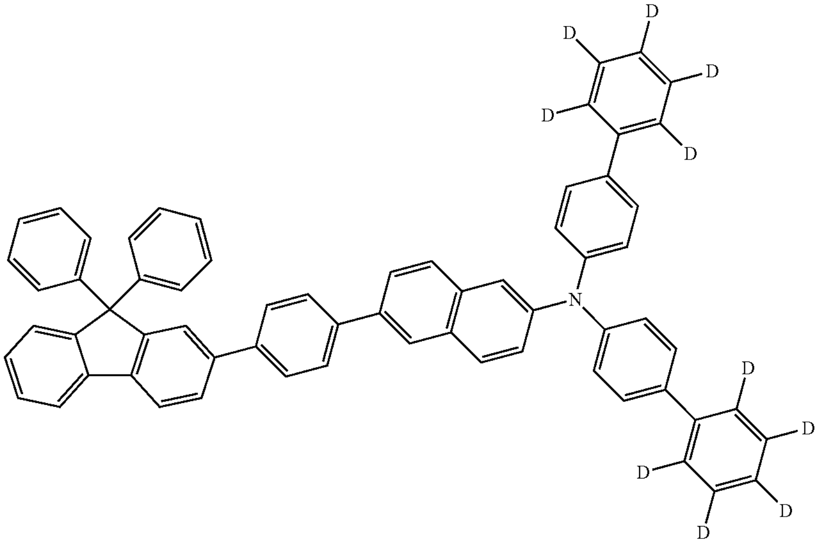
2-38
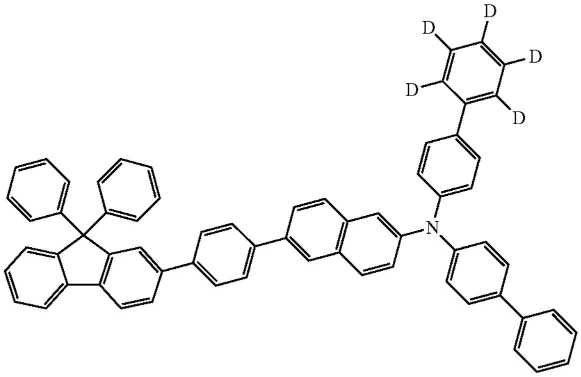
2-39
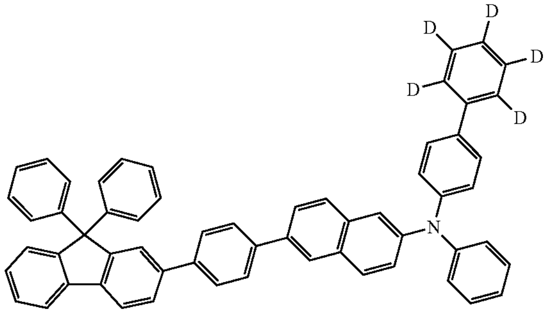

-continued
2-40
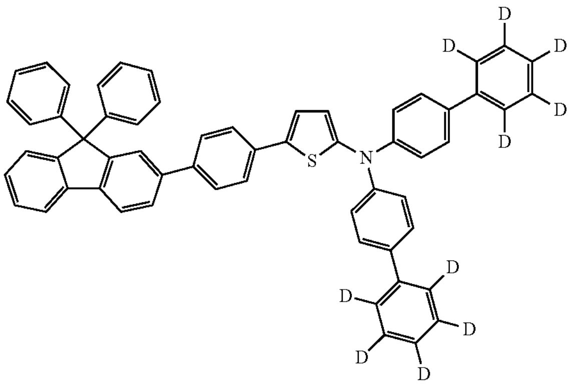
2-41
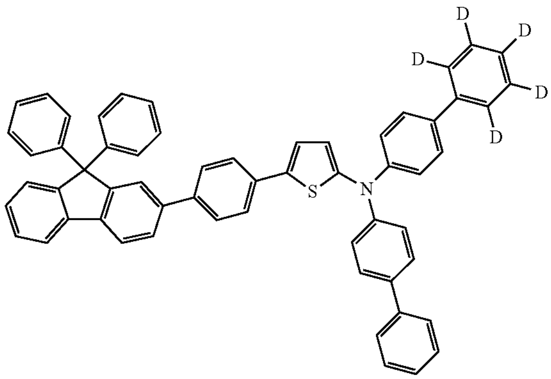
2-42
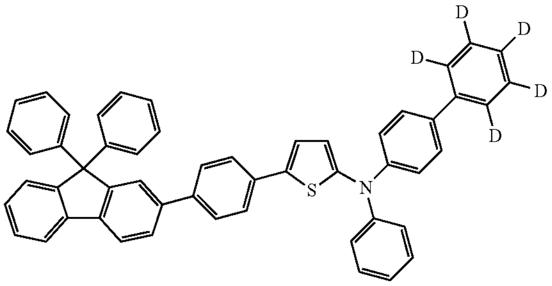
2-43
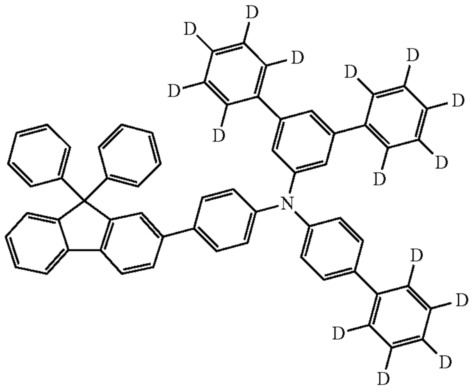
2-44
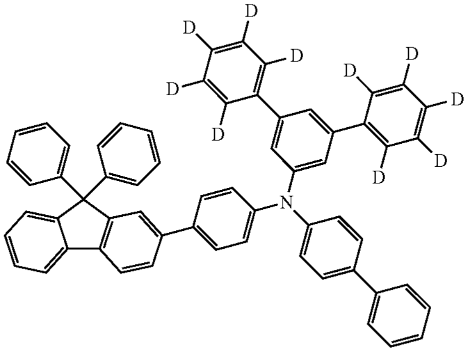
2-45
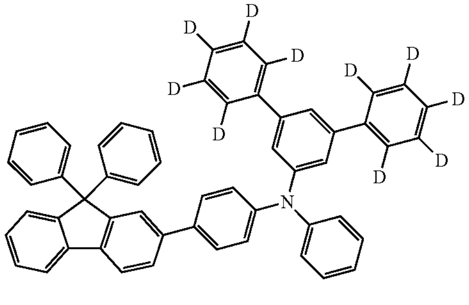
2-46
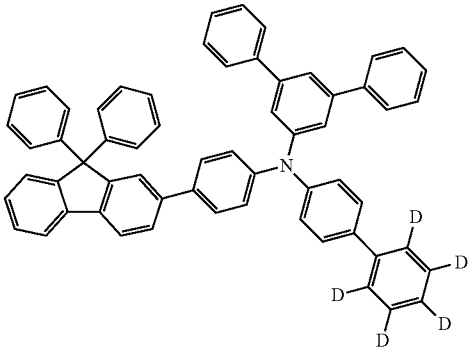
2-47
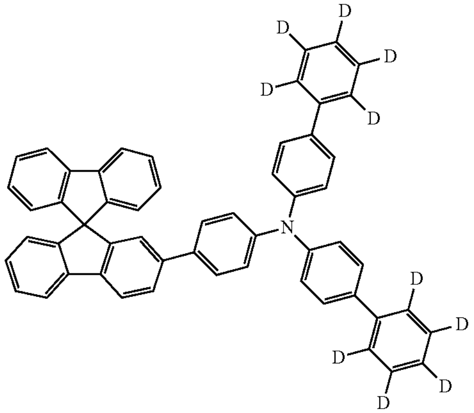

-continued
2-48
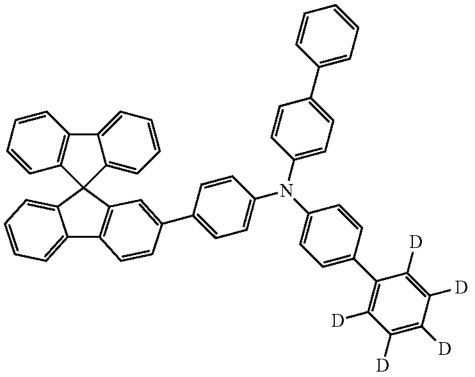
2-49
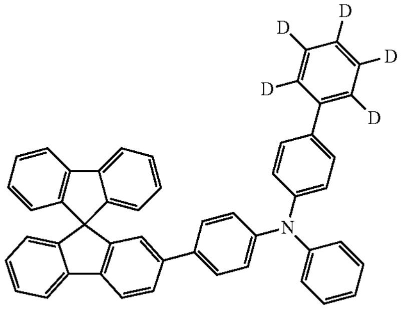
2-50
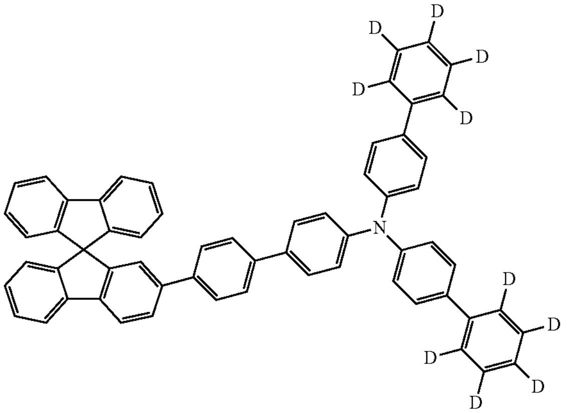
2-51
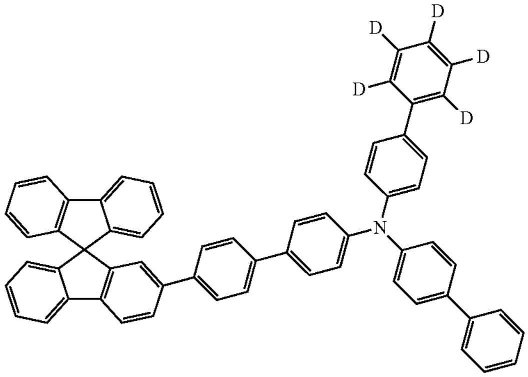
2-52
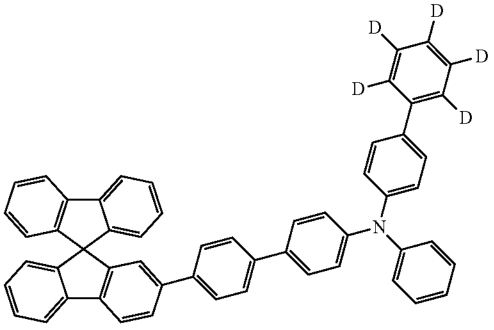
2-53
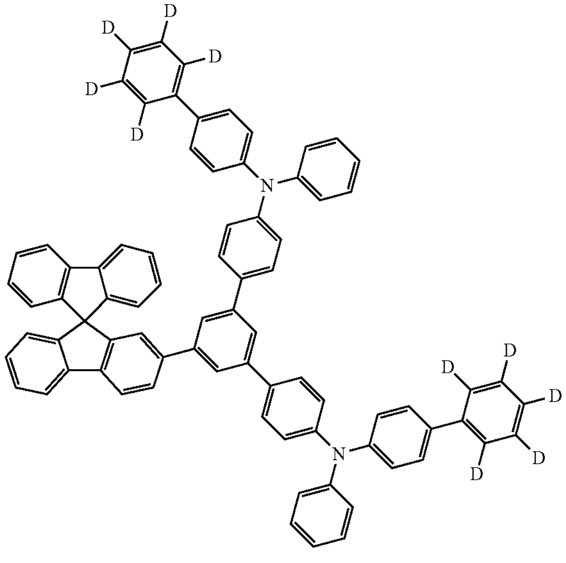

-continued
2-54
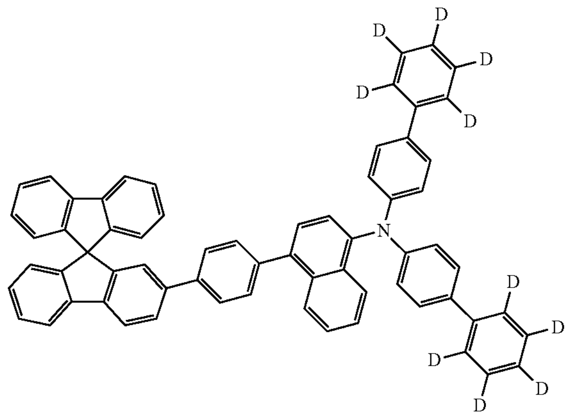
2-55
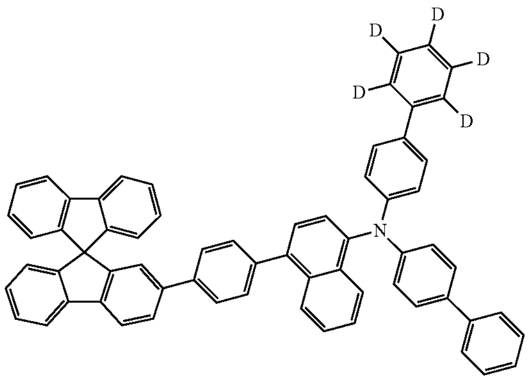
2-56
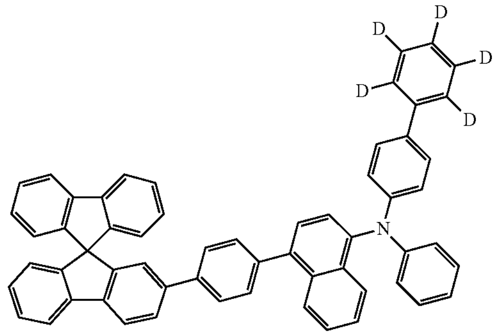
2-57
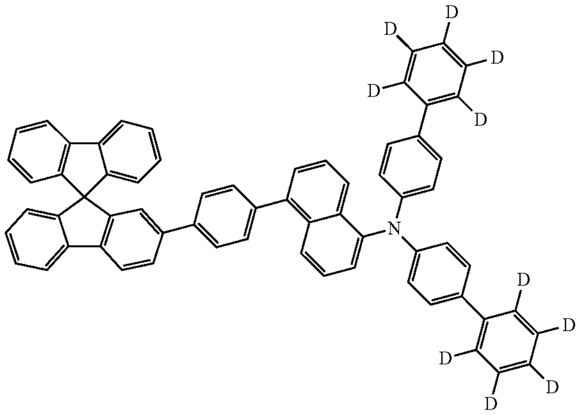
2-58
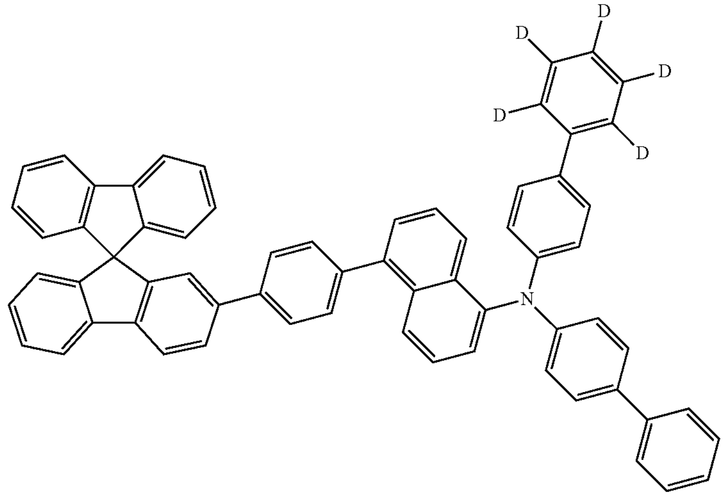

-continued
2-59
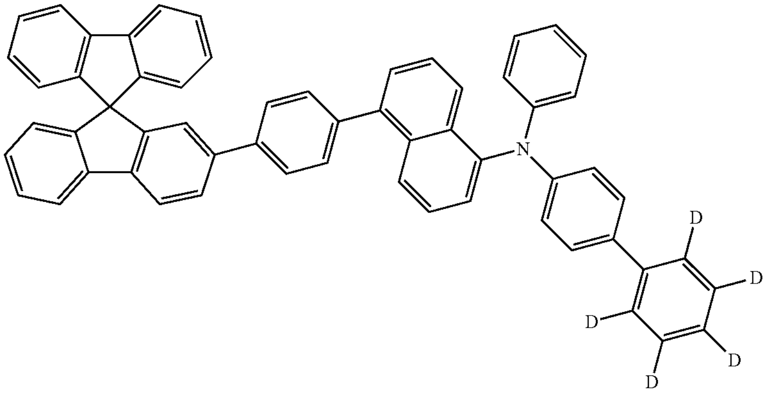
2-60
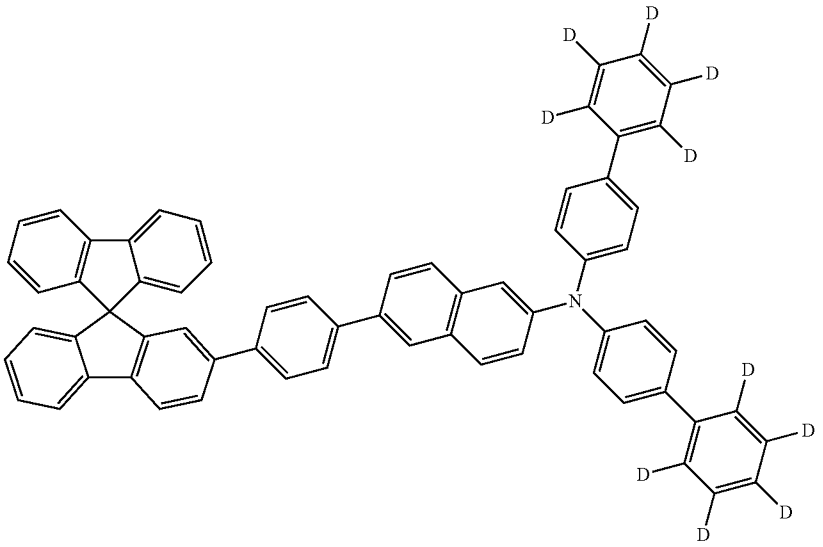
2-61
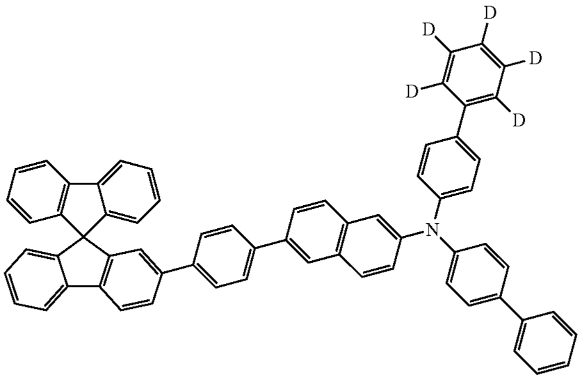
2-62
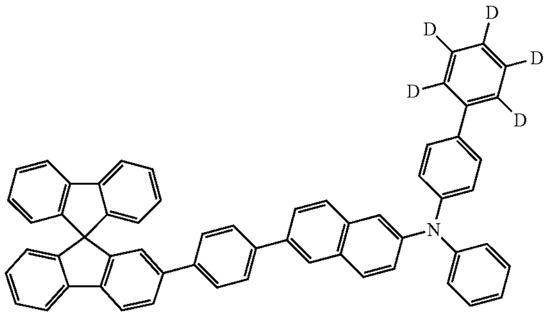

-continued
2-63
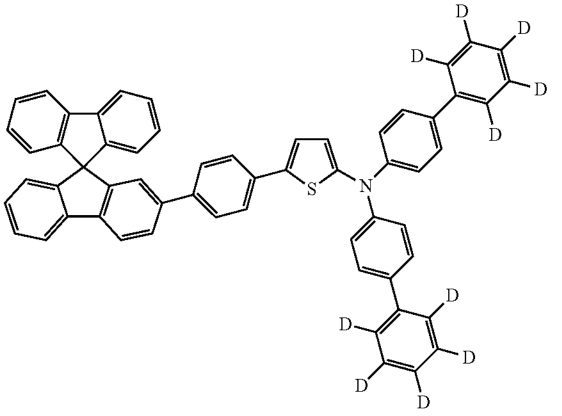
2-64
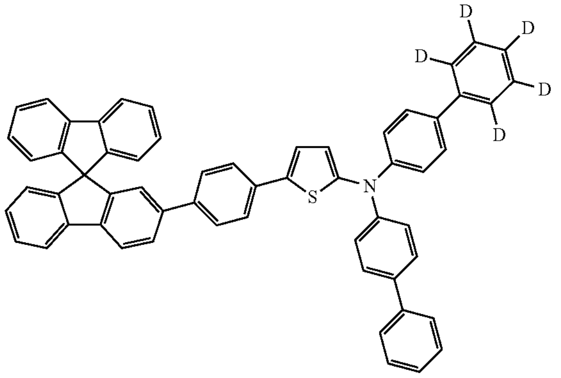
2-65
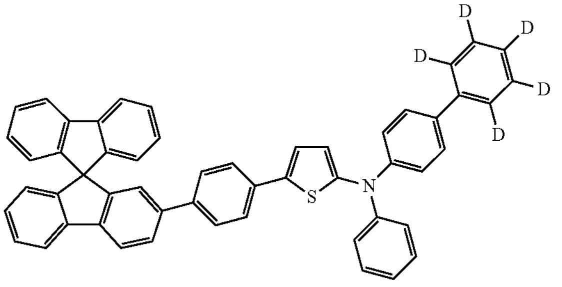
2-66
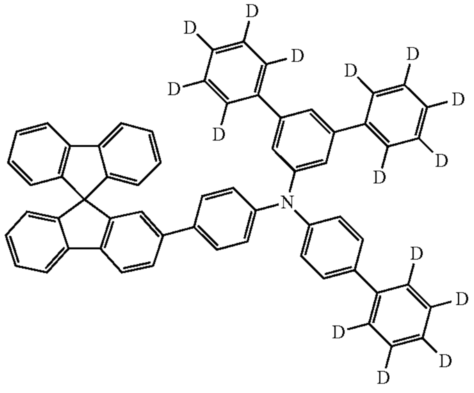
2-67
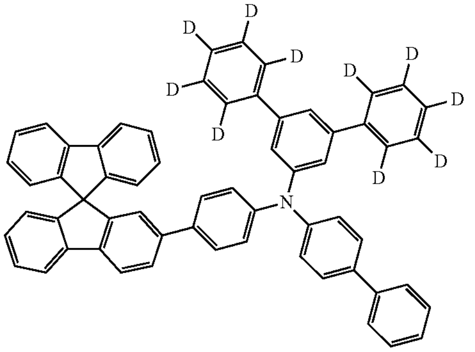
2-68
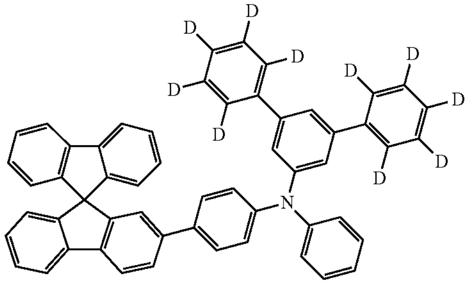
2-69
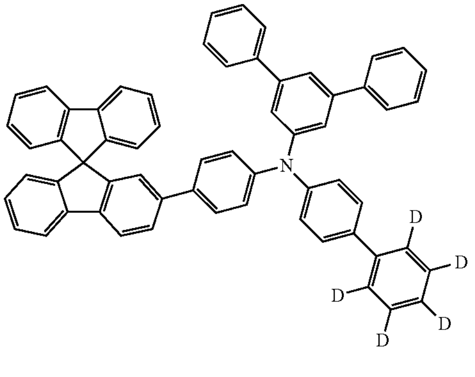
2-70
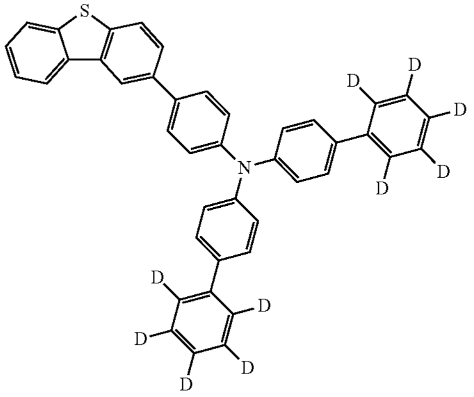

-continued
2-71
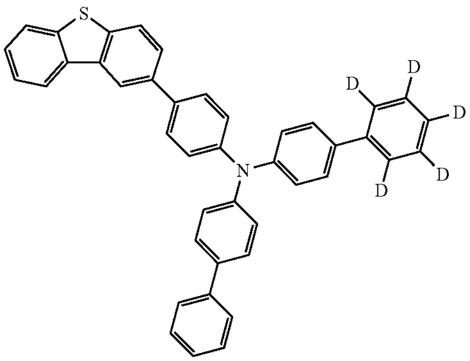
2-72
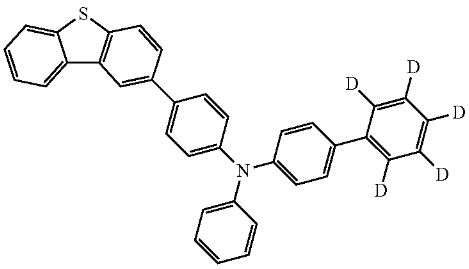
2-73
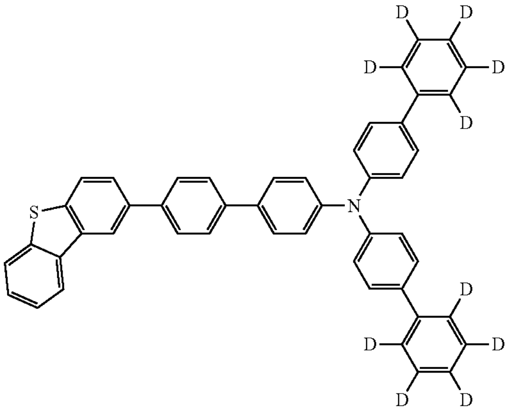
2-74
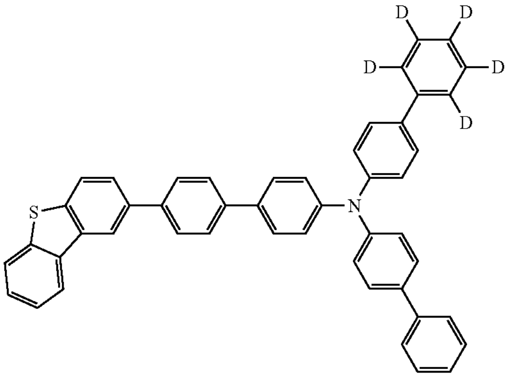
2-75
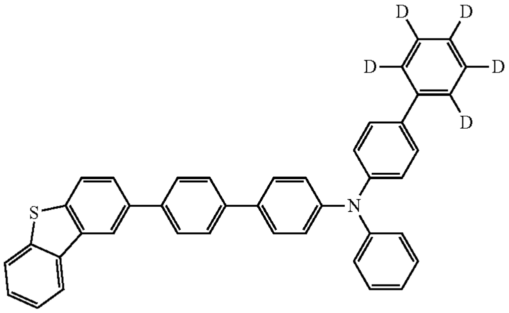
2-76
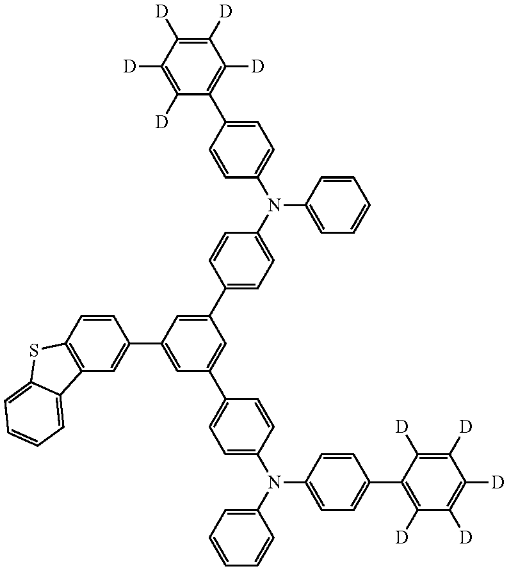

-continued
2-77
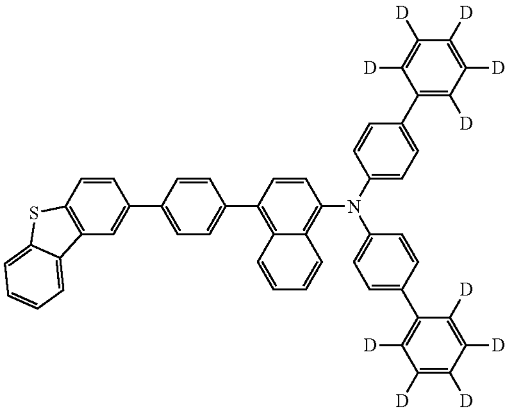
2-78
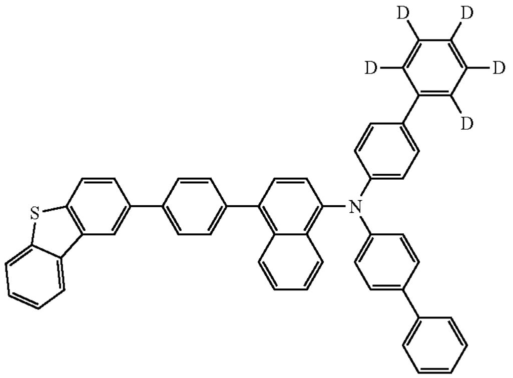
2-79
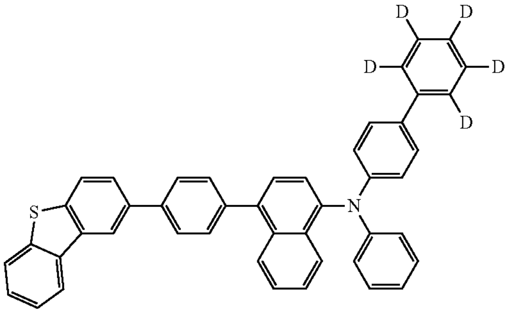
2-80
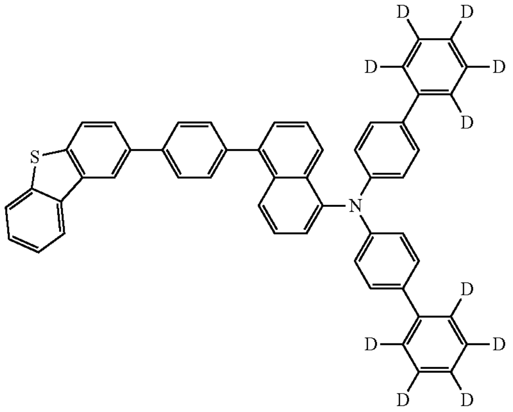
2-81
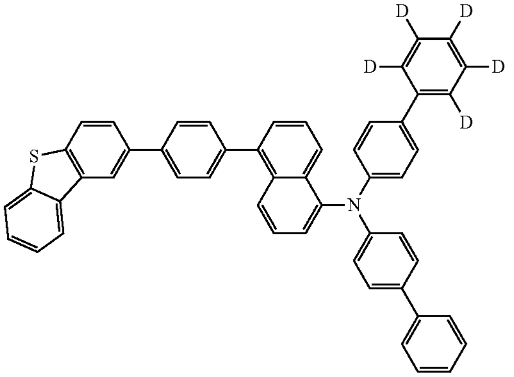
2-82
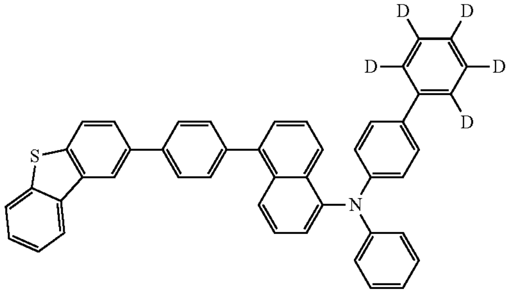
2-83
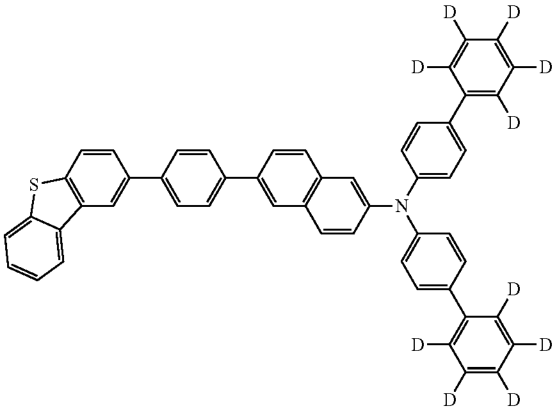
2-84
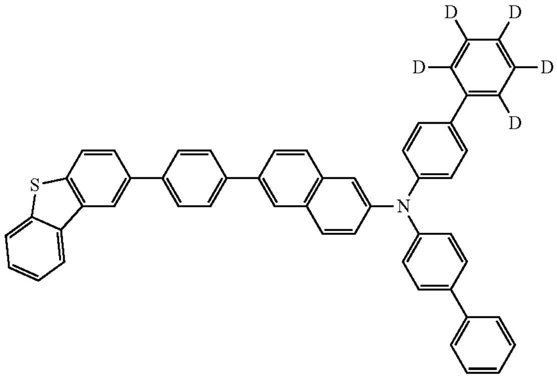

-continued
2-85
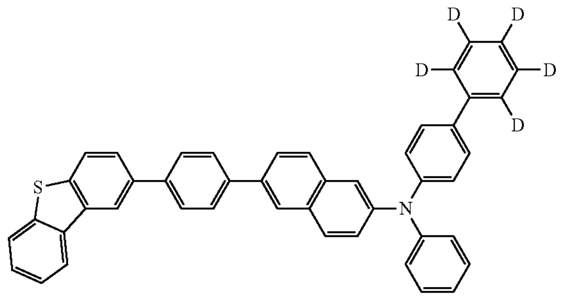
2-86
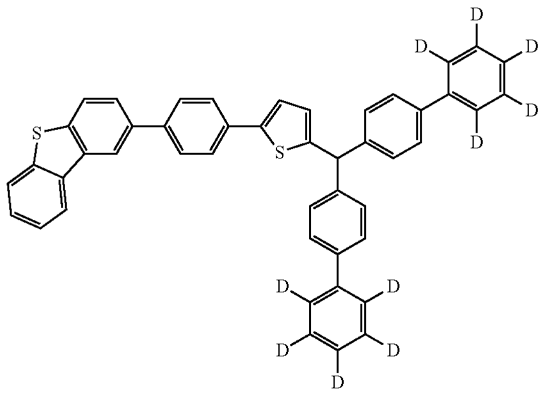
2-87
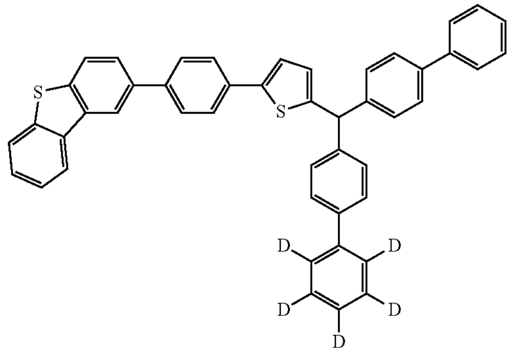
2-88
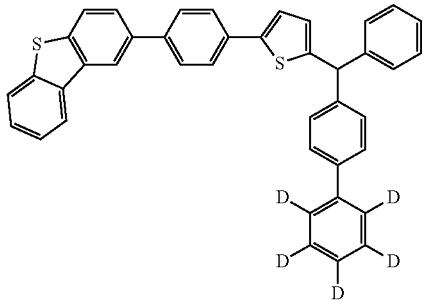
2-89
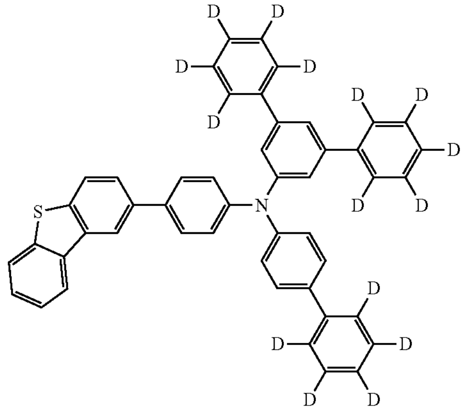
2-90
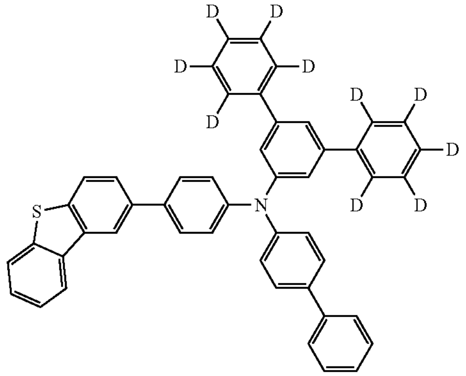
2-91
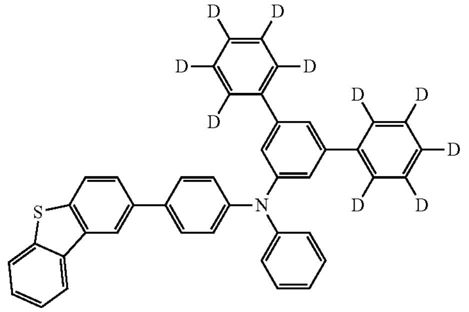
2-92
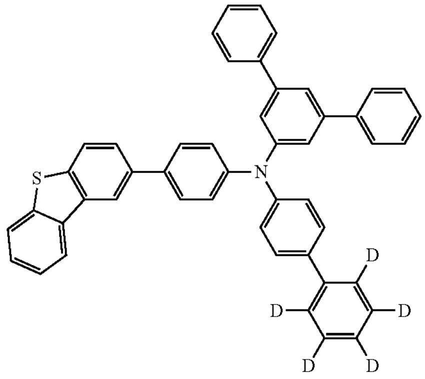

-continued
2-93
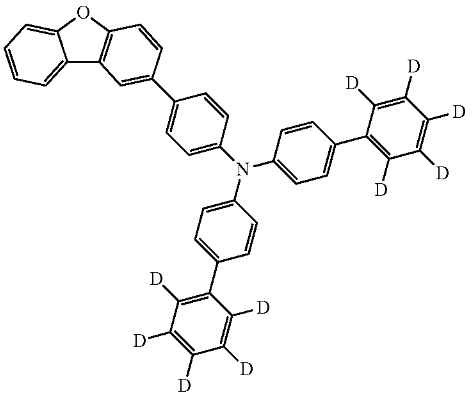
2-94
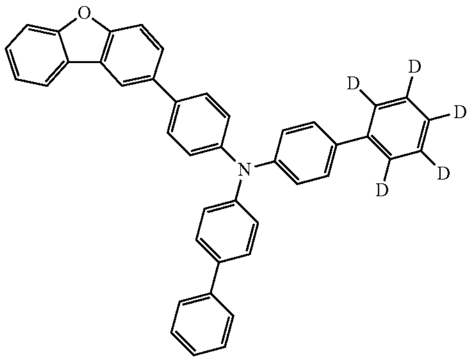
2-95
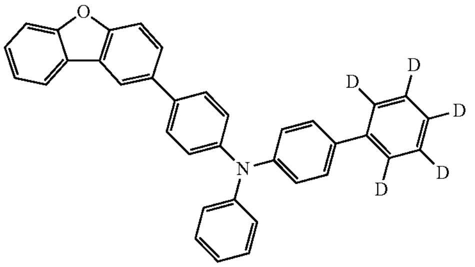
2-96
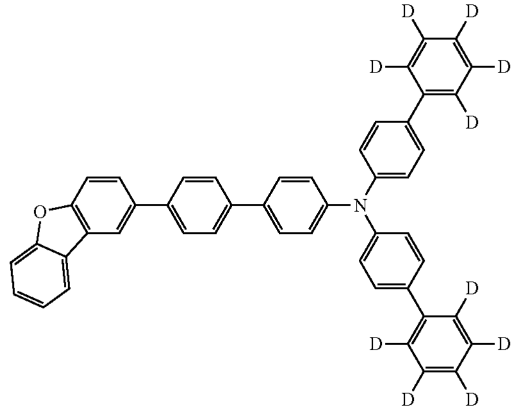
2-97
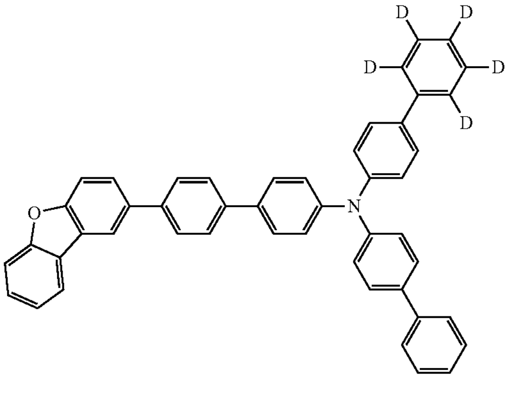
2-98
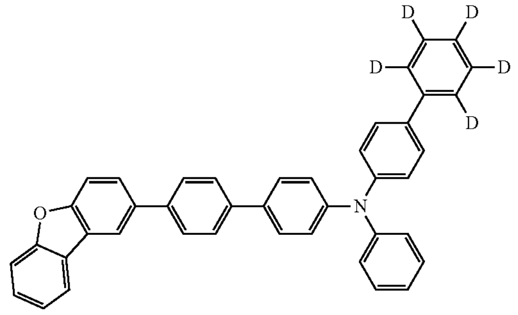

-continued
2-99
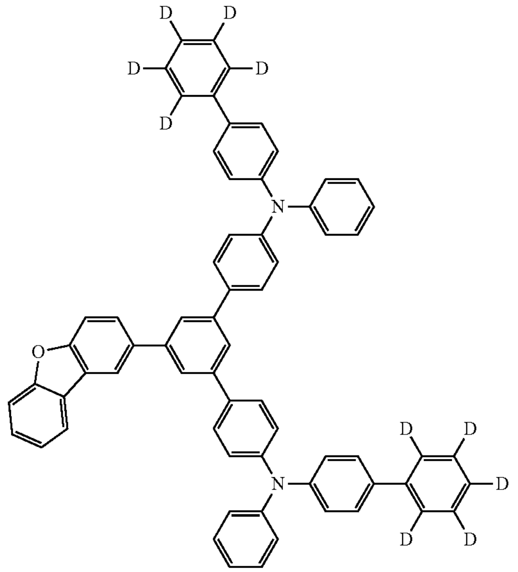
2-100
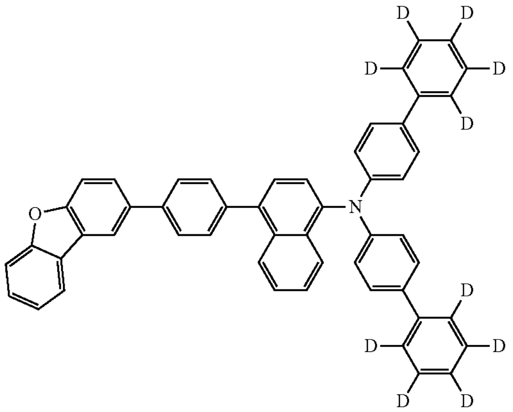
2-101
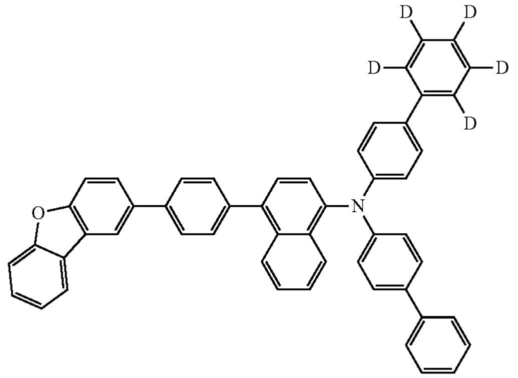
2-102
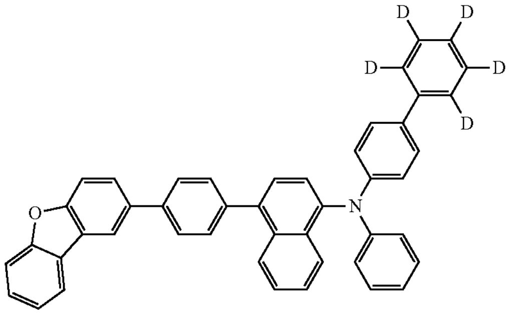
2-103
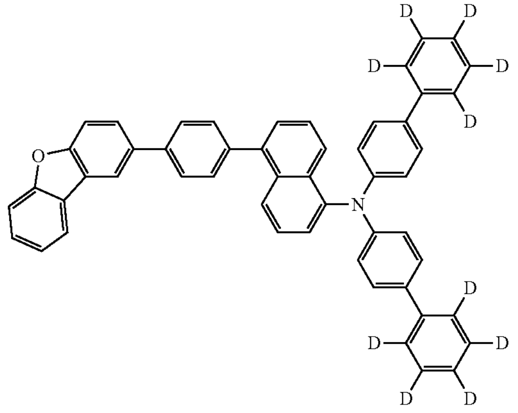
2-104
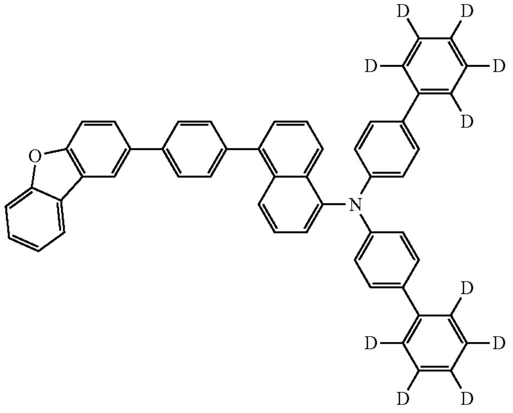

-continued
2-105
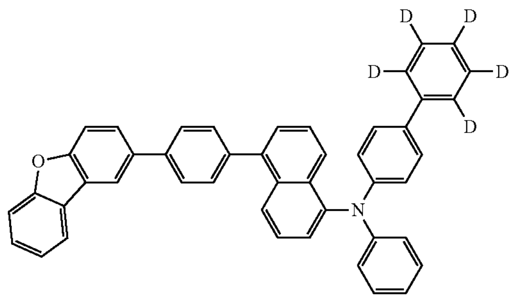
2-106
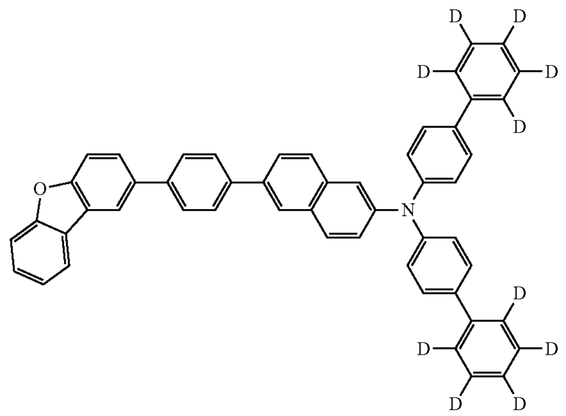
2-107
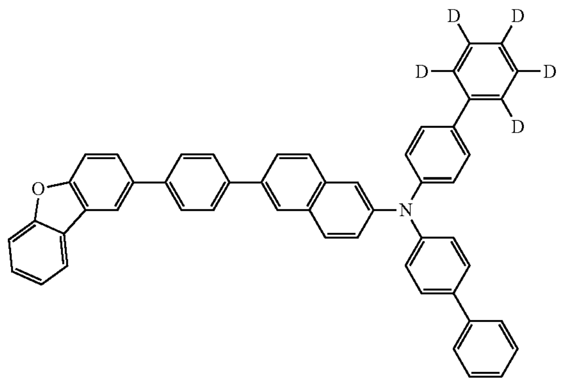
2-108
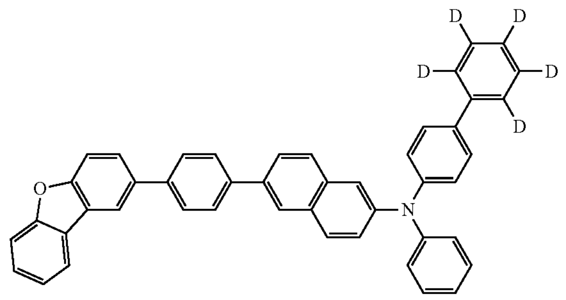
2-109
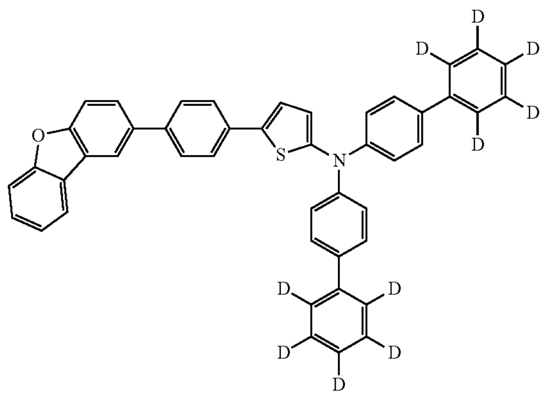
2-110
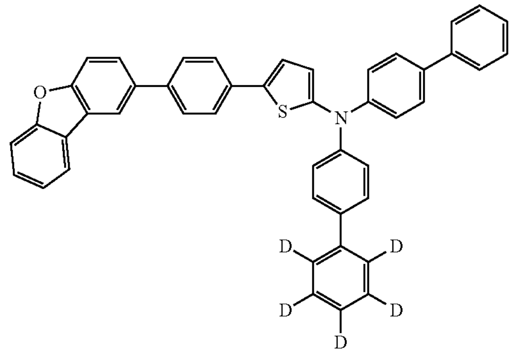
2-111
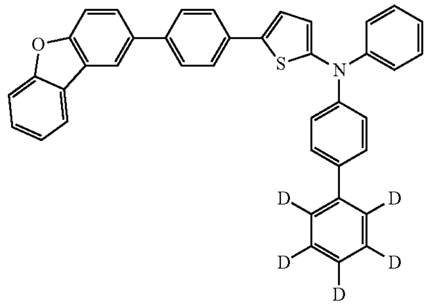
2-112
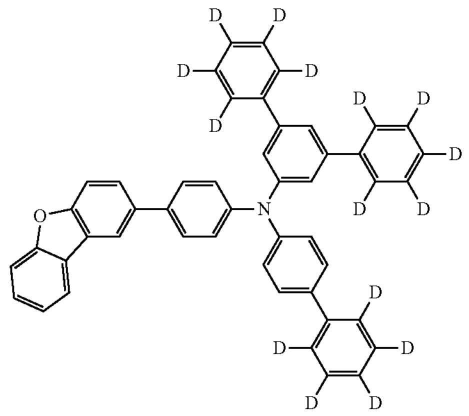

-continued
2-113
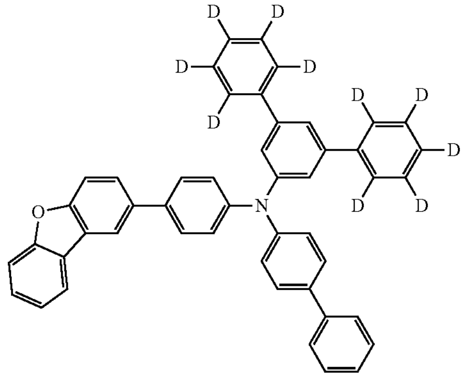
2-114
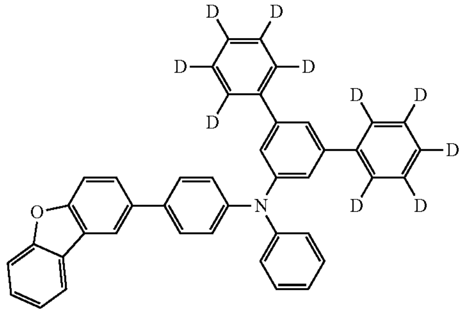
2-115
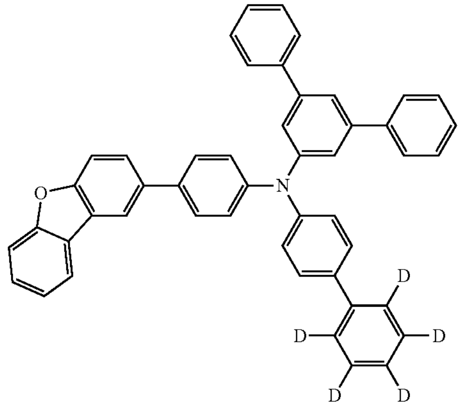
2-116
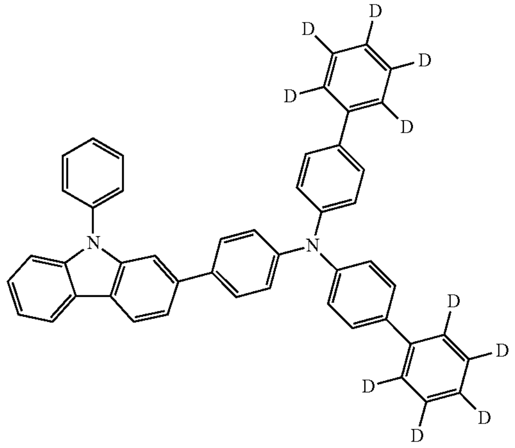
2-117
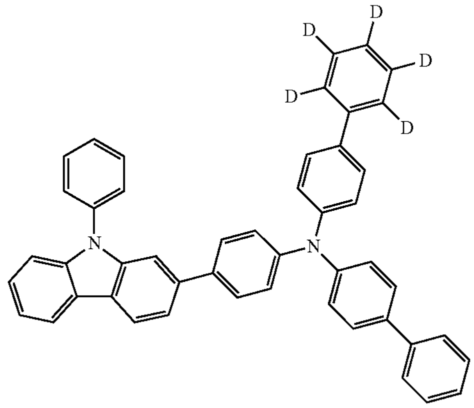
2-118
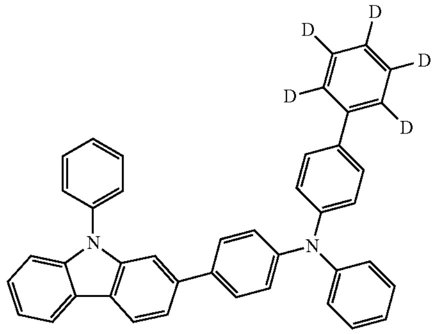

-continued
2-119
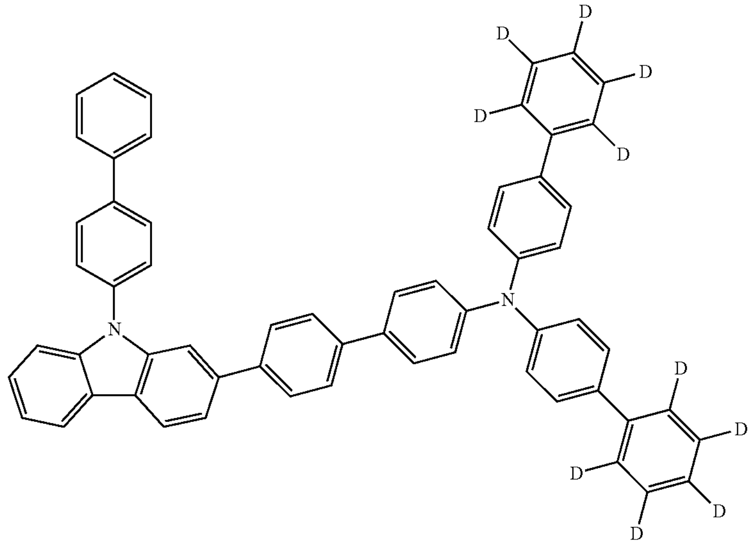
2-120
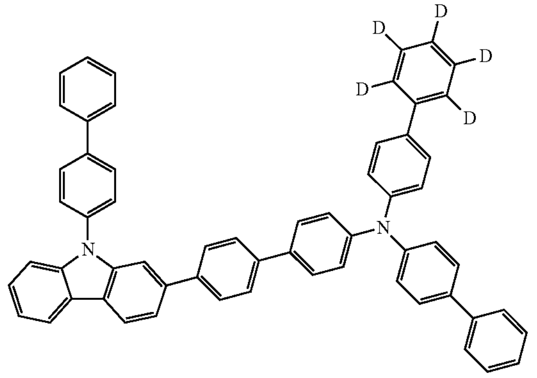
2-121
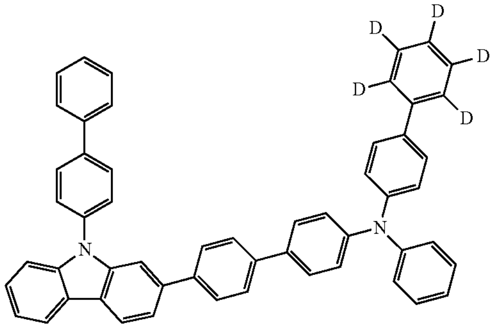
2-122
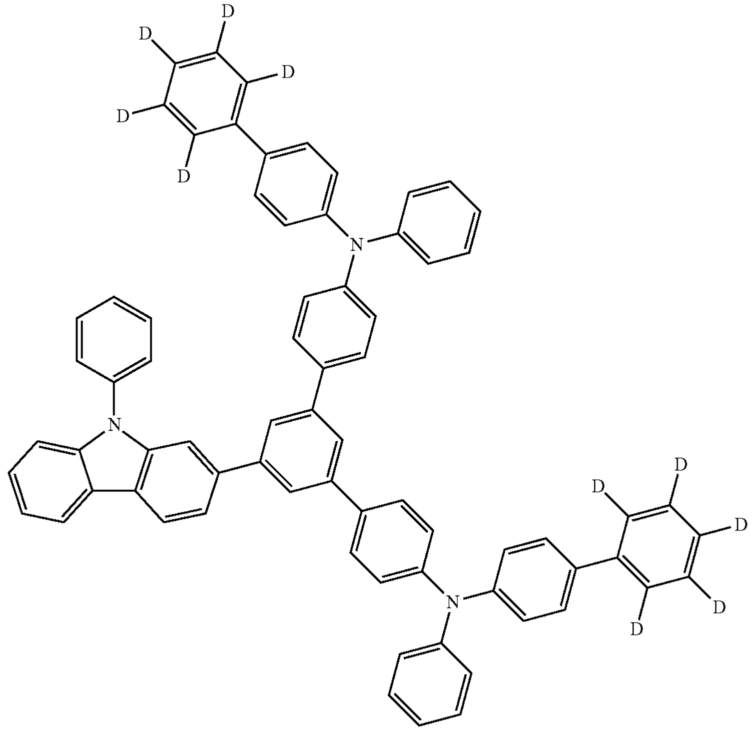

-continued
2-123
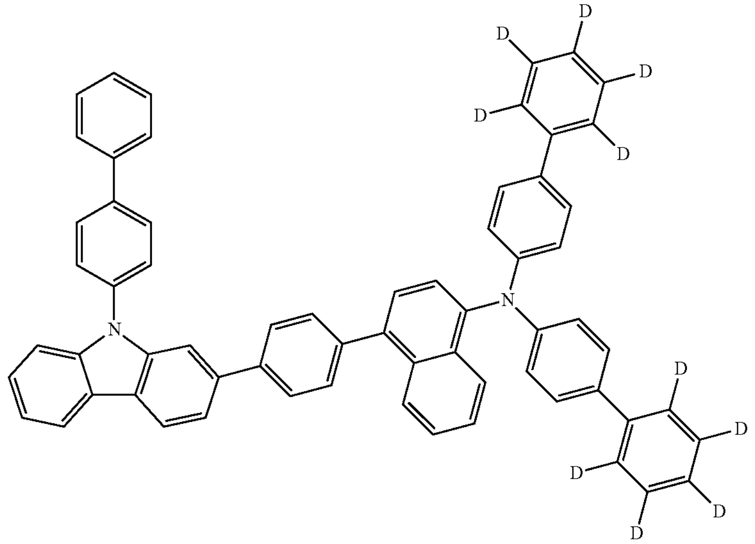
2-124
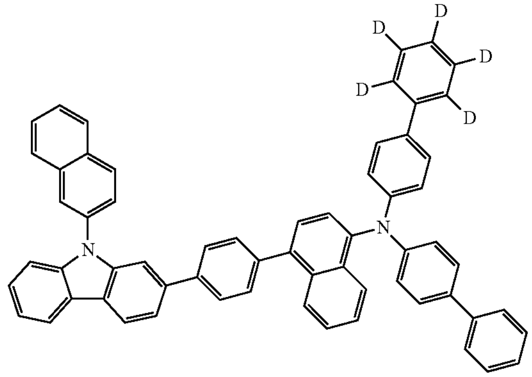
2-125
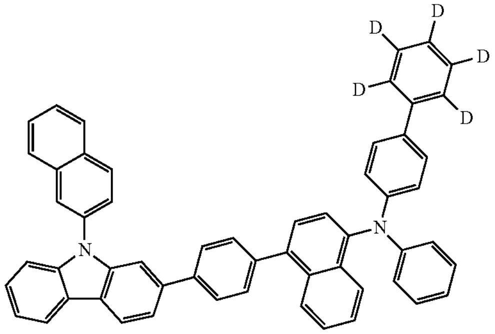
2-126
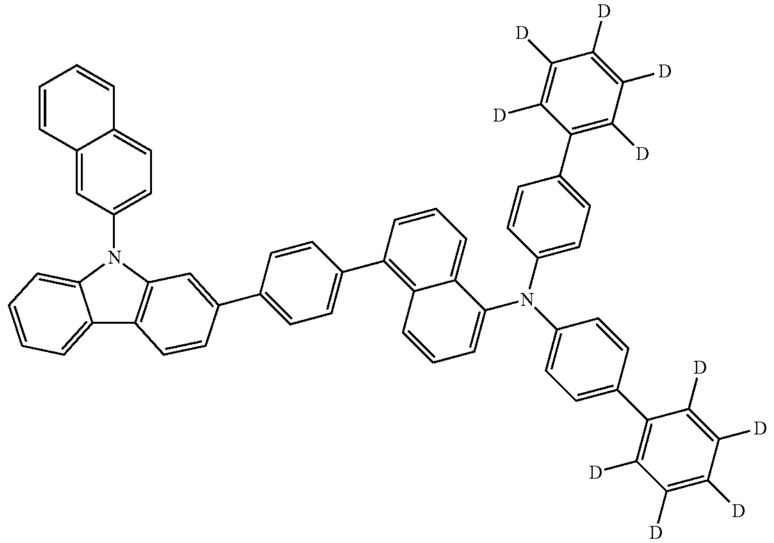

-continued
2-127
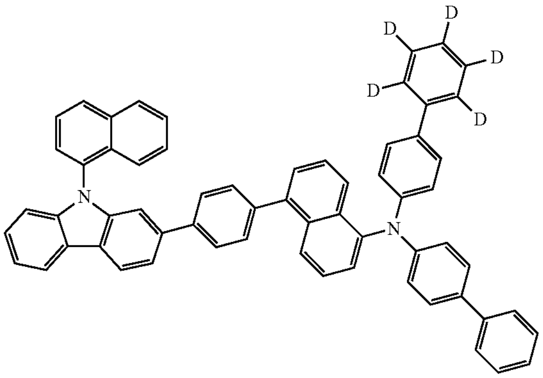
2-128
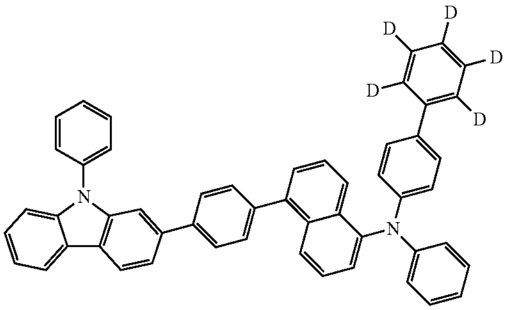
2-129
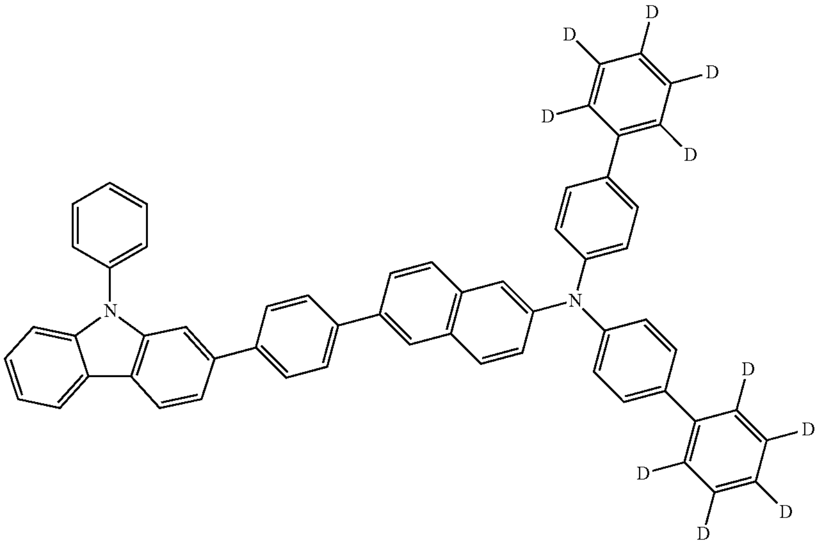
2-130
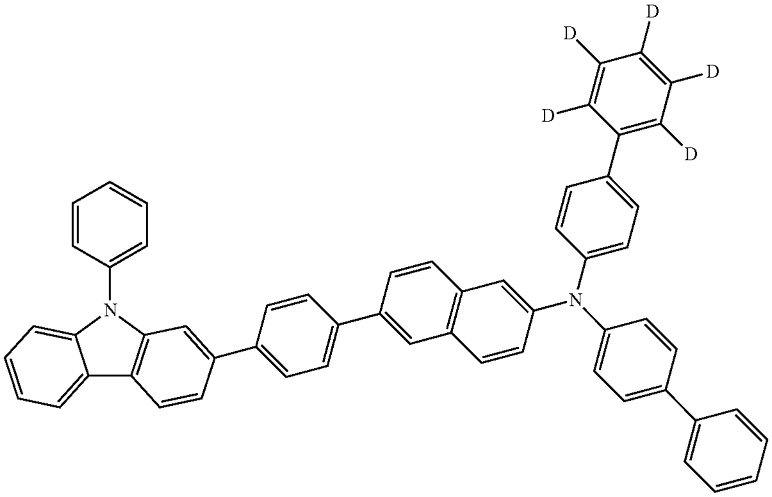

-continued
2-131
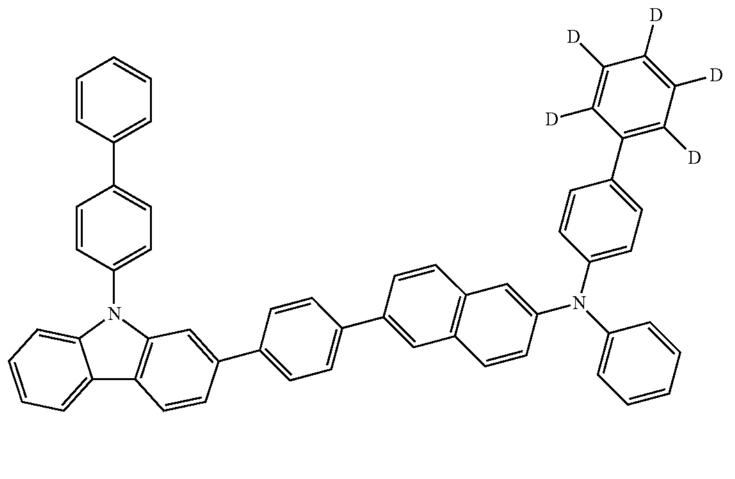
2-132
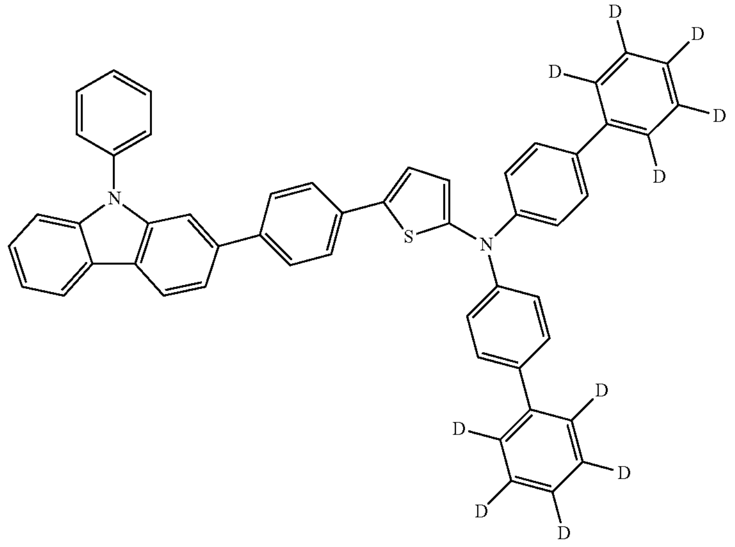
2-133
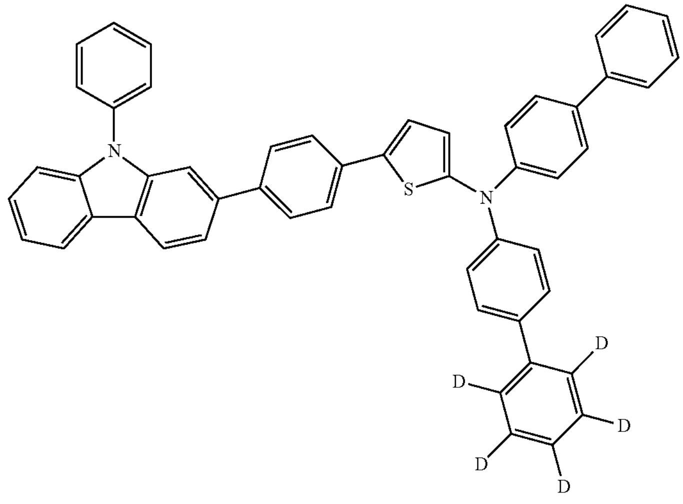

-continued
2-134
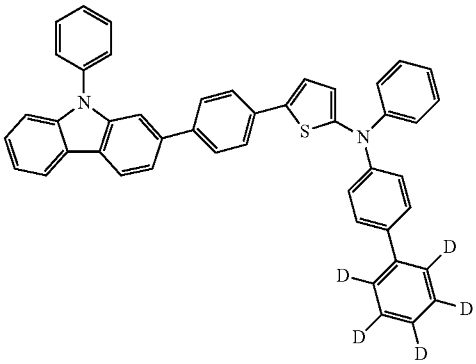
2-135
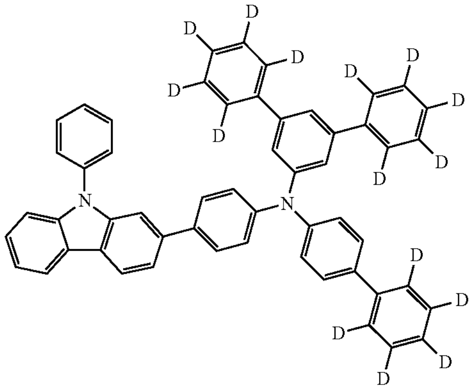
2-136
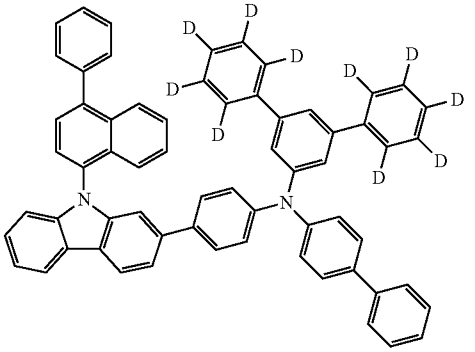
2-137
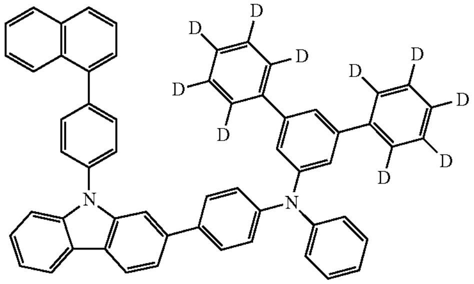
2-138
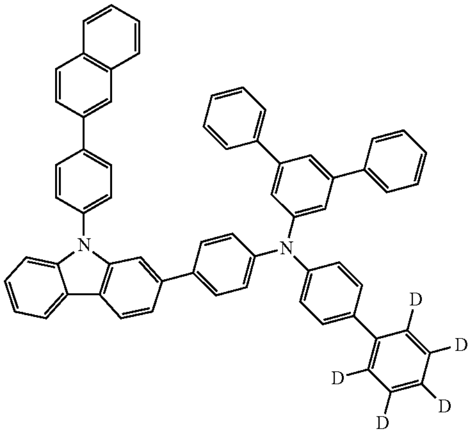
2-139
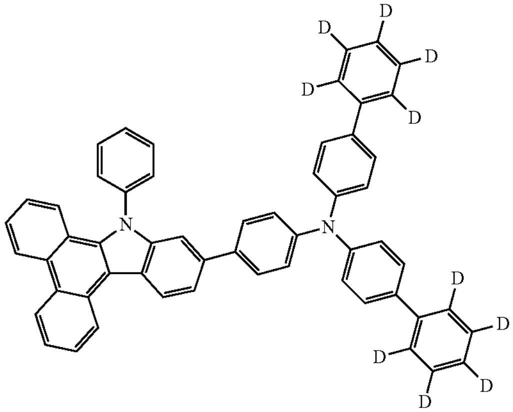
2-140
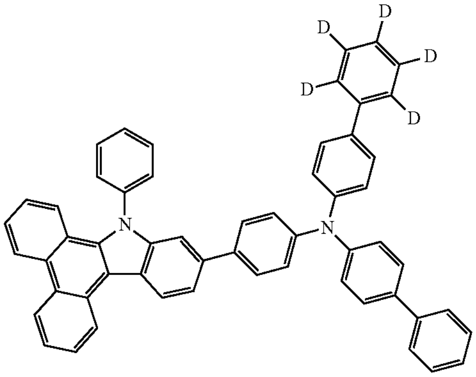
2-141
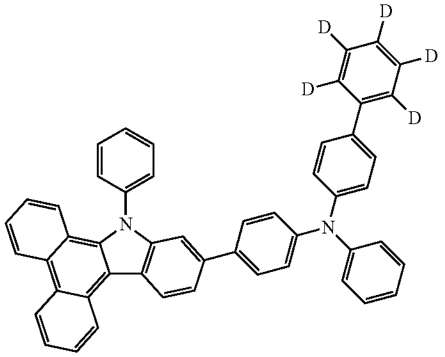

-continued
2-142
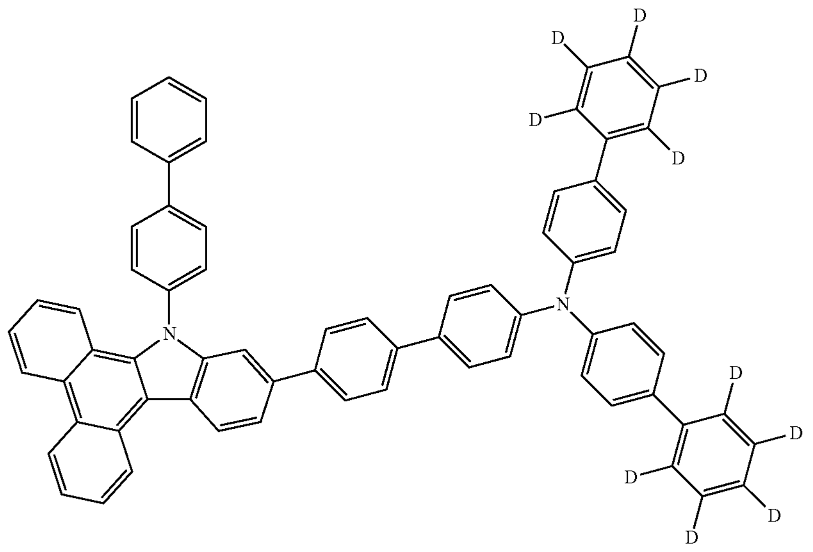
2-143
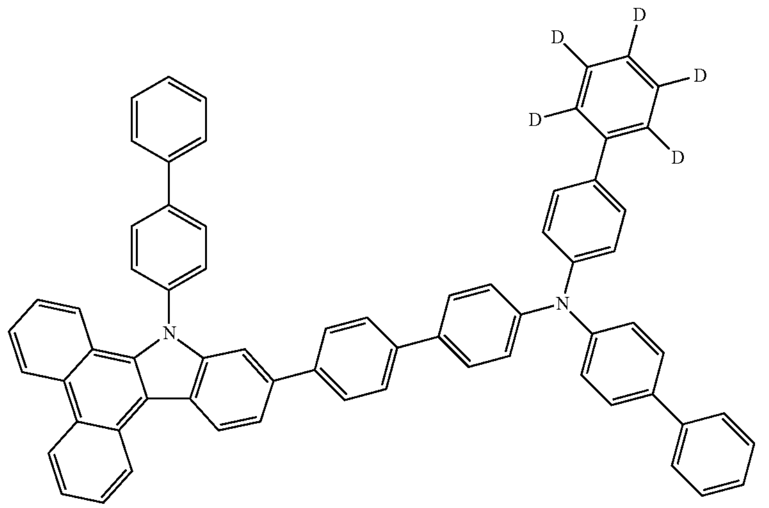
2-144
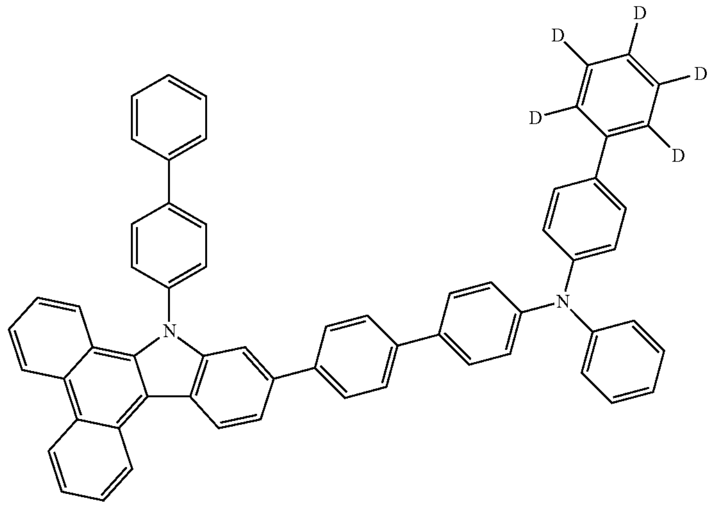

-continued
2-145
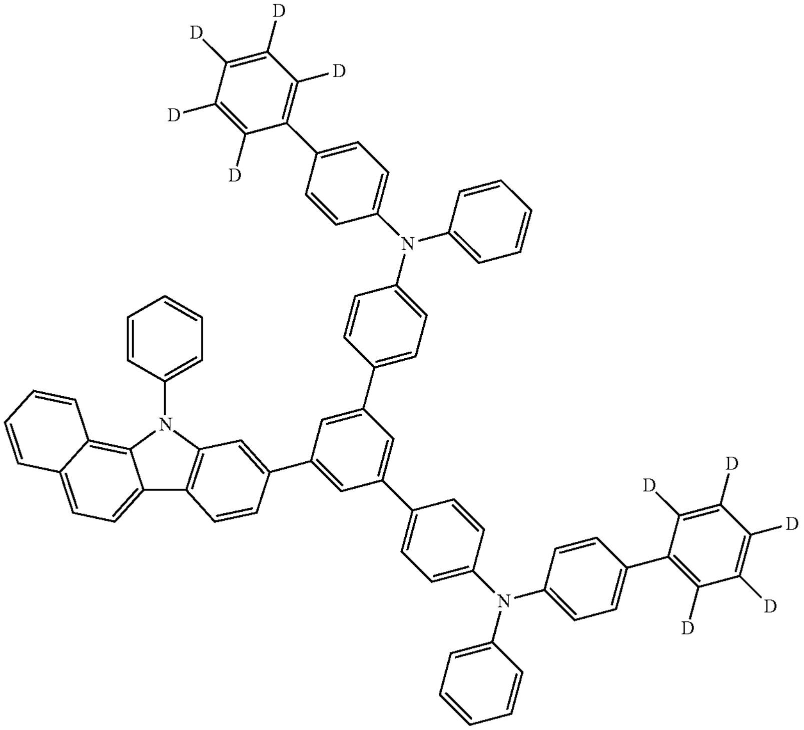
2-146
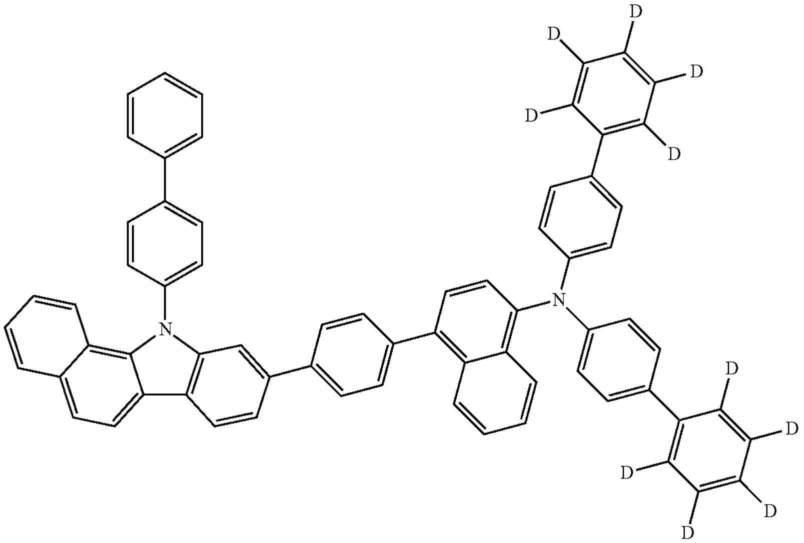
2-147
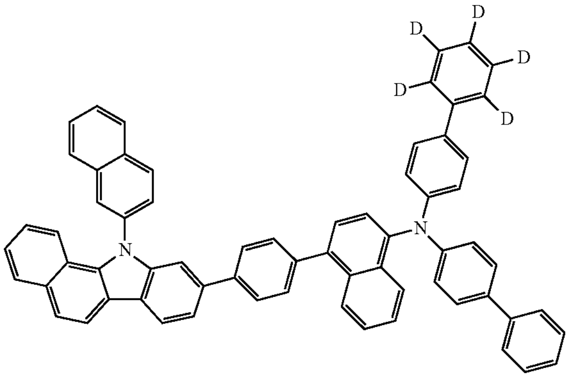
2-148
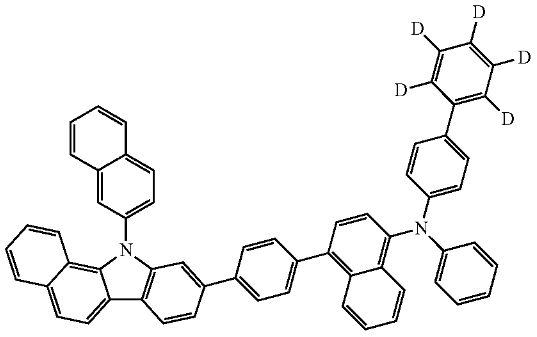

-continued
2-149
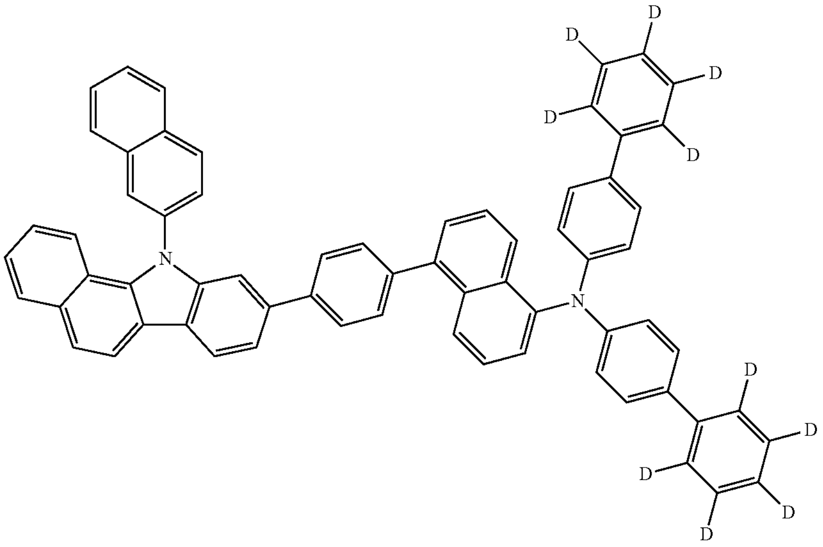
2-150
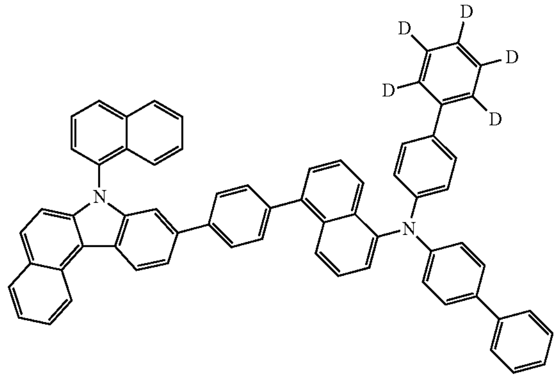
2-151
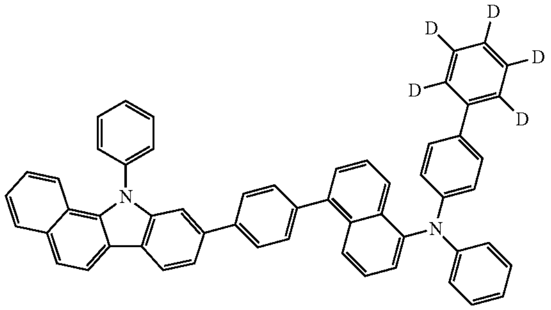
2-152
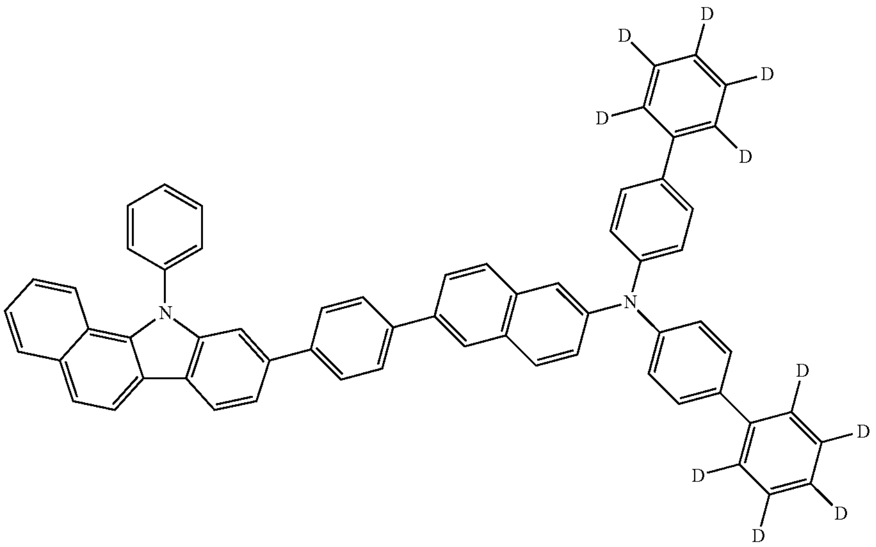

-continued
2-153
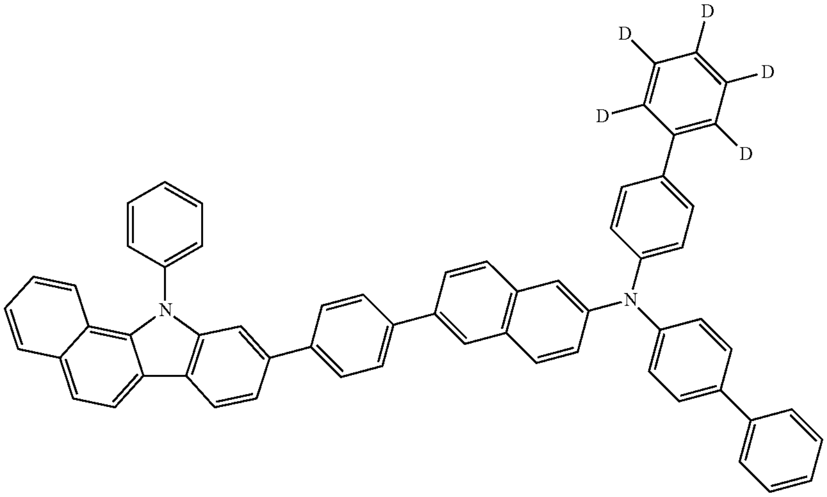
2-154
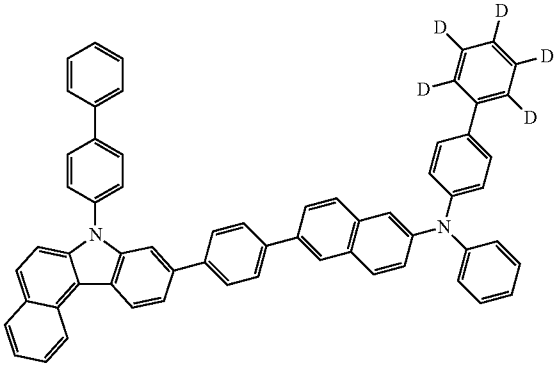
2-155
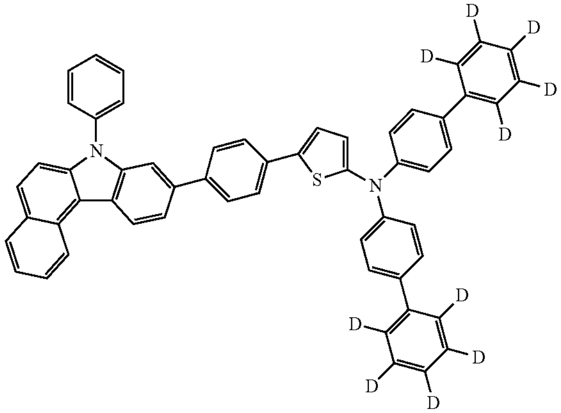
2-156
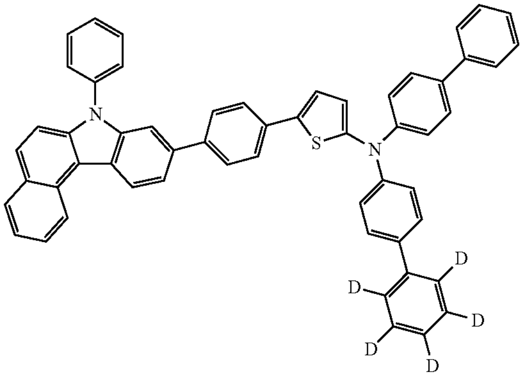
2-157
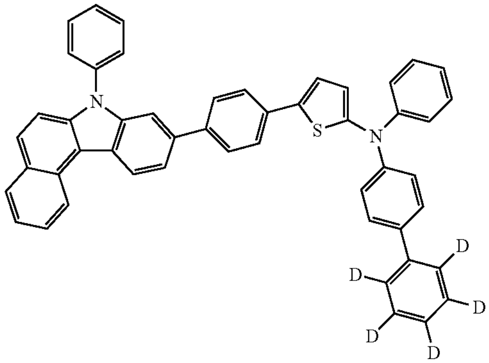

-continued
2-158
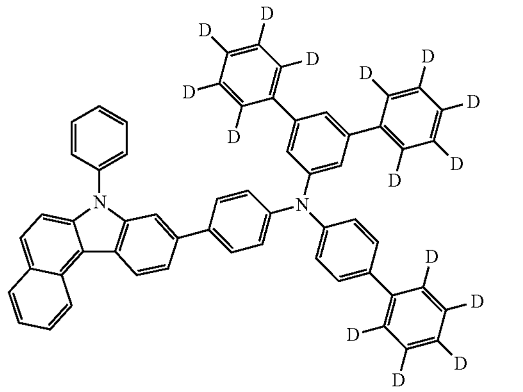
2-159
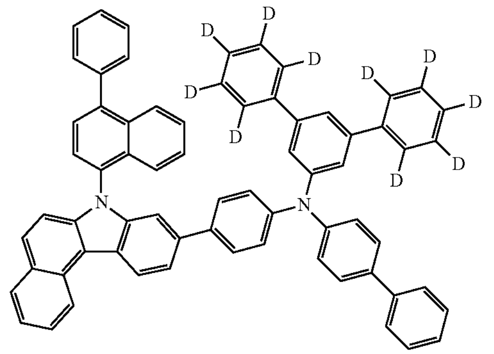
2-160
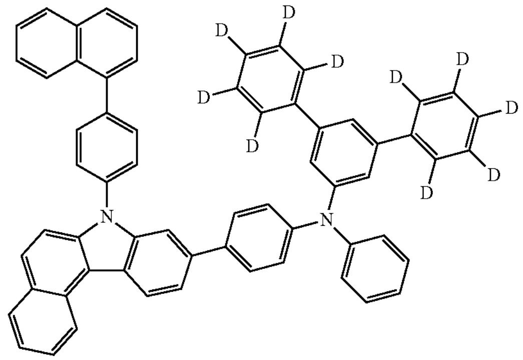
2-161
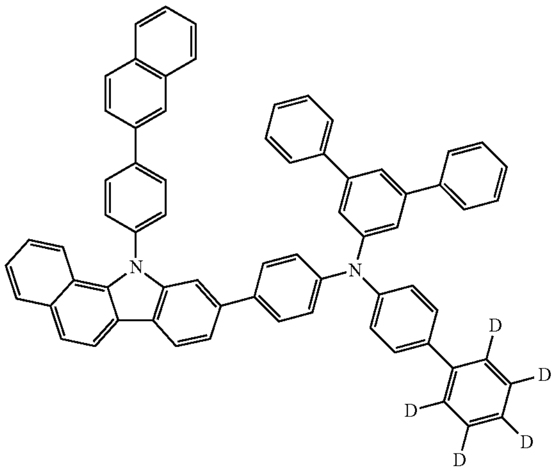
2-162
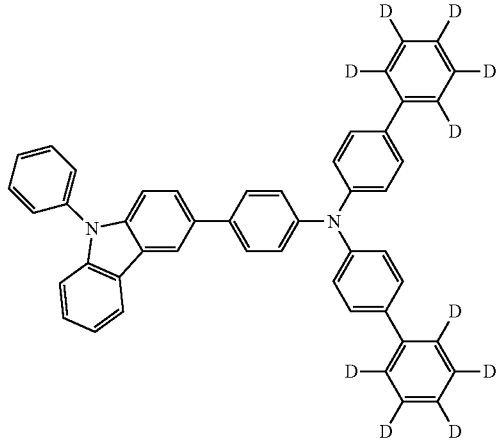
2-163
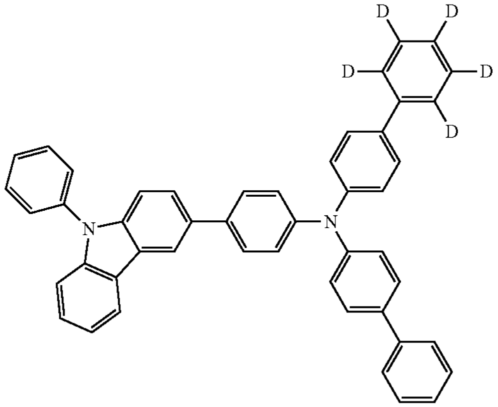

-continued
2-164
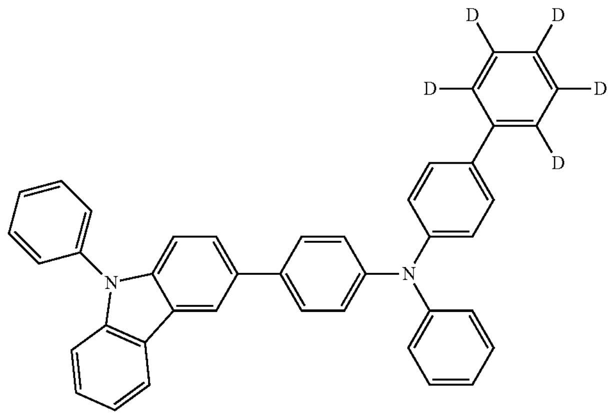
2-165
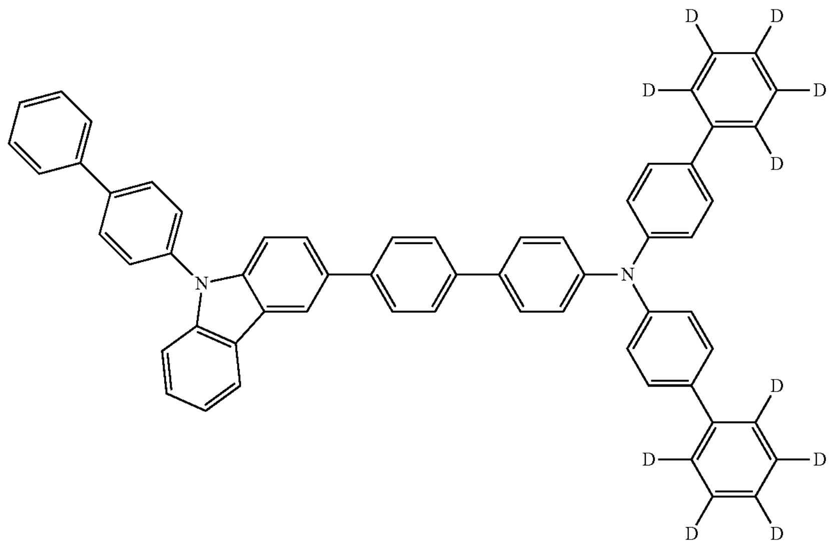
2-166
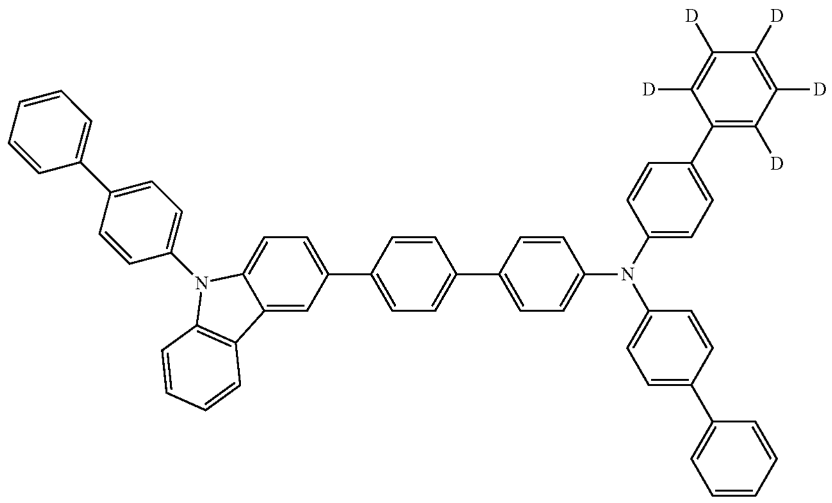

-continued
2-167
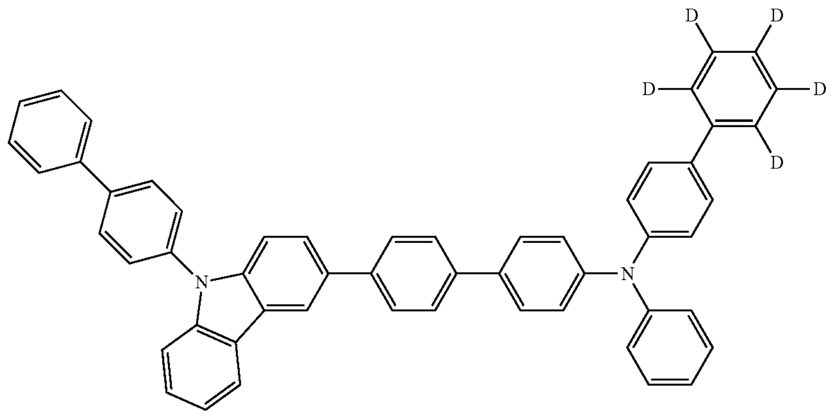
2-168
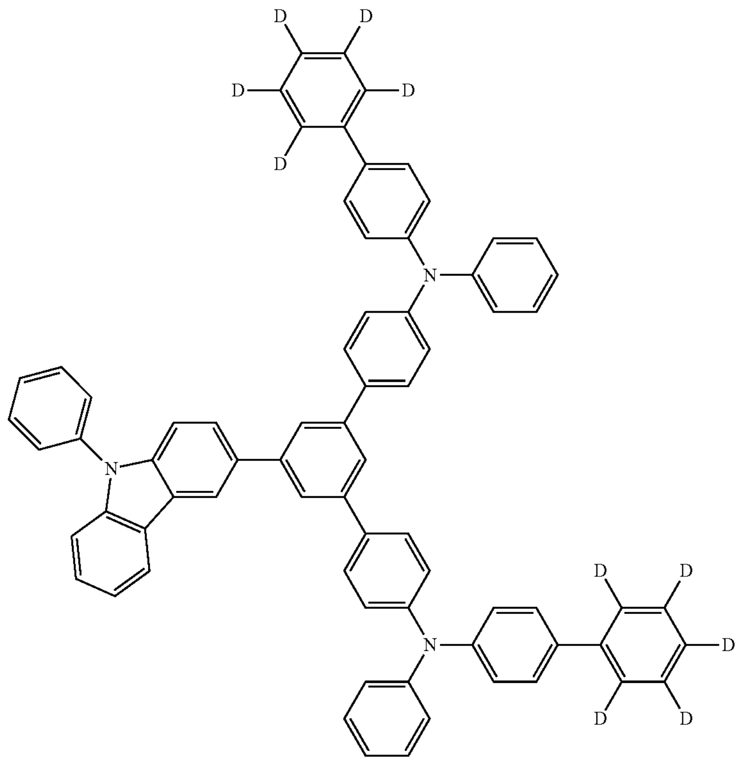

-continued
2-169
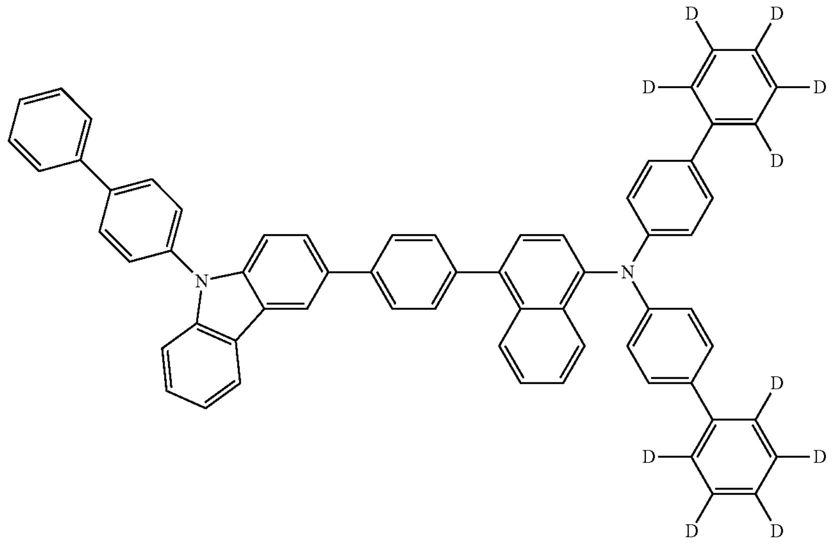
2-170
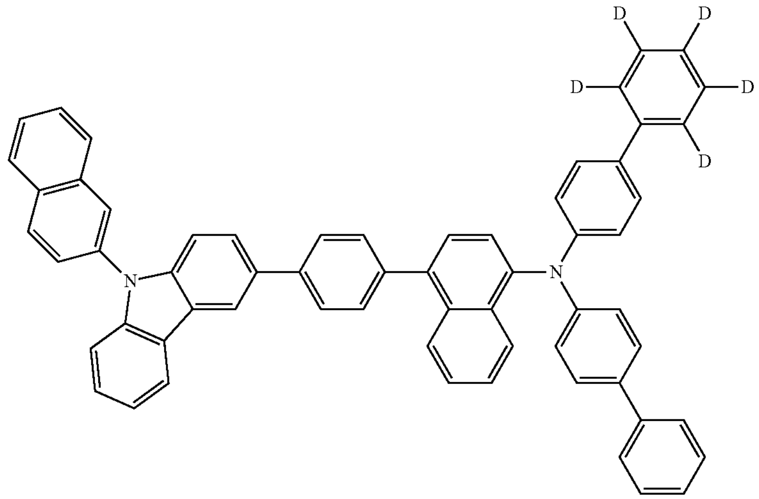
2-171
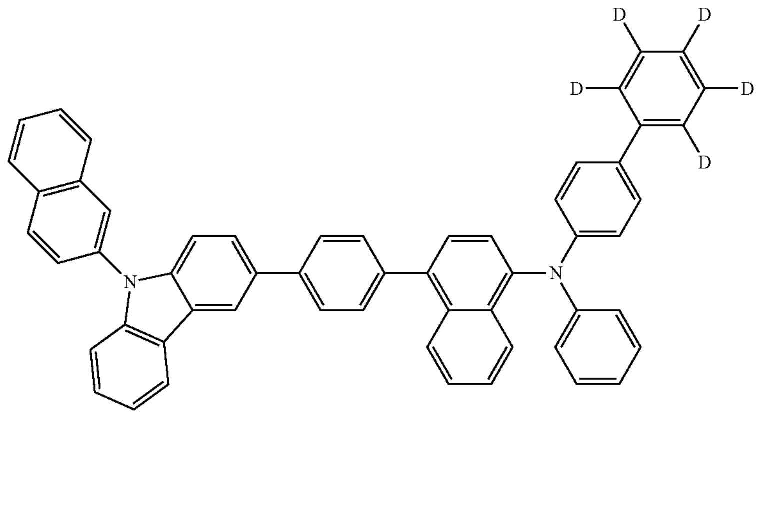

-continued
2-172
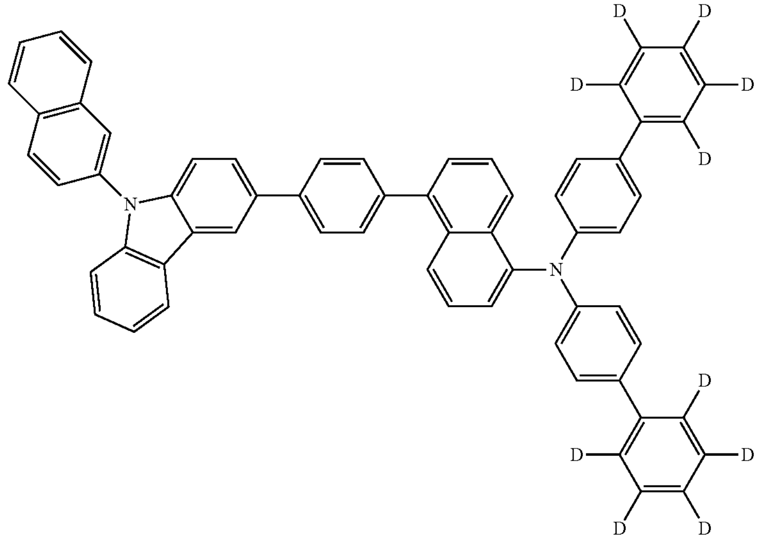
2-173
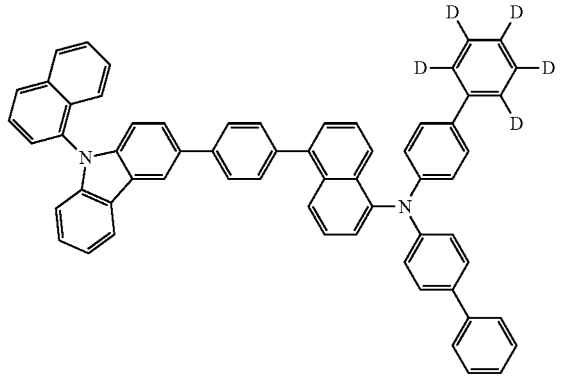
2-174
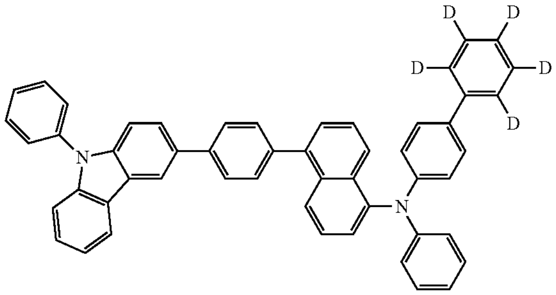
2-175
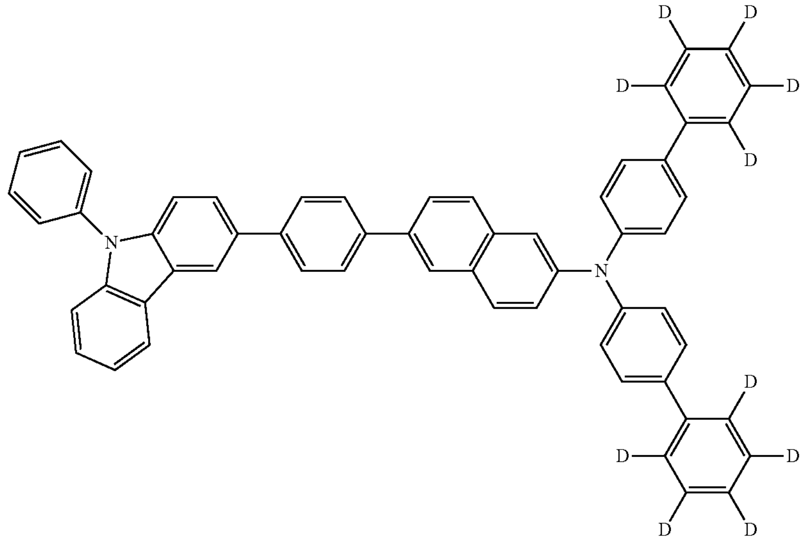

-continued
2-176
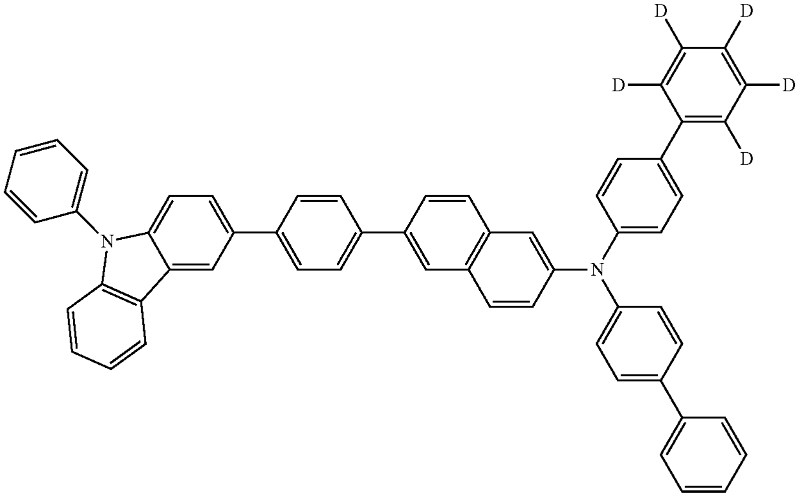
2-177
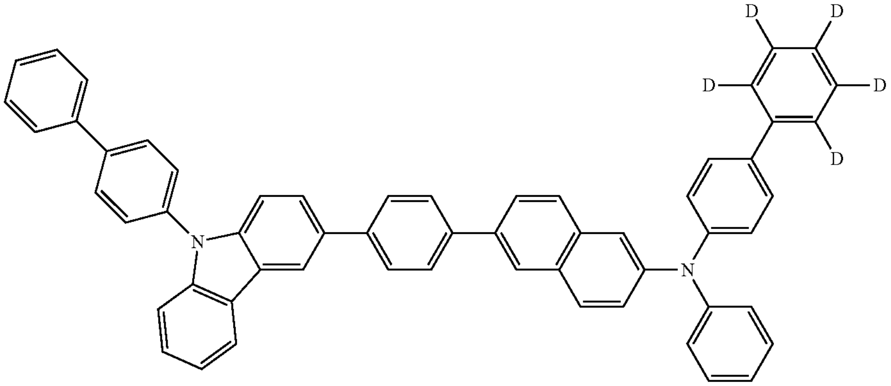
2-178
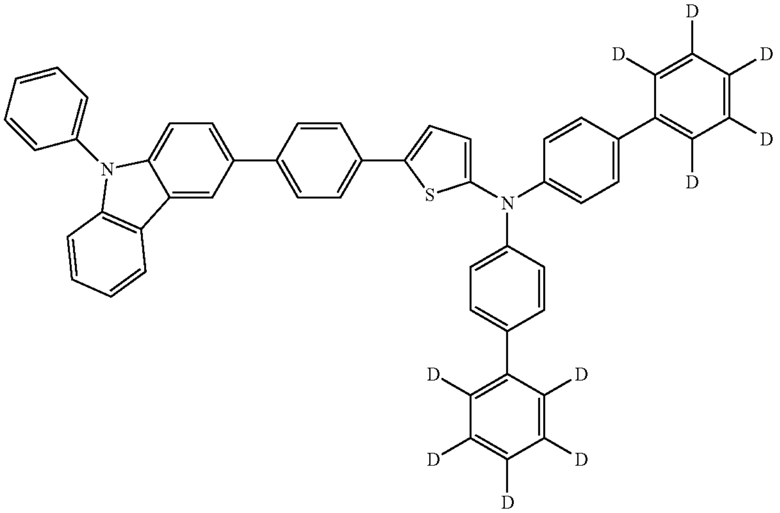

-continued
2-179
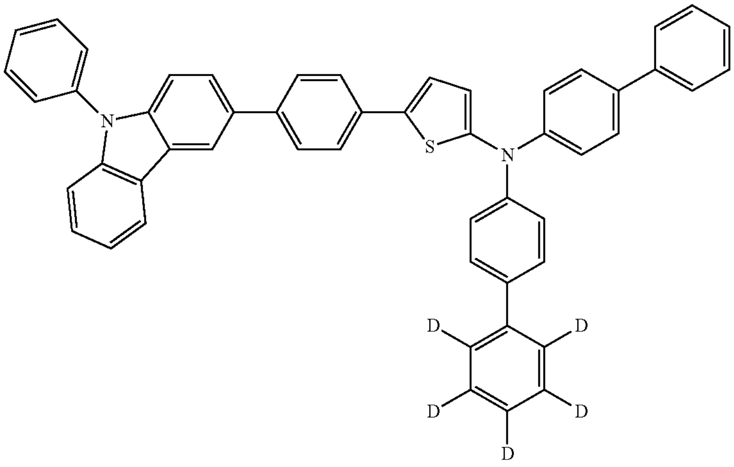
2-181
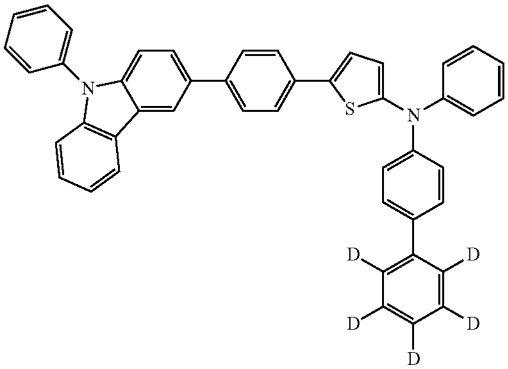
2-180
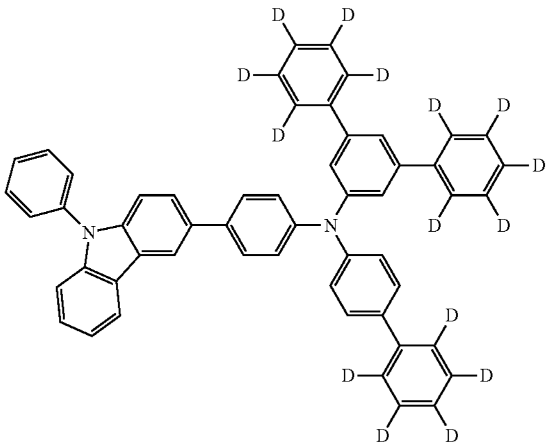
2-182
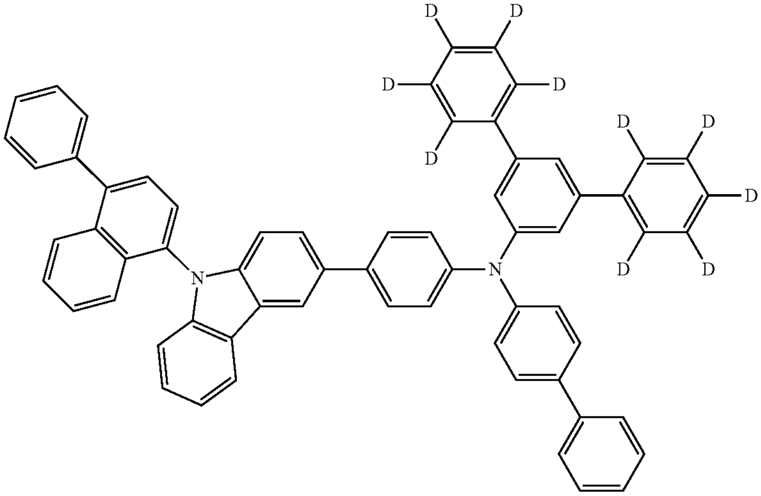

-continued
2-183
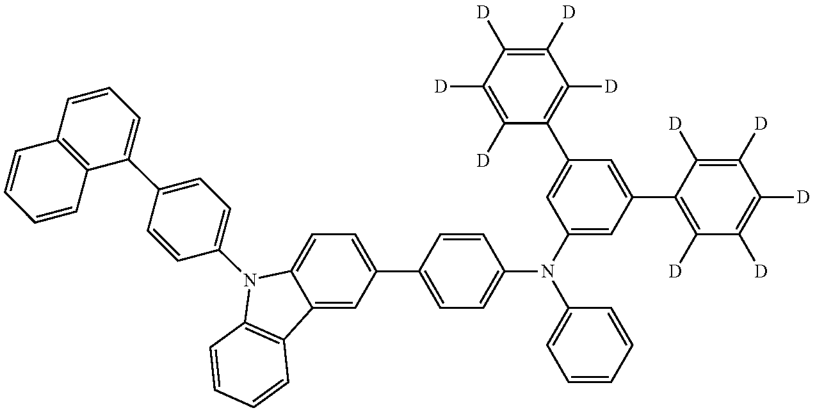
2-184
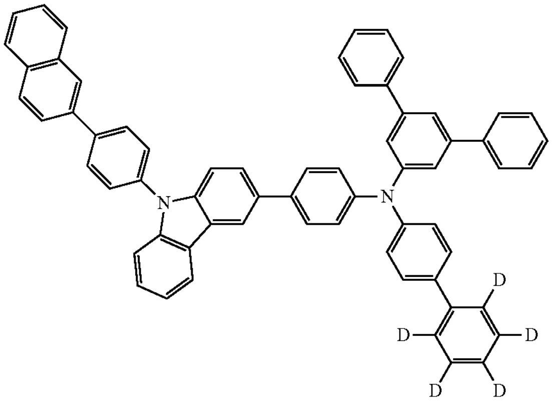
2-185
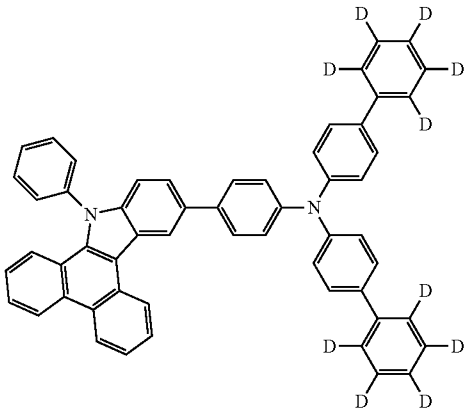
2-186
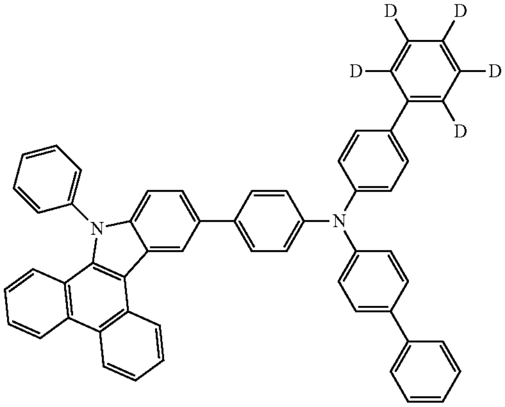
2-187
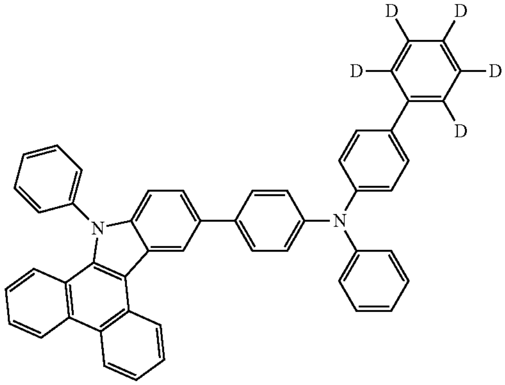

-continued
2-188
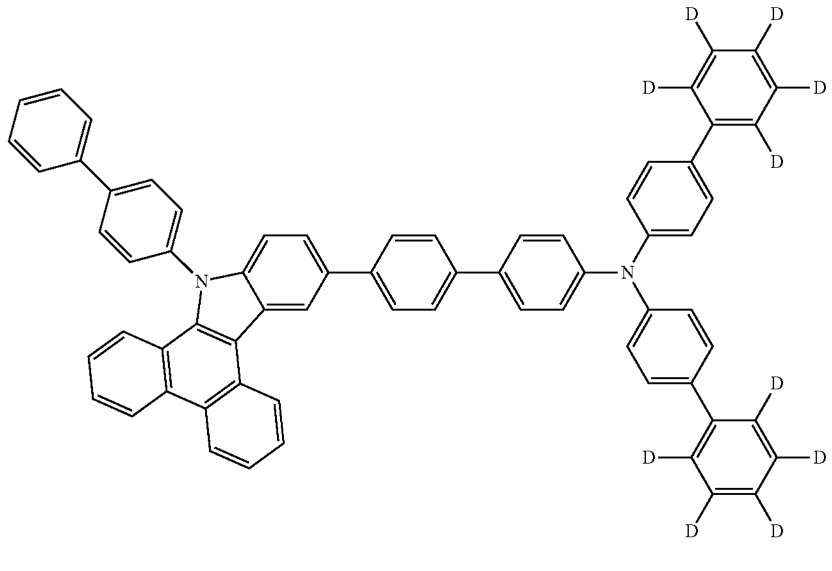
2-189
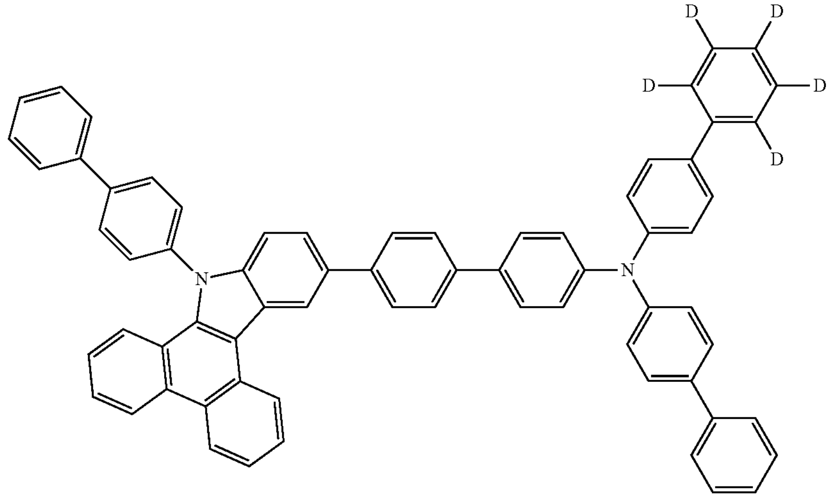
2-190
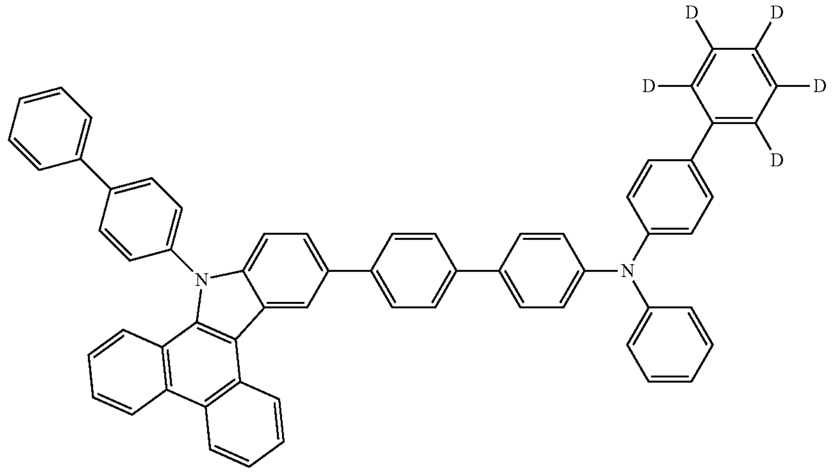

-continued
2-191
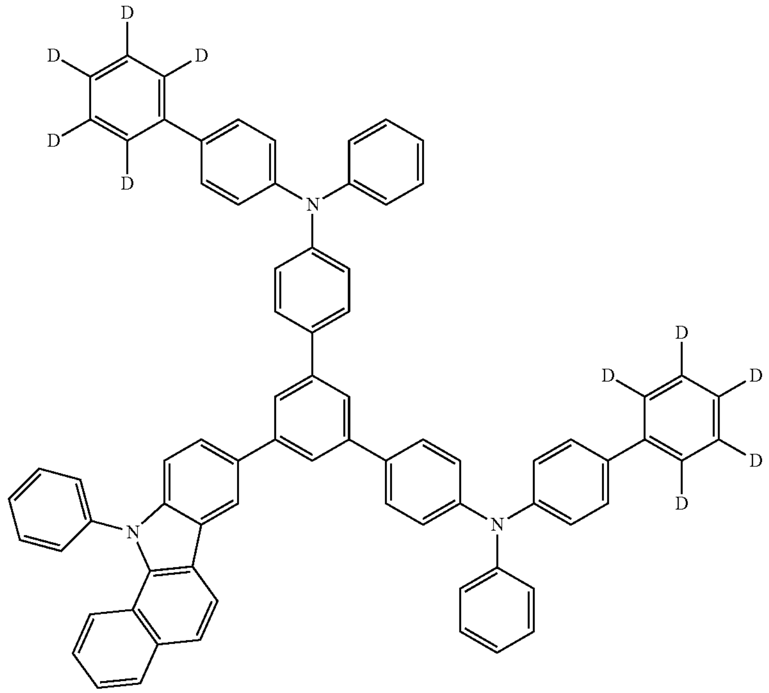
2-192
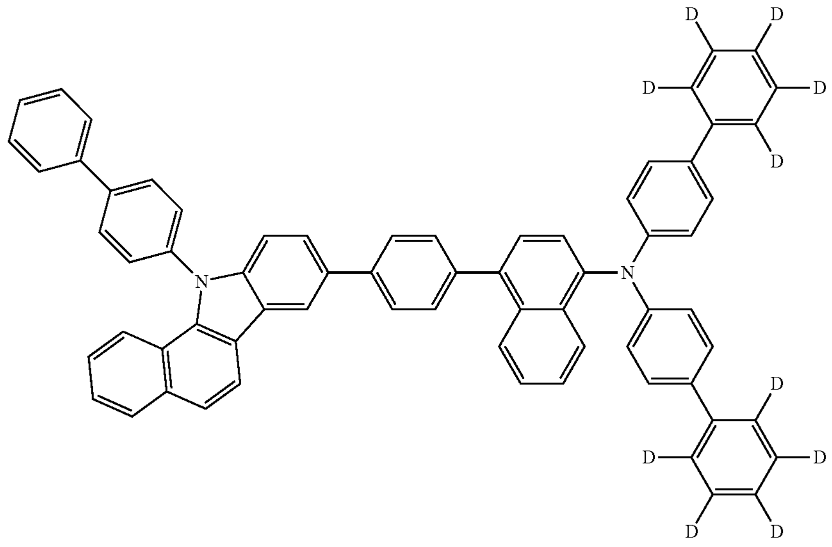

-continued
2-193
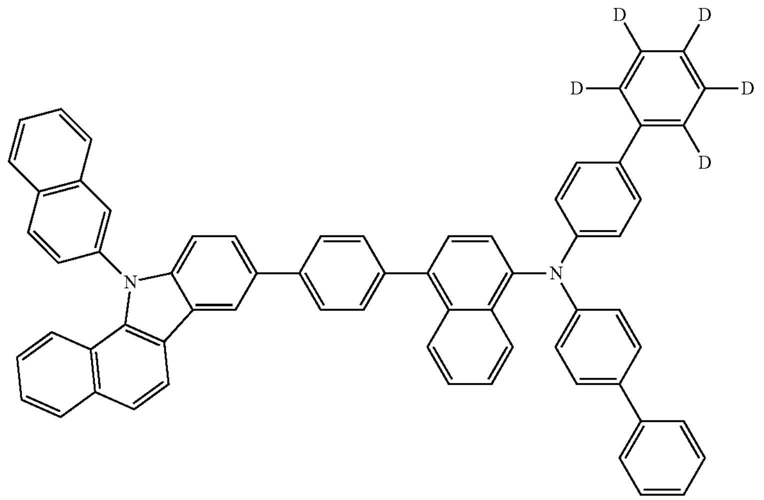
2-194
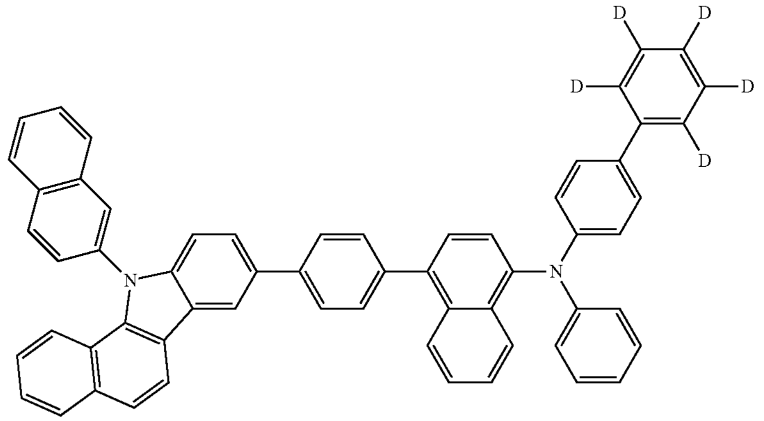
2-195
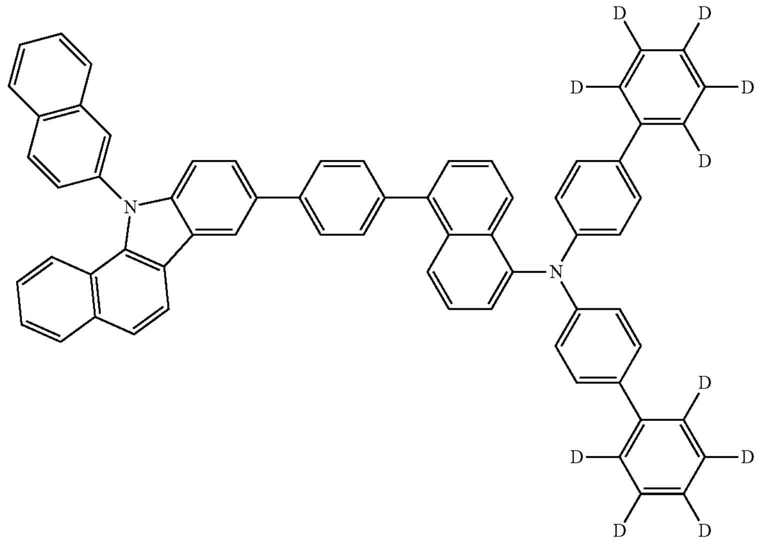

-continued
2-196
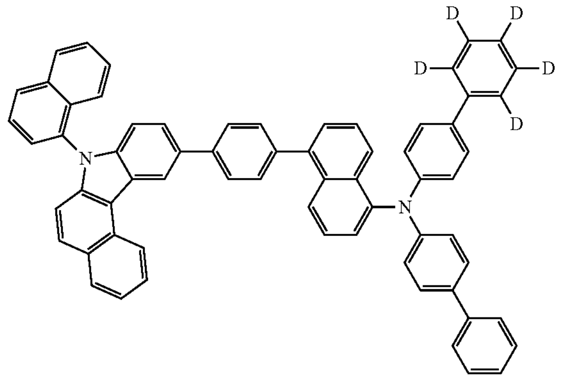
2-197
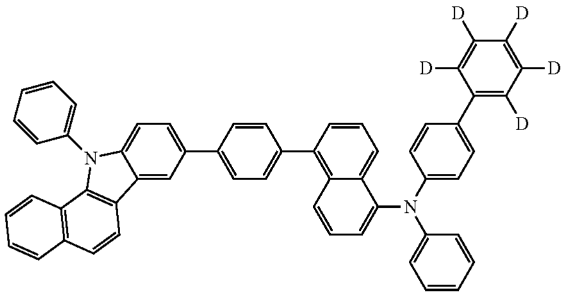
2-198
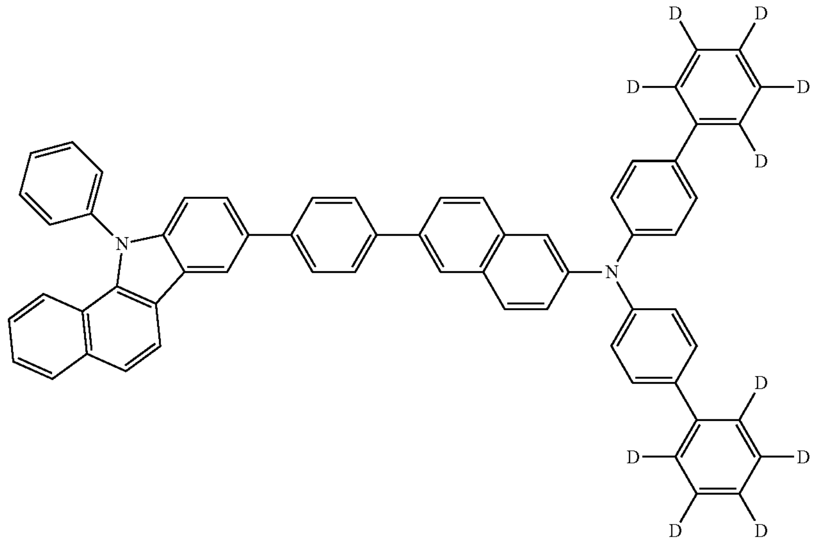
2-199
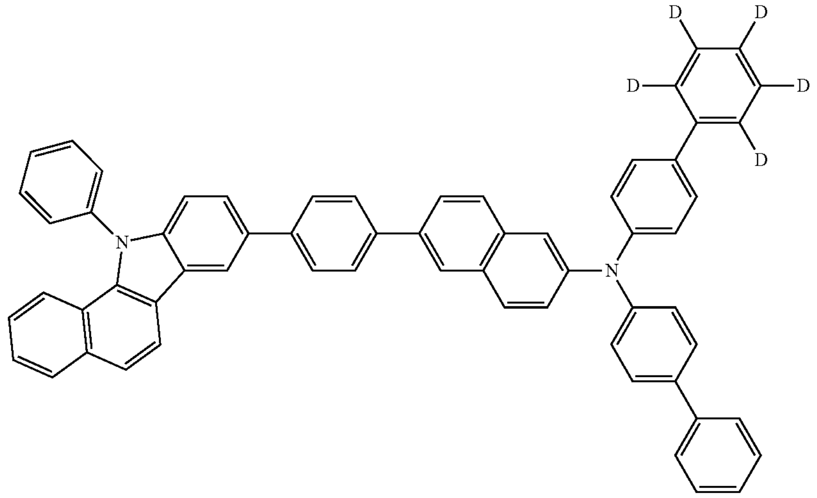

-continued
2-200
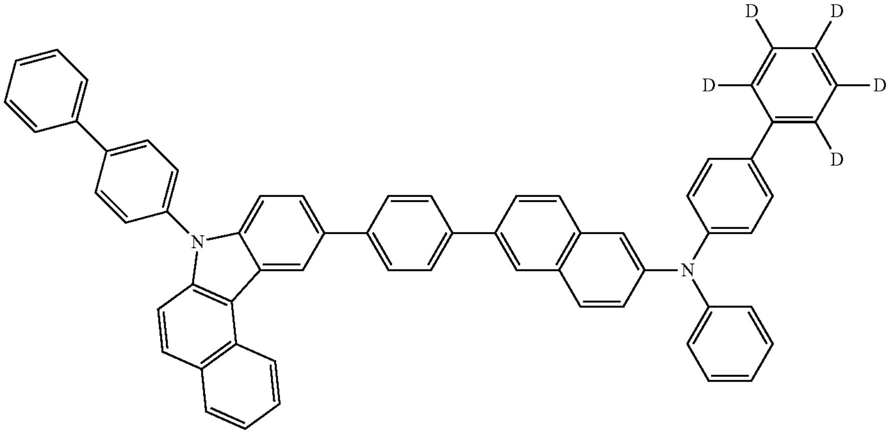
2-201
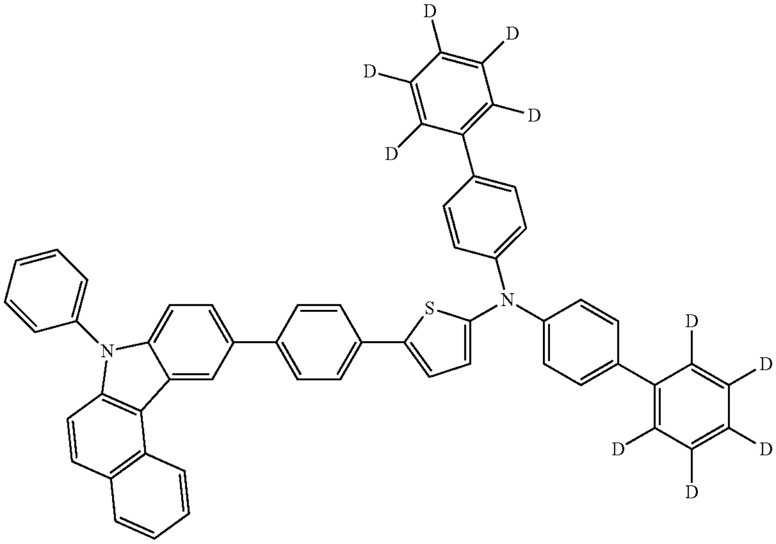
2-202
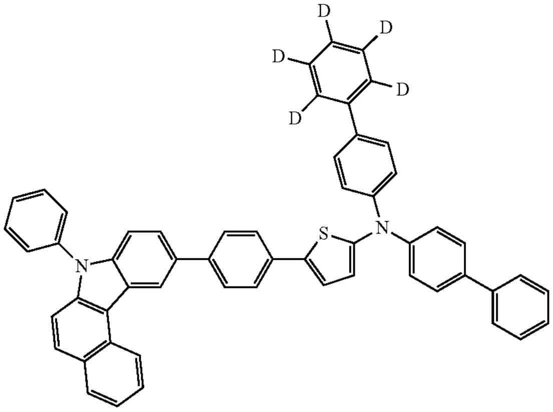
2-203
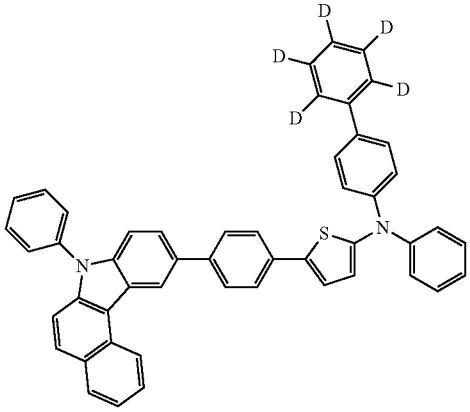

-continued
2-204
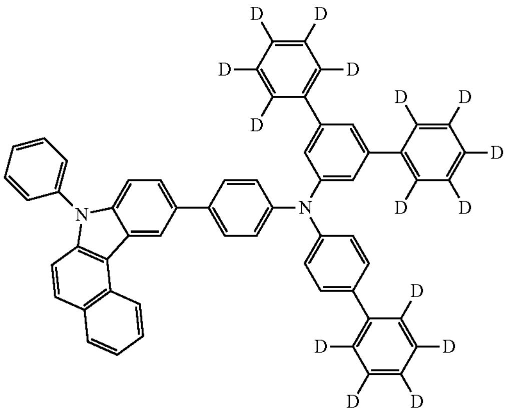
2-205
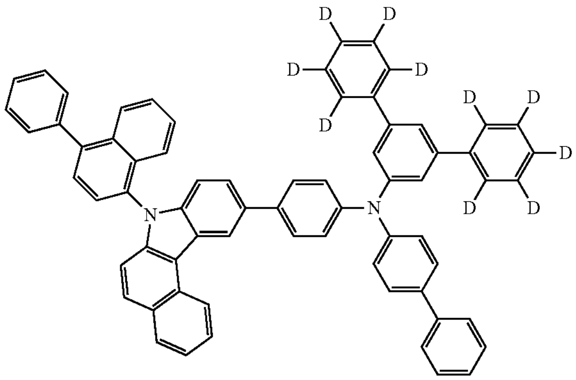
2-206
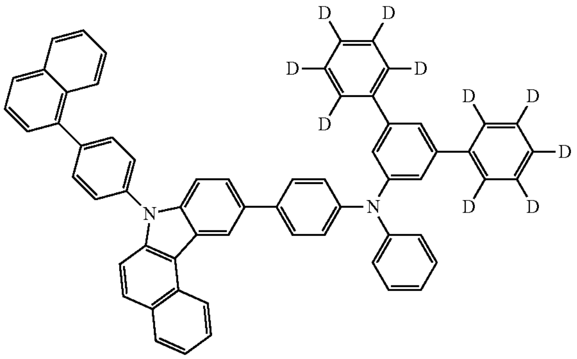
2-207
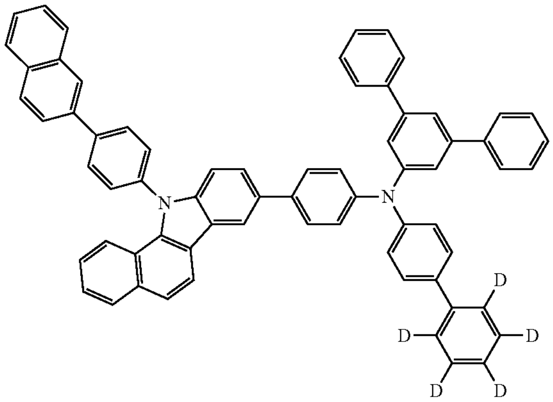
3-1
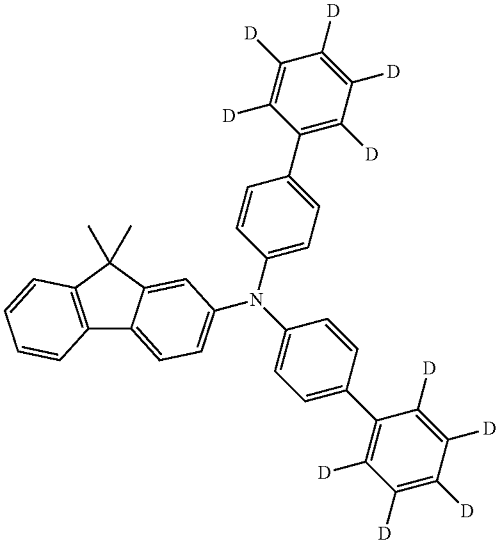
3-2
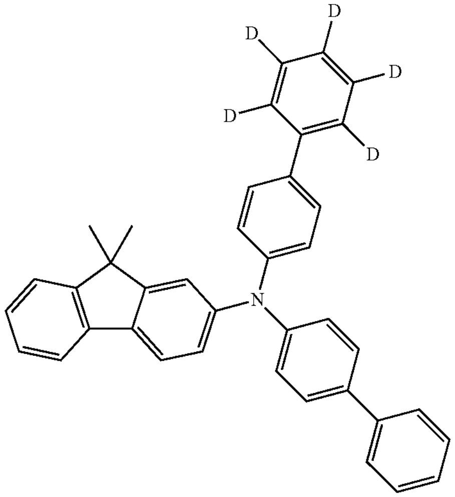

-continued
3-3
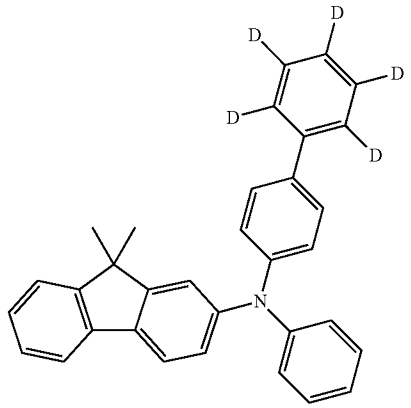
3-4
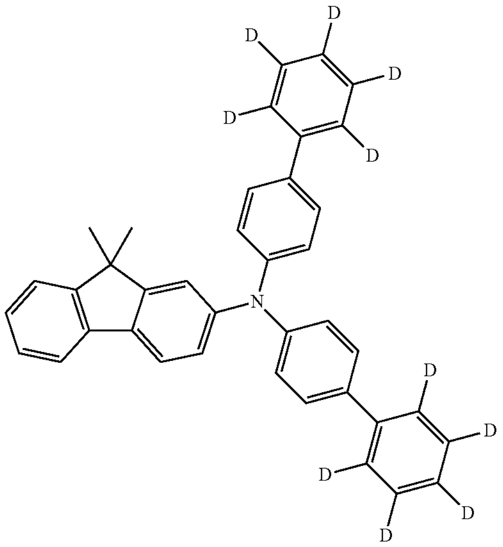
3-5
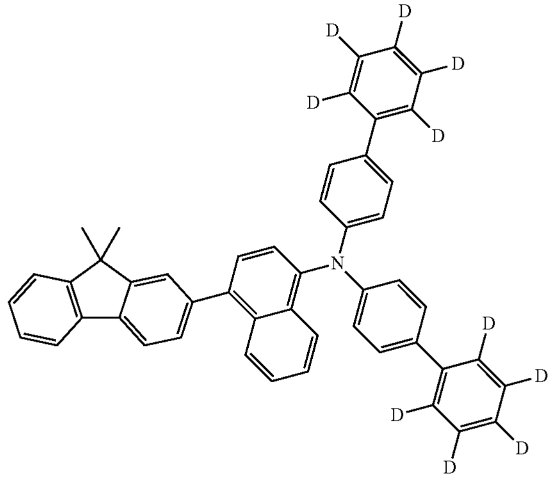
3-6
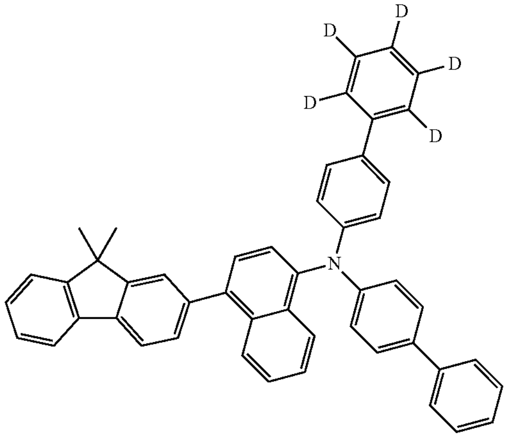
3-7
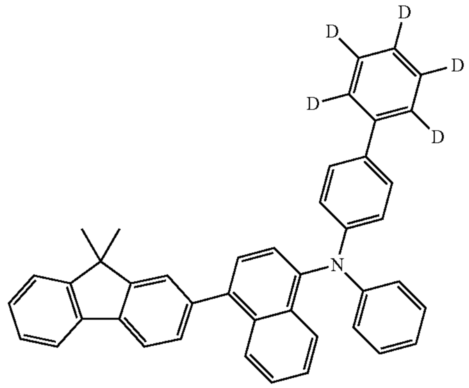
3-8
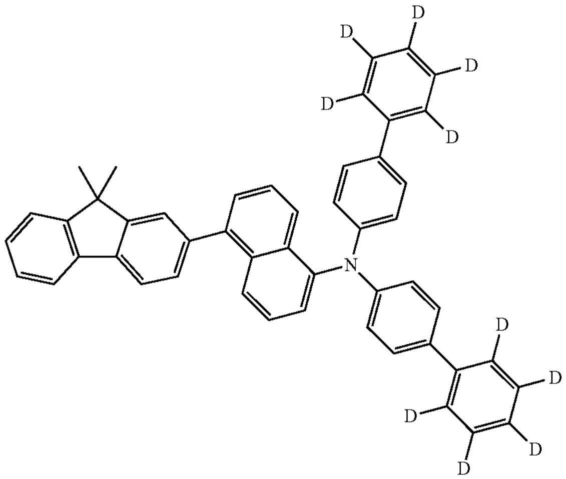

-continued
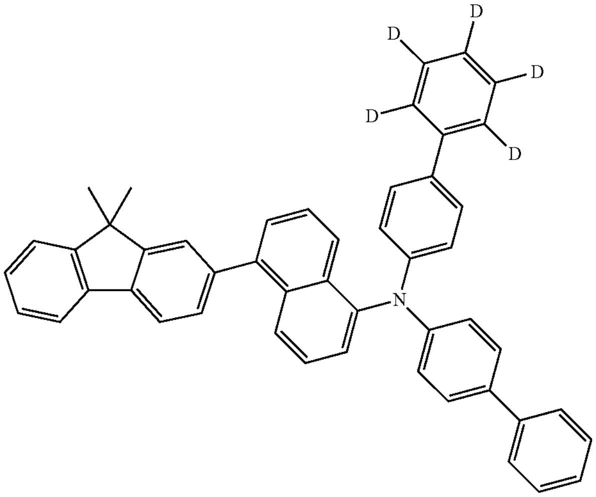
3-9
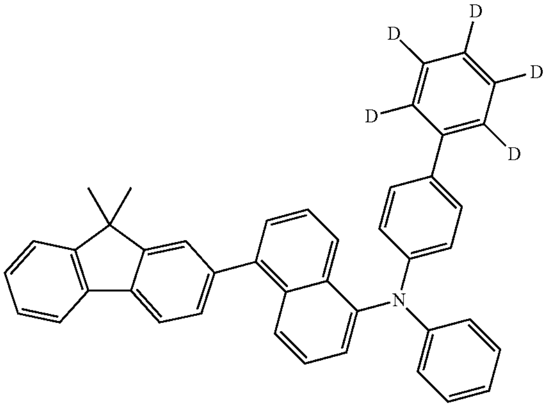
3-10
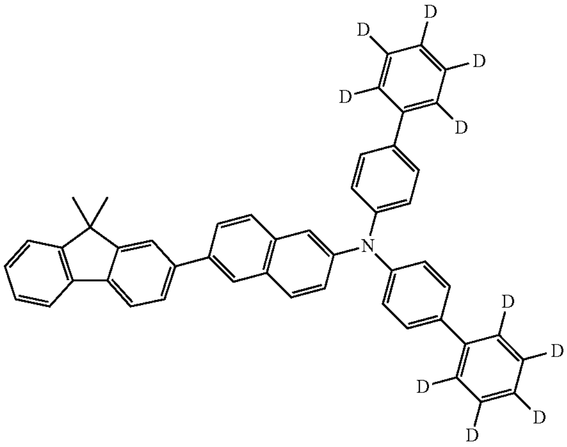
3-11
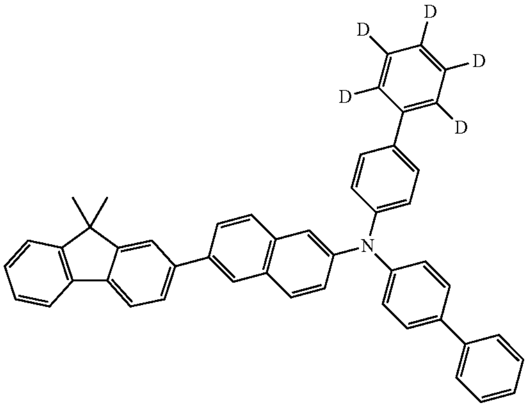
3-12
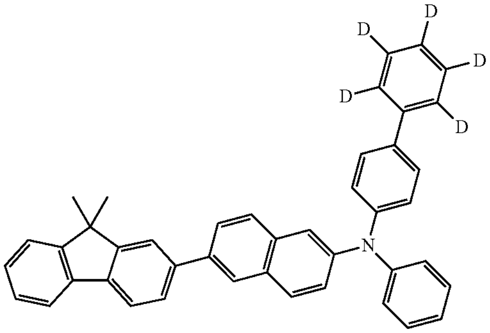
3-13
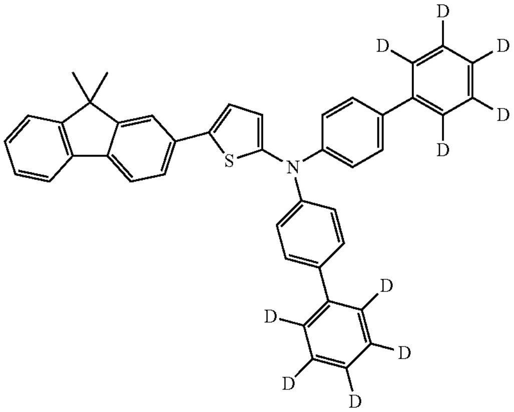
3-14

-continued
3-15
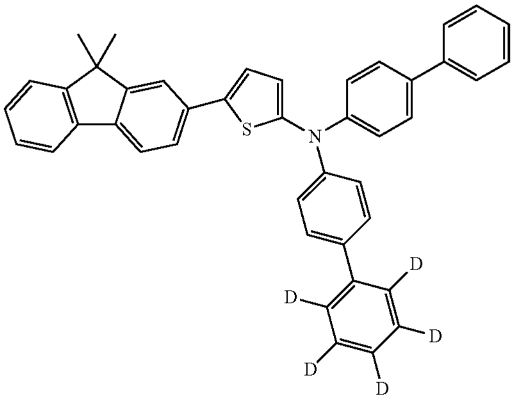
3-16
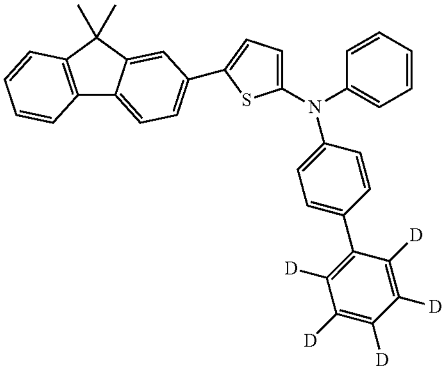
3-17
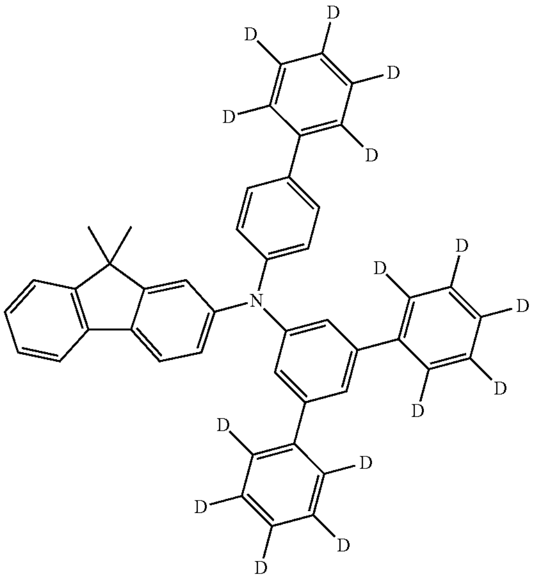
3-18
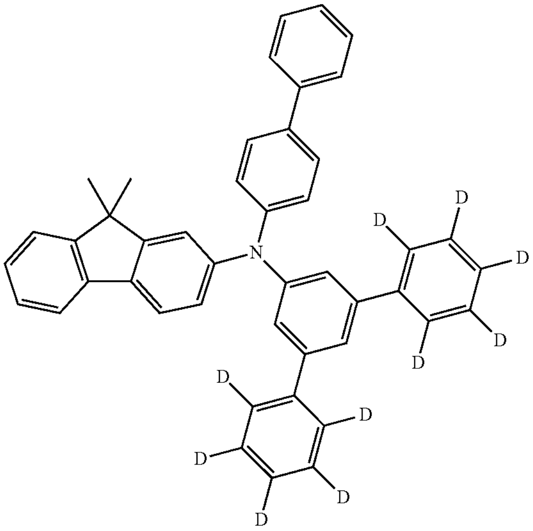
3-20
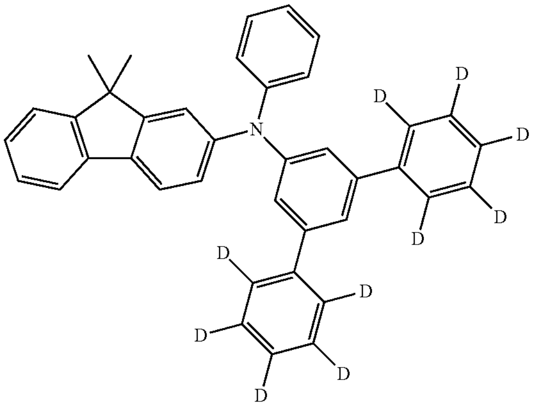
3-19
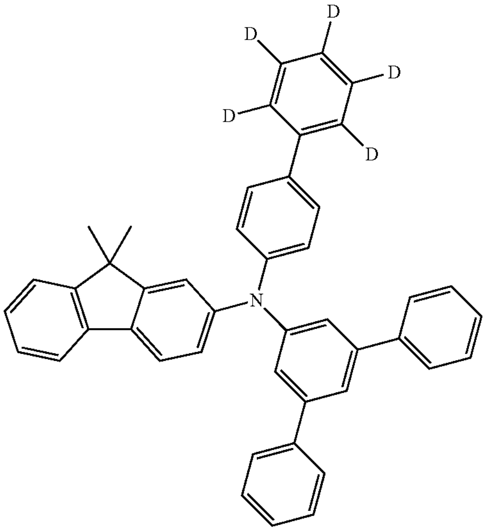

-continued
3-21
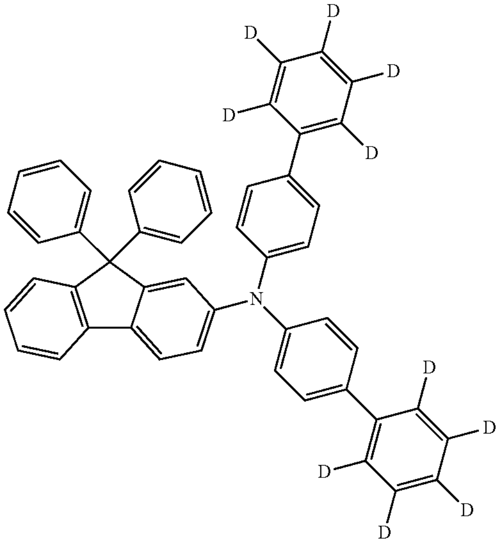
3-22
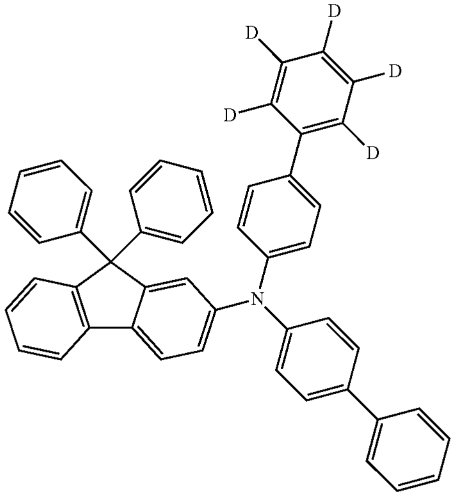
3-23
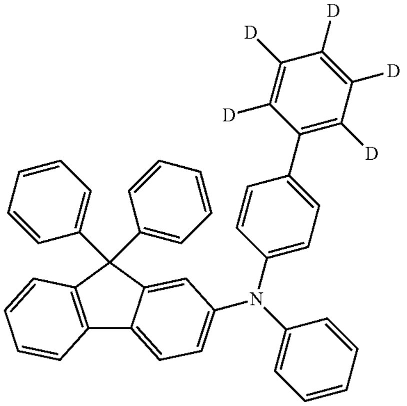
3-24
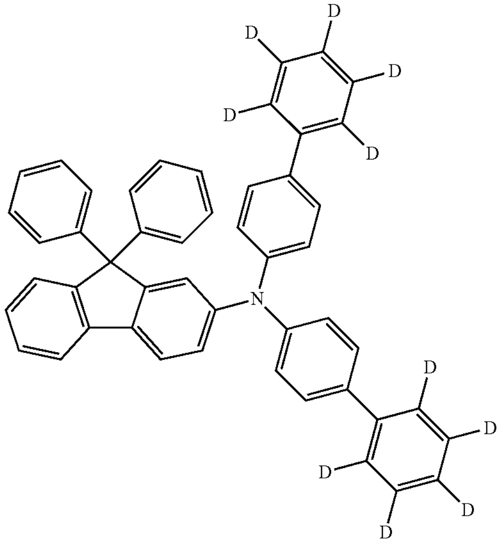
3-25
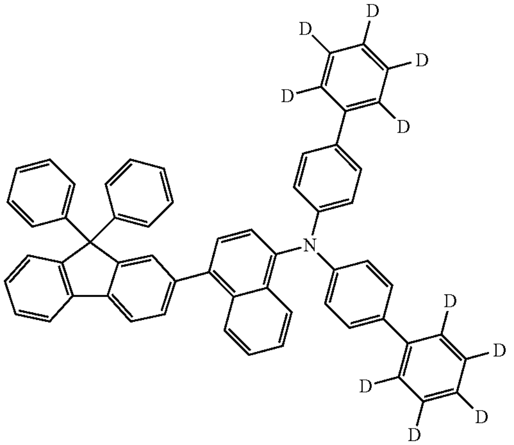
3-26
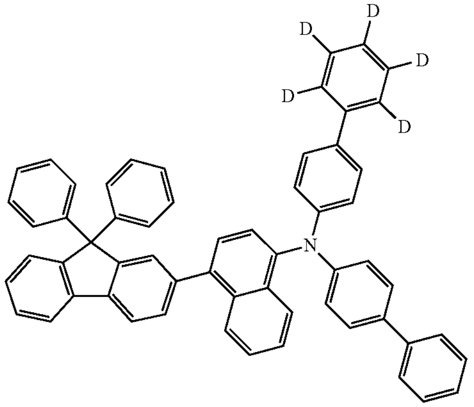

-continued
3-27
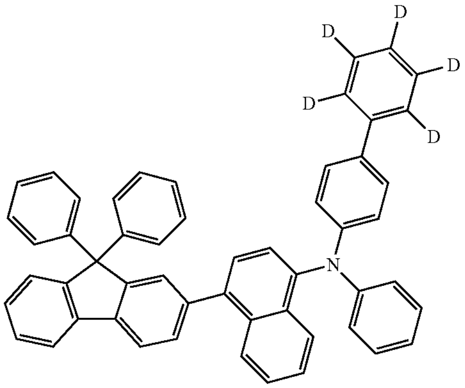
3-28
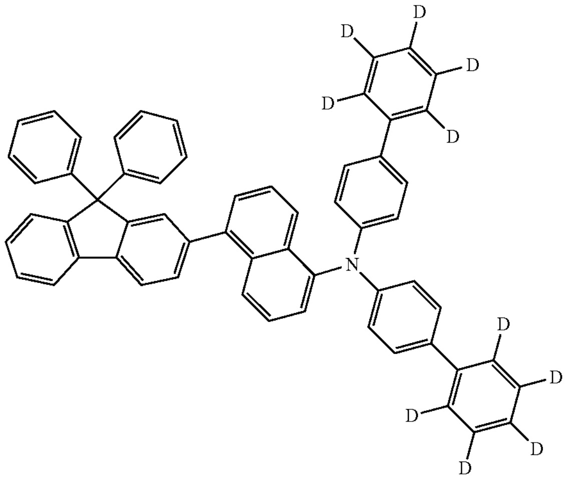
3-29
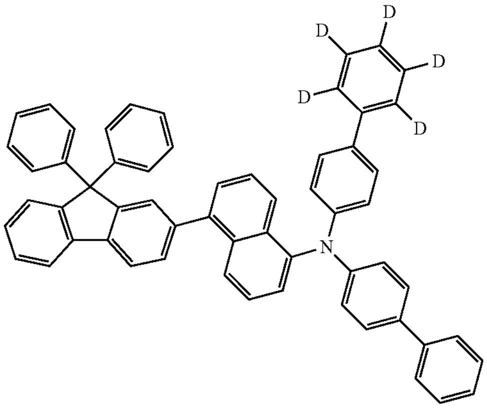
3-30
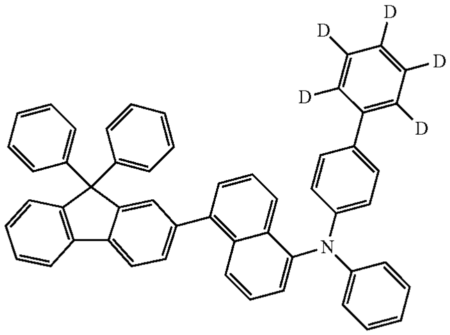
3-31
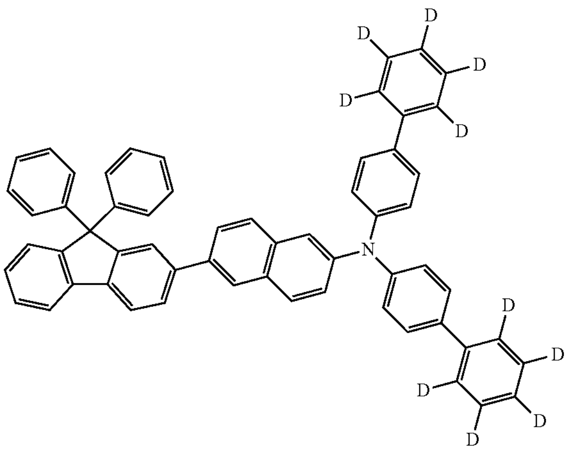
3-32
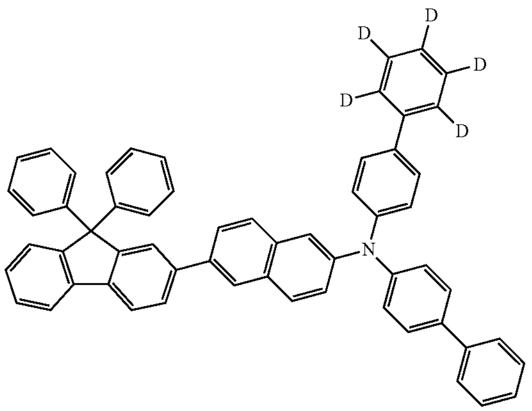

-continued
3-33
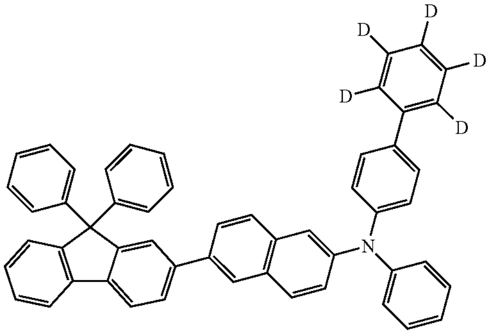
3-34
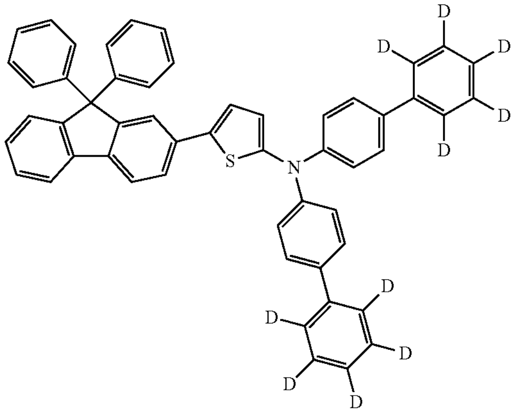
3-35
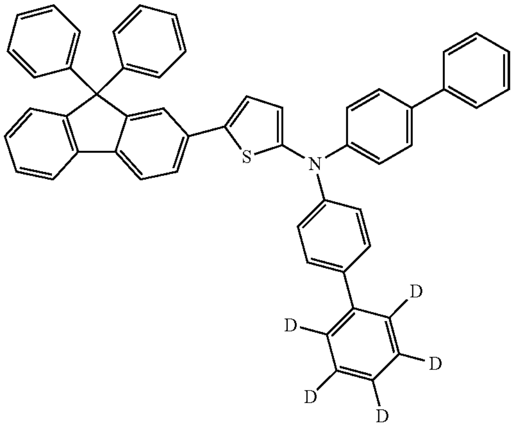
3-36
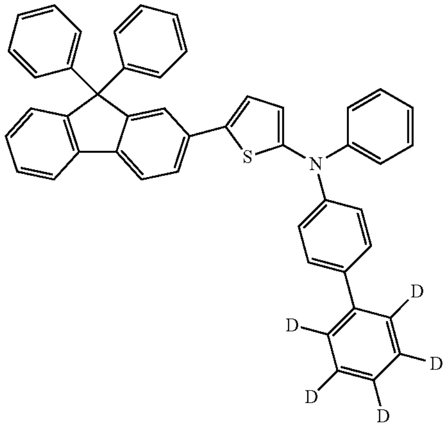
3-37
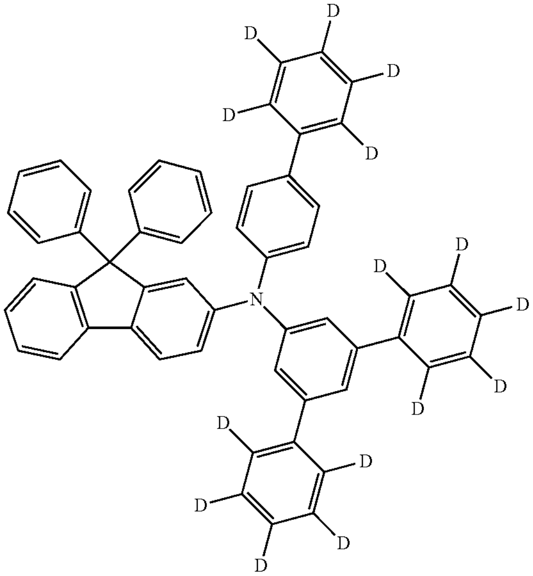
3-38
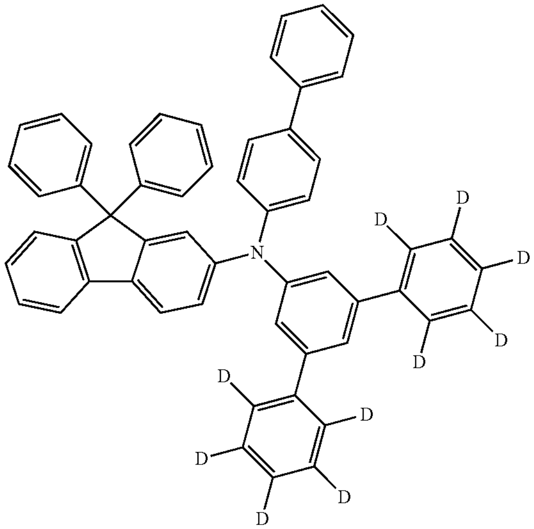

-continued
3-39
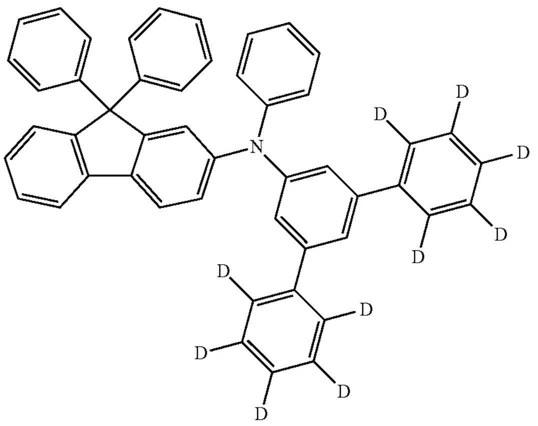
3-40
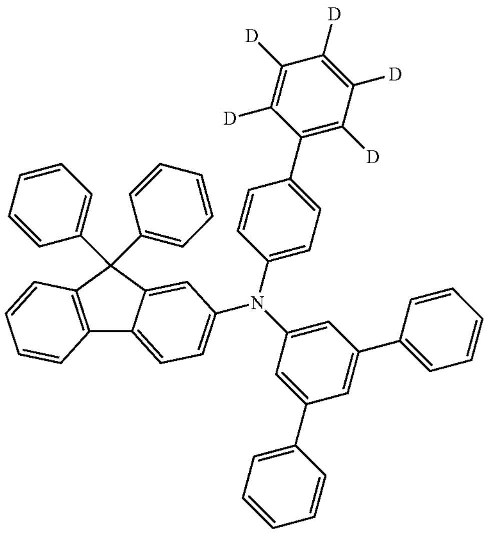
3-41
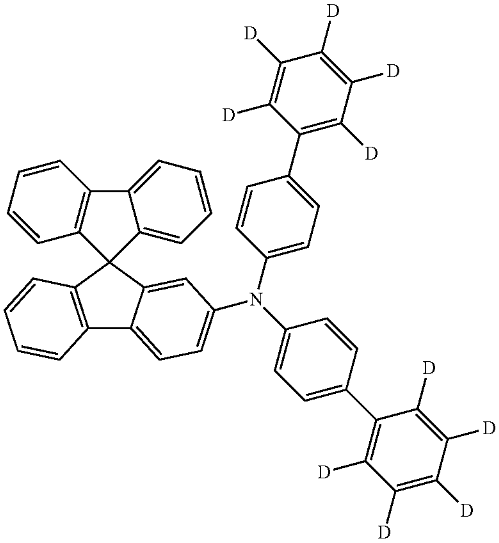
3-42
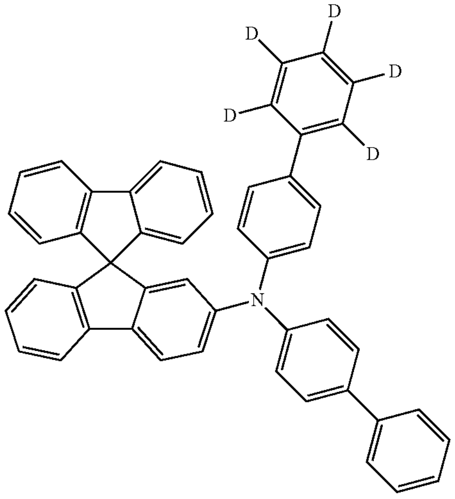
3-43
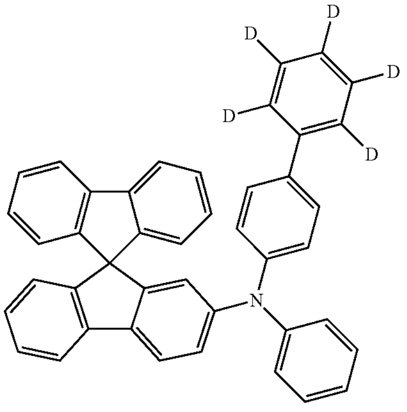
3-44
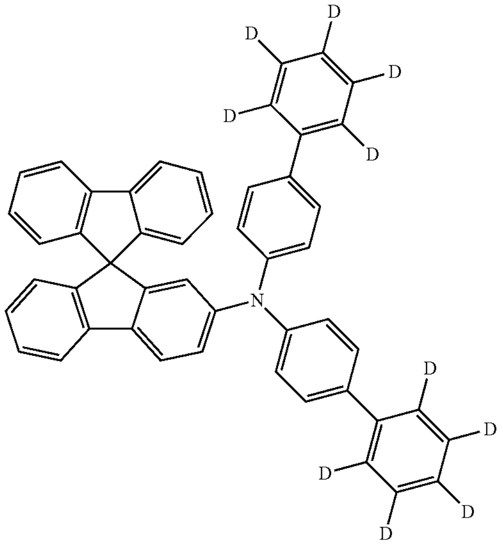

-continued
3-45
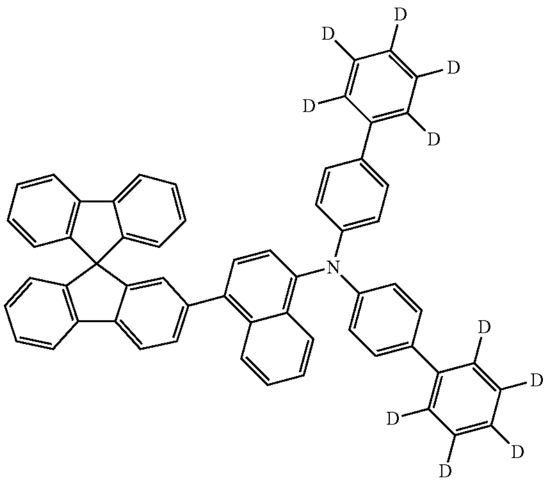
3-46
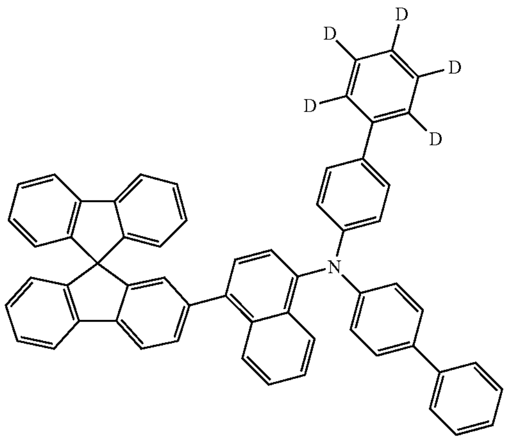
3-47
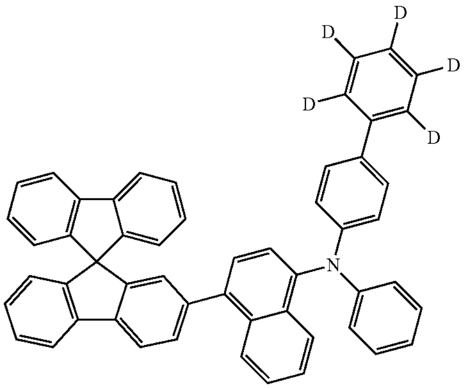
3-48
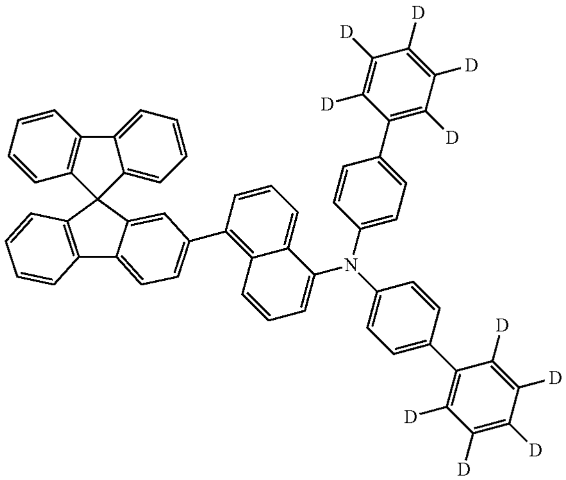
3-49
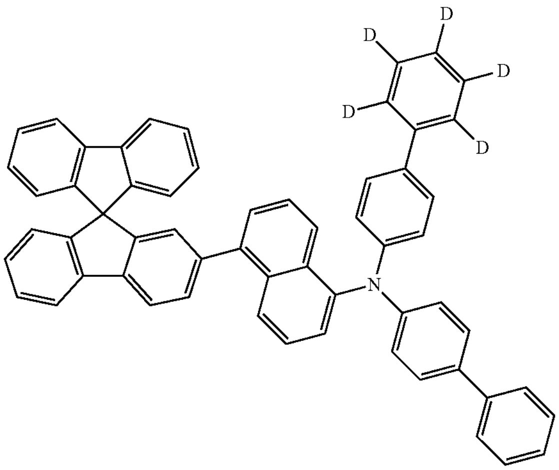
3-50
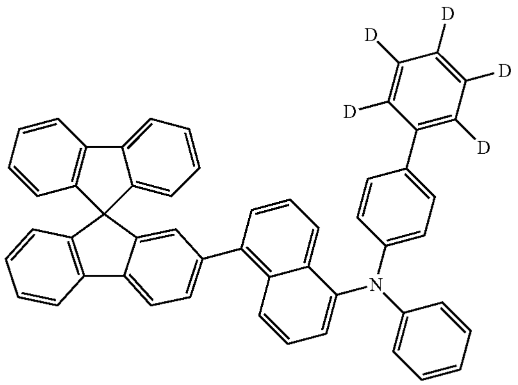

-continued
3-51
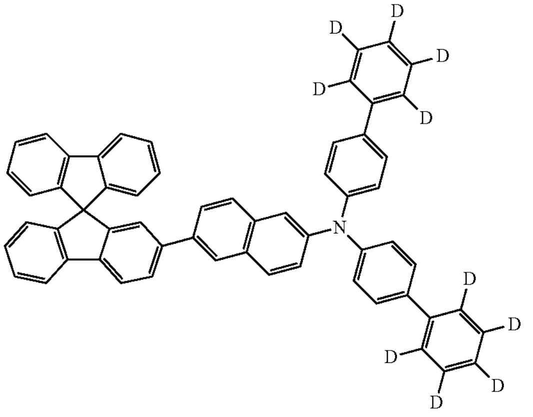
3-52
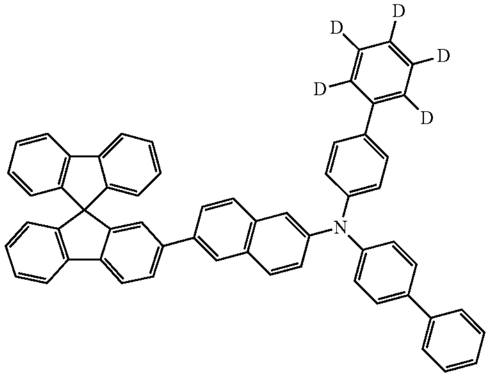
3-53
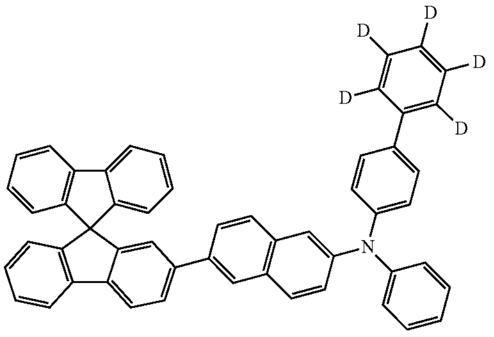
3-54
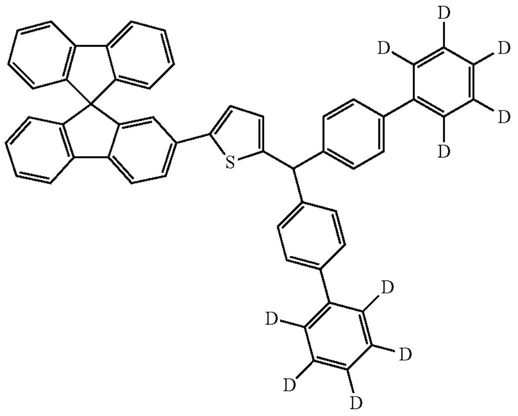
3-55
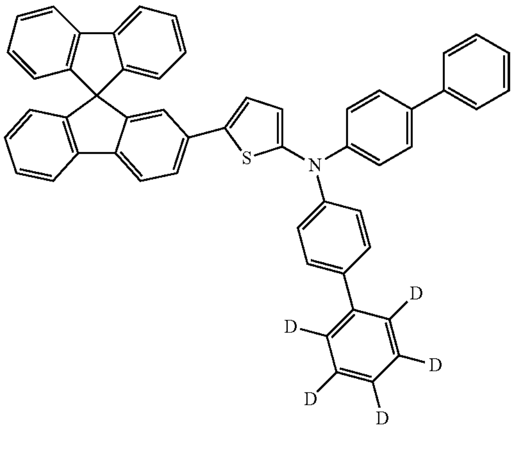
3-56
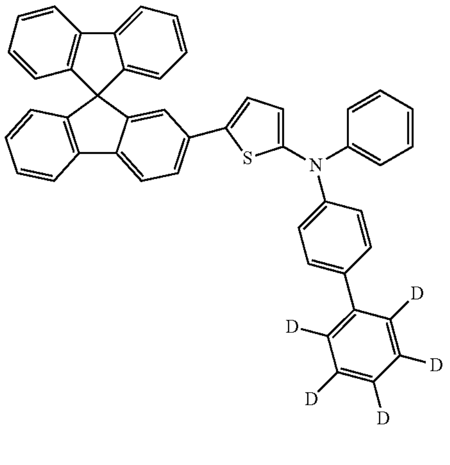

-continued
3-57
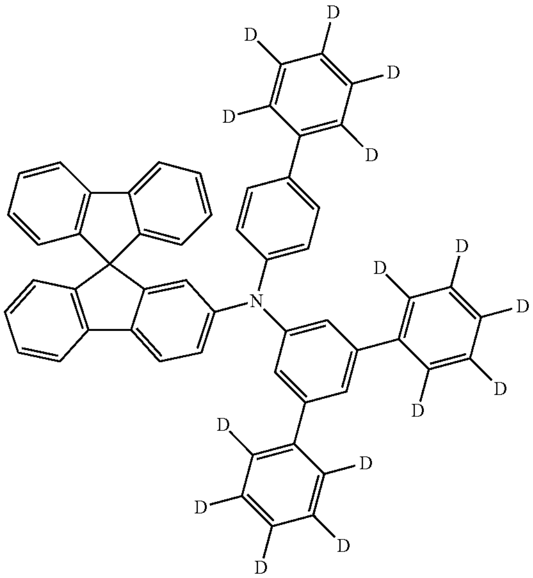
3-58
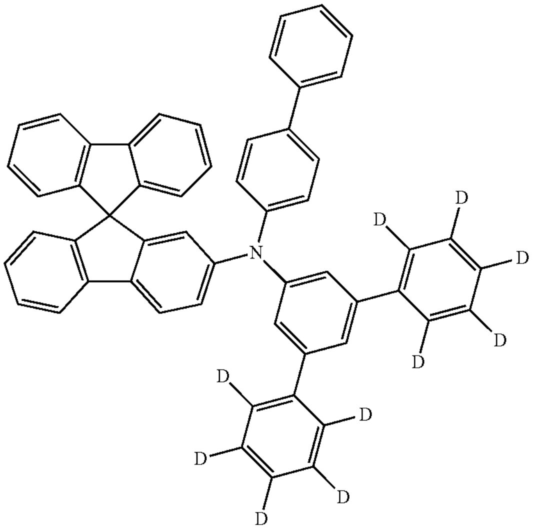
3-59
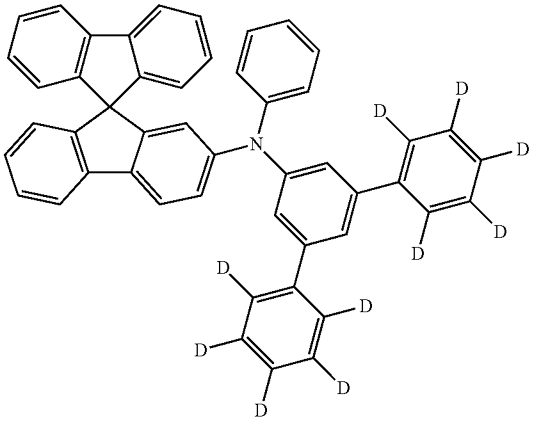
3-60
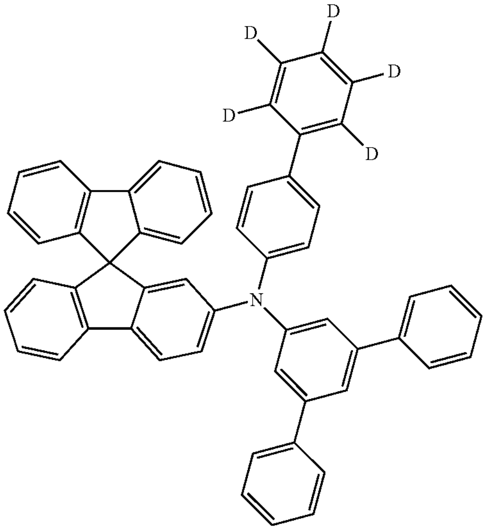
3-61
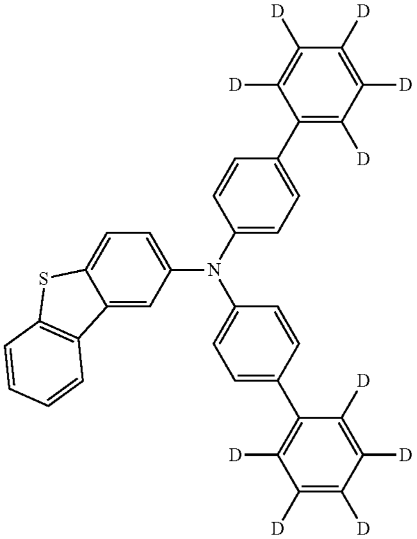
3-62
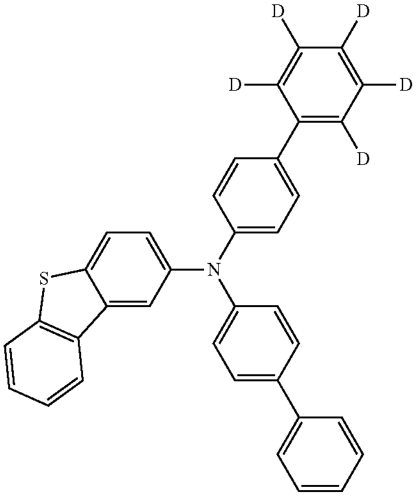

-continued
3-63
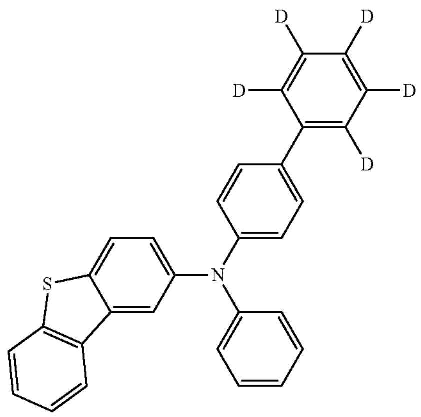
3-64
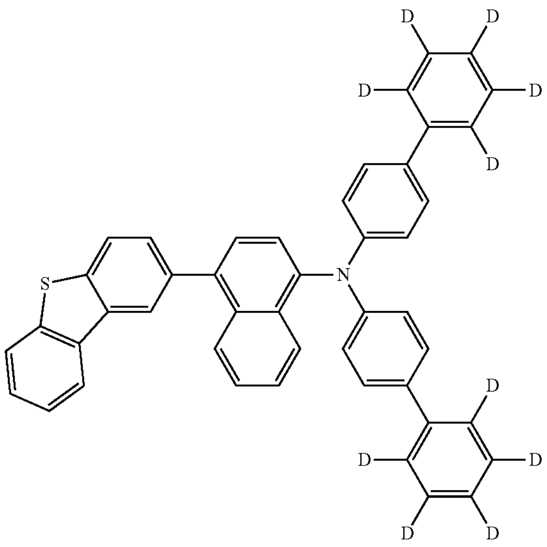
3-65
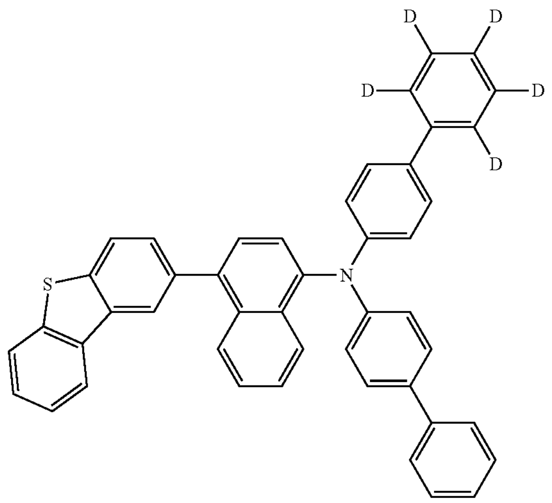
3-66
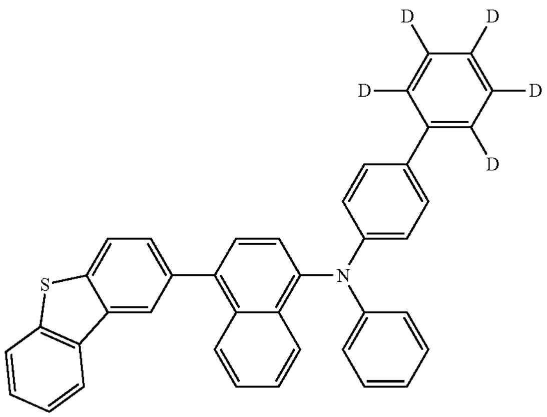
3-67
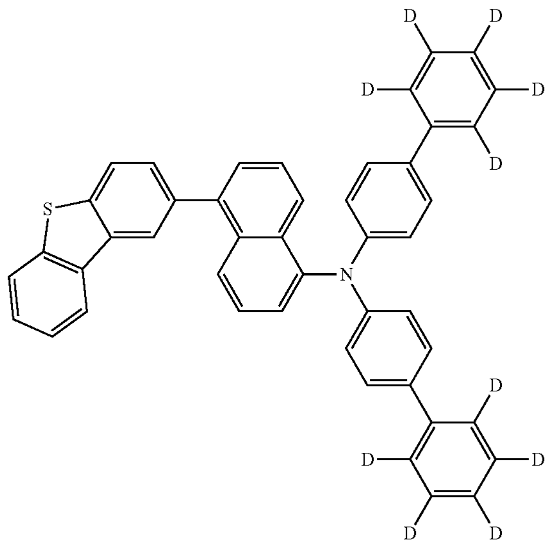
3-68
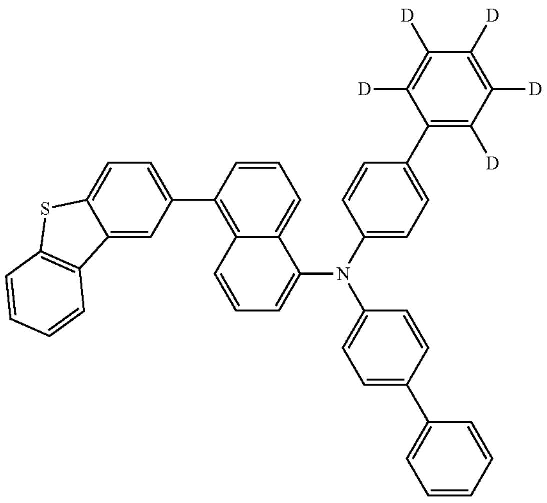

-continued
3-69
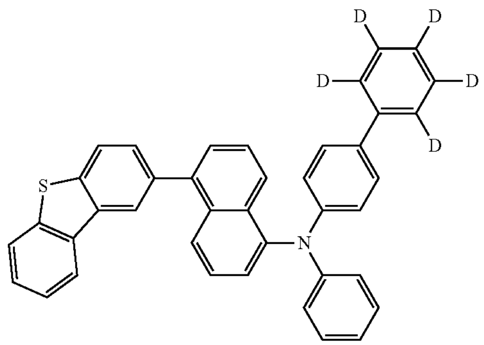
3-70
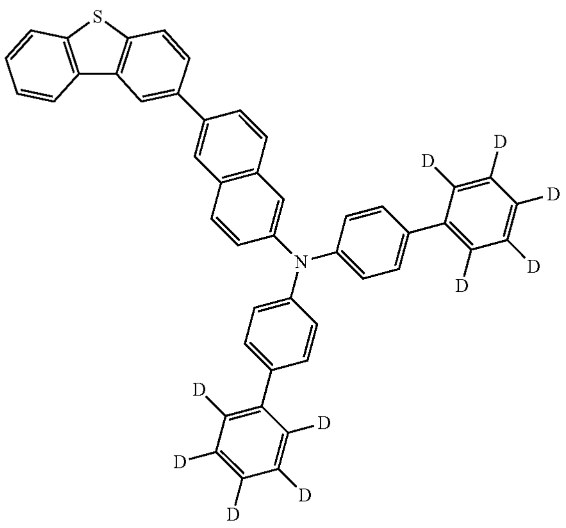
3-71
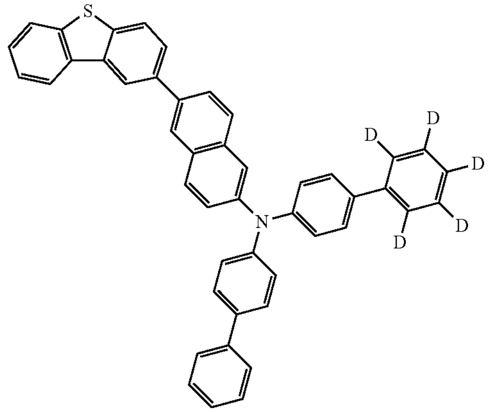
3-72
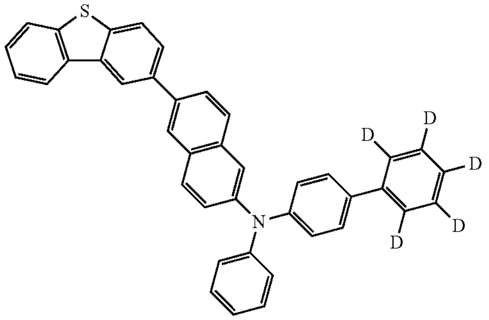
3-73
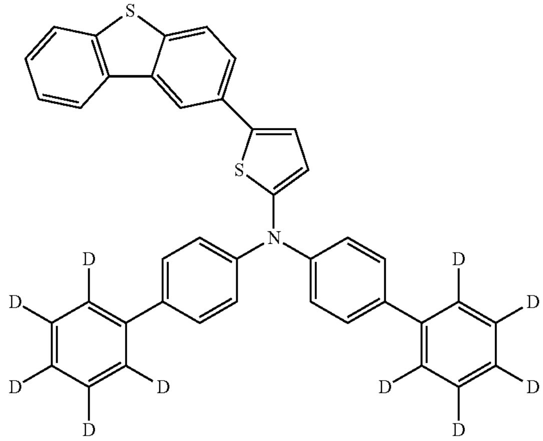
3-74
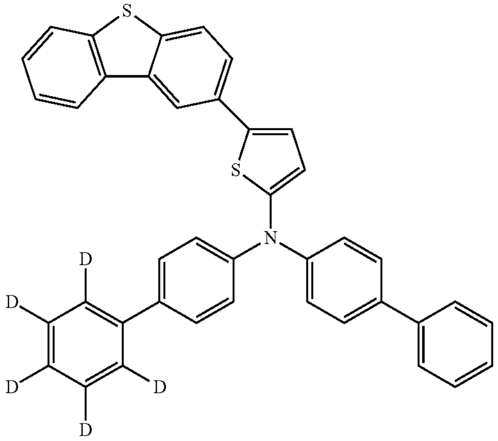

-continued
3-75
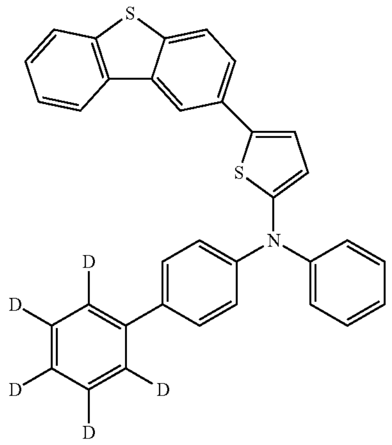
3-76
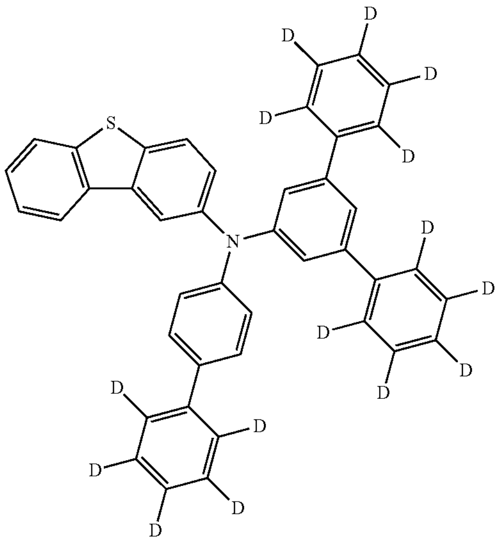
3-77
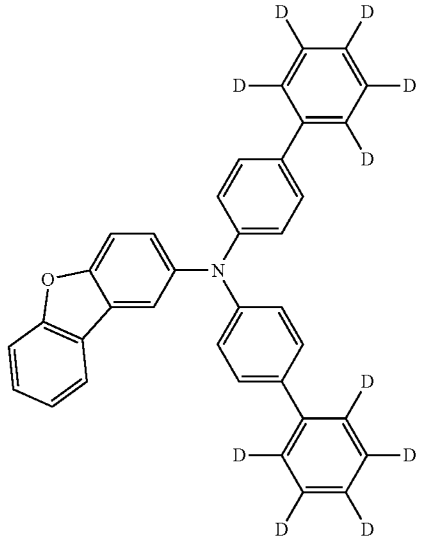
3-78
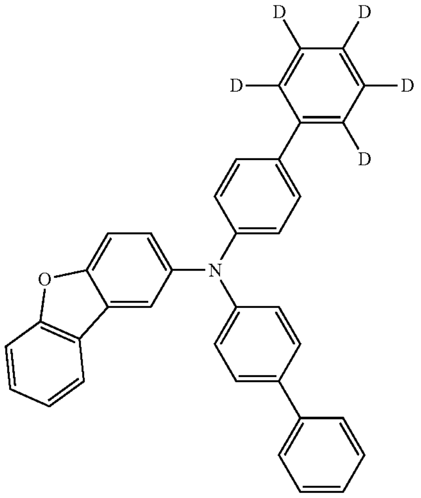
3-79
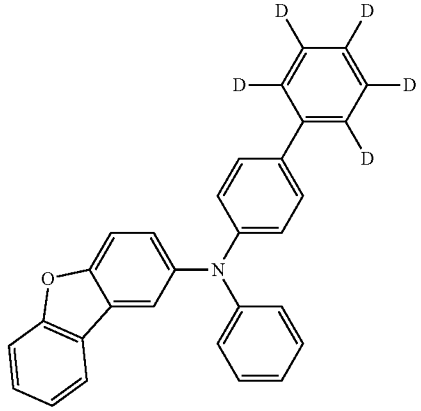
3-80
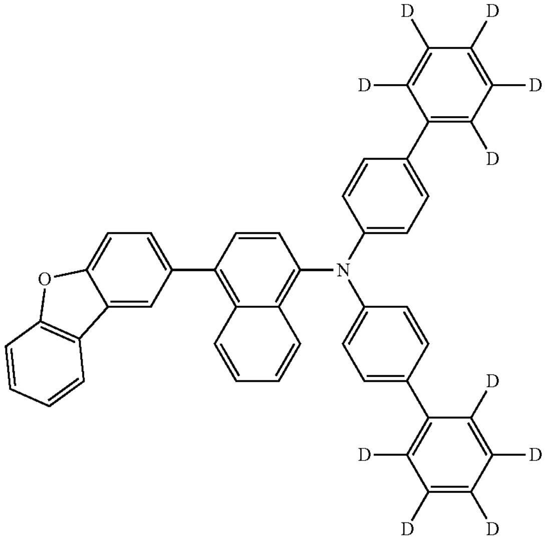

-continued
3-81
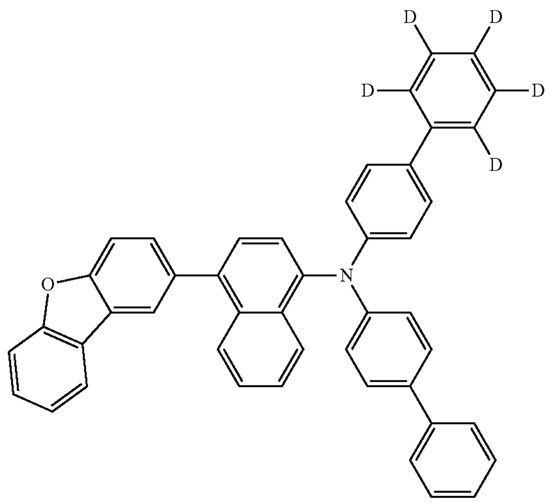
3-82
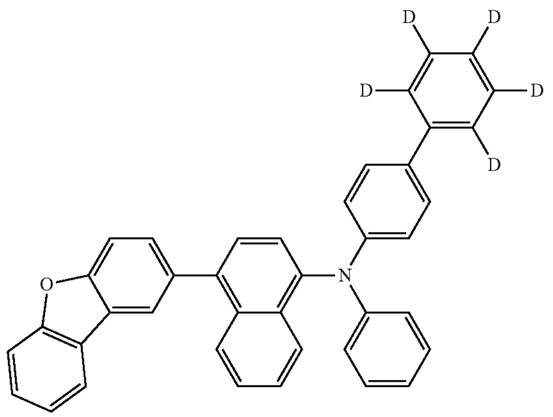
3-83
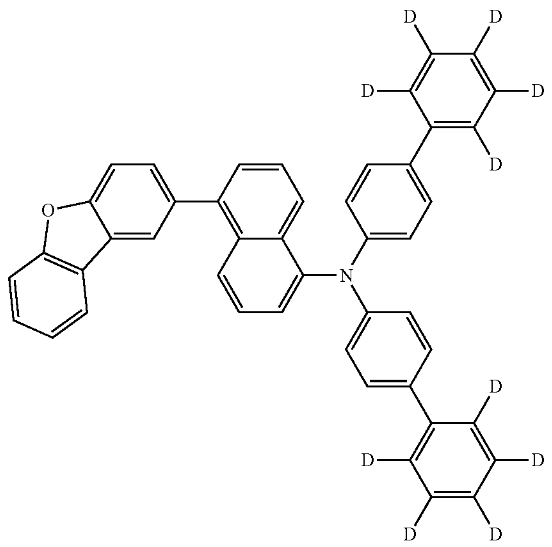
3-84
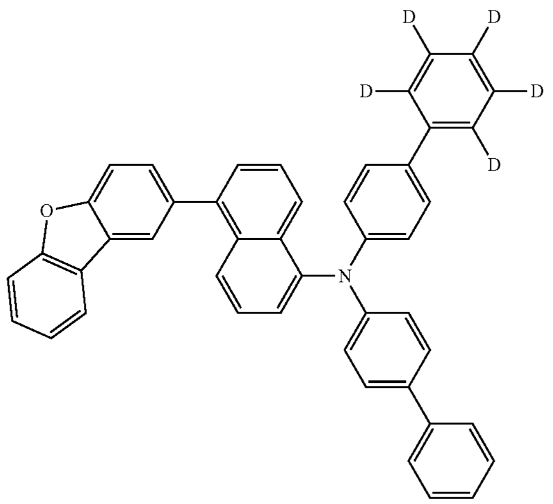
3-85
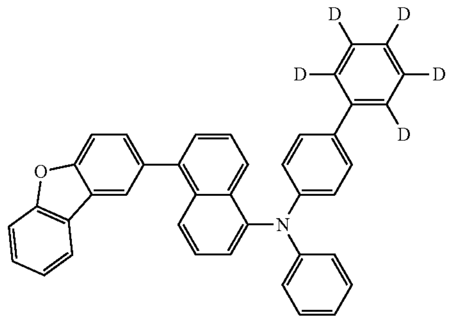
3-86
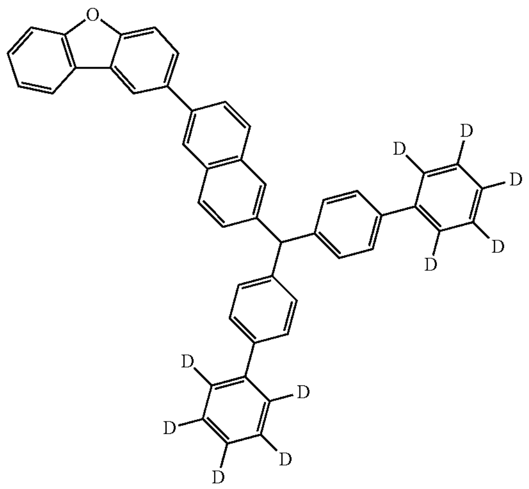

-continued
3-87
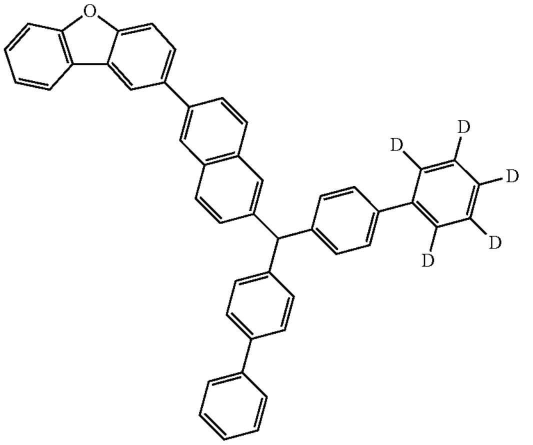
3-88
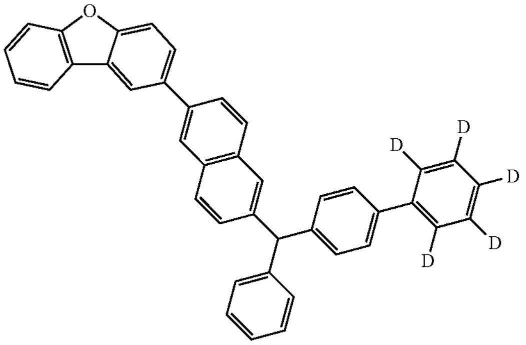
3-89
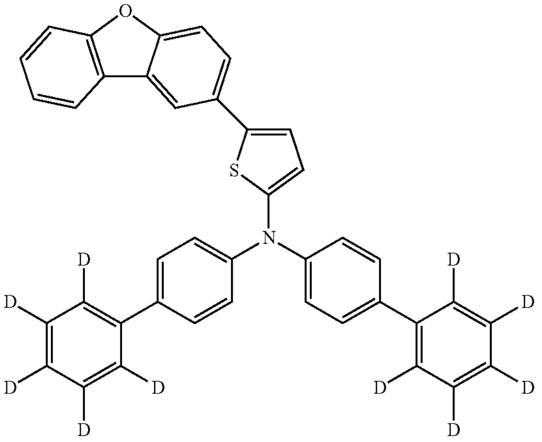
3-90
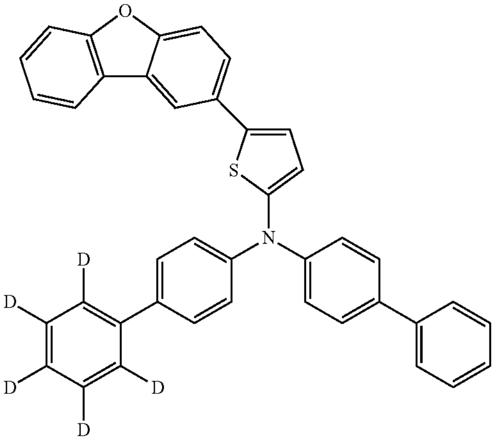
3-91
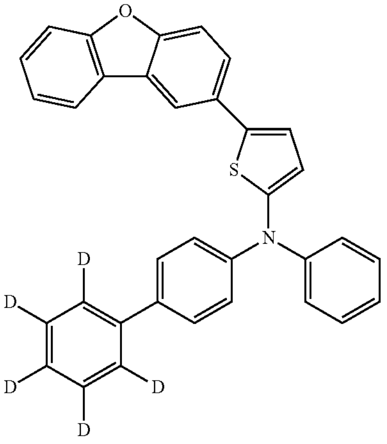
3-92
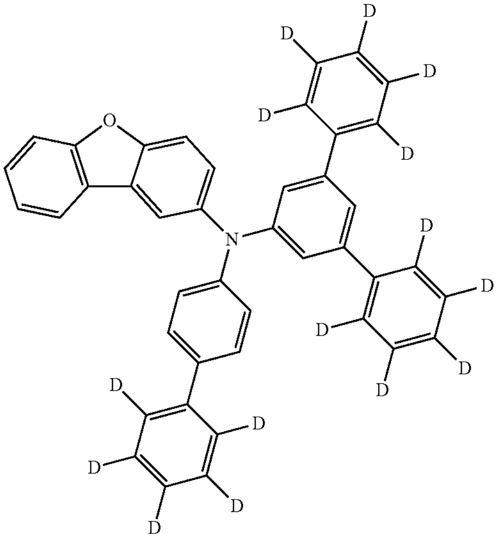

-continued
3-93
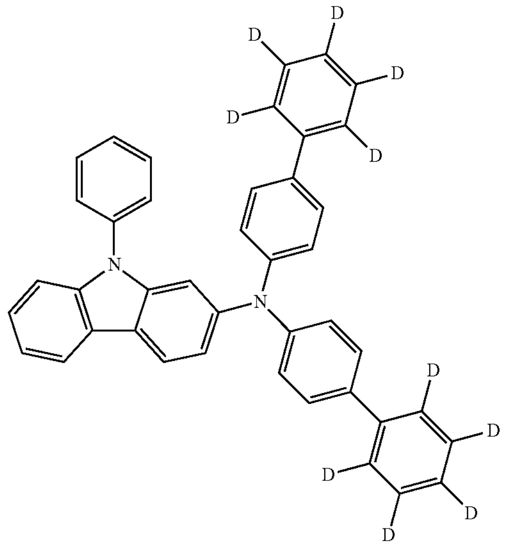
3-94
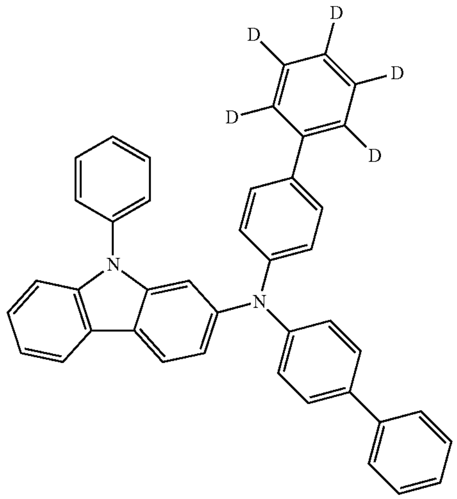
3-95
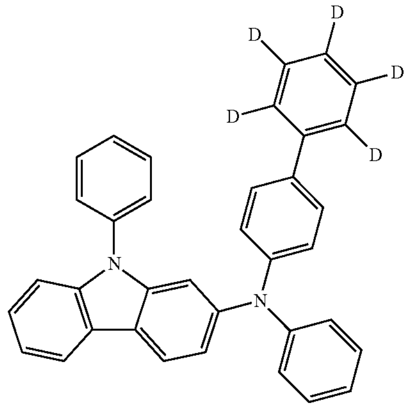
3-96
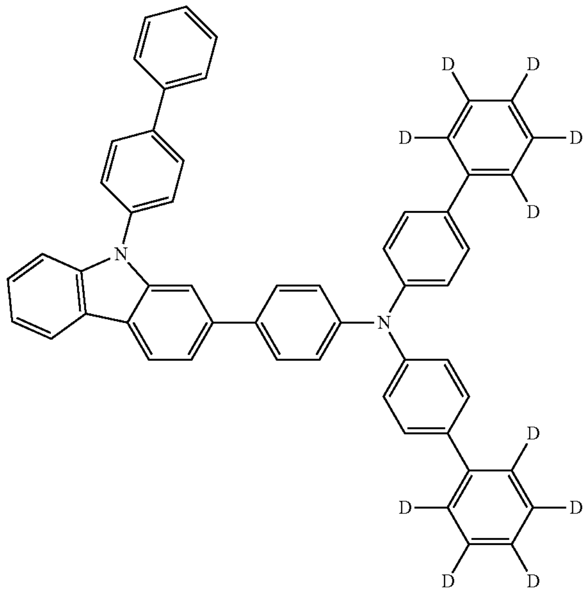
3-97
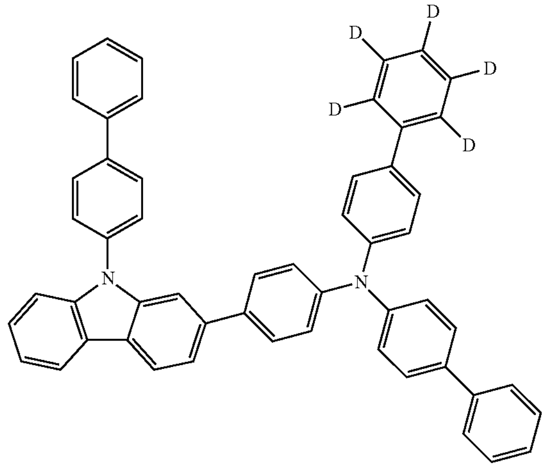
3-98
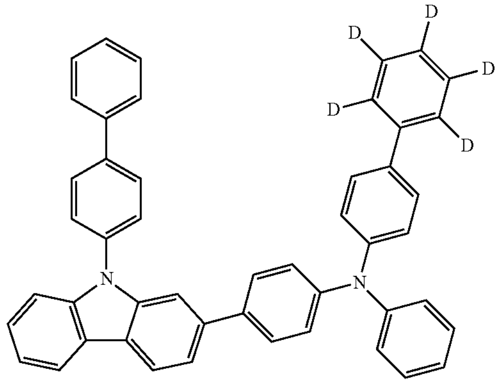

-continued
3-99
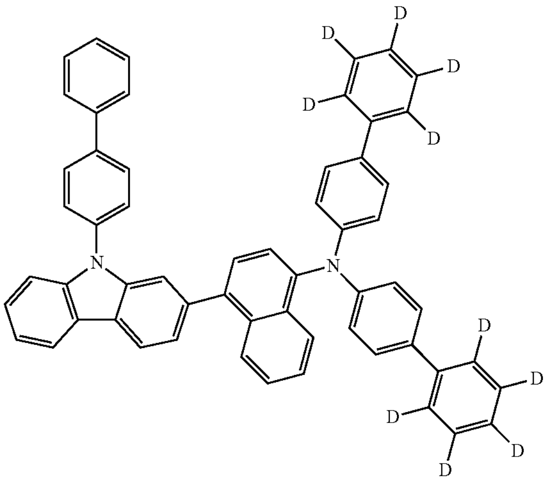
3-100
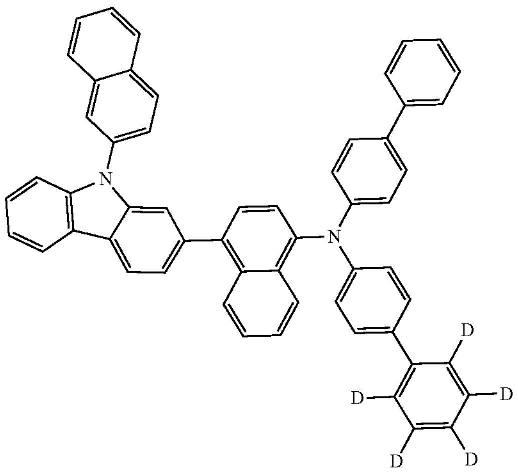
3-101
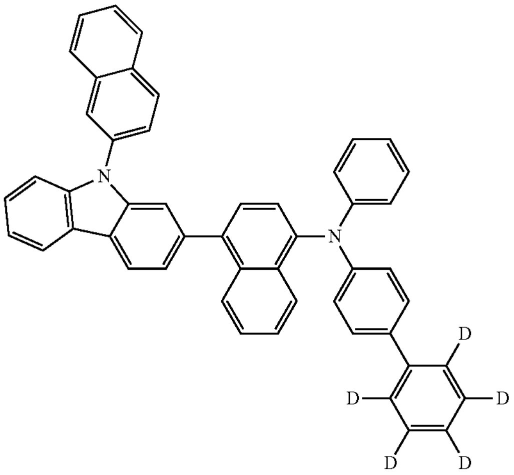
3-102
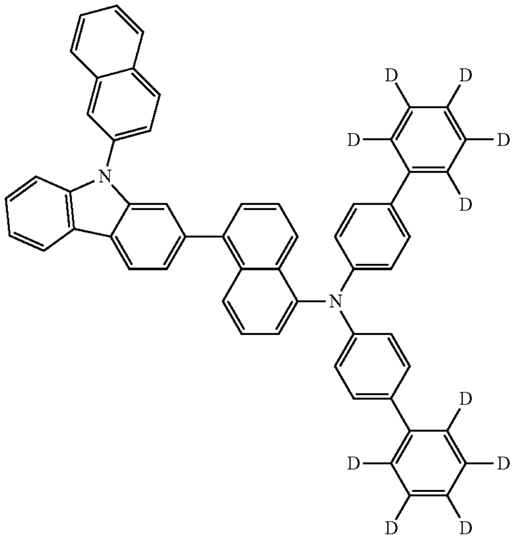
3-104
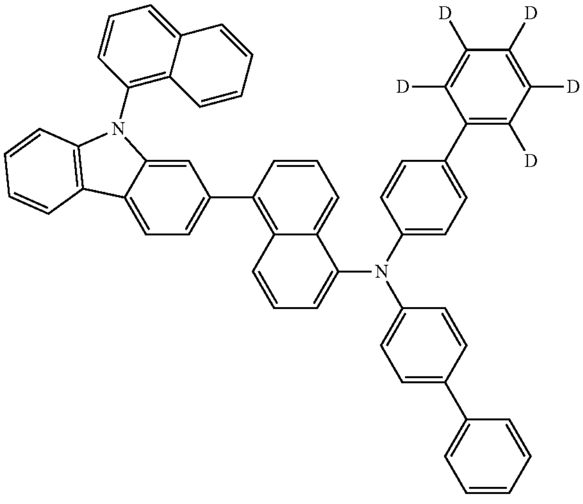
3-103
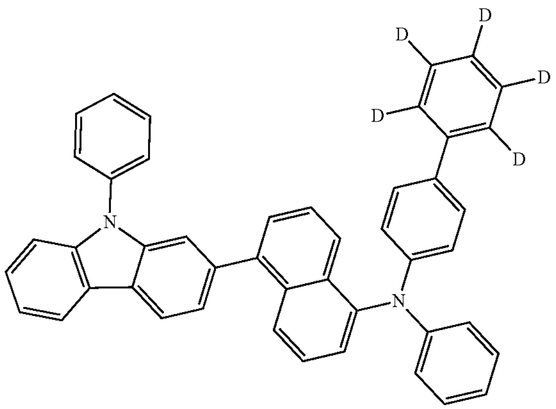

-continued
3-105
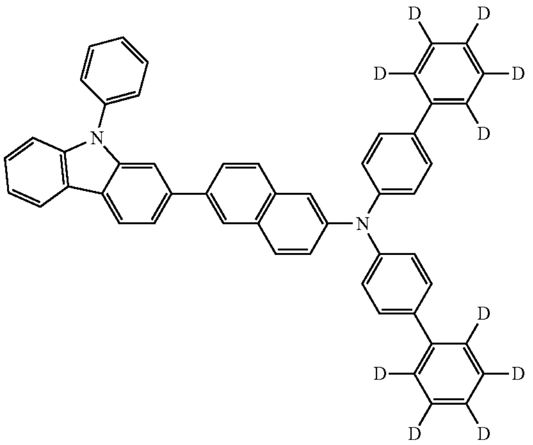
3-106
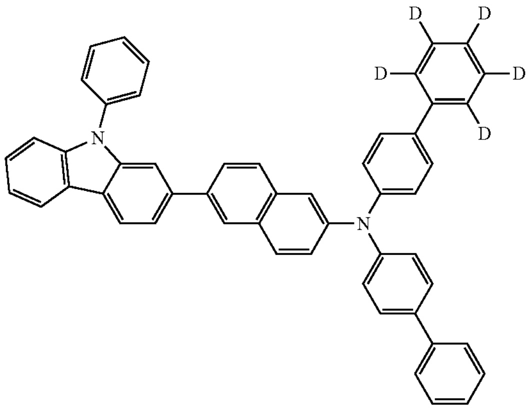
3-107
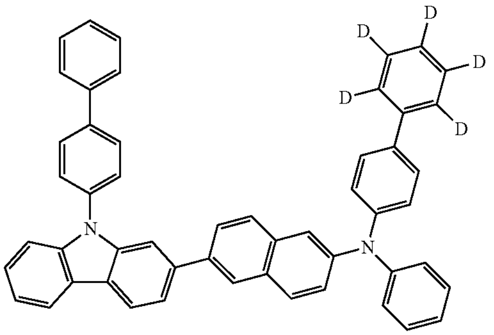
3-108
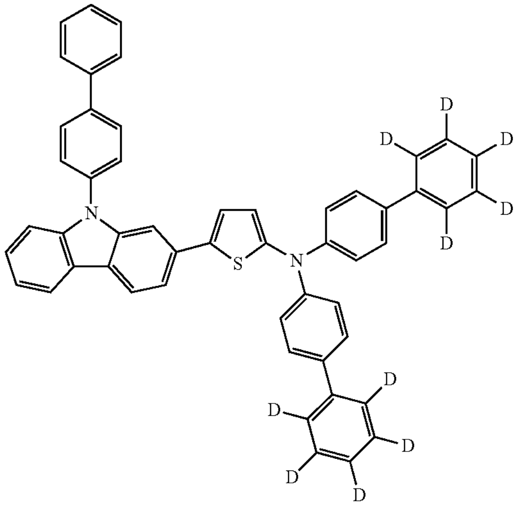
3-109
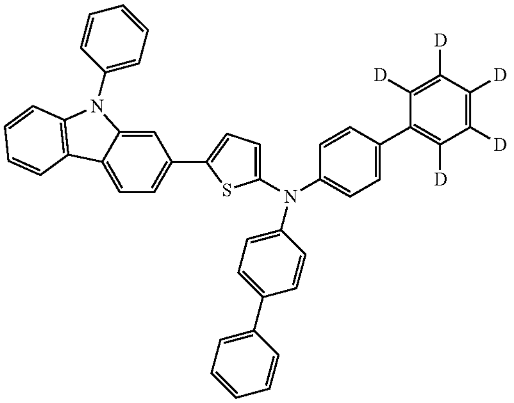
3-110
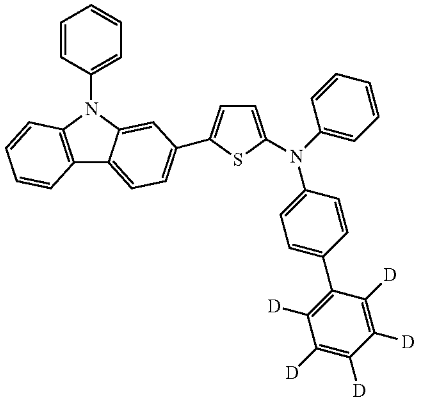

-continued
3-111
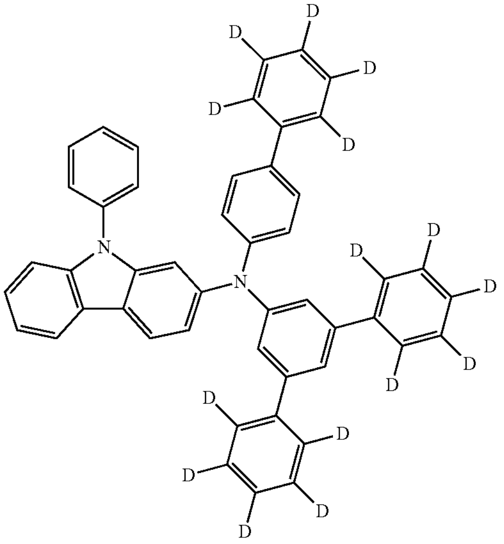
3-112
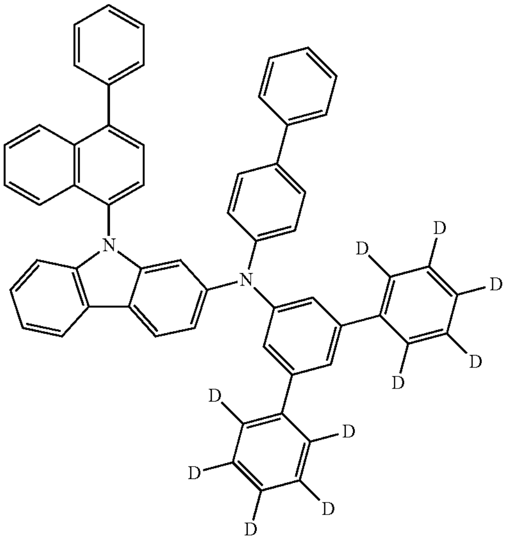
3-113
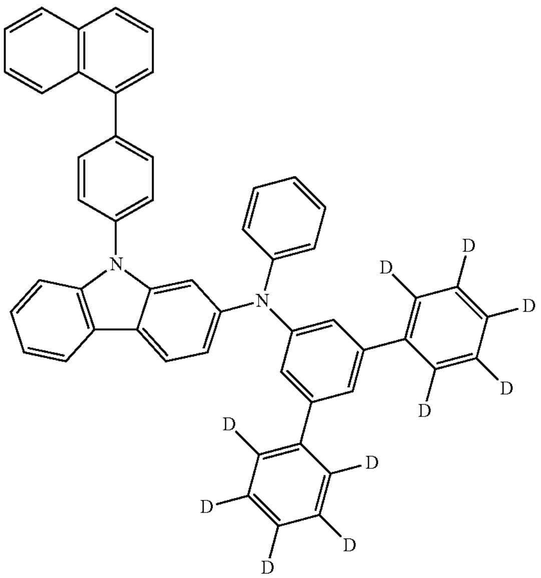
3-114
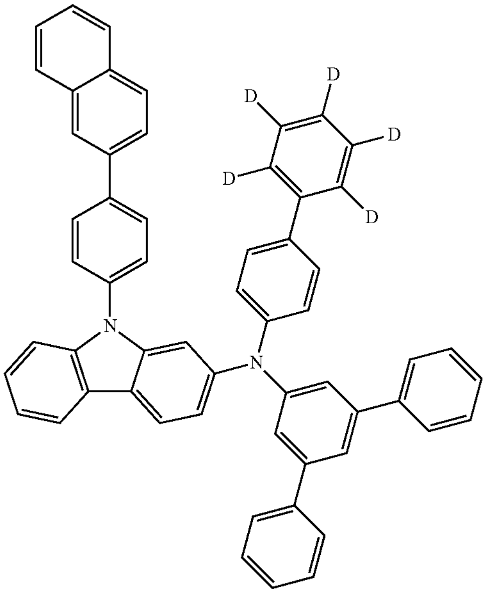
3-115
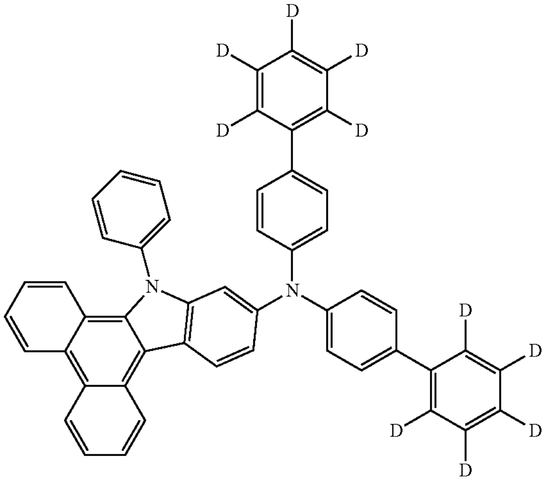
3-116
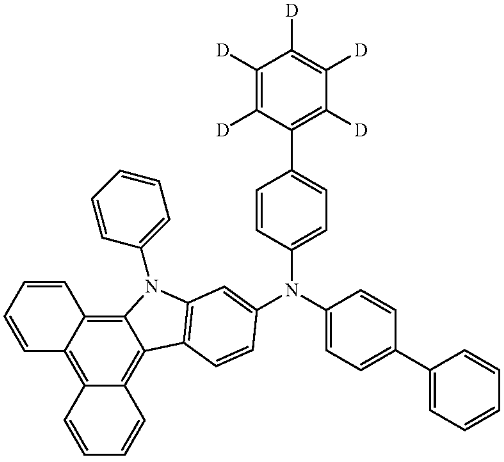

-continued
3-117
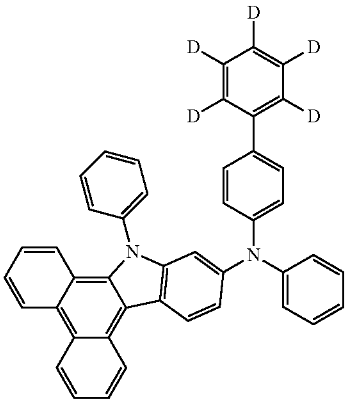
3-118
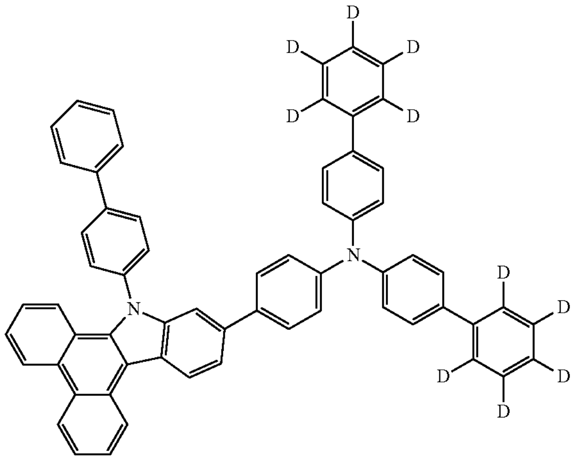
3-119
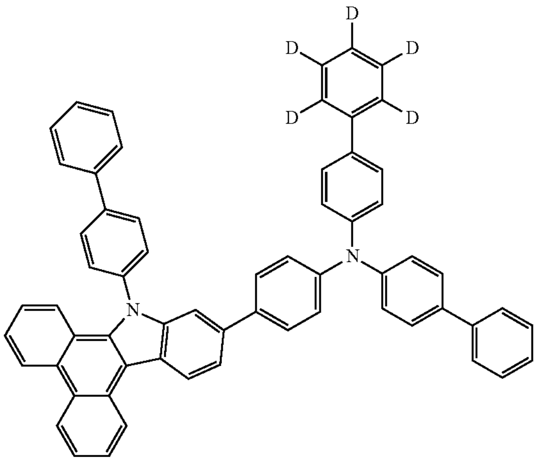
3-120
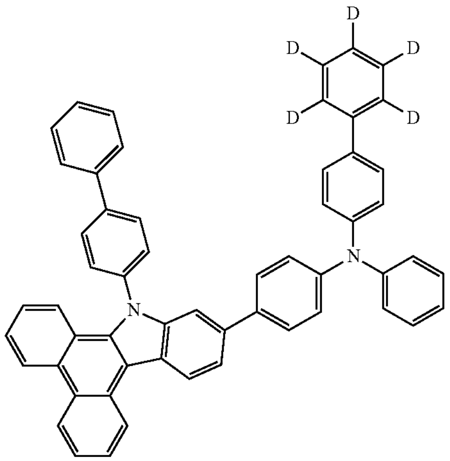
3-121
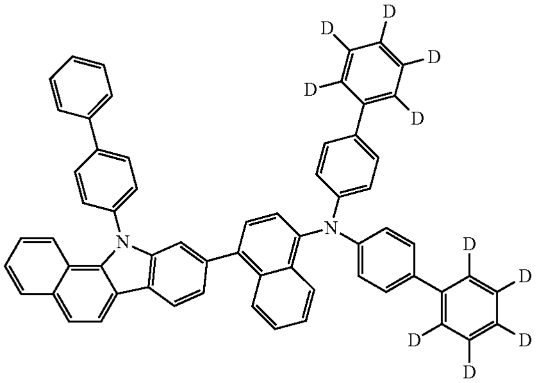
3-122
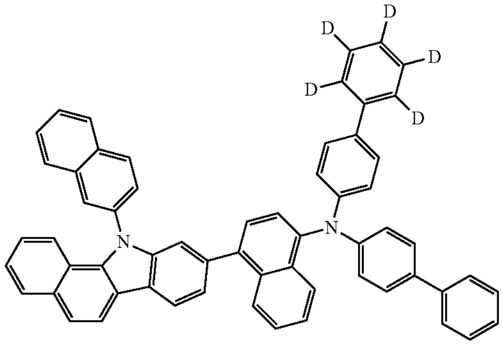

-continued
3-123
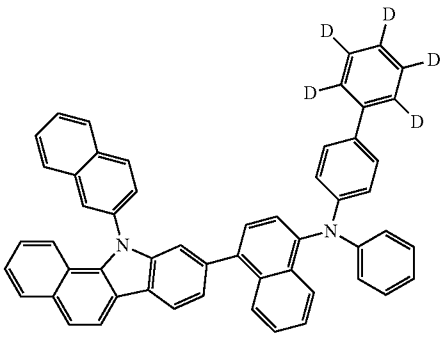
3-124
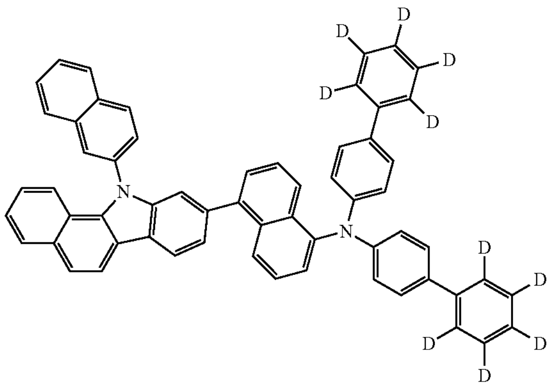
3-125
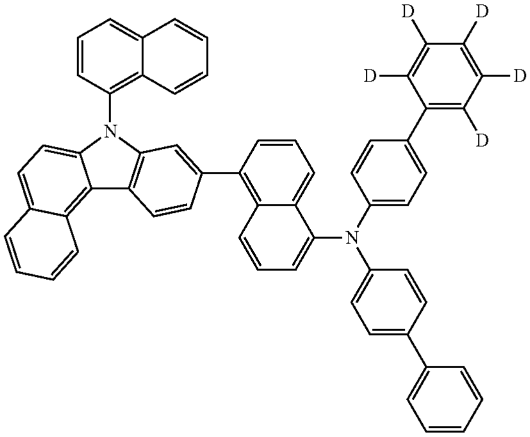
3-126
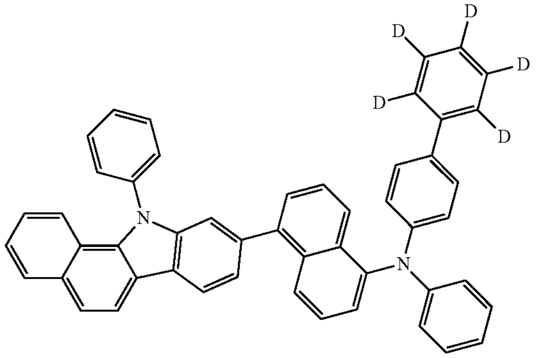
3-127
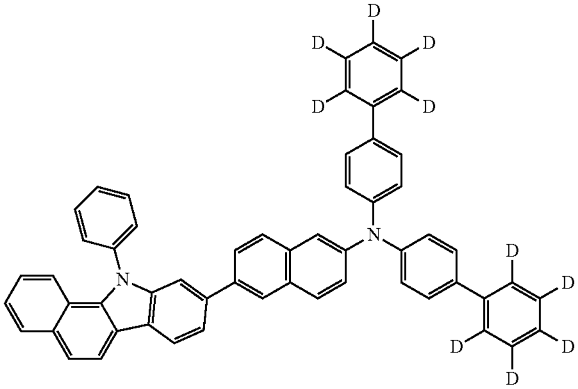
3-128
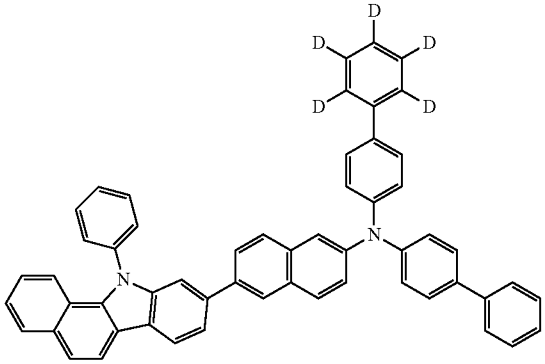

-continued
3-129
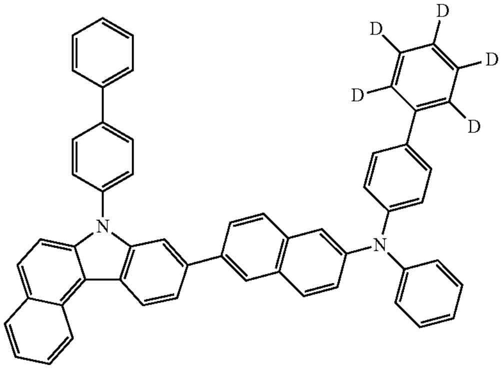
3-130
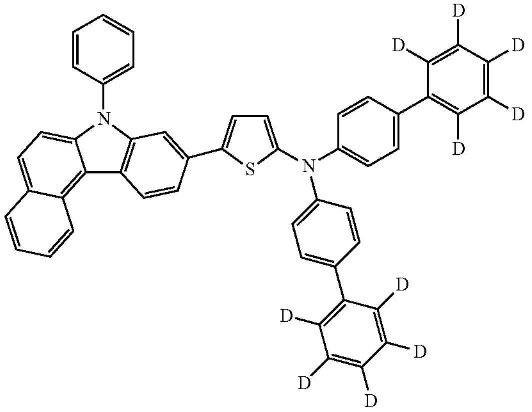
3-131
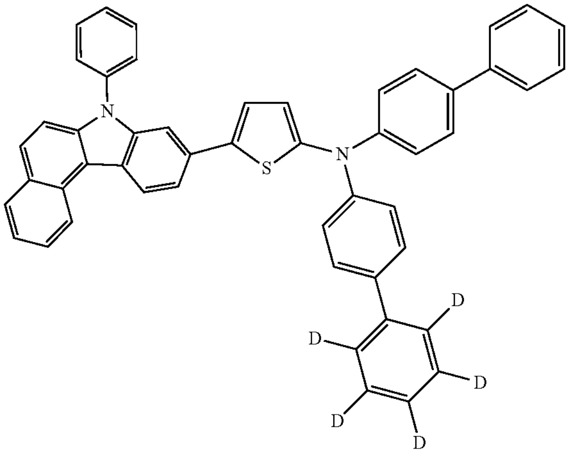
3-132
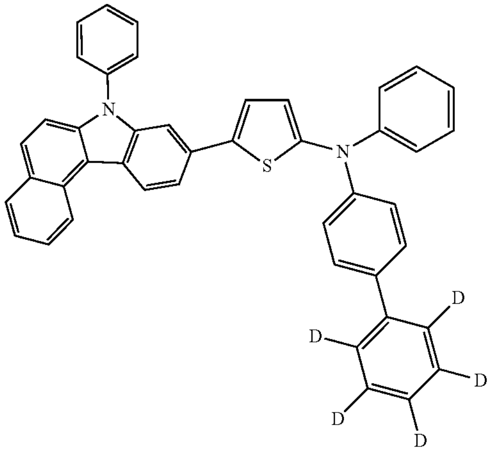
3-133
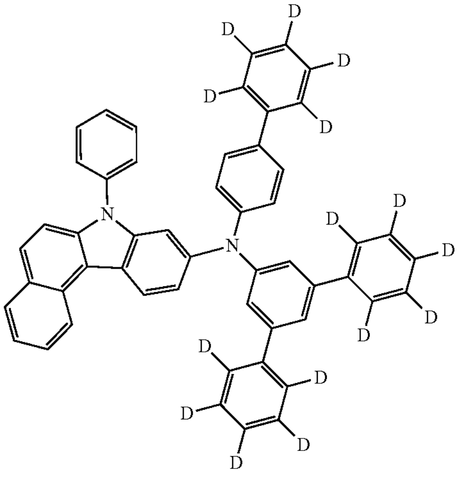
3-134
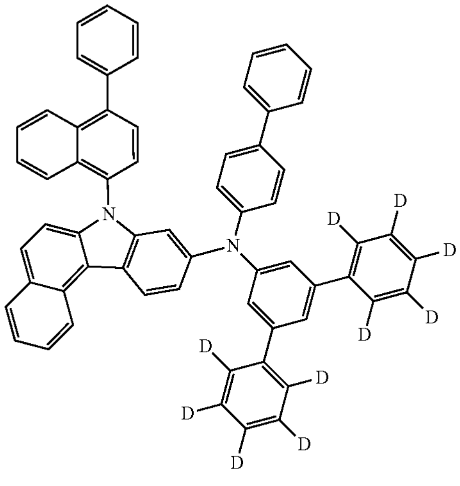

-continued
3-135
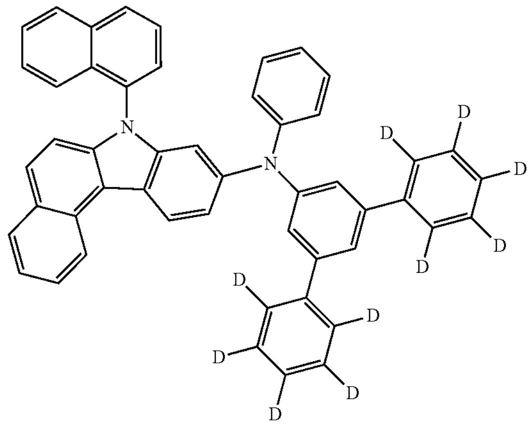
3-136
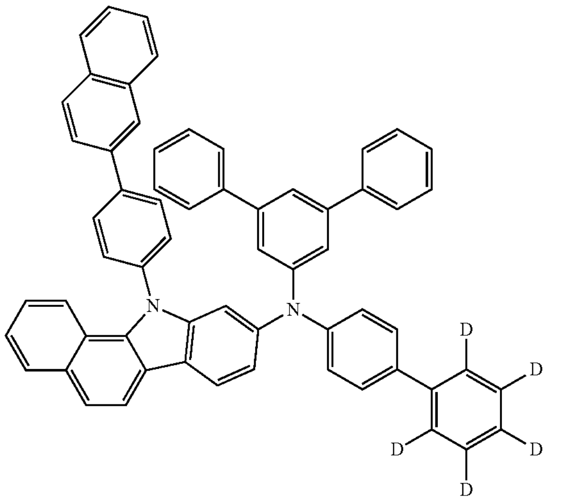
3-137
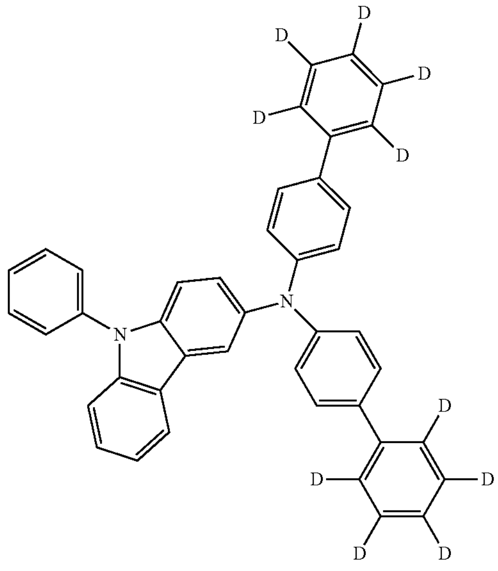
3-138
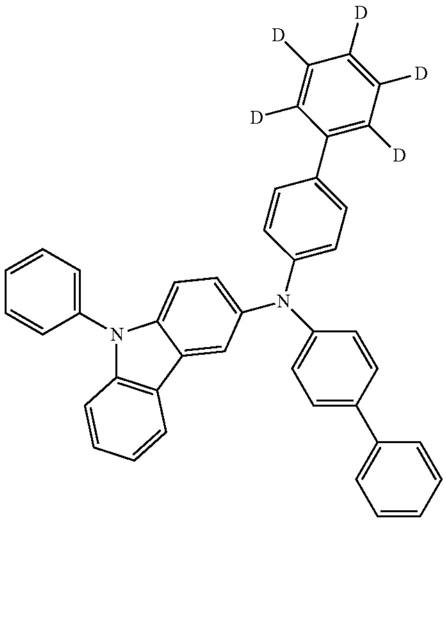
3-139
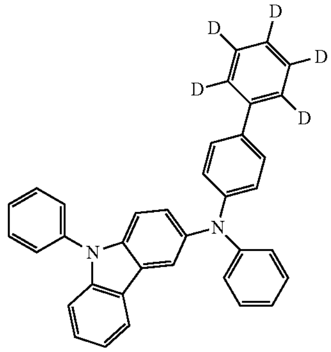
3-140
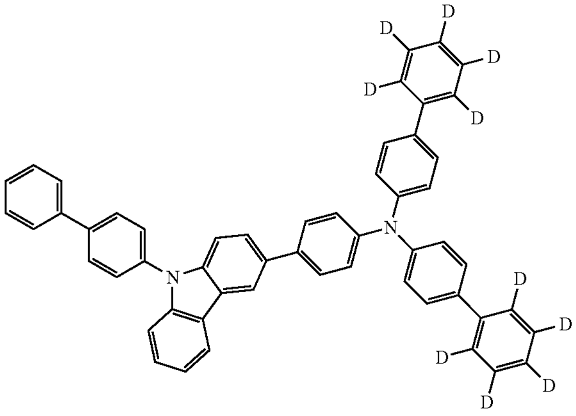

-continued
3-141
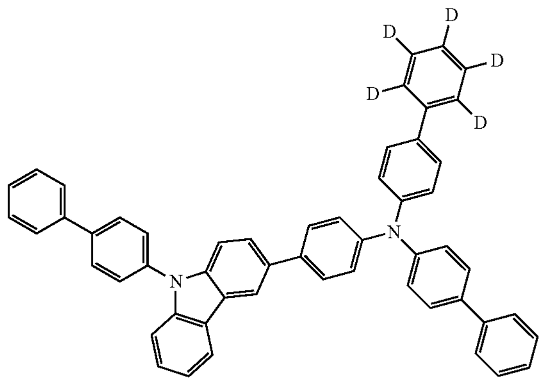
3-142
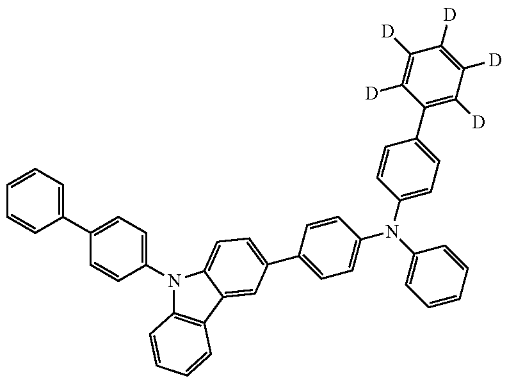
3-143
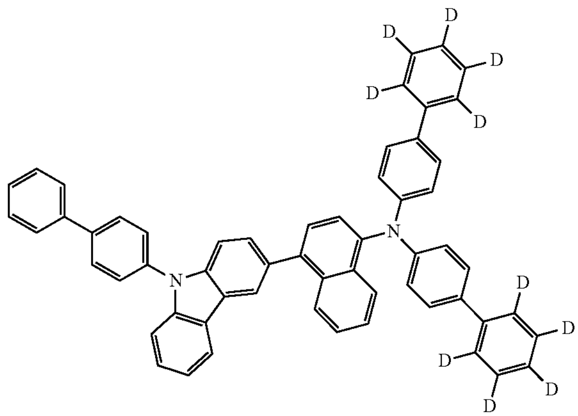
3-144
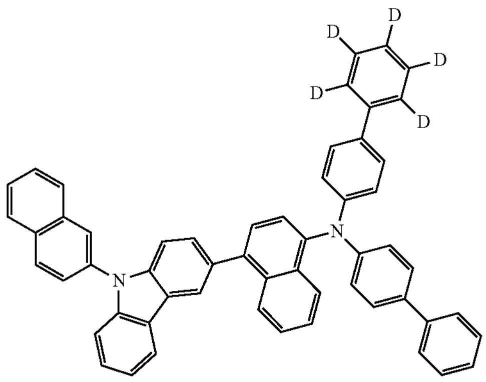
3-145
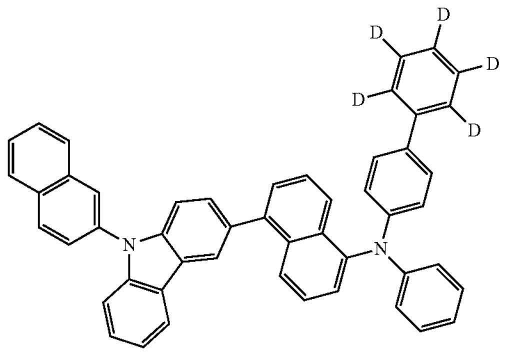
3-146
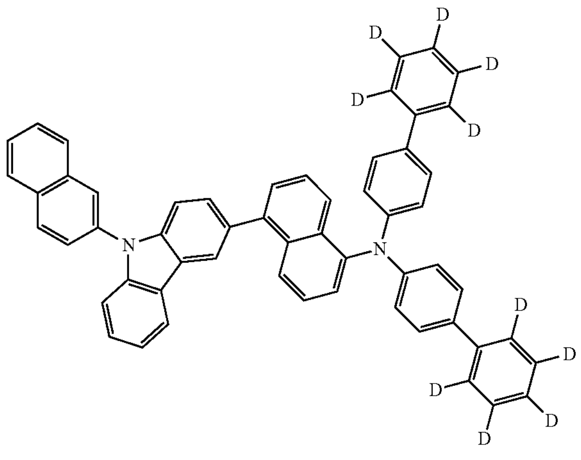

-continued
3-147
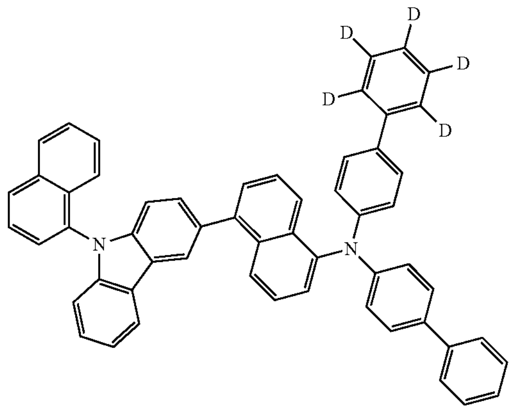
3-148
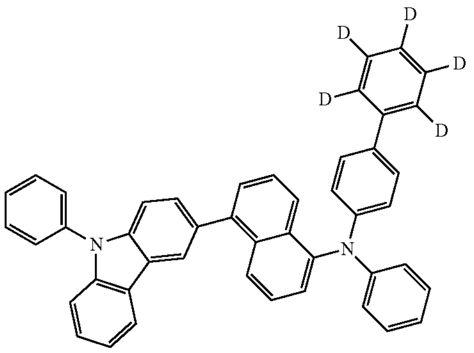
3-149
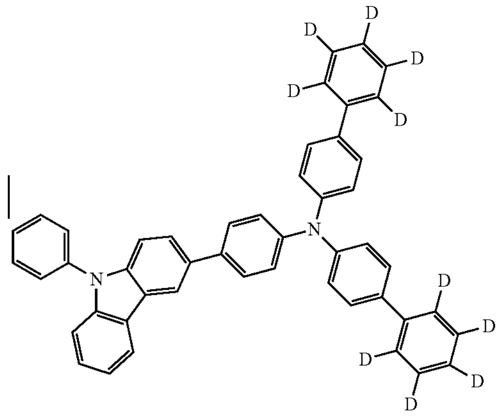
3-150
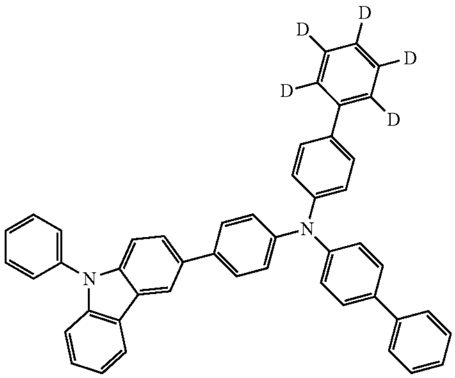
3-151
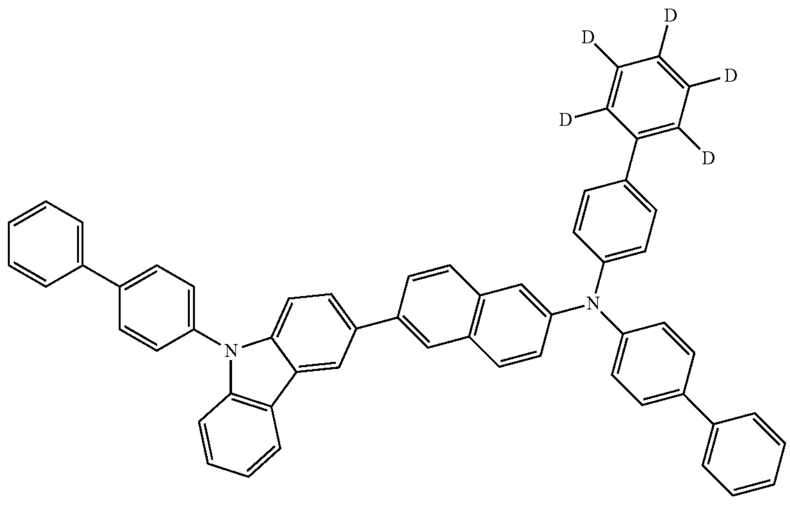

-continued
3-152
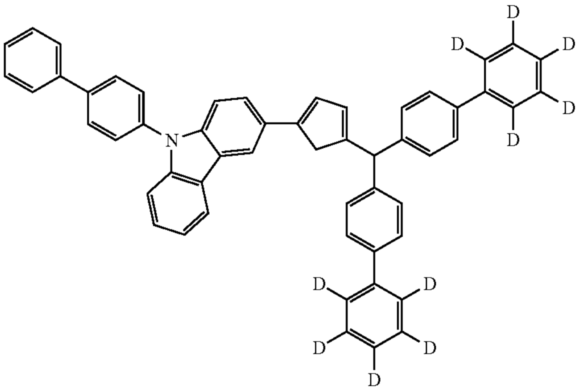
3-153
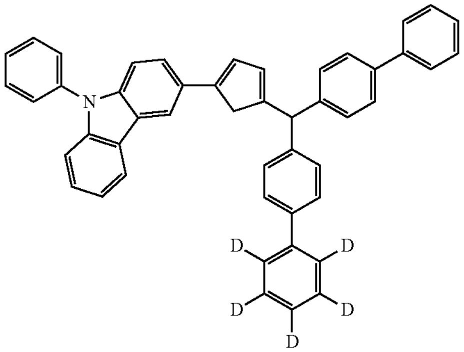
3-154
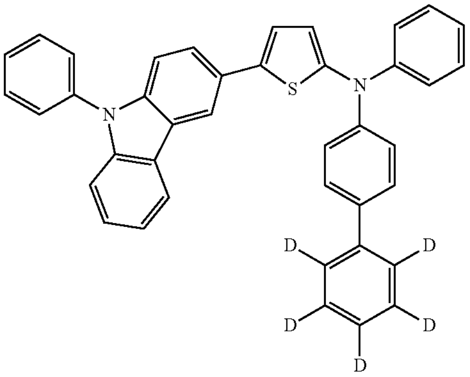
3-155
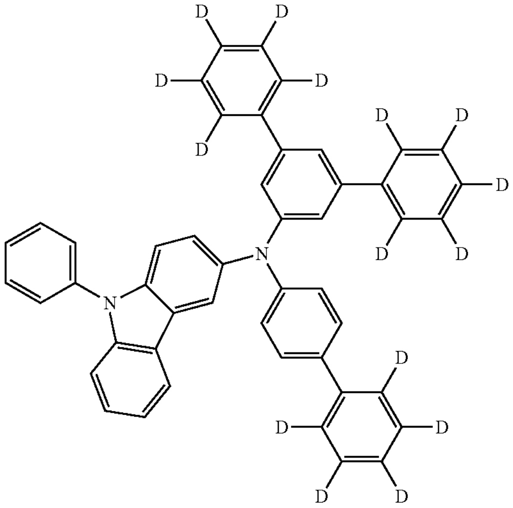
3-156
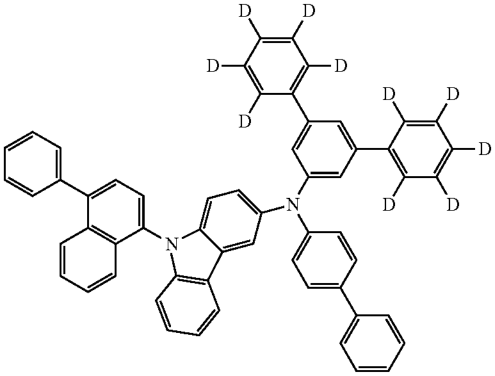
3-157
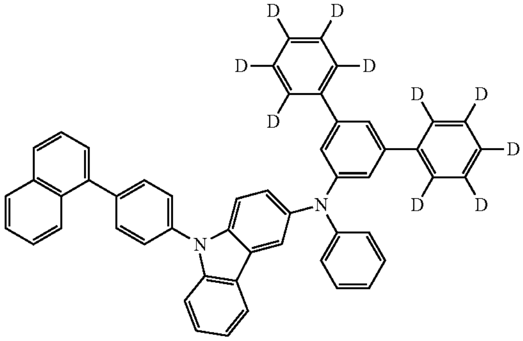

-continued
3-158
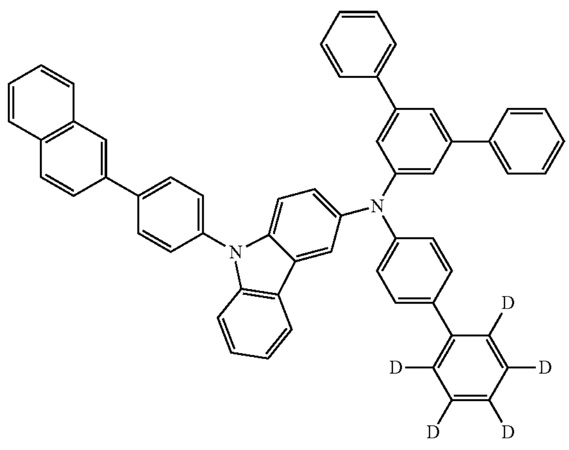
3-159
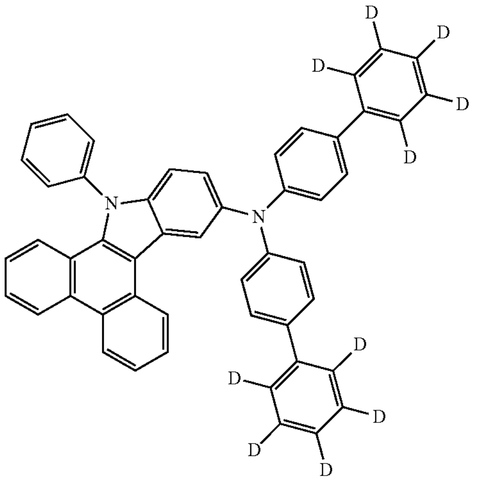
3-160
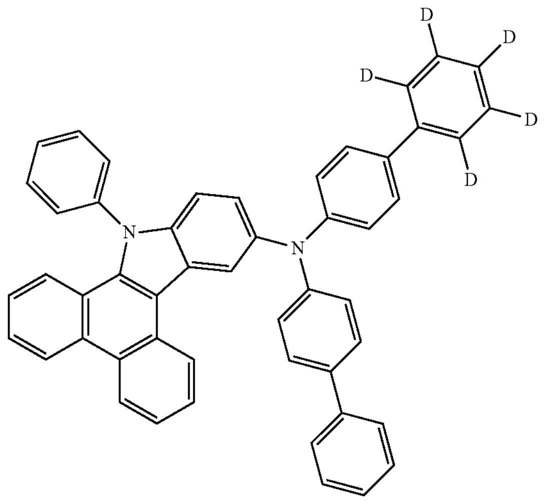
3-161
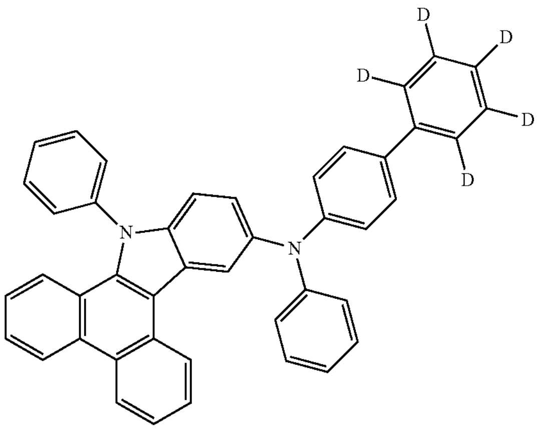
3-162
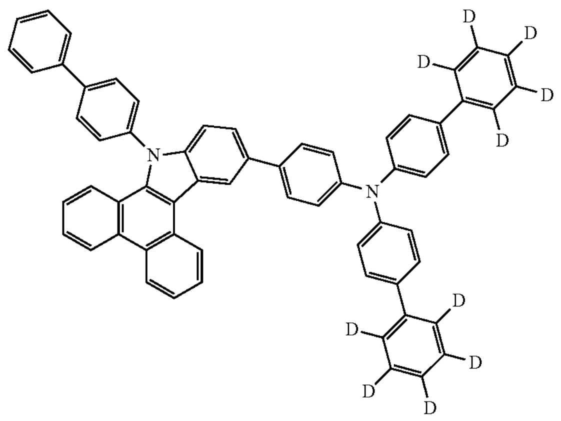
3-163
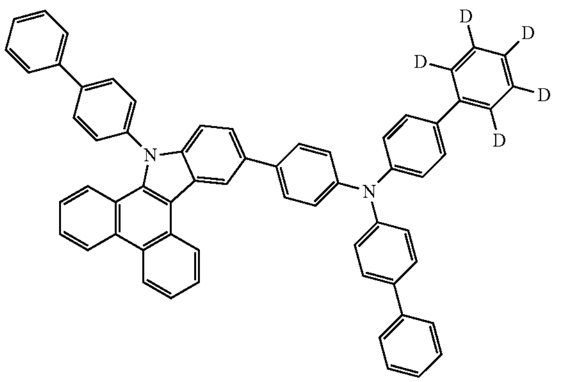

-continued
3-164
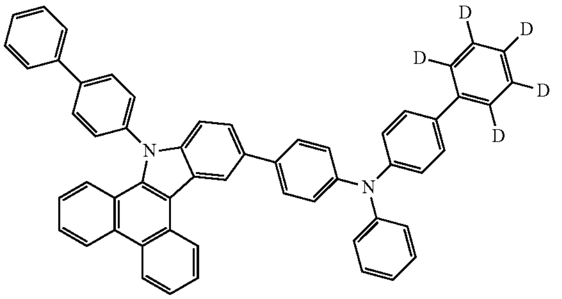
3-165
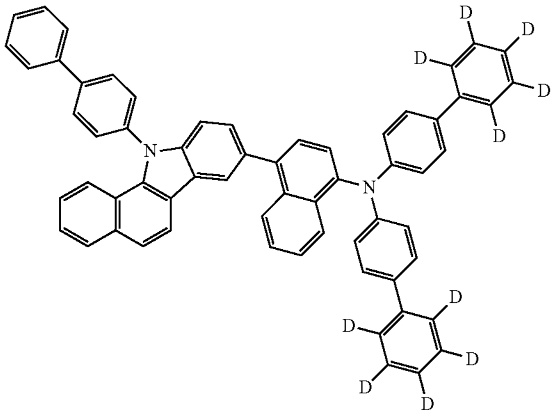
3-166
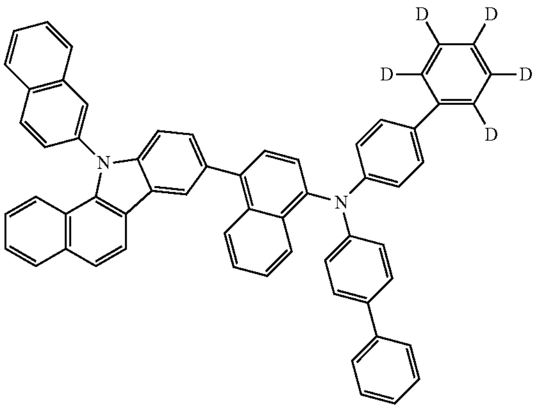
3-167
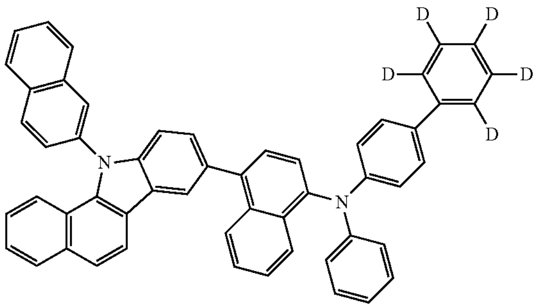
3-168
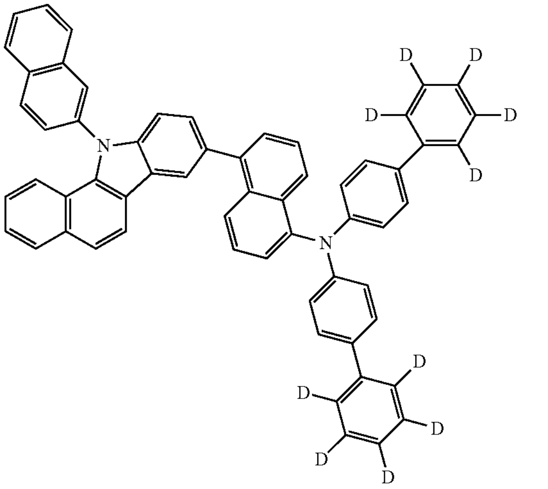
3-169
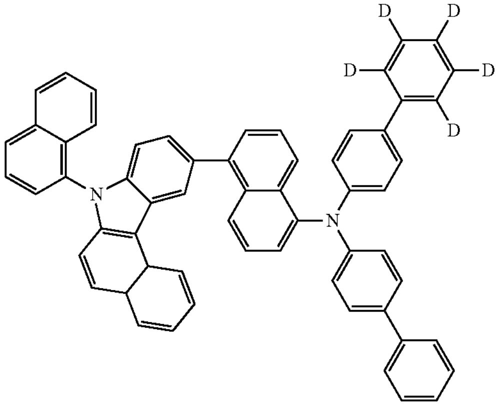

-continued
3-170
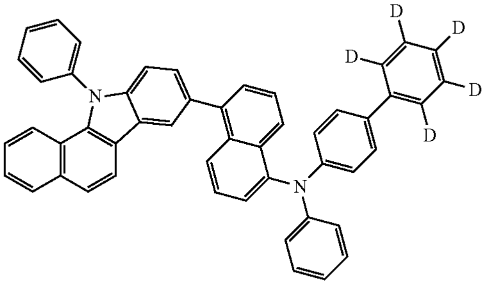
3-171
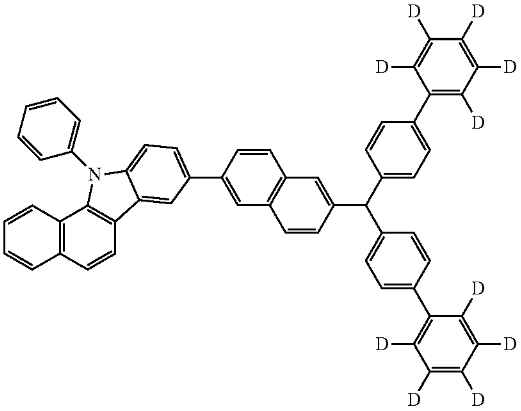
3-172
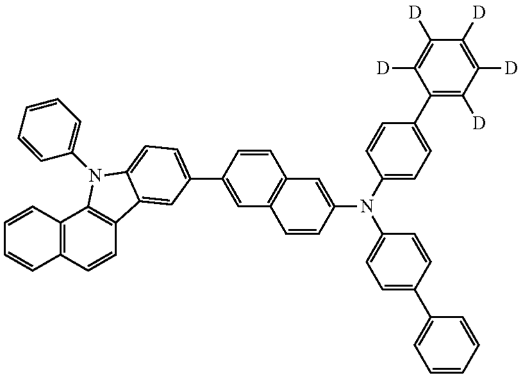
3-173
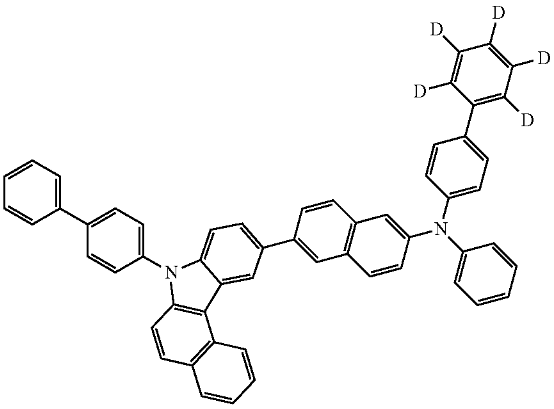
3-174
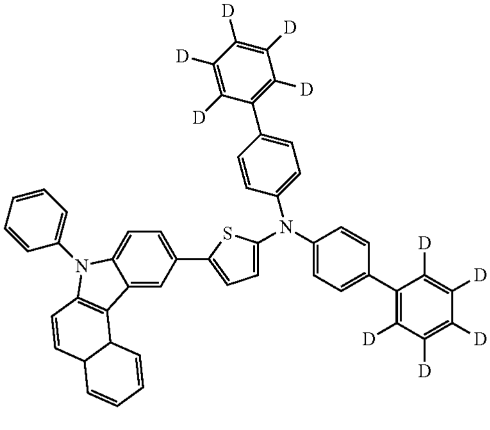
3-175
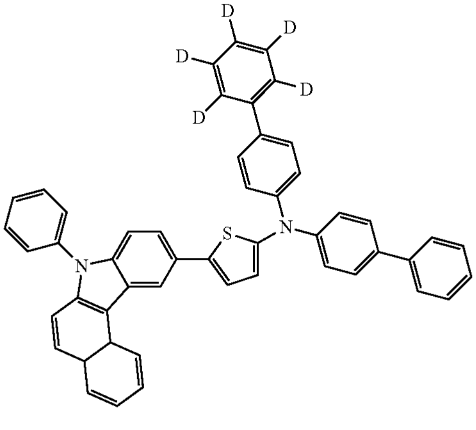

-continued
3-176
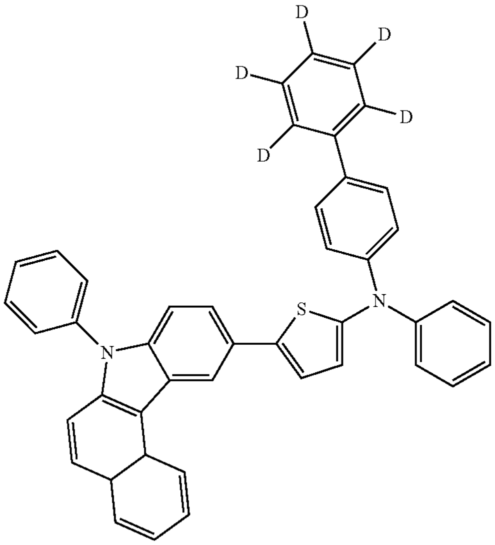
3-177
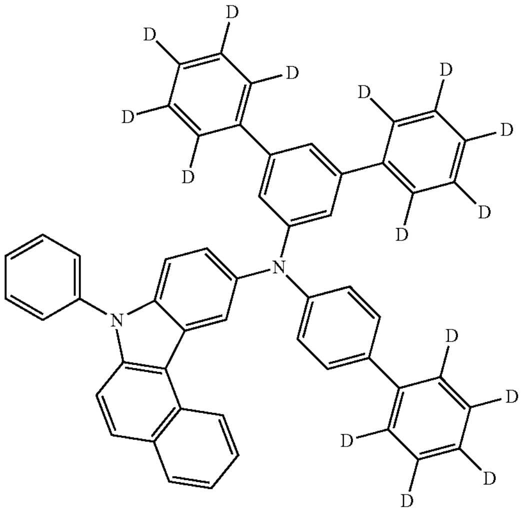
3-178
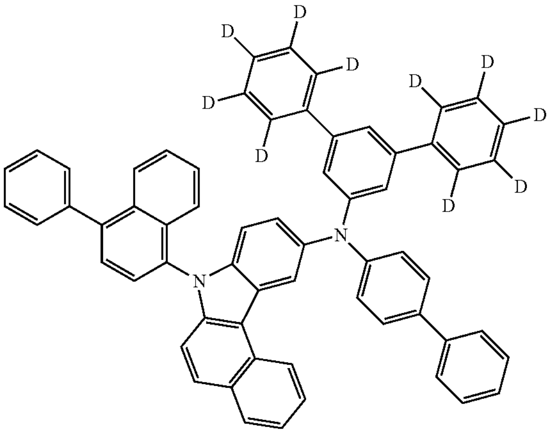
3-179
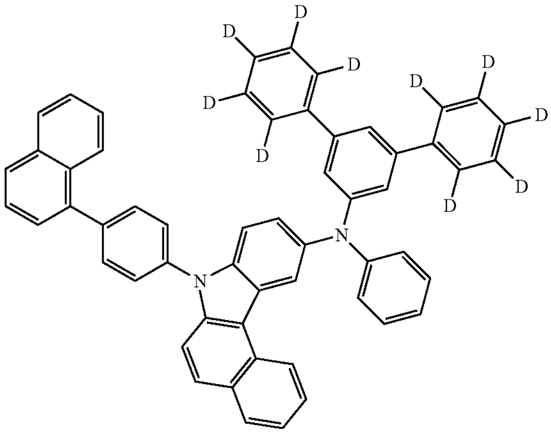
3-180
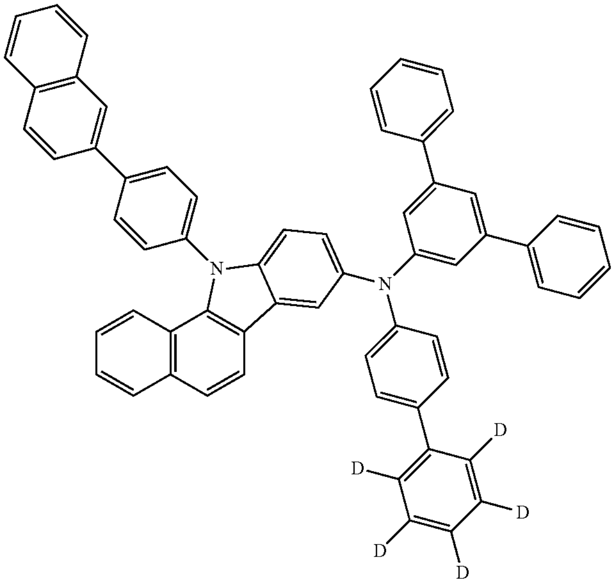

As described above, based on the research result obtained by the inventors of the present invention, the present invention provides compounds represented by Formulas 1 to 4.

The compounds represented by Formulas 1 to 4, as described below, can the characteristics of an organic material layer in an organic electro-luminescence element to the maximum, and at the same time can satisfy the requirement of a hole injection layer material having high uniformity and low degree of crystallinity during formation of a thin film, the requirement of a hole injection layer material that can delay penetration/diffusion of metal oxide from an anode electrode to an organic layer (one of causes of life span reduction) and has a stable property against Joule heating caused by driving of a device, that is, a high glass transition temperature, and the requirement of a highly heat-resistant material that can stand for a long time in a deposition method in the formation of an organic electro-luminescence element.

As described above, the inventors of the present invention found that the compounds substituted with heavy hydrogen, represented by Formulas 1 to 4 showed better thermodynamic behaviors compared to a non-substituted compound. Also, in a compound including carbon and heavy hydrogen, a higher luminous efficiency can be achieved due to the difference in a bond length between carbon-hydrogen and carbon-heavy hydrogen. This is because in such a compound with a smaller bond length, the intermolecular van der waals force is decreased by the smaller bond length. Also, it was found that when a compound is substituted with heavy hydrogen, Zero Point Energy, that is, ground state energy, is lowered, and the bond length of heavy hydrogen-carbon is shortened. Accordingly, the Molecular hardcore volume is reduced, thereby reducing Electronical polarizability. This weakens the Intermolecular interaction, thereby increasing the thin film volume.

Due to this characteristic of the compounds substituted with heavy hydrogen, represented by Formulas 1 to 4, it is possible to reduce the degree of crystallinity of a thin film. In other words, an amorphous state of the thin film can be achieved. Thus, it was determined that the characteristic will be very effective in the achievement of an amorphous state generally required for improving a life span and a driving characteristic of an organic electro-luminescence element.

As a result, it was found that the compounds substituted with heavy hydrogen, represented by Formulas 1 to 4, show a lower visible ray absorption than a material of a carbon-hydrogen bond. Then, it was determined that this characteristic can be advantageous in an increase of the efficiency in a luminous element such as an organic electro-luminescence element. Also, it was determined that the compounds substituted with heavy hydrogen, represented by Formulas 1 to 4, can highly increase heat resistance.

EXAMPLES

Hereinafter, the present invention will be described more specifically with reference to Preparation Examples and Experimental Examples. However, the following examples are only for illustrative purposes and are not intended to limit the scope of the invention.

Preparation Example

Hereinafter, Preparation Examples or Synthesis Examples of the compounds represented by Formulas 1 to 4 will be described.

However, since there are many compounds represented by Formulas 1 to 4, some compounds from among the compounds will be exemplified. A person skilled in the art of the invention should realize that other compounds can be prepared through Preparation Examples as described below although they are not exemplified.

Hereinafter, compounds were synthesized according to the above described synthesis method, and were employed in an organic material layer of an organic electronic element, e.g., an organic electro-luminescence element. Then, they were compared to generally used compounds.

General synthesis method
[Reaction Scheme 1]

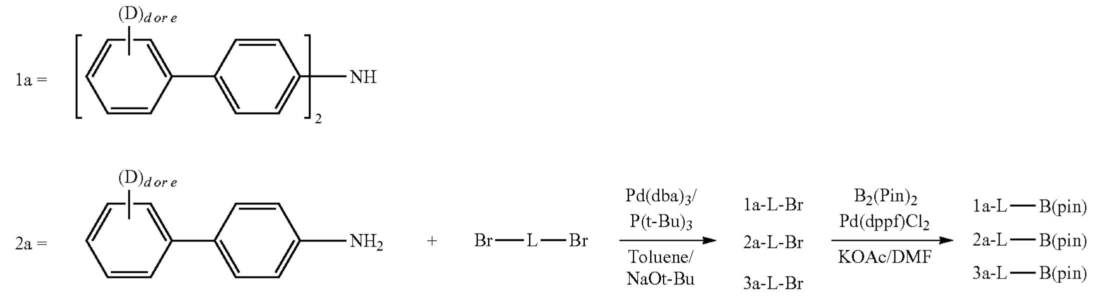

2-1 2-2

-continued
3a =
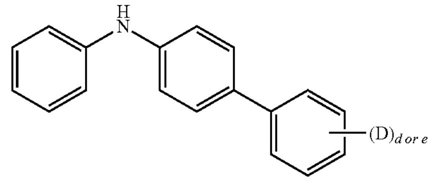
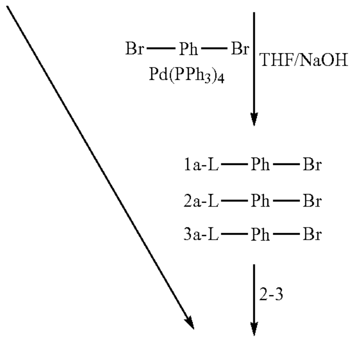
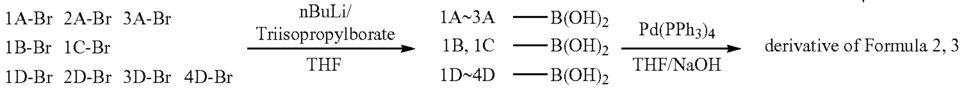
In Reaction Scheme 1, intermediates are as follows.
1A-Br =
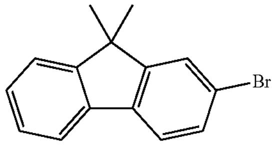
2A-Br =
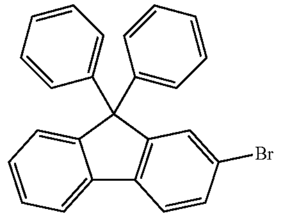
3A-Br =
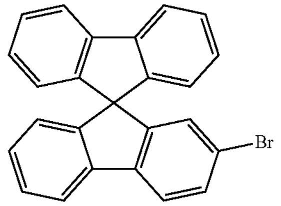
1B-Br =
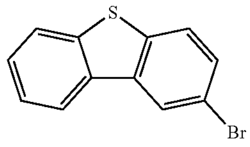
1C-Br =
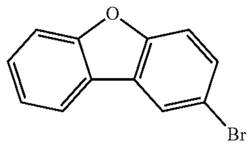
lbs
1D-Br =
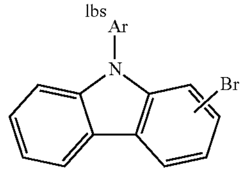
-continued
2D-Br =
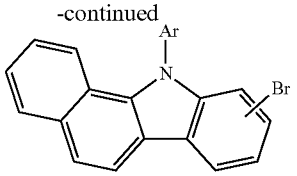
3D-Br =
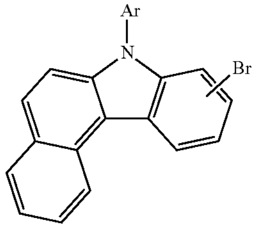
4D-Br =
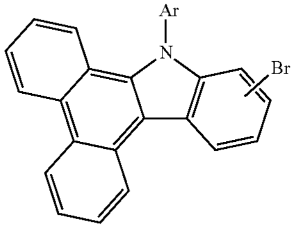
Synthesis Examples of Starting Material
Synthesis of starting material 1A-Br (2-Bromo-9,9-dimethyl-9H-fluorene)
[Reaction Scheme 2]
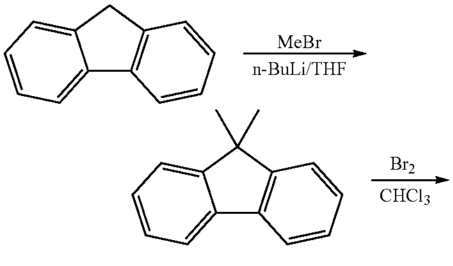
1A-1

-continued

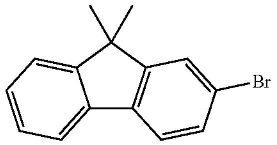

1A-Br

Synthesis of 1A-1 (9,9-Dimethyl-9H-fluorene)

A 500 mL 3-neck round-bottom flask was charged with fluorene (22 g, 130 mmol) and anhydrous THF (100 mL) under nitrogen atmosphere. The resultant mixture was stirred while cooled to −78° C. Then, the mixture was further stirred for 30 minutes, while its temperature was maintained. Then, 2.6M n-BuLi (120 mL, 320 mmol) in hexane solution was dropped to the cooled mixture.

The reaction flask was maintained at −78° C. while stirred for 1 hour. A solution including methyl bromide (28 g, 300 mmol) dissolved in THF (60 mL) was dropped to the reaction flask. The temperature of the reaction flask was slowly raised to room temperature, and the reaction was carried out for 24 hours. After the reaction was completed, the resultant product was extracted with isopropyl ether, water, and brine, and the organic layer was dried with $MgSO_4$. The obtained organic layer was purified by silica gel short column, concentrated, and recrystallized with methylene chloride and hexane so as to give 25 g of 1A-1 (98%).

Synthesis of 1A-Br (2-Bromo-9,9-dimethyl-9H-fluorene)

For a dark reaction, a hood for the reaction is blocked from light, and a 500 mL 3-neck round-bottom flask was charged with 1A-1 (9.7 g, 50 mmol), chloroform (100 mL), and $FeCl_2$ (0.2 g). The reaction flask was cooled to 0° C., and $Br_2$ (12 g, 75 mmol) was dropped thereto. Then, the reaction was carried out for 24 hours.

After the reaction was completed, the produced precipitate was separated by filtering, and washed with water, and ethanol. The obtained solid was heat-dried so as to give 15 g of 1A-Br (85%).

Synthesis of starting material 2A-Br (2-Bromo-9,9-diphenyl-9H-fluorene)

[Reaction Scheme 3]

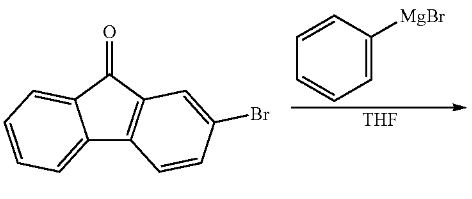

-continued

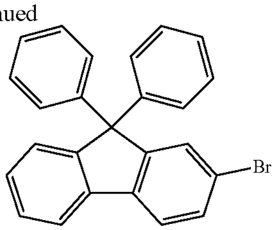

2A-Br

A 2 L round-bottom flask was charged with 2-Bromo-fluorenone (8.65 g 33.38 mmol), and anhydrous THF (850 mL). The reaction flask was cooled to −78° C., and 1M phenyl magnesium bromide (18 g, 100 mmol) dissolved in THF was dropped thereto. Then, the reaction was carried out for 3 hours.

Then, at room temperature, the reaction was carried out for 12 hours. After the reaction was completed, the produced precipitate was separated by filtering, and washed with water, and ethanol. The obtained solid was heat-dried so as to give 8.9 g of a required product (67%).

Synthesis of starting material 3A-Br (2-Bromo-9,9'-spirobi[filuorene])

[Reaction Scheme 4]

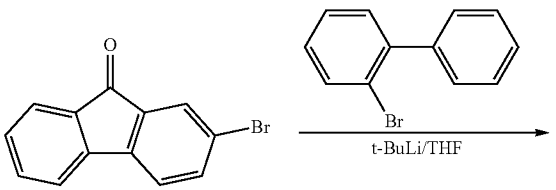

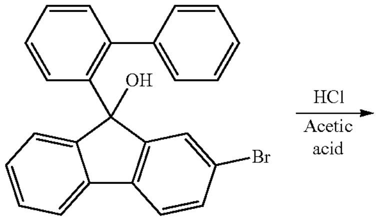

3A-1

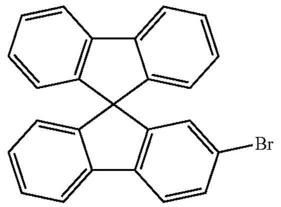

3A-Br

Synthesis of 3A-1 (9-(biphenyl-2-yl)-2-bromo-9H-fluoren-9-ol)

A 1 L 3-neck round-bottom flask was charged with 2-Bromo-9H-fluoren-9-one (41.5 q, 160 mmol) and anhydrous THF (900 mL) under nitrogen atmosphere. The resultant mixture was stirred while cooled to −78° C. Then, the mixture was further stirred for 30 minutes, while its temperature was maintained. Then, 2.6M n-BuLi (64 mL, 160 mmol) in hexane solution was dropped to the cooled mixture. The reaction flask was maintained at −78° C. while stirred for 1 hour.

A solution including 2-bromobiphenyl (37.3 g, 160 mmol) dissolved in THF (60 mL) was dropped to the reaction flask. The temperature of the reaction flask was slowly raised to room temperature, and the reaction was carried out for 24 hours. After the reaction was completed, the resultant product was extracted with isopropyl ether, water, and brine, and the organic layer was dried with $MgSO_4$. The obtained organic layer was purified by silica gel short column, concentrated, and recrystallized with methylene chloride and hexane so as to give 35.7 g of 3A-1 (54%).

Synthesis of 3A-Br (2-Bromo-9,9'-spirobi[fluorene])

A 1 L round-bottom flask was charged with 3A-1 (35.7 g, 86.38 mmol), and acetic acid (96 mL). The resultant mixture was stirred and dissolved in a solvent. The reaction temperature was lowered to 0° C., and hydrochloric acid (112 mL) was slowly dropped thereto. During the dropping of hydrochloric acid, it was determined if a solid is slowly produced. Then, when the amount of the solid is not increased any more, the reaction was ended. The produced precipitate was separated by filtering, and washed with water, and ethanol. The obtained solid was heat-dried so as to give 27.3 g of 3A-Br (80%).

Synthesis of starting material 1D-Br-1 (3-bromo-9-phenyl-9H-carbazole)

[Reaction Scheme 5]

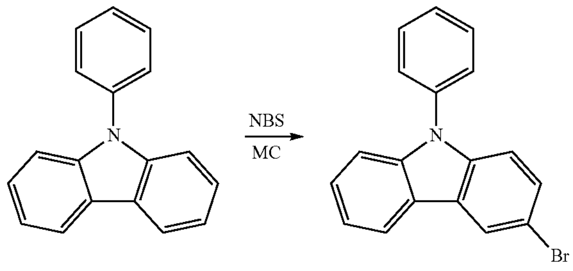

A 500 mL reaction flask was charged with 9-phenyl carbazole (20 g, 82.2 mmol), NBS (15.36 g, 86.31 mmol), and methylene chloride (200 mL), and the reaction was carried out at room temperature for 5 hours. After the reaction was completed, the resultant product was extracted with methylene chloride and $Na_2CO_3$ aqueous solution, dried with $MgSO_4$, and concentrated. Then, the produced compound was purified by short phase Column (methylene chloride:hexane=1:1), and recrystallized with methylene chloride and hexane so as to give 23 g of a required product (87%).

Synthesis of starting material 1D-Br-2 (2-bromo-9-phenyl-9H-carbazole)

Synthesis of intermediate 1 (4-Bromo-2-nitrobiphenyl)

[Reaction Scheme 6]

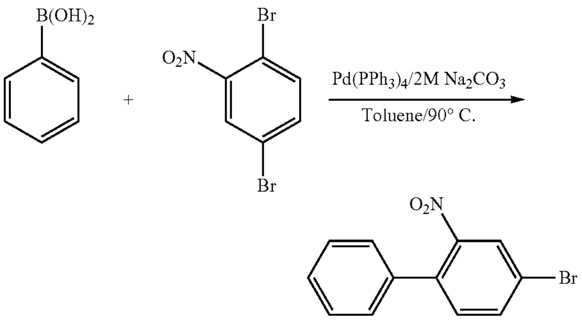

A 500 mL round-bottom flask was charged with toluene (250 mL), phenyl boronic acid (10 g, 82 mmol), 2,5-dibromonitrobenzene (23.1 g, 82.3 mmol), $Pd(PPh_3)_4$ (2.8 g, 2.5 mmol), and 2M $Na_2CO_3$ aqueous solution (124 mL). Then, at 90° C., the mixture was heated under reflux for 6 hours. After the reaction was completed, the resultant product was diluted with addition of distilled water at room temperature. Then, the resultant product was extracted with methylene chloride and water. The organic layer was dried with $MgSO_4$, and concentrated. Then, the produced compound was purified by silica gel column (methylene chloride:hexane=1:1) to give 19.2 g of a required product (84.2%).

Synthesis of intermediate 1 (2-Bromocarbazole)

[Reaction Scheme 7]

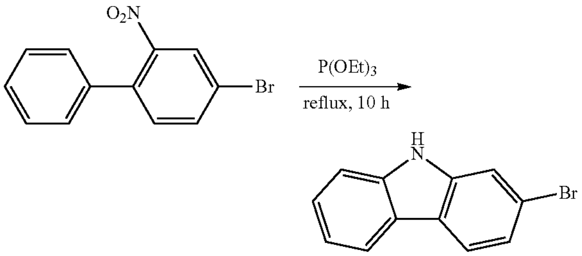

A 250 mL round-bottom flask was charged with 4-Bromo-2-nitrobenzene (19.2 g, 69.04 mmol), and triethyl phosphate (84 mL, 483.28 mmol). At 160° C.~165° C., the mixture was heated under reflux for 14 hours. After the reaction was completed, the remaining triethyl phosphate was removed by vacuum distillation. The resultant product was diluted with a mixed solvent of MeOH:$H_2O$=1:1, and the produced solid was filtered. The obtained solid was washed with a mixed solvent of MeOH:$H_2O$=1:1 and petroleum ether.

The solid was dissolved in methylene chloride, dried with $MgSO_4$, and concentrated, and purified by silica gel column (petroleum ether:methylene chloride=2:1). Then, 10.2 g of a required product (60%) was obtained.

Synthesis of 1D-Br-2: (2-bromo-9-phenyl-9H-carbazole)

[Reaction Scheme 8]

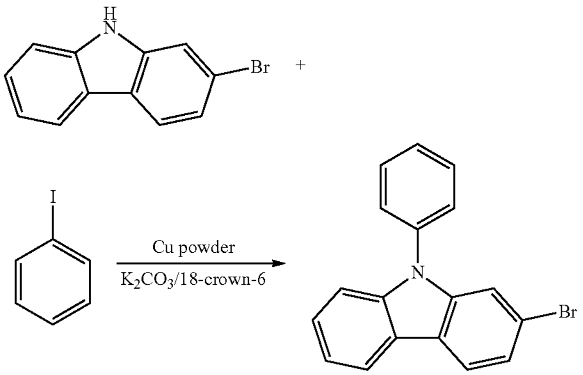

A 250 mL round-bottom flask was charged with 2-Bromocarbazole (6 g, 24.38 mmol), iodobenzene (9.95 g, 48.76 mmol), $K_2CO_3$ (10.11 g, 73.14 mmol), Cu powder (1.55 g, 24.38 mmol), 18-crown-6 (3.22 g, 12.19 mmol), and o-dichlorobenzene (150 mL), and the mixture was heated under reflux for 24 hours. After the reaction was completed, the resultant product was extracted with methylene chloride and water. The obtained organic layer was washed with 5% hydrochloric acid, and brine. The organic layer was dried with $MgSO_4$, and concentrated. The resultant compound was purified by silica gel column (ethyl acetate:hexane=1:1) to give 5.5 g of a required product (70%).

Synthesis of starting material 2D-Br-1 (8-bromo-11-phenyl-11H-benzo[a]carbazole)

[Reaction Scheme 9]

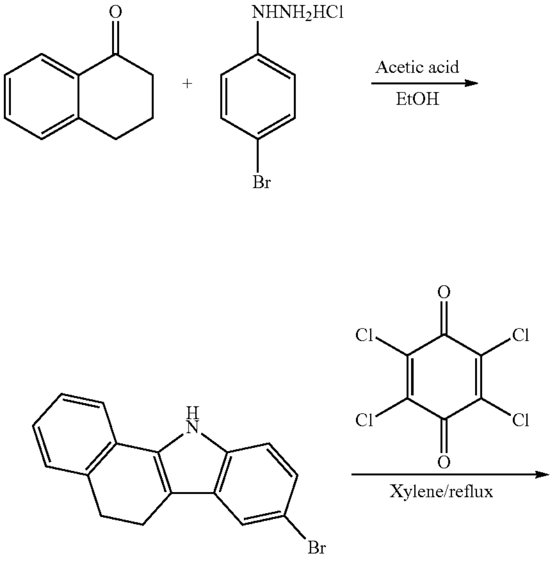

intermediate 1

-continued

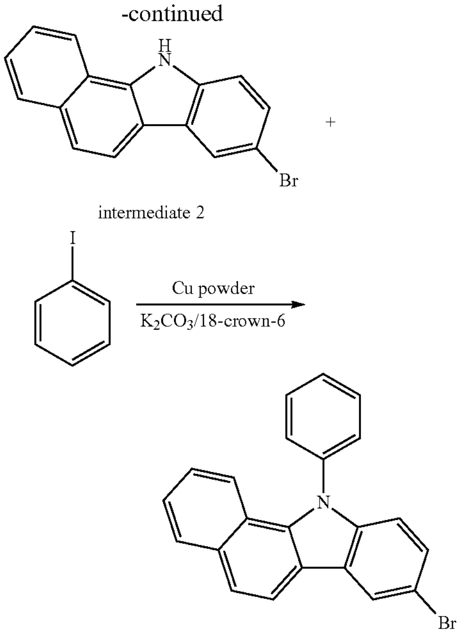

intermediate 2

2D-Br-1

Synthesis of intermediate 1: 8-bromo-6,11-dihydro-5H-benzo[a]carbazole

A 1 L round-bottom flask was charged with α-Tetralone (21.6 g, 1.48 mmol), and 4-bromophenylhydrazinechloride (20.4 g, 91 mmol), and a small amount of acetic acid was added thereto. Then, ethanol (300 Ml) was added thereto, and the resultant mixture was refluxed for 4 hours under nitrogen atmosphere. After the reaction was completed, the resultant product was cooled to room temperature. The produced precipitate was filtered, and dried to give 19.6 g of intermediate 1 (86%).

Synthesis of intermediate 2: 8-bromo-11H-benzo[a]carbazole

A 1 L round-bottom flask was charged with intermediate 1 (24.1 g, 80.5 mmol), tetrachloro-1,4-benzoquinone (27.45 g, 111.7 mmol), and xylene, and refluxed under nitrogen atmosphere. After the reaction was completed, the reaction was ended through the addition of 10% NaOH aqueous solution. Then, the resultant product was extracted with methylene chloride, water, and brine, and the organic layer was dried with $MgSO_4$. The organic solution was concentrated and recrystallized with EtOH to give 22.9 g of intermediate 2 (96%).

Synthesis of 2D-Br-1: 8-bromo-11-phenyl-11H-benzo[a]carbazole 17.1 g of 2D-Br-1 (68%) was obtained in the same manner as described in the synthesis method of 1D-Br-2 except that intermediate 2 (20 g, 67.53 mmol), iodobenzene (27.6 g, 135.06 mmol), $K_2CO_3$ (28 g, 202.59 mmol), Cu powder (4.3 g, 67.53 mmol), 18-crown-6 (8.92 g, 33.77 mmol), and o-dichlorobenzene (415 mL) were used.

Synthesis of starting material 2D-Br-2 (9-bromo-11-phenyl-11H-benzo[a]carbazole)
[Reaction Scheme 10]
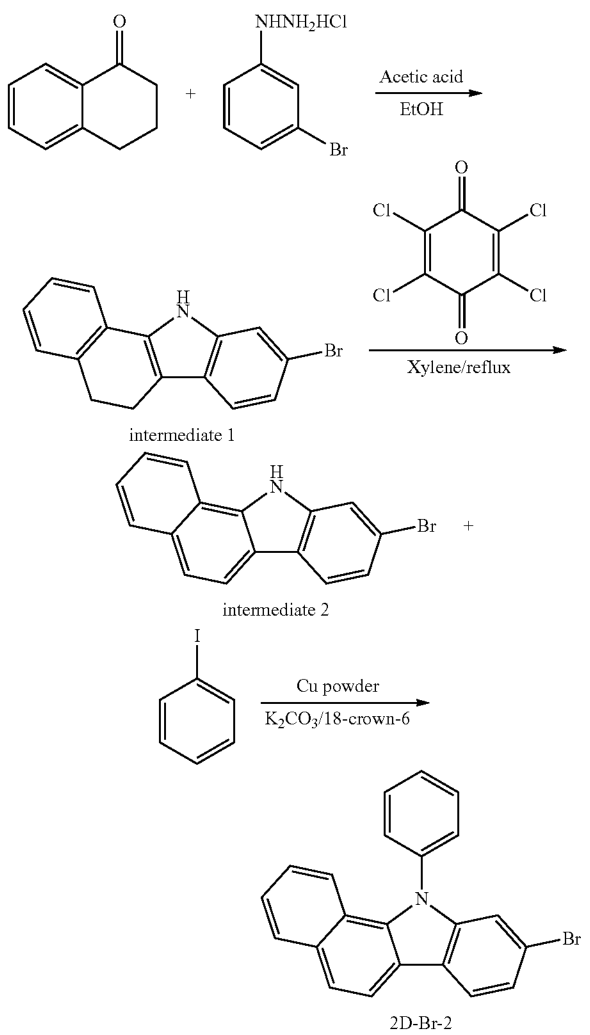
15.1 g of 2D-Br-2 (60%) was obtained in the same manner as described in the synthesis method of 2D-Br-1 except that intermediate 2 (20 g, 67.53 mmol), iodobenzene (27.6 g, 135.06 mmol), $K_2CO_3$ (28 g, 202.59 mmol), Cu powder (4.3 g, 67.53 mmol), 18-crown-6 (8.92 g, 33.77 mmol), and o-dichlorobenzene (415 mL) were used.
Synthesis of starting material 3D-Br
[Reaction Scheme 11]
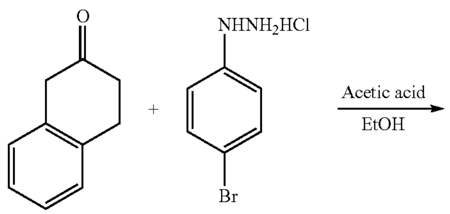
-continued
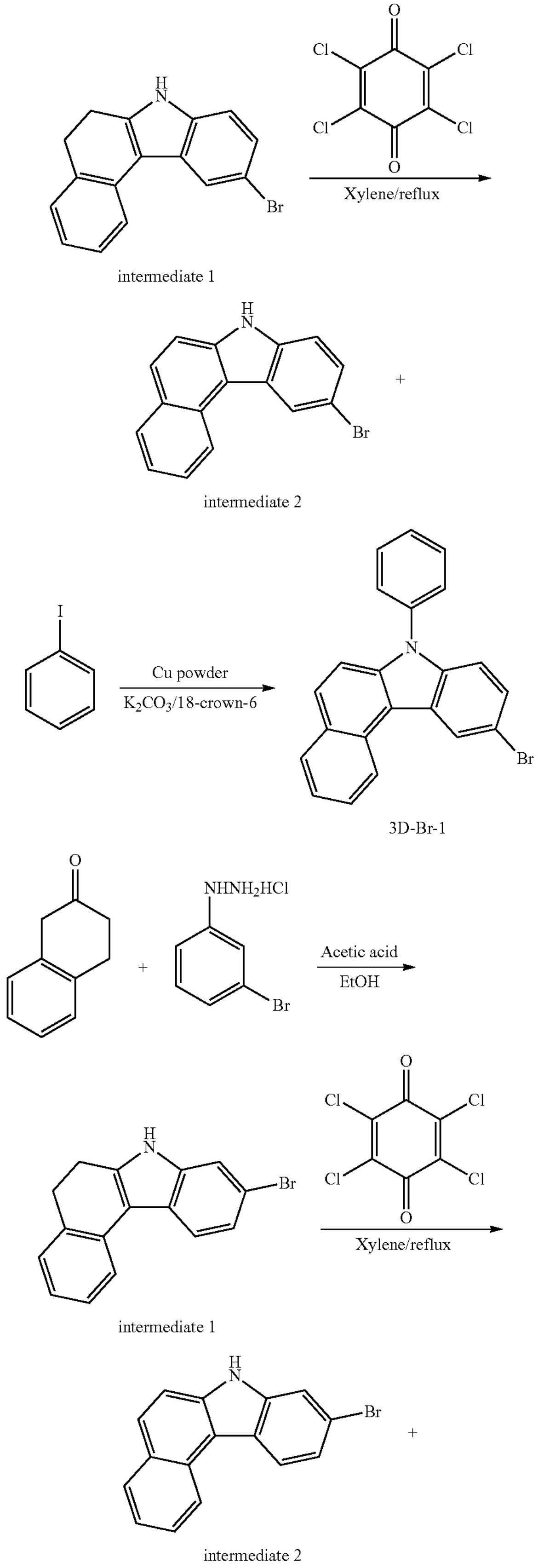

-continued

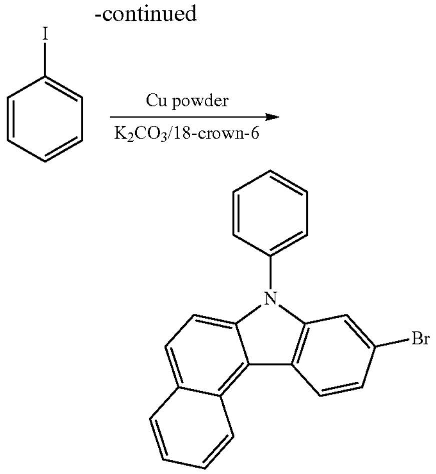

3D-Br-2

This material was obtained in the same manner as the synthesis method of 1D-Br-1 or 1D-Br-2.

Synthesis of starting material 4D-Br-1 (12-bromo-9-phenyl-9H-dibenzo[a,c]carbazole)

Synthesis of intermediate 1: 9-(5-bromo-2-nitrophenyl)phenanthrene

[Reaction Scheme 12]

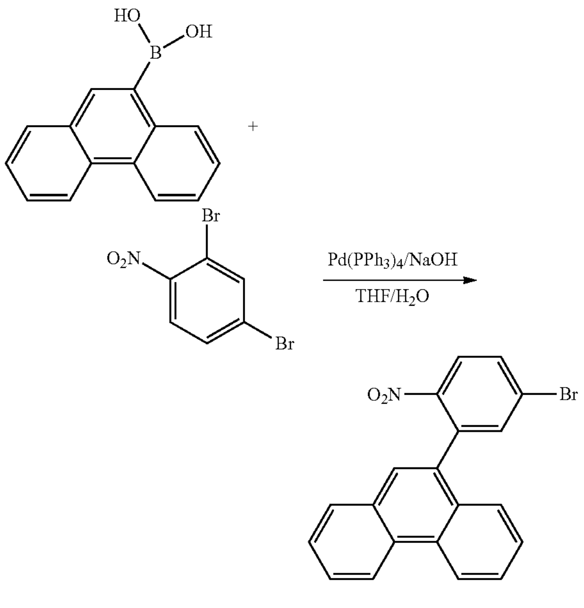

A 2 L round-bottom flask was charged with phenanthracene-9-boronic acid (76.61 g, 345 mmol), THF (700 mL), and $H_2O$ (350 mL), and the materials were dissolved. The resultant mixture was sequentially added with 2,4-dibromo-1-nitrobenzene (146 g, 518 mmol), NaOH (42 g, 1035 mmol), and $Pd(PPh_3)_4$ (20 g, 17.3 mmol), and subjected to a reaction at 80° C. for 24 hours. After the reaction was completed, the resultant product was extracted with methylene chloride, water, and brine, and the organic layer was dried with $MgSO_4$. The obtained organic layer was purified by silica gel column (methylene chloride:hexane=1:3) so as to give 80.4 g of a required product (62%).

Synthesis of intermediate 2: 12-bromo-9H-dibenzo[a,c]carbazole

[Reaction Scheme 13]

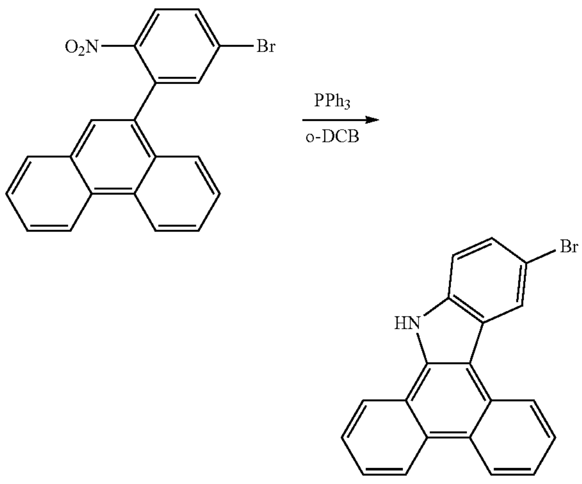

A 2 L round-bottom flask was charged with intermediate 1 (80.4 g, 213 mmol), and $PPh_3$ (139 g, 531 mmol) and o-dichlorobenzene (700 mL), and the materials were dissolved. The resultant mixture was subjected to a reaction at 190° C. for 24 hours.

After the reaction was completed, o-dichlorobenzene was removed, and the remaining filtrate was extracted with methylene chloride and water. The resultant product was purified by short phase column (methylene chloride: hexane=1:2) so as to give 44.3 g of a required product (60%).

Synthesis of 4D-Br-1: 12-bromo-9-phenyl-9H-dibenzo[a,c]carbazole

[Reaction Scheme 14]

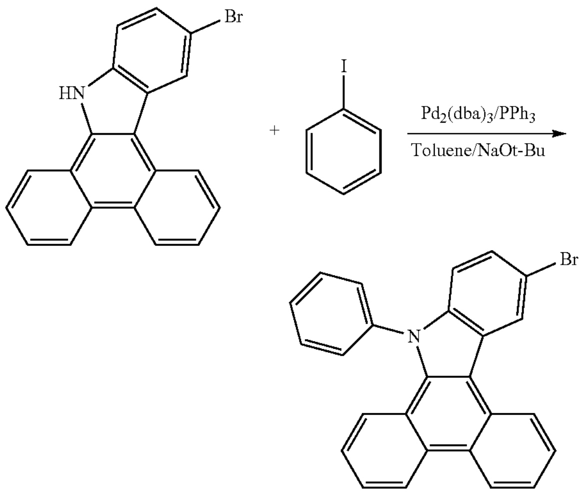

A 500 mL round-bottom flask was charged with 3a-3 compound (5 g, 14.442 mmol), Iodobenzene (4.42 g, 21.663 mmol), $Pd_2(dba)_3$ (0.4 g, 0.433 mmol), $PPh_3$ (0.38 g, 1.444 mmol), NaOt-Bu (4.164 g, 43.33 mmol), and toluene (150 mL), and the mixture was subjected to a reaction at 100° C. for 8 hours.

After the reaction was completed, the resultant product was extracted with ether and water. The organic layer was dried with $MgSO_4$, and purified by short phase column (methylene chloride). Then, the solvent of the obtained organic matter was removed. The resultant product was recrystallized by methylene chloride and hexane to give 3.72 g of a required product (61%).

Synthesis of starting material 4D-Br-2 (11-bromo-9-phenyl-9H-dibenzo[a,c]carbazole)

Synthesis of intermediate 1: 9-(4-bromo-2-nitrophenyl)phenanthrene

[Reaction Scheme 15]

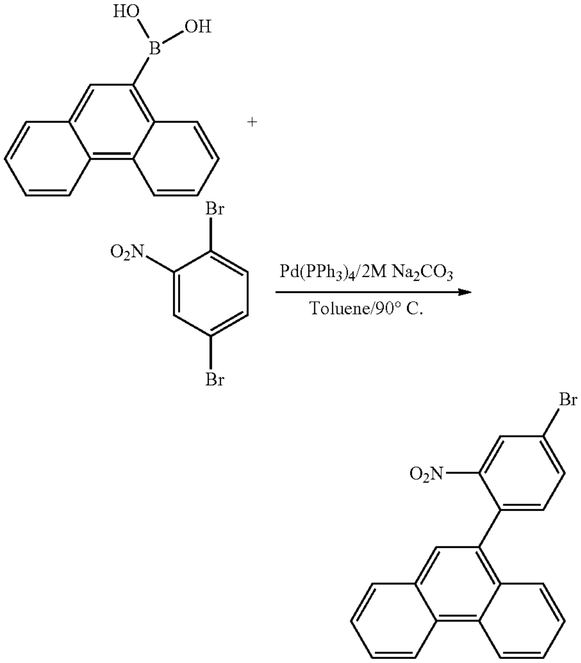

A 500 mL round-bottom flask was charged with toluene (250 mL), phenanthracene-9-boronic acid (18.2 g, 82 mmol), 2,5-dibromonitrobenzene (23.1 g, 82.3 mmol), $Pd(PPh_3)_4$ (2.8 g, 2.5 mmol), and 2M $Na_2CO_3$ aqueous solution (124 mL).

Then, at 90° C., the mixture was heated under reflux for 6 hours. After the reaction was completed, the resultant product was diluted with addition of distilled water at room temperature. Then, the resultant product was extracted with methylene chloride and water. The organic layer was dried with $MgSO_4$, and concentrated. Then, the produced compound was purified by silica gel column (methylene chloride:hexane=1:2) to give 26.36 g of a required product (85%).

Synthesis of intermediate 2: 11-bromo-9H-dibenzo[a,c]carbazole

[Reaction Scheme 16]

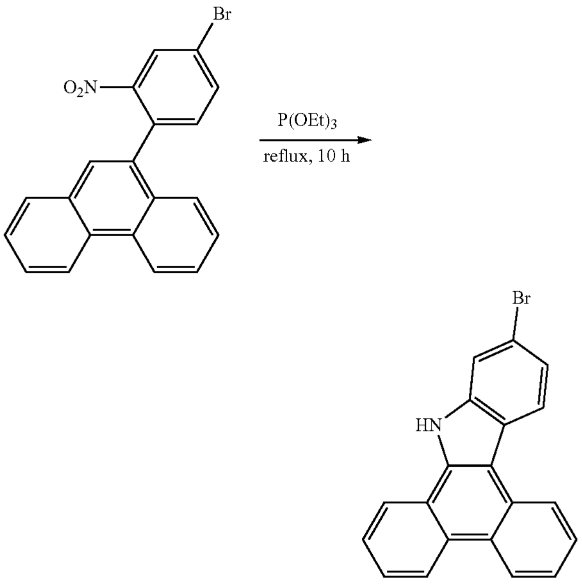

A 250 mL round-bottom flask was charged with 9-(4-bromo-2-nitrophenyl)phenanthrene (26.36 g, 69.69 mmol), and triethyl phosphate (84.84 mL, 487.86 mmol), and the mixture was heated under reflux at 160° C. to 165° C. for 14 hours. After the reaction was completed, the remaining triethyl phosphate was removed by vacuum distillation. The resultant product was diluted with a mixed solvent of MeOH:$H_2O$=1:1, and the produced solid was filtered. The obtained solid was washed with a mixed solvent of MeOH:$H_2O$=1:1 and petroleum ether. The solid was dissolved in methylene chloride, dried with $MgSO_4$, and concentrated, and purified by silica gel column (petroleum ether:methylene chloride=2:1). Then, 14.96 g (62%) of a required product was obtained.

Synthesis of 4D-Br-2: 11-bromo-9-phenyl-9H-dibenzo[a,c]carbazole

[Reaction Scheme 17]

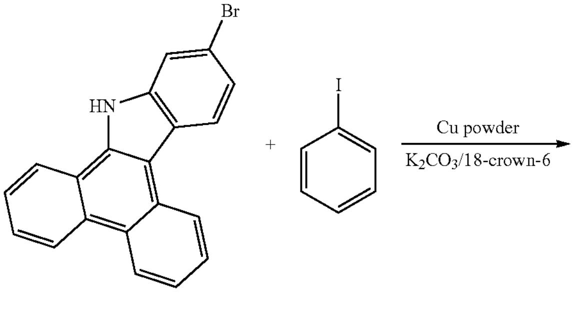

-continued

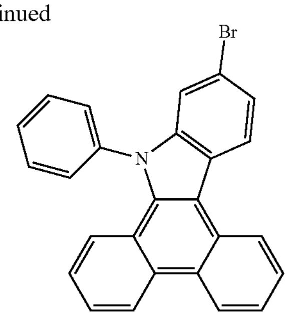

A 250 mL round-bottom flask was charged with 11-bromo-9H-dibenzo[a,c]carbazole (7 g, 20.22 mmol), iodobenzene (8.25 g, 40.44 mmol), $K_3CO_3$ (8.384 g, 60.66 mmol), Cu powder (1.29 g, 20.22 mmol), 18-crown-6 (2.672 g, 10.11 mmol), and o-dichlorobenzene (130 mL), and the mixture was heated under reflux for 24 hours. After the reaction was completed, the resultant product was extracted with methylene chloride and water. The obtained organic layer was washed with 5% hydrochloric acid, and brine. The organic layer was dried with $MgSO_4$, and concentrated. The resultant compound was purified by silica gel column (ethyl acetate:hexane=1:1.5) to give 6.06 g of a required product (71%).

1B-Br (2-bromodibenzo[b,d]thiophene), and 1C-Br (2-bromodibenzo[b,d]furan) were generally used reagents, which were bought.

Synthesis of Intermediate 2-1, and 2-2

Synthesis Examples of 1a~3a

[Reaction Scheme 18]

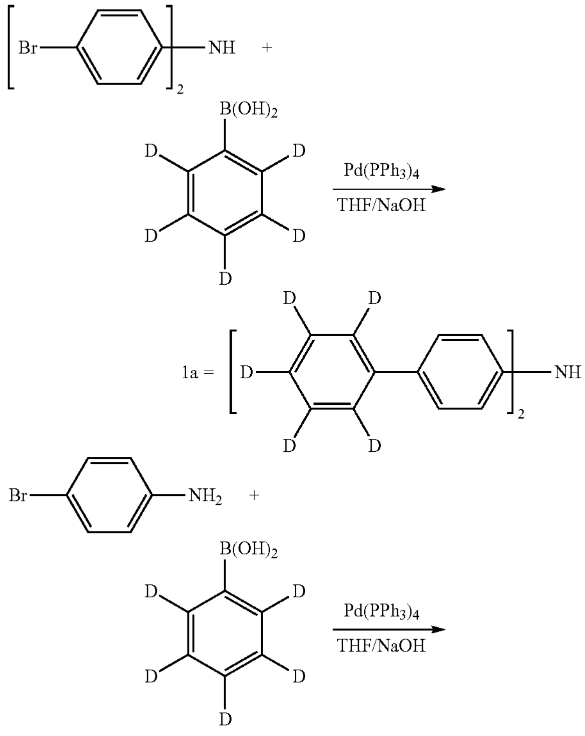

-continued

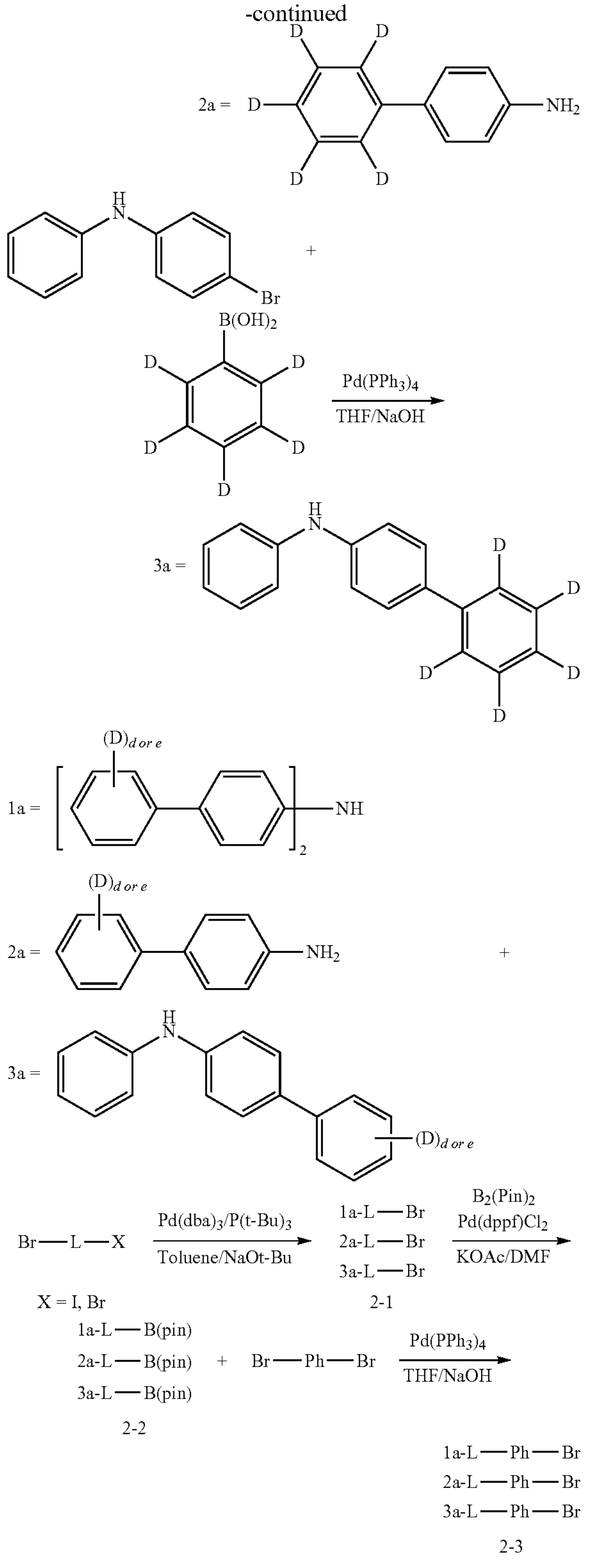

Synthesis Method of 2-1

A round-bottom flask was charged with a compound (1.2 equivalents) of 1, an amine compound (1 equivalent), $Pd_2(dba)_3$ (0.05 mmol), $PPh_3$ (0.1 equivalents), NaOt-Bu (3 equivalents), and toluene (10.5 mL/1 mmol). The mixture was subjected to a reaction at 100° C. After the reaction was completed, the resultant product was extracted with ether and water. The organic layer was dried with $MgSO_4$, and concentrated. Then, the produced organic matter was purified by silica gel column and recrystallized to give a required product.

Synthesis Method of 2-2

A round-bottom flask was charged with a compound (1 equivalent) of 2-1, Bis(pinacolato)diboron (1 equivalent), $Pd(dppf)Cl_2$ (0.03 equivalents). KOAc (3 equivalents), and DMF (6.3 mL/1 mmol). The mixture was heated under reflux at 130° C.

After the reaction was completed, the resultant product was extracted with ether and water. The obtained organic layer was dried with $MgSO_4$, and concentrated. Then, the concentrated product was purified by silica gel column and recrystallized to give a required product.

Synthesis Method of 2-3

A round-bottom flask was charged with a compound (1 equivalent) of 2-2, Br-L-Br (1.1 equivalents), $Pd(PPh_3)_4$ (0.03~0.05 equivalents), NaOH (3 equivalents), THF (3 mL/1 mmol), and water (1.5 mL/1 mmol).

Then, at 80° C. to 90° C., the mixture was heated under reflux. After the reaction was completed, the resultant product was diluted with addition of distilled water at room temperature. Then, the resultant product was extracted with methylene chloride and water. The organic layer was dried with $MgSO_4$, and concentrated. Then, the produced compound was purified by silica gel column and recrystallized to give a required product.

Kinds and Synthesis Examples of a Sub Intermediate

[Formula 5]

Sub-1

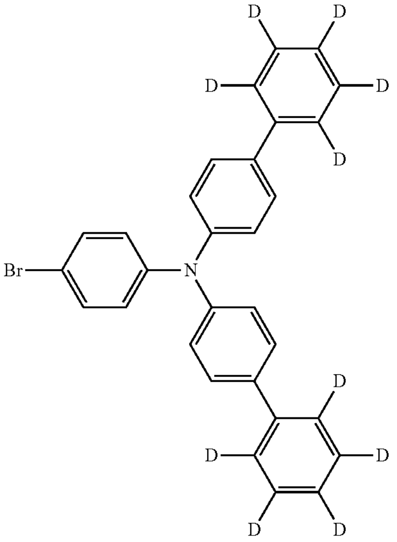

-continued

Sub-2

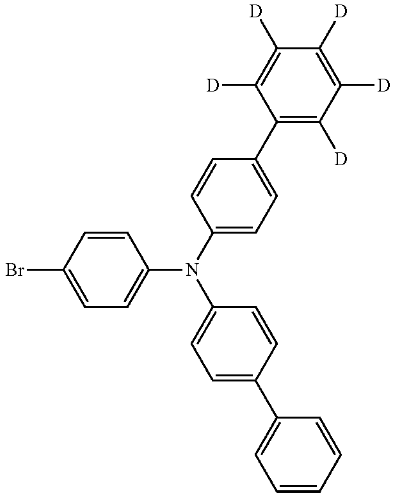

Sub-3

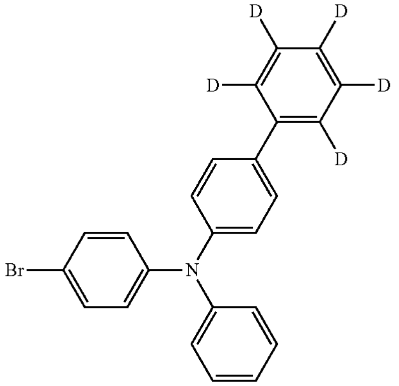

Sub-4

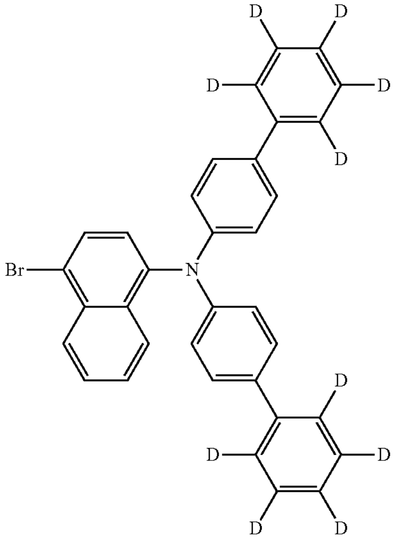

-continued
Sub-5
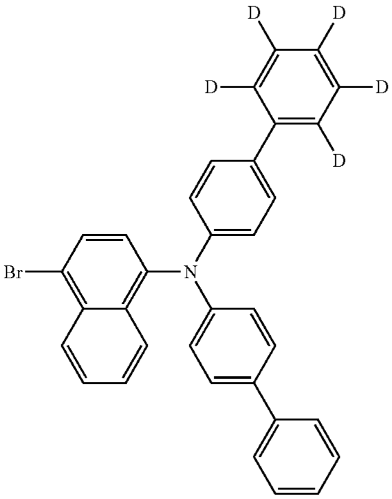
Sub-6
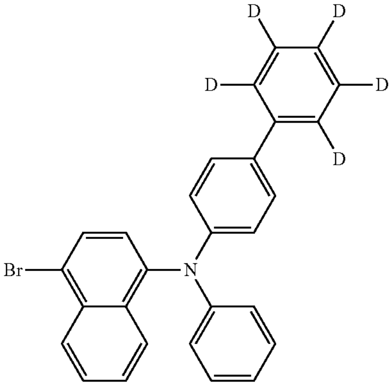
Sub-7
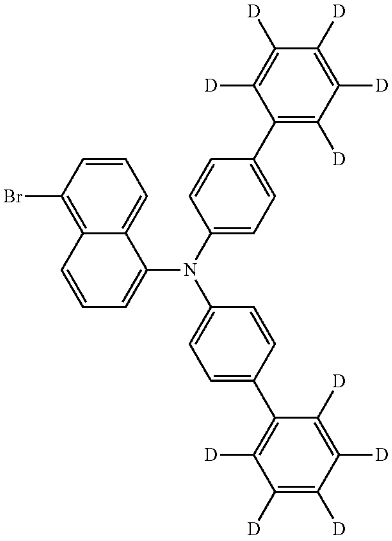
-continued
Sub-8
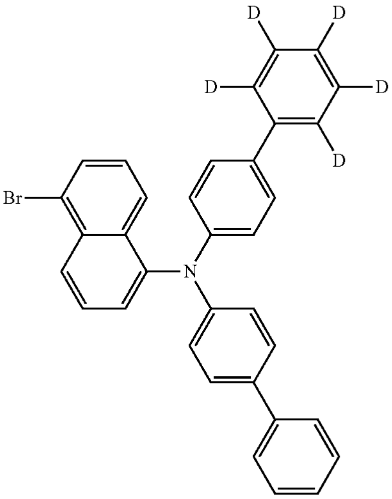
Sub-9
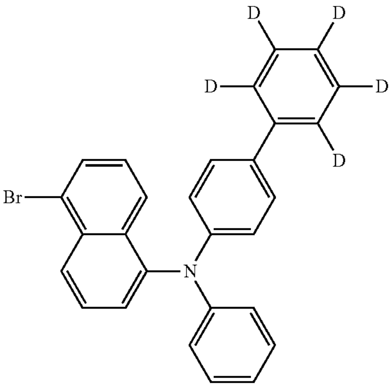
Sub-10
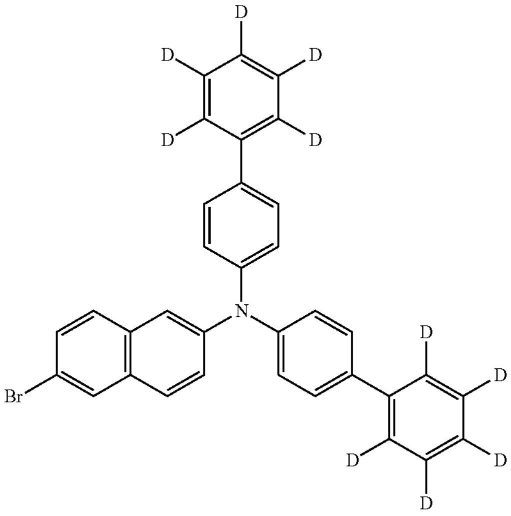

-continued
Sub-11
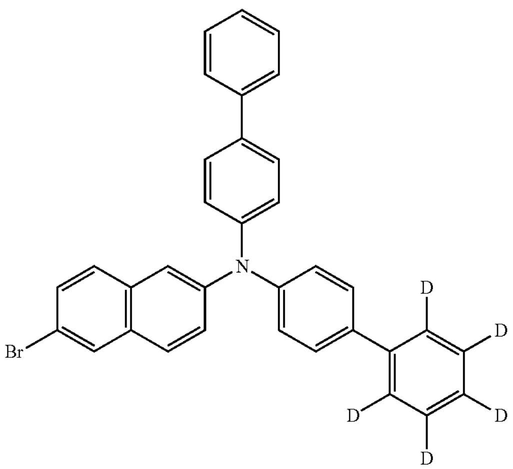
Sub-12
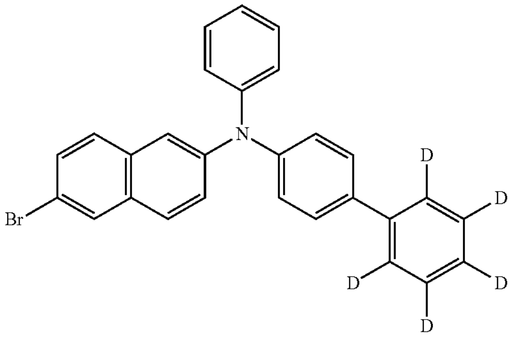
Sub-13
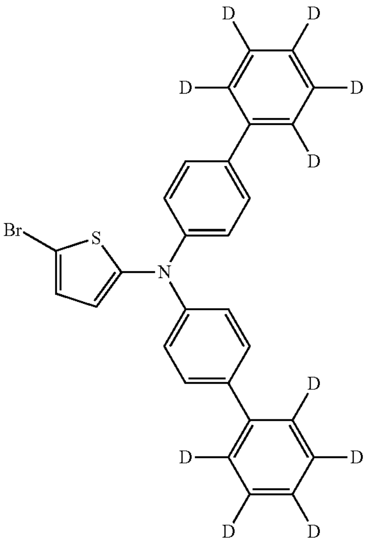
-continued
Sub-14
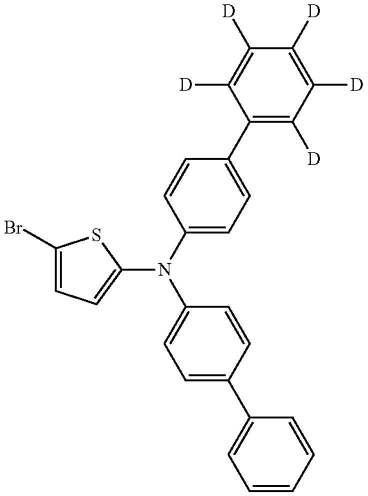
Sub-15
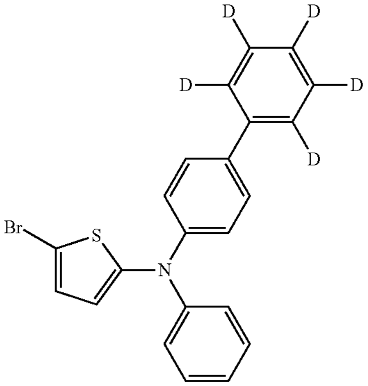
Sub-16
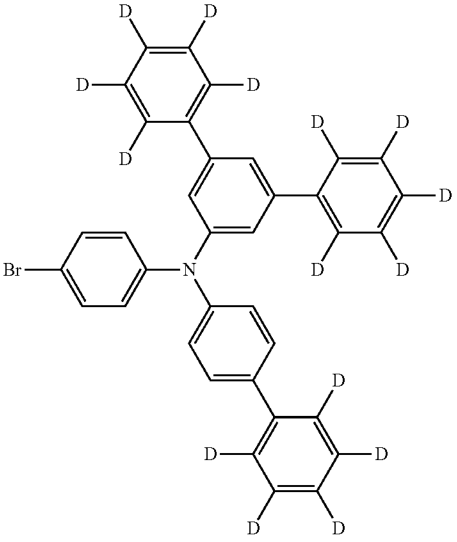

-continued

Sub-17

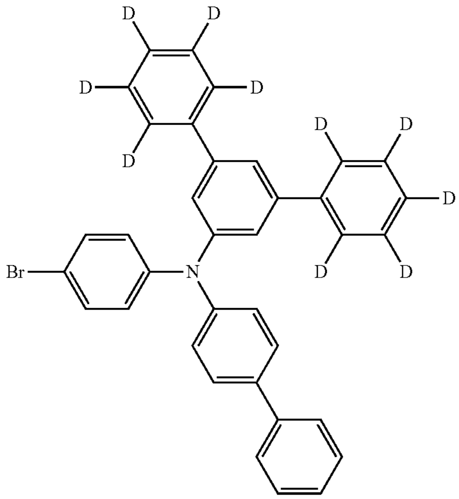

Sub-18

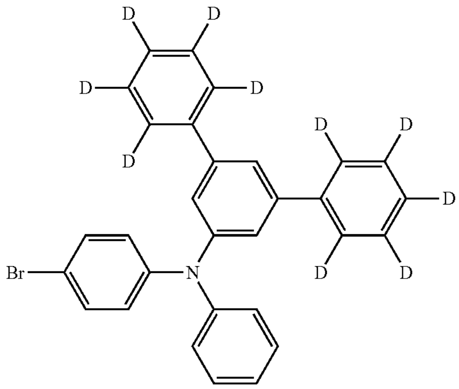

Sub-19

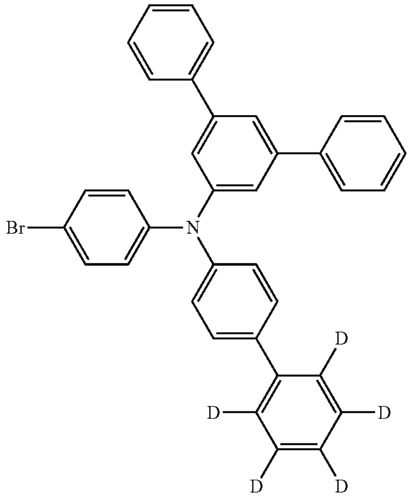

Synthesis of Sub 1

17 g of a product (yield: 70%) was obtained in the same manner as described in the synthesis method of 2-1, except that 1-Bromo-4-iodobenzene (16.97 g, 60 mmol), dibiphenyl-d10-4-amine (16.57 g, 50 mmol), $Pd_2(dba)_3$ (2.3 g, 2.5 mmol), $PPh_3$ (1.31 g, 5 mmol), NaOt-Bu (14.42 g, 150 mmol), and toluene (525 mL) were used.

Synthesis of Sub 2

16.4 g of a product (yield: 68%) was obtained in the same manner as described in the synthesis method of 2-1, except that 1-Bromo-4-iodobenzene (16.97 g, 60 mol), dibiphenyl-d5-4-amine (16.32 g, 50 mmol), $Pd_2(dba)_3$ (2.3 g, 2.5 mmol), $PPh_3$ (1.31 g, 5 mmol), NaOt-Bu (14.42 g, 150 mmol), and toluene (525 mL) were used.

Synthesis of Sub 3

14.6 g of a product (yield: 72%) was obtained in the same manner as described in the synthesis method of 2-1, except that 1-Bromo-4-iodobenzene (16.97 g, 60 mmol), N-phenylbiphenyl-d5-4-amine (12.52 g, 50 mmol), $Pd_2(dba)_3$ (2.3 g, 2.5 mmol), $PPh_3$ (1.31 g, 5 mmol), NaOt-Bu (14.42 g, 150 mmol), and toluene (525 mL) were used.

Synthesis of Sub 4

17.4 g of a product (yield: 65%) was obtained in the same manner as described in the synthesis method of 2-1, except that 1,4-dibromonaphthalene (17.2 g, 60 mmol), dibiphenyl-d10-4-amine (16.57 g, 50 mmol), $Pd_2(dba)_3$ (2.3 g, 2.5 mmol), $PPh_3$ (1.31 g, 5 mmol), NaOt-Bu (14.42 g, 150 mmol), and toluene (525 mL) were used.

Synthesis of Sub 5

16.5 g of a product (yield: 62%) was obtained in the same manner as described in the synthesis method of 2-1, except that 1,4-dibromonaphthalene (17.2 g, 60 mmol), dibiphenyl-d5-4-amine (16.32 g, 50 mmol), $Pd_2(dba)_3$ (2.3 g, 2.5 mmol), $PPh_3$ (1.31 g, 5 mmol), NaOt-Bu (14.42 g, 150 mmol), and toluene (525 mL) were used.

Synthesis of Sub 6

14.6 g of a product (yield: 64%) was obtained in the same manner as described in the synthesis method of 2-1, except that 1,4-dibromonaphthalene (17.2 g, 60 mmol), N-phenylbiphenyl-d5-4-amine (12.52 g, 50 mmol), $Pd_2(dba)_3$ (2.3 g, 2.5 mmol), $PPh_3$ (1.31 g, 5 mmol), NaOt-Bu (14.42 g, 150 mmol), and toluene (525 mL) were used.

Synthesis of Sub 7

18 g of a product (yield: 67%) was obtained in the same manner as described in the synthesis method of 2-1, except that 1,5-dibromonaphthalene (17.2 g, 60 mmol), dibiphenyl-d10-4-amine (16.57 g, 50 mmol), $Pd_2(dba)_3$ (2.3 g, 2.5 mmol), $PPh_3$ (1.31 g, 5 mmol), NaOt-Bu (14.42 g, 150 mmol), and toluene (525 mL) were used.

Synthesis of Sub 8

17 g of a product (yield: 64%) was obtained in the same manner as described in the synthesis method of 2-1, except that 1,5-dibromonaphthalene (17.2 g, 60 mmol), dibiphenyl-d5-4-amine (16.32 g, 50 mmol), $Pd_2(dba)_3$ (2.3 g, 2.5 mmol), $PPh_3$ (1.31 g, 5 mmol), NaOt-Bu (14.42 g, 150 mmol), and toluene (525 mL) were used.

Synthesis of Sub 9

14.8 g of a product (yield: 65%) was obtained in the same manner as described in the synthesis method of 2-1, except that 1,5-dibromonaphthalene (17.2 g, 60 mmol), N-phenylbiphenyl-d5-4-amine (12.52 g, 50 mmol), $Pd_2(dba)_3$ (2.3 g, 2.5 mmol), $PPh_3$ (1.31 g, 5 mmol), NaOt-Bu (14.42 g, 150 mmol), and toluene (525 mL) were used.

Synthesis of Sub 10

17.7 g of a product (yield: 66%) was obtained in the same manner as described in the synthesis method of 2-1, except that 2,6-dibromonaphthalene (17.2 g, 60 mmol), dibiphenyl-d10-4-amine (16.57 g, 50 mmol), $Pd_2(dba)_3$ (2.3 g, 2.5 mmol), $PPh_3$ (1.31 g, 5 mmol), NaOt-Bu (14.42 g, 150 mmol), and toluene (525 mL) were used.

Synthesis of Sub 11

17.6 g of a product (yield: 66%) was obtained in the same manner as described in the synthesis method of 2-1, except that 2,6-dibromonaphthalene (17.2 g, 60 mmol), dibiphenyl-d5-4-amine (16.32 g, 50 mmol), $Pd_2(dba)_3$ (2.3 g, 2.5 mmol), $PPh_3$ (1.31 g, 5 mmol), NaOt-Bu (14.42 g, 150 mmol), and toluene (525 mL) were used.

Synthesis of Sub 12

14.6 g of a product (yield: 64%) was obtained in the same manner as described in the synthesis method of 2-1, except that 2,6-dibromonaphthalene (17.2 g, 60 mmol), N-phenyl-biphenyl-d5-4-amine (12.52 g, 50 mmol), $Pd_2(dba)_3$ (2.3 g, 2.5 mmol), $PPh_3$ (1.31 g, 5 mmol), NaOt-Bu (14.42 g, 150 mmol), and toluene (525 mL) were used.

Synthesis of Sub 13

15.5 g of a product (yield: 63%) was obtained in the same manner as described in the synthesis method of 2-1, except that 2,5-dibromothiophene (14.5 g, 60 mmol), dibiphenyl-d10-4-amine (16.57 g, 50 mmol), $Pd_2(dba)_3$ (2.3 g, 2.5 mmol), $PPh_3$ (1.31 g, 5 mmol), NaOt-Bu (14.42 g, 150 mmol), and toluene (525 mL) were used.

Synthesis of Sub 14

15.6 g of a product (yield: 64%) was obtained in the same manner as described in the synthesis method of 2-1, except that 2,5-dibromothiophene (14.5 g, 60 mmol), dibiphenyl-d5-4-amine (16.32 g, 50 mmol), $Pd_2(dba)_3$ (2.3 g, 2.5 mmol), $PPh_3$ (1.31 g, 5 mmol), NaOt-Bu (14.42 g, 150 mmol), and toluene (525 mL) were used.

Synthesis of Sub 15

13.2 g of a product (yield: 64%) was obtained in the same manner as described in the synthesis method of 2-1, except that 2,5-dibromothiophene (14.5 g, 60 mmol), N-phenylbiphenyl-d5-4-amine (12.52 g, 50 mmol), $Pd_2(dba)_3$ (2.3 g, 2.5 mmol), $PPh_3$ (1.31 g, 5 mmol), NaOt-Bu (14.42 g, 150 mmol), and toluene (525 mL) were used.

Synthesis of Sub 16

20.7 g of a product (yield: 73%) was obtained in the same manner as described in the synthesis method of 2-1, except that 1-Bromo-4-iodobenzene (16.97 g, 60 mmol), amine derivative (20.63 g, 50 mmol), $Pd_2(dba)_3$ (2.3 g, 2.5 mmol), $PPh_3$ (1.31 g, 5 mmol), NaOt-Bu (14.42 g, 150 mmol), and toluene (525 mL) were used.

Synthesis of Sub 17

20 g of a product (yield: 71%) was obtained in the same manner as described in the synthesis method of 2-1, except that 1-Bromo-4-iodobenzene (16.97 g, 60 mmol), amine derivative (20.4 g, 50 mmol), $Pd_2(dba)_3$ (2.3 g, 2.5 mmol), $PPh_3$ (1.31 g, 5 mmol), NaOt-Bu (14.42 g, 150 mmol), and toluene (525 mL) were used.

Synthesis of Sub 18

17.5 g of a product (yield: 72%) was obtained in the same manner as described in the synthesis method of 2-1, except that 1-Bromo-4-iodobenzene (16.97 g, 60 mmol), amine derivative (16.6 g, 50 mmol), $Pd_2(dba)_3$ (2.3 g, 2.5 mmol), $PPh_3$ (1.31 g, 5 mmol), NaOt-Bu (14.42 g, 150 mmol), and toluene (525 mL) were used.

Synthesis of Sub 19

20.1 g of a product (yield: 72%) was obtained in the same manner as described in the synthesis method of 2-1, except that 1-Bromo-4-iodobenzene (16.97 g, 60 mmol), amine derivative (20.1 g, 50 mmol), $Pd_2(dba)_3$ (2.3 g, 2.5 mmol), $PPh_3$ (1.31 g, 5 mmol), NaOt-Bu (14.42 g, 150 mmol), and toluene (525 mL) were used.

Synthesis of a Final Compound

[Reaction Scheme 19]

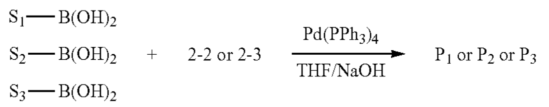

Synthesis Method

A round-bottom flask was charged with a compound (1 equivalent) of 3a-$B(OH)_2$, 4a-$B(OH)_2$ or 5a-$B(OH)_2$, a compound 2-1 or 2-3 (1.1 equivalents), $Pd(PPh_3)_4$ (0.03~0.05 equivalents), NaOH (3 equivalents), THF (3 mL/1 mmol), and water (1.5 mL/1 mmol).

Then, at 80° C. to 90° C., the mixture was heated under reflux. After the reaction was completed, the resultant product was diluted with addition of distilled water at room temperature. Then, the resultant product was extracted with methylene chloride and water. The organic layer was dried with $MgSO_4$, and concentrated. Then, the produced compound was purified by silica gel column and recrystallized to give a required product. The product was analyzed by FD-MS (mass spectrometer), and the results are noted in Table 1 below.

TABLE 1

| compound | FD-MS | compound | FD-MS |
|---|---|---|---|
| 2-1 | m/z = 599.34 ($C_{45}H_{25}D_{10}N$ = 599.83) | 2-2 | m/z = 594.31 ($C_{45}H_{30}D_5N$ = 594.80) |
| 2-3 | m/z = 518.28 ($C_{39}H_{26}D_5N$ = 518.70) | 2-4 | m/z = 675.37 ($C_{61}H_{29}D_{10}N$ = 675.92) |
| 2-5 | m/z = 670.34 ($C_{51}H_{34}D_5N$ = 670.89) | 2-6 | m/z = 594.31 ($C_{45}H_{30}D_5N$ = 594.80) |
| 2-7 | m/z = 918.48 ($C_{69}H_{42}D_{10}N_2$ = 919.23) | 2-8 | m/z = 725.39 ($C_{55}H_{31}D_{10}N$ = 725.98) |
| 2-9 | m/z = 720.36 ($C_{55}H_{36}D_5N$ = 720.95) | 2-10 | m/z = 644.32 ($C_{49}H_{32}D_5N$ = 644.86) |
| 2-11 | m/z = 725.39 ($C_{55}H_{31}D_{10}N$ = 725.98) | 2-12 | m/z = 720.36 ($C_{55}H_{36}D_5N$ = 720.95) |
| 2-13 | m/z = 644.32 ($C_{49}H_{32}D_5N$ = 644.86) | 2-14 | m/z = 725.39 ($C_{55}H_{31}D_{10}N$ = 725.98) |
| 2-15 | m/z = 720.36 ($C_{55}H_{35}D_5N$ = 720.95) | 2-16 | m/z = 644.32 ($C_{49}H_{32}D_5N$ = 644.86) |
| 2-17 | m/z = 681.33 ($C_{49}H_{27}D_{10}NS$ = 681.95) | 2-18 | m/z = 676.30 ($C_{49}H_{32}D_5NS$ = 676.92) |
| 2-19 | m/z = 600.26 ($C_{43}H_{28}D_5NS$ = 600.82) | 2-20 | m/z = 680.40 ($C_{51}H_{24}D_{15}N$ = 680.95) |
| 2-21 | m/z = 675.37 ($C_{51}H_{29}D_{10}N$ = 675.92) | 2-22 | m/z = 599.34 ($C_{45}H_{25}D_{10}N$ = 599.83) |
| 2-23 | m/z = 670.34 ($C_{51}H_{34}D_5N$ = 670.89) | 2-24 | m/z = 723.37 ($C_{55}H_{29}D_{10}N$ = 723.97) |
| 2-25 | m/z = 718.34 ($C_{55}H_{34}D_5N$ = 718.94) | 2-26 | m/z = 642.31 ($C_{49}H_{30}D_5N$ = 642.84) |

TABLE 1-continued

| | | | |
|---|---|---|---|
| 2-27 | m/z = 799.40 ($C_{61}H_{33}D_{10}N$ = 800.06) | 2-28 | m/z = 794.37 ($C_{61}H_{38}D_5N$ = 795.03) |
| 2-29 | m/z = 718.34 ($C_{55}H_{34}D_5N$ = 718.94) | 2-30 | m/z = 1042.51 ($C_{79}H_{46}D_{10}N_2$ = 1043.36) |
| 2-31 | m/z = 849.42 ($C_{65}H_{35}D_{10}N$ = 850.12) | 2-32 | m/z = 844.39 ($C_{65}H_{40}D_5N$ = 845.09) |
| 2-33 | m/z = 768.36 ($C_{59}H_{36}D_5N$ = 768.99) | 2-34 | m/z = 849.42 ($C_{65}H_{55}D_{10}N$ = 850.12) |
| 2-35 | m/z = 844.39 ($C_{65}H_{40}D_5N$ = 845.09) | 2-36 | m/z = 768.36 ($C_{59}H_{36}D_5N$ = 768.99) |
| 2-37 | m/z = 849.42 ($C_{65}H_{35}D_{10}N$ = 850.12) | 2-38 | m/z = 844.39 ($C_{65}H_{40}D_5N$ = 845.09) |
| 2-39 | m/z = 768.36 ($C_{59}H_{36}D_5N$ = 768.99) | 2-40 | m/z = 805.36 ($C_{59}H_{31}D_{10}NS$ = 806.09) |
| 2-41 | m/z = 800.33 ($C_{59}H_{36}D_5NS$ = 801.06) | 2-42 | m/z = 724.30 ($C_{53}H_{32}D_5NS$ = 724.96) |
| 2-43 | m/z = 804.43 ($C_{61}H_{28}D_{15}N$ = 805.09) | 2-44 | m/z = 799.40 ($C_{61}H_{33}D_{10}N$ = 800.06) |
| 2-45 | m/z = 723.37 ($C_{55}H_{29}D_{10}N$ = 723.97) | 2-46 | m/z = 794.37 ($C_{61}H_{38}D_5N$ = 795.03) |
| 2-47 | m/z = 721.36 ($C_{55}H_{27}D_{10}N$ = 721.95) | 2-48 | m/z = 716.32 ($C_{55}H_{32}D_5N$ = 716.92) |
| 2-49 | m/z = 640.29 ($C_{49}H_{28}D_5N$ = 640.82) | 2-50 | m/z = 797.39 ($C_{61}H_{31}D_{10}N$ = 798.05) |
| 2-51 | m/z = 792.36 ($C_{61}H_{36}D_5N$ = 793.02) | 2-52 | m/z = 716.32 ($C_{55}H_{32}D_5N$ = 716.92) |
| 2-53 | m/z = 1040.49 ($C_{79}H_{44}D_{10}N_2$ = 1041.35) | 2-54 | m/z = 847.40 ($C_{65}H_{33}D_{10}N$ = 848.11) |
| 2-55 | m/z = 842.37 ($C_{65}H_{38}D_5N_2$ = 843.07) | 2-56 | m/z = 766.34 ($C_{59}H_{34}D_5N$ = 766.98) |
| 2-57 | m/z = 847.40 ($C_{65}H_{33}D_{10}N$ = 848.11) | 2-58 | m/z = 842.37 ($C_{65}H_{38}D_5N$ = 843.07) |
| 2-59 | m/z = 766.34 ($C_{59}H_{34}D_5N$ = 766.98) | 2-60 | m/z = 847.40 ($C_{65}H_{33}D_{10}N$ = 848.11) |
| 2-61 | m/z = 842.37 ($C_{65}H_{38}D_5N$ = 843.07) | 2-62 | m/z = 766.34 ($C_{59}H_{34}D_5N$ = 766.98) |
| 2-63 | m/z = 803.34 ($C_{59}H_{29}D_{10}NS$ = 804.07) | 2-64 | m/z = 798.31 ($C_{58}H_{34}D_5NS$ = 799.04) |
| 2-65 | m/z = 722.28 ($C_{53}H_{30}D_5NS$ = 722.95) | 2-66 | m/z = 802.42 ($C_{61}H_{26}D_{15}N$ = 803.08) |
| 2-67 | m/z = 797.39 ($C_{61}H_{31}D_{10}N$ = 798.05) | 2-68 | m/z = 721.36 ($C_{55}H_{27}D_{10}N$ = 721.95) |
| 2-69 | m/z = 792.36 ($C_{61}H_{36}D_5N$ = 793.02) | 2-70 | m/z = 589.26 ($C_{42}H_{19}D_{10}NS$ = 589.81) |
| 2-71 | m/z = 584.23 ($C_{42}H_{24}D_5NS$ = 584.78) | 2-72 | m/z = 508.20 ($C_{36}H_{20}D_5NS$ = 508.69) |
| 2-73 | m/z = 665.30 ($C_{48}H_{23}D_{10}NS$ = 665.91) | 2-74 | m/z = 660.26 ($C_{48}H_{28}D_5NS$ = 660.88) |
| 2-75 | m/z = 584.23 ($C_{42}H_{24}D_5NS$ = 584.78) | 2-76 | m/z = 908.40 ($C_{66}H_{35}D_{10}N_2S$ = 909.21) |
| 2-77 | m/z = 715.31 ($C_{52}H_{25}D_{10}NS$ = 715.97) | 2-78 | m/z = 710.28 ($C_{52}H_{30}D_5NS$ = 710.94) |
| 2-79 | m/z = 634.25 ($C_{46}H_{26}D_5NS$ = 634.84) | 2-80 | m/z = 715.31 ($C_{52}H_{25}D_{10}NS$ = 715.97) |
| 2-81 | m/z = 710.28 ($C_{52}H_{30}D_5NS$ = 710.94) | 2-82 | m/z = 634.25 ($C_{46}H_{26}D_5NS$ = 634.84) |
| 2-83 | m/z = 715.31 ($C_{52}H_{25}D_{10}NS$ = 715.97) | 2-84 | m/z = 710.28 ($C_{52}H_{30}D_5NS$ = 710.94) |
| 2-85 | m/z = 634.25 ($C_{46}H_{26}D_5NS$ = 634.84) | 2-86 | m/z = 671.25 ($C_{46}H_{21}D_{10}NS_2$ = 671.94) |
| 2-87 | m/z = 666.22 ($C_{46}H_{26}D_5NS_2$ = 666.91) | 2-88 | m/z = 590.19 ($C_{40}H_{22}D_5NS_2$ = 590.81) |
| 2-89 | m/z = 670.33 ($C_{48}H_{18}D_{15}NS$ = 670.94) | 2-90 | m/z = 665.30 ($C_{48}H_{23}D_{10}NS$ = 665.91) |
| 2-91 | m/z = 589.26 ($C_{42}H_{19}D_{10}NS$ = 589.81) | 2-92 | m/z = 660.26 ($C_{48}H_{28}D_5NS$ = 660.88) |
| 2-93 | m/z = 573.29 ($C_{42}H_{19}D_{10}NO$ = 573.75) | 2-94 | m/z = 568.26 ($C_{42}H_{24}D_5NO$ = 568.72) |
| 2-95 | m/z = 492.22 ($C_{36}H_{20}D_5NO$ = 492.62) | 2-96 | m/z = 649.32 ($C_{48}H_{23}D_{10}NO$ = 649.84) |
| 2-97 | m/z = 644.29 ($C_{48}H_{28}D_5NO$ = 644.81) | 2-98 | m/z = 568.26 ($C_{42}H_{24}D_5NO$ = 568.72) |
| 2-99 | m/z = 892.42 ($C_{66}H_{36}D_{10}N_2O$ = 893.15) | 2-100 | m/z = 699.33 ($C_{52}H_{25}D_{10}NO$ = 699.90) |
| 2-101 | m/z = 694.30 ($C_{52}H_{30}D_5NO$ = 694.87) | 2-102 | m/z = 618.27 ($C_{46}H_{26}D_5NO$ = 618.78) |
| 2-103 | m/z = 699.33 $C_{52}H_{25}D_{10}NO$ = 699.90) | 2-104 | m/z = 694.30 ($C_{52}H_{30}D_5NO$ = 694.87) |
| 2-105 | m/z = 618.27 ($C_{46}H_{26}D_5NO$ = 618.78) | 2-106 | m/z = 699.33 ($C_{52}H_{25}D_{10}NO$ = 699.90) |

TABLE 1-continued

| | | | |
|---|---|---|---|
| 2-107 | m/z = 694.30 ($C_{52}H_{30}D_5NO$ = 694.87) | 2-108 | m/z = 618.27 ($C_{46}H_{26}D_5NO$ = 618.78) |
| 2-109 | m/z = 655.28 ($C_{46}H_{21}D_{10}NOS$ = 655.87) | 2-110 | m/z = 650.24 ($C_{46}H_{26}D_5NOS$ = 650.84) |
| 2-111 | m/z = 574.21 ($C_{40}H_{22}D_5NOS$ = 574.74) | 2-112 | m/z = 654.35 ($C_{48}H_{18}D_{15}NO$ = 654.87) |
| 2-113 | m/z = 649.32 ($C_{48}H_{23}D_{10}NO$ = 649.84) | 2-114 | m/z = 573.29 ($C_{42}H_{19}D_{10}NO$ = 573.75) |
| 2-115 | m/z = 644.29 ($C_{48}H_{28}D_5NO$ = 644.81) | 2-116 | m/z = 648.33 ($C_{48}H_{24}D_{10}N_2$ = 648.86) |
| 2-117 | m/z = 643.30 ($C_{48}H_{29}D_5N_2$ = 643.83) | 2-118 | m/z = 567.27 ($C_{42}H_{29}D_5N_2$ = 567.73) |
| 2-119 | m/z = 800.40 ($C_{60}H_{32}D_{10}N_2$ = 801.05) | 2-120 | m/z = 795.37 ($C_{60}H_{37}D_5N_2$ = 796.02) |
| 2-121 | m/z = 719.33 ($C_{54}H_{33}D_5N_2$ = 719.92) | 2-122 | m/z = 967.47 ($C_{72}H_{41}D_{10}N_3$ = 968.26) |
| 2-123 | m/z = 850.41 ($C_{64}H_{34}D_{10}N_2$ = 851.11) | 2-124 | m/z = 819.37 ($C_{62}H_{37}D_5N_2$ = 820.04) |
| 2-125 | m/z = 743.33 ($C_{56}H_{35}D_5N_2$ = 743.95) | 2-126 | m/z = 824.40 ($C_{62}H_{32}D_{10}N_2$ = 825.07) |
| 2-127 | m/z = 819.37 ($C_{62}H_{37}D_5N_2$ = 820.04) | 2-128 | m/z = 693.32 ($C_{62}H_{31}D_5N_2$ = 693.89) |
| 2-129 | m/z = 774.38 ($C_{58}H_{30}D_{10}N_2$ = 775.01) | 2-130 | m/z = 769.35 ($C_{58}H_{35}D_5N_2$ = 769.98) |
| 2-131 | m/z = 769.35 ($C_{58}H_{35}D_5N_2$ = 769.98) | 2-132 | m/z = 730.32 ($C_{52}H_{26}D_{10}N_2S$ = 730.98) |
| 2-133 | m/z = 725.29 ($C_{52}H_{31}D_5N_2S$ = 725.95) | 2-134 | m/z = 649.26 ($C_{46}H_{27}D_5N_2$ = 649.86) |
| 2-135 | m/z = 729.40 ($C_{54}H_{23}D_{15}N_2$ = 729.99) | 2-136 | m/z = 850.41 ($C_{64}H_{34}D_{10}N_2$ = 851.11) |
| 2-137 | m/z = 774.38 ($C_{58}H_{30}D_{10}N_2$ = 775.01) | 2-138 | m/z = 845.38 ($C_{64}H_{39}D_5N_2$ = 846.08) |
| 2-139 | m/z = 748.37 ($C_{56}H_{28}D_{10}N_2$ = 748.98) | 2-140 | m/z = 743.33 ($C_{56}H_{33}D_5N_2$ = 743.95) |

| compound | FD-MS | 화합물 | FD-MS |
|---|---|---|---|
| 2-141 | m/z = 667.30 ($C_{50}H_{29}D_5N_2$ = 667.85) | 2-142 | m/z = 900.43 ($C_{68}H_{36}D_{10}N_2$ = 901.17) |
| 2-143 | m/z = 895.40 ($C_{68}H_{41}D_5N_2$ = 896.14) | 2-144 | m/z = 819.37 ($C_{62}H_{37}D_5N_2$ = 820.04) |
| 2-145 | m/z = 1017.49 ($C_{76}H_{43}D_{10}N_3$ = 1018.32) | 2-146 | m/z = 900.43 ($C_{68}H_{36}D_{10}N_2$ = 901.17) |
| 2-147 | m/z = 869.38 ($C_{66}H_{39}D_5N_2$ = 870.10) | 2-148 | m/z = 793.35 ($C_{60}H_{35}D_5N_2$ = 794.00) |
| 2-149 | m/z = 874.41 ($C_{66}H_{34}D_{10}N_2$ = 875.13) | 2-150 | m/z = 869.38 ($C_{66}H_{39}D_5N_2$ = 870.10) |
| 2-151 | m/z = 743.33 ($C_{56}H_{33}D_5N_2$ = 743.95) | 2-152 | m/z = 824.40 ($C_{62}H_{32}D_{10}N_2$ = 825.07) |
| 2-153 | m/z = 819.37 ($C_{62}H_{37}D_5N_2$ = 820.04) | 2-154 | m/z = 819.37 ($C_{62}H_{37}D_5N_2$ = 820.04) |
| 2-155 | m/z = 780.34 ($C_{56}H_{28}D_{10}N_2S$ = 781.04) | 2-156 | m/z = 775.31 ($C_{56}H_{33}D_5N_2S$ = 776.01) |
| 2-157 | m/z = 699.28 ($C_{50}H_{23}D_5N_2S$ = 699.91) | 2-158 | m/z = 779.41 ($C_{58}H_{25}D_{15}N_2$ = 780.04) |
| 2-159 | m/z = 900.43 ($C_{68}H_{36}D_{10}N_2$ = 901.17) | 2-160 | m/z = 824.40 ($C_{62}H_{32}D_{10}N_2$ = 825.07) |
| 2-161 | m/z = 895.40 ($C_{68}H_{41}D_5N_2$ = 896.14) | 2-162 | m/z = 648.33 ($C_{48}H_{24}D_{10}N_2$ = 648.86) |
| 2-163 | m/z = 643.30 ($C_{48}H_{29}D_5N_2$ = 643.83) | 2-164 | m/z = 567.27 ($C_{42}H_{25}D_5N_2$ = 567.73) |
| 2-165 | m/z = 800.40 ($C_{60}H_{32}D_{10}N_2$ = 801.05) | 2-166 | m/z = 795.37 ($C_{60}H_{37}D_5N_2$ = 796.02) |
| 2-167 | m/z = 719.33 ($C_{54}H_{33}D_5N_2$ = 719.92) | 2-168 | m/z = 967.47 ($C_{72}H_{41}D_{10}N_3$ = 968.26) |
| 2-169 | m/z = 850.41 ($C_{64}H_{34}D_{10}N_2$ = 851.11) | 2-170 | m/z = 819.37 ($C_{62}H_{37}D_5N_2$ = 820.04) |
| 2-171 | m/z = 743.33 ($C_{56}H_{33}D_5N_2$ = 743.95) | 2-172 | m/z = 824.40 ($C_{62}H_{32}D_{10}N_2$ = 825.07) |
| 2-173 | m/z = 819.37 ($C_{62}H_{37}D_5N_2$ = 820.04) | 2-174 | m/z = 693.32 ($C_{52}H_{31}D_5N_2$ = 693.89) |
| 2-175 | m/z = 774.38 ($C_{58}H_{30}D_{10}N_2$ = 775.01) | 2-176 | m/z = 769.35 ($C_{58}H_{35}D_5N_2$ = 769.98) |
| 2-177 | m/z = 769.35 ($C_{58}H_{35}D_5N_2$ = 769.98) | 2-178 | m/z = 730.32 ($C_{52}H_{26}D_{10}N_2S$ = 730.98) |
| 2-179 | m/z = 725.29 ($C_{52}H_{31}D_5N_2S$ = 725.95) | 2-180 | m/z = 649.26 ($C_{46}H_{27}D_5N_2S$ = 649.86) |
| 2-181 | m/z = 729.40 ($C_{54}H_{23}D_{15}N_2$ = 729.99) | 2-182 | m/z = 850.41 ($C_{64}H_{34}D_{10}N_2$ = 851.11) |

TABLE 1-continued

| | | | |
|---|---|---|---|
| 2-183 | m/z = 774.38 ($C_{58}H_{30}D_{10}N_2$ = 775.01) | 2-184 | m/z = 845.38 ($C_{64}H_{39}D_5N_2$ = 846.08) |
| 2-185 | m/z = 748.37 ($C_{56}H_{28}D_{10}N_2$ = 748.98) | 2-186 | m/z = 743.33 ($C_{56}H_{33}D_5N_2$ = 743.95) |
| 2-187 | m/z = 667.30 ($C_{50}H_{29}D_5N_2$ = 667.85) | 2-188 | m/z = 900.43 ($C_{68}H_{36}D_{10}N_2$ = 901.17) |
| 2-189 | m/z = 895.40 ($C_{68}H_{41}D_5N_2$ = 896.14) | 2-190 | m/z = 819.37 ($C_{62}H_{37}D_5N_2$ = 820.04) |
| 2-191 | m/z = 1017.49 ($C_{76}H_{43}D_{10}N_3$ = 1018.32) | 2-192 | m/z = 900.43 ($C_{68}H_{36}D_{10}N_2$ = 901.17) |
| 2-193 | m/z = 869.38 ($C_{66}H_{39}D_5N_2$ = 870.10) | 2-194 | m/z = 793.35 ($C_{60}H_{35}D_5N_2$ = 794.00) |
| 2-195 | m/z = 874.41 ($C_{66}H_{34}D_{10}N_2$ = 875.13) | 2-196 | m/z = 869.38 ($C_{66}H_{39}D_5N_2$ = 870.10) |
| 2-197 | m/z = 743.33 ($C_{56}H_{33}D_5N_2$ = 743.95) | 2-198 | m/z = 824.40 ($C_{62}H_{32}D_{10}N_2$ = 825.07) |
| 2-199 | m/z = 819.37 ($C_{62}H_{37}D_5N_2$ = 820.04) | 2-200 | m/z = 819.37 ($C_{62}H_{37}D_5N_2$ = 820.04) |
| 2-201 | m/z = 780.34 ($C_{56}H_{28}D_{10}N_2S$ = 781.04) | 2-202 | m/z = 775.31 ($C_{56}H_{33}D_5N_2S$ = 776.01) |
| 2-203 | m/z = 699.28 ($C_{50}H_{29}D_5N_2S$ = 699.91) | 2-204 | m/z = 779.41 ($C_{68}H_{25}D_{15}N_2$ = 780.04) |
| 2-205 | m/z = 900.43 ($C_{68}H_{36}D_{10}N_2$ = 901.17) | 2-206 | m/z = 824.40 ($C_{62}H_{32}D_{10}N_2$ = 825.07) |
| 2-207 | m/z = 895.40 ($C_{68}H_{41}D_5N_2$ = 896.14) | | |
| 3-1 | m/z = 523.31 ($C_{39}H_{21}D_{10}N$ = 523.73) | 3-2 | m/z = 518.28 ($C_{39}H_{26}D_5N$ = 518.70) |
| 3-3 | m/z = 442.25 ($C_{33}H_{22}D_5N$ = 442.60) | 3-4 | m/z = 523.31 ($C_{39}H_{21}D_{10}N$ = 523.73) |

| compound | FD-MS | compound | FD-MS |
|---|---|---|---|
| 3-5 | m/z = 649.36 ($C_{49}H_{27}D_{10}N$ = 649.89) | 3-6 | m/z = 644.32 ($C_{49}H_{32}D_5N$ = 644.86) |
| 3-7 | m/z = 568.29 ($C_{43}H_{28}D_5N$ = 568.76) | 3-8 | m/z = 649.36 ($C_{49}H_{27}D_{10}N$ = 649.89) |
| 3-9 | m/z = 644.32 ($C_{49}H_{32}D_5N$ = 644.86) | 3-10 | m/z = 568.29 ($C_{43}H_{28}D_5N$ = 568.76) |
| 3-11 | m/z = 649.36 ($C_{49}H_{27}D_{10}N$ = 649.89) | 3-12 | m/z = 644.32 ($C_{49}H_{32}D_5N$ = 644.86) |
| 3-13 | m/z = 568.29 ($C_{43}H_{28}D_5N$ = 568.76) | 3-14 | m/z = 605.30 ($C_{43}H_{23}D_{10}NS$ = 605.86) |
| 3-15 | m/z = 600.26 ($C_{43}H_{28}D_5NS$ = 600.82) | 3-16 | m/z = 524.23 ($C_{37}H_{24}D_5NS$ = 524.73) |
| 3-17 | m/z = 604.37 ($C_{45}H_{20}D_{15}N$ = 604.86) | 3-18 | m/z = 599.34 ($C_{45}H_{25}D_{10}N$ = 599.83) |
| 3-19 | m/z = 523.31 ($C_{39}H_{21}D_{10}N$ = 523.73) | 3-20 | m/z = 594.31 ($C_{46}H_{30}D_5N$ = 594.80) |
| 3-21 | m/z = 647.34 ($C_{49}H_{25}D_{10}N$ = 647.87) | 3-22 | m/z = 642.31 ($C_{49}H_{30}D_5N$ = 642.84) |
| 3-23 | m/z = 566.28 ($C_{43}H_{26}D_5N$ = 566.74) | 3-24 | m/z = 647.34 ($C_{49}H_{25}D_{10}N$ = 647.87) |
| 3-25 | m/z = 773.39 ($C_{59}H_{31}D_{10}N$ = 774.03) | 3-26 | m/z = 768.36 ($C_{59}H_{36}D_5N$ = 768.99) |
| 3-27 | m/z = 692.32 ($C_{53}H_{32}D_5N$ = 692.90) | 3-28 | m/z = 773.39 ($C_{59}H_{31}D_{10}N$ = 774.03) |
| 3-29 | m/z = 768.36 ($C_{59}H_{36}D_5N$ = 768.99) | 3-30 | m/z = 692.32 ($C_{53}H_{32}D_5N$ = 692.90) |
| 3-31 | m/z = 773.39 ($C_{59}H_{31}D_{10}N$ = 774.03) | 3-32 | m/z = 768.36 ($C_{59}H_{36}D_5N$ = 768.99) |
| 3-33 | m/z = 692.32 ($C_{53}H_{32}D_5N$ = 692.90) | 3-34 | m/z = 729.33 ($C_{53}H_{27}D_{10}NS$ = 729.99) |
| 3-35 | m/z = 648.26 ($C_{47}H_{28}D_5NS$ = 648.87) | 3-36 | m/z = 648.26 ($C_{47}H_{28}D_5NS$ = 648.87) |
| 3-37 | m/z = 728.40 ($C_{56}H_{24}D_{15}N$ = 729.00) | 3-38 | m/z = 723.37 ($C_{56}H_{29}D_{10}N$ = 723.97) |
| 3-39 | m/z = 647.34 ($C_{49}H_{25}D_{10}N$ = 647.87) | 3-40 | m/z = 718.34 ($C_{55}H_{34}D_5N$ = 718.94) |
| 3-41 | m/z = 645.32 ($C_{49}H_{23}D_{10}N$ = 645.85) | 3-42 | m/z = 640.29 ($C_{49}H_{28}D_5N$ = 640.82) |
| 3-43 | m/z = 564.26 ($C_{45}H_{24}D_5N$ = 564.73) | 3-44 | m/z = 645.32 ($C_{49}H_{23}D_{10}N$ = 645.85) |
| 3-45 | m/z = 771.37 ($C_{59}H_{29}D_{10}N$ = 772.01) | 3-46 | m/z = 766.34 ($C_{59}H_{34}D_5N$ = 766.98) |
| 3-47 | m/z = 690.31 ($C_{53}H_{30}D_5N$ = 690.88) | 3-48 | m/z = 771.37 ($C_{59}H_{29}D_{10}N$ = 772.01) |
| 3-49 | m/z = 766.34 ($C_{59}H_{34}D_5N$ = 766.98) | 3-50 | m/z = 690.31 ($C_{53}H_{30}D_5N$ = 690.88) |

TABLE 1-continued

| | | | |
|---|---|---|---|
| 3-51 | m/z = 771.37 ($C_{59}H_{29}D_{10}N$ = 772.01) | 3-52 | m/z = 766.34 ($C_{59}H_{34}D_5N$ = 766.98) |
| 3 53 | m/z = 690.31 ($C_{53}H_{30}D_5N$ = 690.88) | 3-54 | m/z = 727.31 ($C_{53}H_{25}D_{10}NS$ = 727.98) |
| 3-55 | m/z = 722.28 ($C_{53}H_{30}D_5NS$ = 722.95) | 3-56 | m/z = 646.25 ($C_{47}H_{25}D_5NS$ = 646.85) |
| 3-57 | m/z = 726.39 ($C_{55}H_{22}D_{15}N$ = 726.98) | 3-58 | m/z = 721.36 ($C_{55}H_{27}D_{10}N$ = 721.95) |
| 3-59 | m/z = 645.32 ($C_{49}H_{23}D_{10}N$ = 645.85) | 3-60 | m/z = 716.32 ($C_{55}H_{32}D_5N$ = 716.92) |
| 3-61 | m/z = 513.23 ($C_{36}H_{15}D_{10}NS$ = 513.72) | 3-62 | m/z = 508.20 ($C_{36}H_{20}D_5NS$ = 508.69) |
| 3-63 | m/z = 432.17 ($C_{30}H_{16}D_5NS$ = 432.59) | 3-64 | m/z = 639.28 ($C_{46}H_{21}D_{10}NS$ = 639.87) |
| 3-65 | m/z = 634.25 ($C_{46}H_{26}D_5NS$ = 634.84) | 3-66 | m/z = 558.22 ($C_{40}H_{22}D_5NS$ = 558.74) |
| 3-67 | m/z = 639.28 ($C_{46}H_{21}D_{10}NS$ = 639.87) | 3-68 | m/z = 634.25 ($C_{46}H_{26}D_5NS$ = 634.84) |
| 3-69 | m/z = 558.22 ($C_{40}H_{22}D_5NS$ = 558.74) | 3-70 | m/z = 639.28 ($C_{46}H_{21}D_{10}NS$ = 639.87) |
| 3-71 | m/z = 634.25 ($C_{46}H_{26}D_5NS$ = 634.84) | 3-72 | m/z = 558.22 ($C_{40}H_{22}D_5NS$ = 558.74) |
| 3-73 | m/z = 595.22 ($C_{40}H_{17}D_{10}NS_2$ = 595.84) | 3-74 | m/z = 590.19 ($C_{40}H_{22}D_5NS_2$ = 590.81) |
| 3-75 | m/z = 514.16 ($C_{34}H_{18}D_5NS_2$ = 514.71) | 3-76 | m/z = 594.30 ($C_{42}H_{14}D_{15}NS$ = 594.84) |
| 3-77 | m/z = 497.26 ($C_{36}H_{15}D_{10}NO$ = 497.65) | 3-78 | m/z = 492.22 ($C_{36}H_{20}D_5NO$ = 492.62) |
| 3-79 | m/z = 416.19 ($C_{30}H_{16}D_5NO$ = 416.52) | 3-80 | m/z = 623.30 ($C_{46}H_{21}D_{10}NO$ = 623.81) |
| 3-81 | m/z = 618.27 ($C_{46}H_{26}D_5NO$ = 618.78) | 3-82 | m/z = 542.24 ($C_{40}H_{22}D_5NO$ = 542.68) |
| 3-83 | m/z = 623.30 ($C_{46}H_{21}D_{10}NO$ = 623.81) | 3-84 | m/z = 618.27 ($C_{46}H_{26}D_5NO$ = 618.78) |
| 3-85 | m/z = 542.24 ($C_{40}H_{22}D_5NO$ = 542.68) | 3-86 | m/z = 623.30 ($C_{46}H_{21}D_{10}NO$ = 623.81) |
| 3-87 | m/z = 618.27 ($C_{46}H_{26}D_5NO$ = 618.78) | 3-88 | m/z = 542.24 ($C_{40}H_{22}D_5NO$ = 542.68) |
| 3-89 | m/z = 579.24 ($C_{40}H_{17}D_{10}NOS$ = 579.78) | 3-90 | m/z = 574.21 ($C_{40}H_{22}D_5NOS$ = 574.74) |
| 3-91 | m/z = 498.18 ($C_{34}H_{18}D_5NOS$ = 498.65) | 3-92 | m/z = 578.32 ($C_{42}H_{14}D_{15}NO$ = 578.78) |
| 3-93 | m/z = 572.30 ($C_{42}H_{20}D_{10}N_2$ = 572.76) | 3-94 | m/z = 567.27 ($C_{42}H_{25}D_5N_2$ = 567.73) |
| 3-95 | m/z = 491.24 ($C_{36}H_{21}D_5N_2$ = 491.64) | 3-96 | m/z = 724.37 ($C_{54}H_{28}D_{10}N_2$ = 724.95) |
| 3-97 | m/z = 719.33 ($C_{54}H_{33}D_5N_2$ = 719.92) | 3-98 | m/z = 643.30 ($C_{48}H_{29}D_5N_2$ = 643.83) |
| 3-99 | m/z = 774.38 ($C_{58}H_{30}D_{10}N_2$ = 775.01) | 3-100 | m/z = 743.33 ($C_{56}H_{33}D_5N_2$ = 743.95) |
| 3-101 | m/z = 667.30 ($C_{50}H_{29}D_5N_2$ = 667.85) | 3-102 | m/z = 748.37 ($C_{56}H_{28}D_{10}N_2$ = 748.98) |
| 3-103 | m/z = 743.33 ($C_{56}H_{33}D_5N_2$ = 743.95) | 3-104 | m/z = 617.29 ($C_{46}H_{27}D_5N_2$ = 617.79) |
| 3-105 | m/z = 698.35 ($C_{52}H_{26}D_{10}N_2$ = 698.92) | 3-106 | m/z = 693.32 ($C_{52}H_{31}D_5N_2$ = 693.89) |
| 3-107 | m/z = 693.32 ($C_{52}H_{31}D_5N_2$ = 693.89) | 3-108 | m/z = 654.29 ($C_{46}H_{22}D_{10}N_2S$ = 654.89) |
| 3-109 | m/z = 649.26 ($C_{46}H_{27}D_5N_2S$ = 649.86) | 3-110 | m/z = 573.23 ($C_{40}H_{23}D_5N_2S$ = 573.76) |
| 3-111 | m/z = 653.37 ($C_{48}H_{19}D_{15}N_2$ = 653.89) | 3-112 | m/z = 774.38 ($C_{58}H_{30}D_{10}N_2$ = 775.01) |
| 3-113 | m/z = 698.35 ($C_{52}H_{26}D_{10}N_2$ = 698.92) | 3-114 | m/z = 769.35 ($C_{58}H_{35}D_5N_2$ = 769.98) |
| 3-115 | m/z = 672.33 ($C_{50}H_{24}D_{10}N_2$ = 672.88) | 3-116 | m/z = 667.30 ($C_{50}H_{29}D_5N_2$ = 667.85) |
| 3-117 | m/z = 591.27 ($C_{44}H_{25}D_5N_2$ = 591.75) | 3-118 | m/z = 824.40 ($C_{62}H_{32}D_{10}N_2$ = 825.07) |
| 3-119 | m/z = 819.37 ($C_{52}H_{37}D_5N_2$ = 820.04) | 3-120 | m/z = 743.33 ($C_{56}H_{33}D_5N_2$ = 743.95) |
| 3-121 | m/z = 824.40 ($C_{62}H_{32}D_{10}N_2$ = 825.07) | 3-122 | m/z = 793.35 ($C_{60}H_{35}D_5N_2$ = 794.00) |
| 3-123 | m/z = 717.32 ($C_{54}H_{31}D_5N_2$ = 717.91) | 3-124 | m/z = 798.38 ($C_{60}H_{30}D_{10}N_2$ = 799.03) |
| 3-125 | m/z = 793.35 ($C_{60}H_{35}D_5N_2$ = 794.00) | 3-126 | m/z = 667.30 ($C_{50}H_{29}D_5N_2$ = 667.85) |
| 3-127 | m/z = 748.37 ($C_{56}H_{28}D_{10}N_2$ = 748.98) | 3-128 | m/z = 743.33 ($C_{56}H_{33}D_5N_2$ = 743.95) |
| 3-129 | m/z = 743.33 ($C_{56}H_{23}D_5N_2$ = 743.95) | 3-130 | m/z = 704.31 ($C_{50}H_{24}D_{10}N_2S$ = 704.94) |

TABLE 1-continued

| | | | |
|---|---|---|---|
| 3-131 | m/z = 699.28 ($C_{50}H_{29}D_5N_2S$ = 699.91) | 3-132 | m/z = 623.24 ($C_{44}H_{25}D_5N_2S$ = 623.82) |
| 3-133 | m/z = 703.38 ($C_{52}H_{21}D_{15}N_2$ = 703.95) | 3-134 | m/z = 824.40 ($C_{62}H_{32}D_{10}N_2$ = 825.07) |
| 3-135 | m/z = 748.37 ($C_{56}H_{28}D_{10}N_2$ = 748.98) | 3-136 | m/z = 819.37 ($C_{62}H_{37}D_5N_2$ = 820.04) |
| 3-137 | m/z = 572.30 ($C_{42}H_{20}D_{10}N_2$ = 572.76) | 3-138 | m/z = 567.27 ($C_{42}H_{25}D_5N_2$ = 567.73) |
| 3-139 | m/z = 491.24 ($C_{36}H_{21}D_5N_2$ = 491.64) | 3-140 | m/z = 724.37 ($C_{54}H_{28}D_{10}N_2$ = 724.95) |
| 3-141 | m/z = 719.33 ($C_{54}H_{33}D_5N_2$ = 719.92) | 3-142 | m/z = 643.30 ($C_{48}H_{29}D_5N_2$ = 643.83) |
| 3-143 | m/z = 774.38 ($C_{58}H_{30}D_{10}N_2$ = 775.01) | 3-144 | m/z = 743.33 ($C_{56}H_{33}D_5N_2$ = 743.95) |
| 3-145 | m/z = 667.30 ($C_{50}H_{29}D_5N_2$ = 667.85) | 3-146 | m/z = 748.37 ($C_{56}H_{28}D_{10}N_2$ = 748.98) |
| 3-147 | m/z = 743.33 ($C_{56}H_{33}D_5N_2$ = 743.95) | 3-148 | m/z = 617.29 ($C_{46}H_{27}D_5N_2$ = 617.79) |
| 3-149 | m/z = 698.35 ($C_{52}H_{26}D_{10}N_2$ = 698.92) | 3-150 | m/z = 693.32 ($C_{52}H_{31}D_5N_2$ = 693.89) |
| 3-151 | m/z = 693.32 ($C_{52}H_{31}D_5N_2$ = 693.89) | 3-152 | m/z = 654.29 ($C_{46}H_{22}D_{10}N_2S$ = 654.89) |
| 3-153 | m/z = 649.26 ($C_{46}H_{27}D_5N_2S$ = 649.86) | 3-154 | m/z = 573.23 ($C_{40}H_{23}D_5N_2S$ = 573.76) |
| 3-155 | m/z = 653.37 ($C_{48}H_{19}D_{15}N_2$ = 653.89) | 3-156 | m/z = 774.38 ($C_{58}H_{30}D_{10}N_2$ = 775.01) |
| 3-157 | m/z = 698.35 ($C_{52}H_{26}D_{10}N_2$ = 698.92) | 3-158 | m/z = 769.35 ($C_{58}H_{35}D_5N_2$ = 769.98) |
| 3-159 | m/z = 672.33 ($C_{50}H_{24}D_{10}N_2$ = 672.88) | 3-160 | m/z = 667.30 ($C_{50}H_{29}D_5N_2$ = 667.85) |
| 3-161 | m/z = 591.27 ($C_{44}H_{25}D_5N_2$ = 591.75) | 3-162 | m/z = 824.40 ($C_{62}H_{32}D_{10}N_2$ = 825.07) |
| 3-163 | m/z = 819.37 ($C_{62}H_{37}D_5N_2$ = 820.04) | 3-164 | m/z = 743.33 ($C_{56}H_{33}D_5N_2$ = 743.95) |
| 3-165 | m/z = 824.40 ($C_{62}H_{32}D_{10}N_2$ = 825.07) | 3-166 | m/z = 793.35 ($C_{60}H_{35}D_5N_2$ = 794.00) |
| 3-167 | m/z = 717.32 ($C_{54}H_{31}D_5N_2$ = 717.91) | 3-168 | m/z = 798.38 ($C_{60}H_{30}D_{10}N_2$ = 799.03) |
| 3-169 | m/z = 793.35 ($C_{60}H_{36}D_5N_2$ = 794.00) | 3-170 | m/z = 667.30 ($C_{50}H_{29}D_5N_2$ = 667.85) |
| 3-171 | m/z = 748.37 ($C_{56}H_{28}D_{10}N_2$ = 748.98) | 3-172 | m/z = 743.33 ($C_{56}H_{33}D_5N_2$ = 743.95) |
| 3-173 | m/z = 743.33 ($C_{56}H_{23}D_5N_2$ = 743.95) | 3-174 | m/z = 704.31 ($C_{50}H_{24}D_{10}N_2S$ = 704.94) |
| 3-175 | m/z = 699.28 ($C_{50}H_{29}D_5N_2S$ = 699.91) | 3-176 | m/z = 623.24 ($C_{44}H_{25}D_5N_2S$ = 623.82) |
| 3-177 | m/z = 703.38 ($C_{52}H_{21}D_{15}N_2$ = 703.95) | 3-178 | m/z = 824.40 ($C_{62}H_{32}D_{10}N_2$ = 825.07) |
| 3-179 | m/z = 748.37 ($C_{56}H_{28}D_{10}N_2$ = 748.98) | 3-180 | m/z = 819.37 ($C_{62}H_{37}D_5N_2$ = 820.04) |

Also, into a core structure with the above described structure, various substituents can be introduced so that a compound having a peculiar characteristic of the introduced substituent can be synthesized. For example, in the manufacturing of an organic electronic element such as an organic light emitting element, substituents used for a hole injection layer material, a hole transport layer material, an emitting layer material, and an electron transport layer material can be introduced into the structure so that materials satisfying requirements of respective organic material layers can be prepared.

The inventive compound may be used for various purposes in an organic electro-luminescence electronic device according to the kinds and properties of a substituent.

The inventive compound can be freely modified by a core and a substitute, and thus can be employed in various layers as well as a host of a phosphorescent or fluorescent emitting layer.

The inventive organic electronic element may be manufactured by a conventional method and a conventional material for manufacturing an organic electronic element except that the above described compounds are used to form at least one organic material layer.

It is natural that even when the inventive compounds are used in other organic material layers of an organic electroluminescence element, such as an emission assisting layer, an electron injection layer, an electron transport layer, and a hole injection layer, the same effects can be achieved.

Meanwhile, the inventive compound may be used in a soluble process. In other words, through a soluble process of the compound, an organic material layer (to be described later) of an organic electronic element can be formed. In other words, when the compound is used as an organic material layer, the organic material layer may be manufactured with a smaller number of layers by using various polymer materials by means of a soluble process or a solvent process (e.g., spin coating, dip coating, doctor blading, screen printing, inkjet printing or thermal transfer) instead of deposition.

The organic electronic elements, in which compounds according to the present invention can be employed, may include, for example, an organic light-emitting diode (OLED), an organic solar cell, an organic photo conductor (OPC) drum, an organic transistor (organic TFT), and the like.

As one example of the organic electronic elements in which compounds according to the present invention can be used, an organic light-emitting diode (OLED) will be described below, but the present invention is not limited thereto. The above described compounds may be applied to various organic electronic elements.

In another embodiment of the present invention, there is provided an organic electronic element (organic electro-luminescence element) including a first electrode, a second electrode, and an organic material layer interposed between these electrodes, in which at least one of organic material layers includes the compounds according to the present invention.

Figure 2:
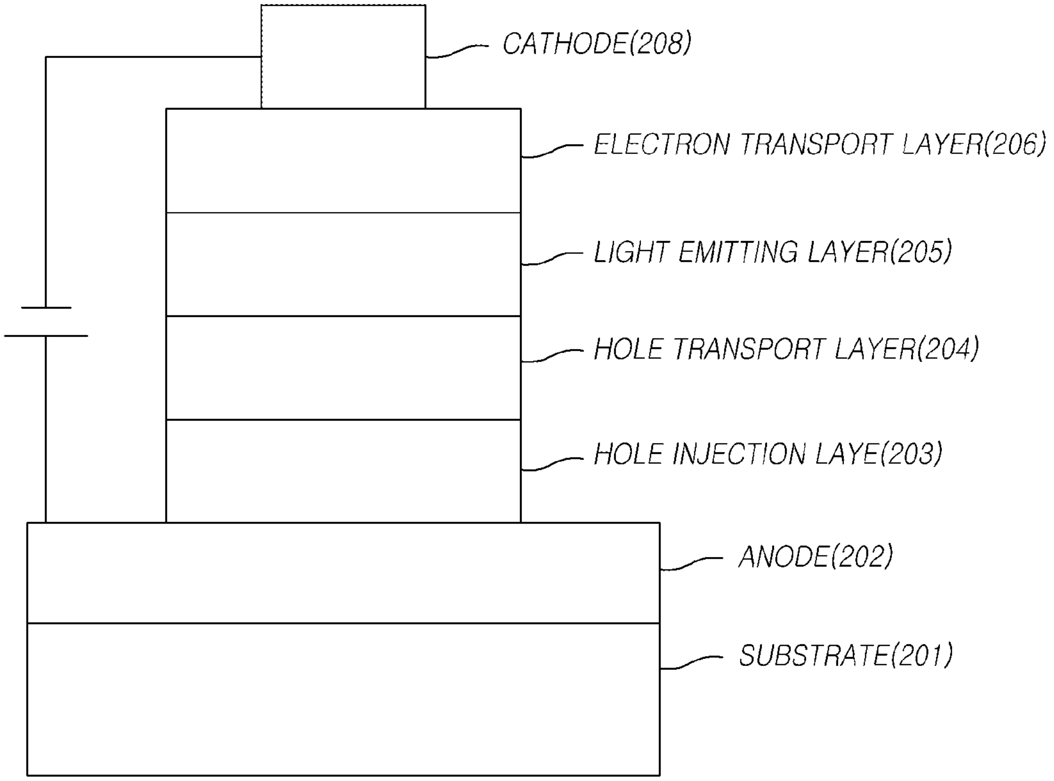
Figure 3:
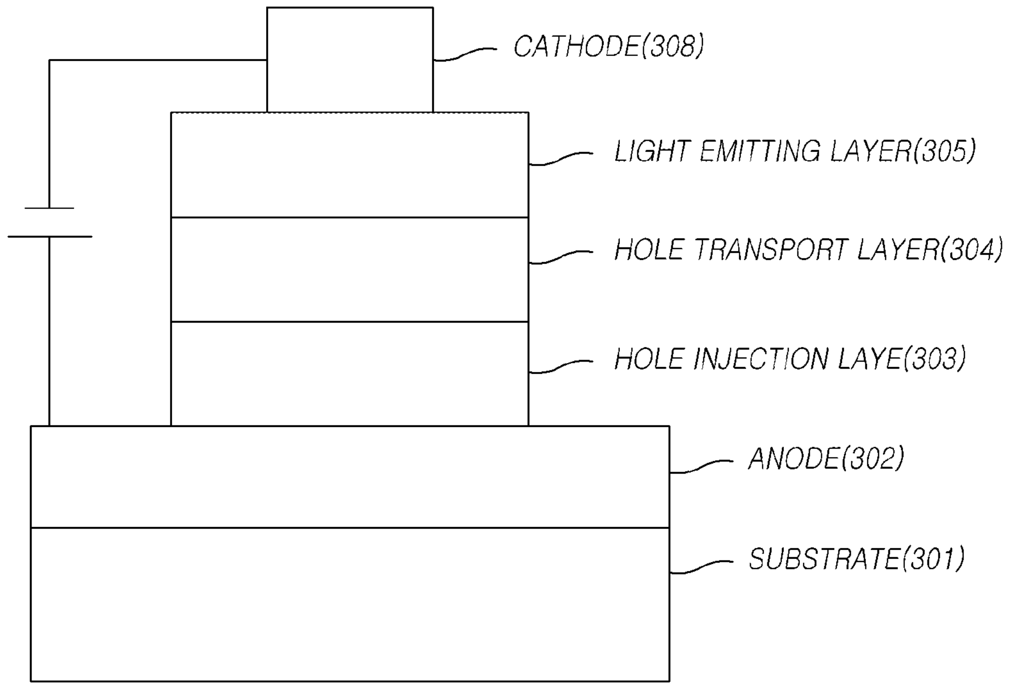
Figure 4:
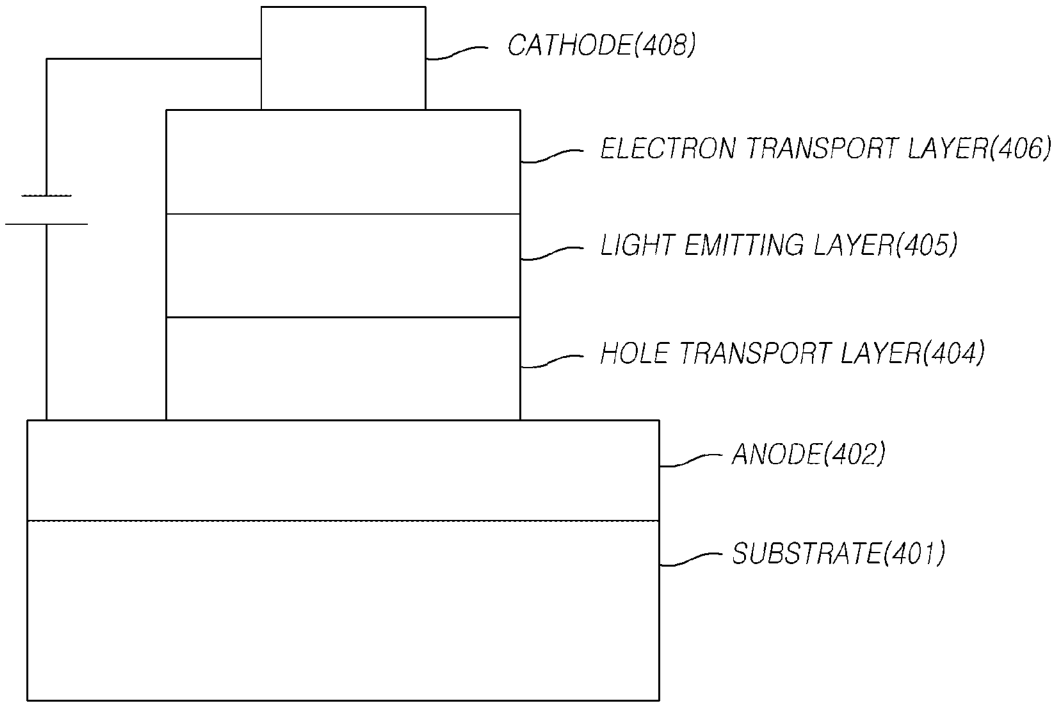
Figure 5:
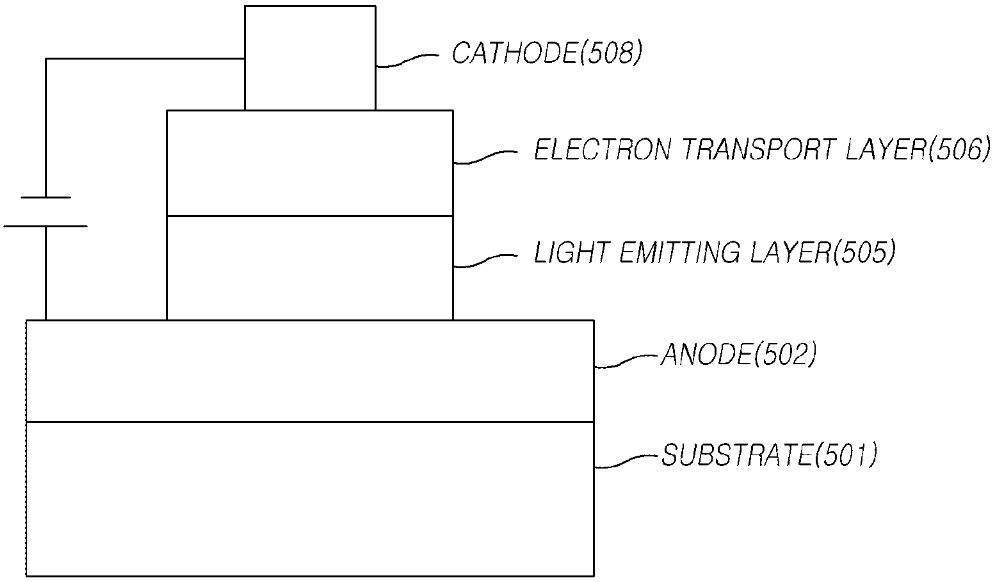
Figure 6:
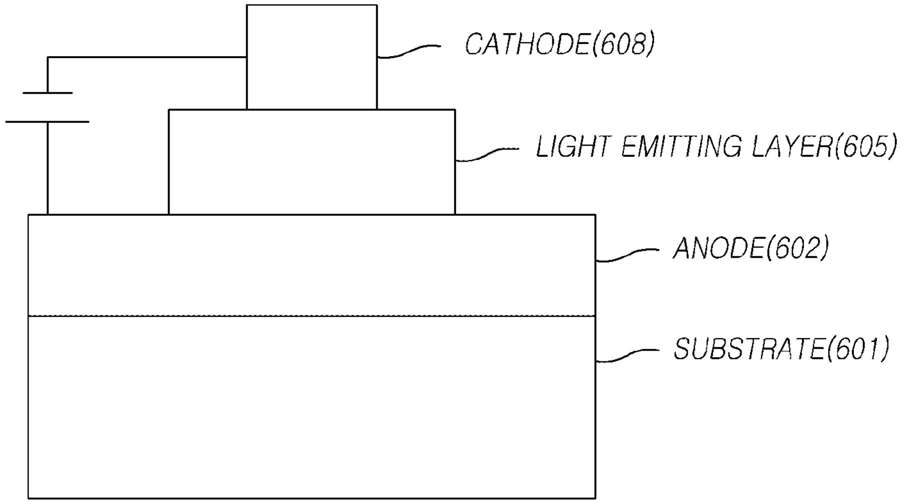

FIGS. 1 to 6 show examples of an organic electro-luminescence element which can employ a compound according to the present invention.

The organic electro-luminescence element according to another embodiment of the present invention may be manufactured by means of a manufacturing method and materials conventionally known in the art in such a manner that it can have a conventionally known structure, except that at least one of organic material layers including a hole injection layer, a hole transport layer, an emitting layer, an electron transport layer, and an electron injection layer is formed in such a manner that it can include the compound according to the present invention.

The structures of the organic electro-luminescence element according to another embodiment of the present invention are shown in FIGS. 1 to 6, but the present invention is not limited to the structures. Herein, the reference numeral 101 indicates a substrate, 102 indicates an anode, 103 indicates a hole injection layer (HIL), 104 indicates a hole transport layer (HTL), 105 indicates an emitting layer (EML), 106 indicates an electron injection layer (EIL), 107 indicates an electron transport layer (ETL), and 108 indicates a cathode.

Although not shown, such an organic electro-luminescence element may further include a hole blocking layer (HBL) for blocking movement of holes, an electron blocking layer (EBL) for blocking movement of electrons, a light emission assisting layer for supporting or assisting light emission, and a protective layer. The protective layer may be formed in such a manner that it, as an uppermost layer, can protect an organic material layer or a cathode.

Herein, the compound according to the present invention may be included in at least one of organic material layers including a hole injection layer, a hole transport layer, an emitting layer, and an electron transport layer.

Specifically, the compound according to the present invention may be substituted for at least one of a hole injection layer, a hole transport layer, an emitting layer, an electron transport layer, an electron injection layer, a hole blocking layer, an electron blocking layer, an light emission assisting layer, and a protective layer, or may be used in combination with these layers so as to form a multi-layered structure. Of course, the compound may be used for not only one layer of the organic material layers but also two or more layers.

Especially, the compound according to the present invention may be used as a material for hole injection, hole transport, electron injection, electron transport, light emission, and passivation (capping). Especially, it may be used alone as a light emitting material, a host or a dopant in host/dopant, and may be used as a hole injection layer or a hole transport layer.

For example, in manufacturing of the organic electro-luminescence element according to another embodiment of the present invention, a metal, a conductive metal oxide, or an alloy thereof may be deposited on a substrate by means of PVD (physical vapor deposition) such as sputtering or e-beam evaporation so as to form an anode, and then an organic material layer including a hole injection layer, a hole transport layer, an emitting layer, an electron transport layer, and an electron injection layer may be formed thereon, and a material capable of being used as a cathode may be deposited thereon.

Besides, on a substrate, a cathode material, an organic material layer, and an anode material may be sequentially deposited so as to provide an organic electronic element. The organic material layer may be formed in a multi-layered structure including a hole injection layer, a hole transport layer, an emitting layer, an electron transport layer, and an electron injection layer, but the present invention is not limited thereto. It may be formed in a single layer structure.

Further, the organic material layer may be manufactured with a smaller number of layers by using various polymer materials by means of a soluble process or a solvent process (e.g., spin coating, dip coating, doctor blading, screen printing, inkjet printing, or thermal transfer) instead of deposition.

In the organic electro-luminescence element according to another embodiment of the present invention, the above described compound may be used in a soluble process such as a spin coating process or an ink jet process.

The substrate is a support for the organic electro-luminescence element, and may employ a silicon wafer, a quartz or glass plate, a metal plate, a plastic film or sheet.

On the substrate, an anode is positioned. Such an anode allows holes to be injected into a hole injection layer positioned thereon. As an anode material, a material having a high work function may be used so that injection of holes into an organic material layer can be smoothly carried out. Specific examples of an anode material used for the present invention may include: metals (such as vanadium, chromium, copper, zinc, gold) or alloys thereof; metal oxides such as zinc oxide, indium oxide, indium tin oxide (ITO), indium zinc oxide (IZO); a metal-oxide combination such as ZnO:Al or $SnO_2$:Sb; and conductive polymers such as poly(3-methylthiophene), poly[3,4-(ethylene-1,2-dioxy) thiophene](PEDT), polypyrrole and polyaniline, but the present invention is not limited thereto.

On the anode, a hole injection layer is positioned. A material for such a hole injection layer is required to have a high efficiency for injecting holes from an anode, and to be able to efficiently transport the injected holes. For this, the material has to have a low ionization potential, a high transparency against visible ray, and a high stability for holes.

As a hole injection material, a material into which holes can be efficiently injected from an anode at a low voltage is used. HOMO (highest occupied molecular orbital) of the hole injection material may range from a work function of an anode material to HOMO of adjacent organic material layers. Specific examples of the hole injection material may include metal porphyrine-, oligothiophene-, and arylamine-based organic materials, hexanitrile hexaazatriphenylene- and quinacridone-based organic materials, perylene-based organic materials, and anthraquinone-, polyaniline-, and polythiophene-based conductive polymers, but the present invention is not limited thereto.

On the hole injection layer, a hole transport layer is positioned. Such a hole transport layer receives holes transferred from the hole injection layer and transfers them to an organic light emitting layer positioned thereon. Further, the hole transport layer has a high hole mobility and a high hole stability and performs a role of blocking electrons. Besides these general requirements, it requires heat-resistance against a device when applied for an automobile display, and thus may be made of a material having a glass transition temperature (Tg) of 70° C. or more.

The examples of a material satisfying these conditions may include NPD (or NPB), spiro-arylamine-based compound, perylene-arylamine-based compound, azacycloheptatriene compound, bis(diphenylvinylphenyl)anthracene, silicongermaniumoxide compound, silicon-based arylamine compound, and the like.

On the hole transport layer, an organic light emitting layer is positioned. Such an organic light emitting layer is made of a material having a high quantum efficiency, in which holes and electrons which are injected from an anode and a cathode, respectively, are recombined so as to emit light. As a light emitting material, a material allowing holes and electrons transferred from a hole transport layer and an electron transport layer, respectively, to be combined so as to emit light in a visible ray range is used. Preferably, a material having a high quantum efficiency against fluorescence or phosphorescence may be used.

As a material or a compound satisfying these conditions, for a green color, Alq3 may be used, and for a blue color, Balq(8-hydroxyquinoline beryllium salt), DPVBi(4,4'-bis(2,2-diphenylethenyl)-1,1'-biphenyl) based material, Spiro material, spiro-DPVBi(Spiro-4,4'-bis(2,2-diphenylethenyl)-1,1'-biphenyl), LiPBO(2-(2-benzoxazoyl)-phenol lithium salt), bis(diphenylvinylphenylvinyl)benzene, aluminum-quinoline metal complex, imidazole, thiazol and oxazole-metal complex, or the like may be used. In order to improve the luminous efficiency of a blue color, perylene, and BczVBi(3,3'[(1,1'-biphenyl)-4,4'-diyldi-2,1-ethenediyl]bis(9-ethyl)-9H-carbazole; DSA (distrylamine)) may be doped in a small amount. For a red color, a green light emitting material may be doped with DCJTB([2-(1,1'-dimethylethyl)-6-[2-(2,3,6,7-tetrahydro-1,1,7,7-tetramethyl-1H,5H-benzo(ij)quinolizin-9-yl)ethenyl]-4H-pyran-4-ylidene]-propanedinitrile) in a small amount.

When a process such as inkjet printing, roll coating, spin coating, is used to form an emitting layer, a polymer such as polyphenylenevinylene (PPV)-based polymer or poly fluorene may be used for an organic light emitting layer.

On the organic light emitting layer, an electron transport layer is positioned. Such an electron transport layer requires a material which has a high efficiency for electrons injected from a cathode positioned thereon, and can efficiently transport the injected electrons. For this, a material having a high electron affinity, a high electron mobility, and a high electron stability is required.

Specific examples of an electron transport material satisfying these conditions may include Al complex of 8-hydroxyquinoline; complex including $Alq_3$; organic radical compound; and hydroxyflavone-metal complex, but the present invention is not limited thereto.

On the electron transport layer, an electron injection layer is layered. The electron injection layer may be manufactured by using a metal complex compound (such as Balq, $Alq_3$, $Be(bq)_2$, $Zn(BTZ)_2$, $Zn(phq)_2$, PBD, spiro-PBD, TPBI, and Tf-6P) or a low molecular material including an aromatic compound having an imidazole ring or a boron compound. Herein, the electron injection layer may be formed in a thickness range of 100 Å to 300 Å.

On the electron injection layer, a cathode is positioned. Such a cathode performs a role of injecting electrons into the electron injection layer. As a material for the cathode, the same material as that used for an anode may be used. In order to achieve efficient electron injection, a metal having a low work function may be used. Especially, metals such as tin, magnesium, indium, calcium, sodium, lithium, aluminum, silver, or alloys thereof may be used. Further, a double-layered electrode (e.g., lithium fluoride and aluminum, lithium oxide and aluminum, and strontium oxide and aluminum) with a thickness of 100 μm or less may be used.

As described above, the compound according to the present invention may be used as a hole injection material, a hole transport material, a light emitting material, an electron transport material and an electron injection material, which are appropriate for fluorescent and phosphorescent elements of all colors (such as red, green, blue, white). Also, the compound may be used as a material of a host (or a dopant) of various colors.

The organic electro-luminescence element according to the present invention may be manufactured in a front luminescent type, a rear luminescent type, or a both-side luminescent type according to its materials.

Meanwhile, the present invention provides a terminal which includes a display device and a control part for driving the display device, the display device including the above described organic electronic element. The terminal means a wired/wireless communication terminal which is currently used or will be used in the future. The above described terminal according to the present invention may be a mobile communication terminal such as a cellular phone, and may include all kinds of terminals such as a PDA, an electronic dictionary, a PMP, a remote control, a navigation unit, a game player, various kinds of TVs, and various kinds of computers.

COMPARATIVE EXAMPLE

In Examples, the inventive compounds were used in a hole transport layer, while In Comparative Examples, compounds represented by Formulas below were used as a hole transport material.

[Formula 6]

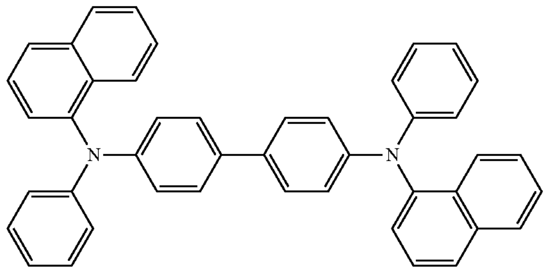

-continued

[Formula 7]

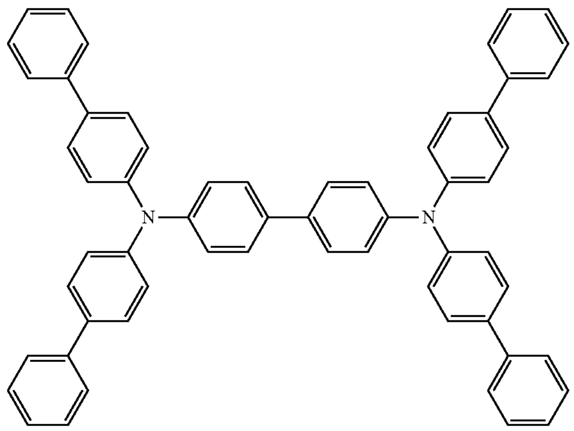

Especially, in order to determine the effect of heavy hydrogen substitution of the compounds, in Comparative Example (3) to Comparative Example (17), compounds substituted with hydrogen instead of heavy hydrogen were synthesized in the same manner as described in the above described synthesis method. Herein, as noted in Table 2, in order to express the hydrogen substitution, the compounds were accompanied by 'H'. For example, the compound in Comparative Example (3) corresponds to the compound 2-1 of Formula 4 except that the compound is substituted with hydrogen instead of heavy hydrogen. This rule is applied to other Comparative Examples in the same manner.

TABLE 2

| Comparative Example | compound |
|---|---|
| Comparative Example(1) | compound of Formula 6 |
| Comparative Example(2) | compound of Formula 7 |

TABLE 2-continued

| Comparative Example | compound |
|---|---|
| Comparative Example(3) | compound(2-1H) |
| Comparative Example(4) | compound(2-2H) |
| Comparative Example(5) | compound(2-17H) |
| Comparative Example(6) | compound(2-28H) |
| Comparative Example(7) | compound(2-60H) |
| Comparative Example(8) | compound(2-97H) |
| Comparative Example(9) | compound(2-116H) |
| Comparative Example(10) | compound(2-139H) |
| Comparative Example(11) | compound(2-162H) |
| Comparative Example(12) | compound(2-163H) |
| Comparative Example(13) | compound(2-185H) |
| Comparative Example(14) | compound(3-1H) |
| Comparative Example(15) | compound(3-2H) |
| Comparative Example(16) | compound(3-61H) |
| Comparative Example(17) | compound(3-138H) |

Manufacturing of Organic Electro-Luminescence Element

Then, an organic electro-luminescence element was manufactured through a conventional method by using the synthesized compounds as a light emitting host material of an emitting layer or as a hole transport layer.

First, on an ITO layer (anode) formed on a glass substrate, a copper phthalocyanine (hereinafter, referred to as CuPc) film as a hole injection layer was vacuum-deposited with a thickness of 10 nm. Then, on this film, each of the compounds according to Examples and Comparative Examples, noted in Table 1 or 2, were vacuum-deposited as a hole transport layer with a thickness of 20 nm. Then, a comparison test was carried out. Then, in the comparison test, BD-052X (Idemitsu) was used as a light emitting dopant, and 9,10-di-(naphthalene-2-anthracene)=AND] was used as a host material, and the doping concentration was fixed at 4%. Then, as an electron injection layer, tris(8-quinolinol) aluminum was film-formed with a thickness of 40 nm. Next, LiF (alkali-metal halide) was deposited with a thickness of 0.2 nm, and Al was deposited with a thickness of 150 nm. The Al/LiF was used as a cathode while the organic electro-luminescence element was fabricated.

TABLE 3

| | Compound | driving voltage | Current (mA/cm$^2$) | Luminance (cd/m$^2$) | Efficiency (cd/A) | T(90) | With respect to NPB (%) |
|---|---|---|---|---|---|---|---|
| Comparative Example(1) | compound of Formula 6 | 6.1 | 9.9 | 300.0 | 3.0 | 63.6 | 100% |
| Comparative Example(2) | compound of Formula 7 | 4.9 | 7.5 | 300.0 | 4.0 | 65.0 | 102% |
| Comparative Example(3) | compound(2-1H) | 5.6 | 8.7 | 300.0 | 3.4 | 64.5 | 101% |
| Comparative Example(4) | compound(2-2H) | 6.1 | 6.7 | 300.0 | 4.5 | 59.3 | 93% |
| Comparative Example(5) | compound(2-17H) | 4.7 | 8.7 | 300.0 | 3.4 | 52.0 | 82% |
| Comparative Example(6) | compound(2-28H) | 5.3 | 9.8 | 300.0 | 3.1 | 54.8 | 86% |
| Comparative Example(7) | compound(2-60H) | 5.4 | 9.0 | 300.0 | 3.3 | 54.2 | 85% |
| Comparative Example(8) | compound(2-97H) | 4.9 | 6.8 | 300.0 | 4.4 | 52.0 | 82% |
| Comparative Example(9) | compound(2-116H) | 4.8 | 7.8 | 300.0 | 3.8 | 56.4 | 89% |
| Comparative Example(10) | compound(2-139H) | 5.3 | 7.9 | 300.0 | 3.8 | 79.0 | 124% |
| Comparative Example(11) | compound(2-162H) | 5.4 | 7.4 | 300.0 | 4.1 | 58.3 | 92% |
| Comparative Example(12) | compound(2-163H) | 5.9 | 7.2 | 300.0 | 4.2 | 53.1 | 83% |
| Comparative Example(13) | compound(2-185H) | 5.1 | 7.6 | 300.0 | 3.9 | 77.5 | 122% |

TABLE 3-continued

| | Compound | driving voltage | Current ($mA/cm^2$) | Luminance ($cd/m^2$) | Efficiency (cd/A) | T(90) | With respect to NPB (%) |
|---|---|---|---|---|---|---|---|
| Comparative Example(14) | compound(3-1H) | 6.2 | 6.9 | 300.0 | 4.4 | 70.7 | 111% |
| Comparative Example(15) | compound(3-2H) | 4.6 | 9.9 | 300.0 | 3.0 | 59.0 | 93% |
| Comparative Example(16) | compound(3-61H) | 5.7 | 7.8 | 300.0 | 3.9 | 57.3 | 90% |
| Comparative Example(17) | compound(3-138H) | 6.3 | 8.6 | 300.0 | 3.5 | 61.2 | 96% |
| Example(1) | compound(2-1) | 5.2 | 9.4 | 300.0 | 3.2 | 146.3 | 230% |
| Example(2) | compound(2-2) | 4.7 | 7.6 | 300.0 | 4.0 | 145.7 | 229% |
| Example(3) | compound(2-3) | 5.7 | 7.5 | 300.0 | 4.0 | 142.0 | 223% |
| Example(4) | compound(2-4) | 5.7 | 6.2 | 300.0 | 4.9 | 110.8 | 174% |
| Example(5) | compound(2-5) | 4.4 | 5.8 | 300.0 | 5.2 | 96.7 | 152% |
| Example(6) | compound(2-6) | 5.9 | 9.4 | 300.0 | 3.2 | 94.1 | 148% |
| Example(7) | compound(2-7) | 4.4 | 6.3 | 300.0 | 4.8 | 148.4 | 233% |
| Example(8) | compound(2-8) | 4.7 | 6.0 | 300.0 | 5.0 | 147.9 | 232% |
| Example(9) | compound(2-9) | 5.0 | 6.6 | 300.0 | 4.5 | 95.7 | 150% |
| Example(10) | compound(2-10) | 5.4 | 5.7 | 300.0 | 5.2 | 109.4 | 172% |
| Example(11) | compound(2-11) | 4.7 | 8.3 | 300.0 | 3.6 | 92.8 | 146% |
| Example(12) | compound(2-12) | 5.3 | 5.6 | 300.0 | 5.4 | 129.5 | 204% |
| Example(13) | compound(2-13) | 4.3 | 7.4 | 300.0 | 4.0 | 115.0 | 181% |
| Example(14) | compound(2-14) | 4.2 | 8.9 | 300.0 | 3.4 | 139.1 | 219% |
| Example(15) | compound(2-15) | 5.9 | 6.4 | 300.0 | 4.7 | 118.3 | 186% |
| Example(16) | compound(2-16) | 4.8 | 7.4 | 300.0 | 4.1 | 147.8 | 232% |
| Example(17) | compound(2-17) | 5.4 | 6.7 | 300.0 | 4.5 | 117.8 | 185% |
| Example(18) | compound(2-18) | 4.2 | 6.1 | 300.0 | 4.9 | 126.3 | 199% |
| Example(19) | compound(2-19) | 4.5 | 6.0 | 300.0 | 5.0 | 146.0 | 229% |
| Example(20) | compound(2-20) | 5.4 | 7.7 | 300.0 | 3.9 | 143.9 | 226% |
| Example(21) | compound(2-21) | 4.8 | 5.9 | 300.0 | 5.1 | 96.9 | 152% |
| Example(22) | compound(2-22) | 5.2 | 7.0 | 300.0 | 4.3 | 91.5 | 144% |
| Example(23) | compound(2-23) | 4.2 | 7.0 | 300.0 | 4.3 | 105.9 | 166% |
| Example(24) | compound(2-24) | 5.2 | 10.0 | 300.0 | 3.0 | 110.8 | 174% |
| Example(25) | compound(2-25) | 4.6 | 6.6 | 300.0 | 4.5 | 106.7 | 168% |
| Example(26) | compound(2-26) | 5.6 | 8.6 | 300.0 | 3.5 | 148.7 | 234% |
| Example(27) | compound(2-27) | 4.6 | 6.3 | 300.0 | 4.7 | 106.6 | 168% |
| Example(28) | compound(2-28) | 4.9 | 7.5 | 300.0 | 4.0 | 138.9 | 218% |
| Example(29) | compound(2-29) | 5.6 | 8.5 | 300.0 | 3.5 | 122.7 | 193% |
| Example(30) | compound(2-30) | 4.4 | 5.8 | 300.0 | 5.2 | 95.1 | 149% |
| Example(31) | compound(2-31) | 5.1 | 7.7 | 300.0 | 3.9 | 134.6 | 212% |
| Example(32) | compound(2-32) | 4.5 | 6.8 | 300.0 | 4.4 | 123.0 | 193% |
| Example(33) | compound(2-33) | 5.7 | 5.3 | 300.0 | 5.7 | 94.6 | 149% |
| Example(34) | compound(2-34) | 4.3 | 8.3 | 300.0 | 3.6 | 123.4 | 194% |
| Example(35) | compound(2-35) | 4.1 | 8.1 | 300.0 | 3.7 | 119.7 | 188% |
| Example(36) | compound(2-36) | 4.5 | 5.6 | 300.0 | 5.4 | 112.1 | 176% |
| Example(37) | compound(2-37) | 5.5 | 8.8 | 300.0 | 3.4 | 93.9 | 148% |
| Example(38) | compound(2-38) | 5.5 | 8.3 | 300.0 | 3.6 | 110.9 | 174% |
| Example(39) | compound(2-39) | 4.1 | 6.1 | 300.0 | 4.9 | 113.6 | 179% |
| Example(40) | compound(2-40) | 5.2 | 5.5 | 300.0 | 5.4 | 91.7 | 144% |
| Example(41) | compound(2-41) | 5.7 | 8.9 | 300.0 | 3.4 | 113.8 | 179% |
| Example(42) | compound(2-42) | 5.2 | 6.5 | 300.0 | 4.6 | 132.9 | 209% |
| Example(43) | compound(2-43) | 4.2 | 6.7 | 300.0 | 4.5 | 100.7 | 158% |
| Example(44) | compound(2-44) | 4.2 | 5.4 | 300.0 | 5.5 | 103.9 | 163% |
| Example(45) | compound(2-45) | 4.1 | 5.5 | 300.0 | 5.5 | 122.2 | 192% |
| Example(46) | compound(2-46) | 5.6 | 7.5 | 300.0 | 4.0 | 130.1 | 204% |
| Example(47) | compound(2-47) | 5.6 | 8.4 | 300.0 | 3.6 | 103.2 | 162% |
| Example(48) | compound(2-48) | 4.9 | 5.9 | 300.0 | 5.1 | 143.9 | 226% |
| Example(49) | compound(2-49) | 4.7 | 8.8 | 300.0 | 3.4 | 101.3 | 159% |
| Example(50) | compound(2-50) | 4.0 | 7.2 | 300.0 | 4.1 | 117.1 | 184% |
| Example(51) | compound(2-51) | 5.2 | 9.2 | 300.0 | 3.3 | 113.8 | 179% |
| Example(52) | compound(2-52) | 5.5 | 5.7 | 300.0 | 5.3 | 127.3 | 200% |
| Example(53) | compound(2-53) | 5.5 | 7.5 | 300.0 | 4.0 | 114.3 | 180% |
| Example(54) | compound(2-54) | 5.4 | 8.4 | 300.0 | 3.6 | 106.7 | 168% |
| Example(55) | compound(2-55) | 4.5 | 6.6 | 300.0 | 4.5 | 132.6 | 208% |
| Example(56) | compound(2-56) | 4.4 | 6.7 | 300.0 | 4.5 | 126.8 | 199% |
| Example(57) | compound(2-57) | 4.1 | 9.2 | 300.0 | 3.3 | 146.8 | 231% |
| Example(58) | compound(2-58) | 5.1 | 9.0 | 300.0 | 3.3 | 129.2 | 203% |
| Example(59) | compound(2-59) | 4.5 | 9.0 | 300.0 | 3.3 | 90.7 | 142% |
| Example(60) | compound(2-60) | 4.4 | 9.8 | 300.0 | 3.1 | 108.3 | 170% |
| Example(61) | compound(2-61) | 4.1 | 5.3 | 300.0 | 5.7 | 108.5 | 170% |
| Example(62) | compound(2-62) | 5.9 | 5.4 | 300.0 | 5.5 | 102.3 | 161% |
| Example(63) | compound(2-63) | 5.4 | 9.6 | 300.0 | 3.1 | 97.7 | 154% |
| Example(64) | compound(2-64) | 4.0 | 9.5 | 300.0 | 3.2 | 148.3 | 233% |
| Example(65) | compound(2-65) | 4.5 | 9.9 | 300.0 | 3.0 | 142.7 | 224% |
| Example(66) | compound(2-66) | 5.3 | 7.4 | 300.0 | 4.0 | 148.7 | 234% |
| Example(67) | compound(2-67) | 4.3 | 6.9 | 300.0 | 4.3 | 109.4 | 172% |
| Example(68) | compound(2-68) | 4.0 | 6.3 | 300.0 | 4.7 | 146.5 | 230% |
| Example(69) | compound(2-69) | 4.1 | 8.5 | 300.0 | 3.5 | 125.5 | 197% |

TABLE 3-continued

| | Compound | driving voltage | Current ($mA/cm^2$) | Luminance ($cd/m^2$) | Efficiency (cd/A) | T(90) | With respect to NPB (%) |
|---|---|---|---|---|---|---|---|
| Example(70) | compound(2-70) | 4.5 | 6.4 | 300.0 | 4.7 | 111.3 | 175% |
| Example(71) | compound(2-71) | 5.5 | 10.0 | 300.0 | 3.0 | 146.5 | 230% |
| Example(72) | compound(2-72) | 5.0 | 5.9 | 300.0 | 5.1 | 100.1 | 157% |
| Example(73) | compound(2-73) | 5.2 | 6.3 | 300.0 | 4.8 | 126.4 | 199% |
| Example(74) | compound(2-74) | 5.9 | 8.5 | 300.0 | 3.5 | 121.6 | 191% |
| Example(75) | compound(2-75) | 5.5 | 5.4 | 300.0 | 5.6 | 136.1 | 214% |
| Example(76) | compound(2-76) | 4.5 | 7.3 | 300.0 | 4.1 | 93.5 | 147% |
| Example(77) | compound(2-77) | 4.6 | 7.5 | 300.0 | 4.0 | 130.1 | 204% |
| Example(78) | compound(2-78) | 5.5 | 6.8 | 300.0 | 4.4 | 116.0 | 182% |
| Example(79) | compound(2-79) | 4.1 | 6.2 | 300.0 | 4.8 | 140.6 | 221% |
| Example(80) | compound(2-80) | 5.4 | 9.1 | 300.0 | 3.3 | 133.0 | 209% |
| Example(81) | compound(2-81) | 5.2 | 8.0 | 300.0 | 3.7 | 143.0 | 225% |
| Example(82) | compound(2-82) | 4.7 | 5.5 | 300.0 | 5.4 | 113.6 | 179% |
| Example(83) | compound(2-83) | 5.4 | 6.2 | 300.0 | 4.9 | 105.5 | 166% |
| Example(84) | compound(2-84) | 4.8 | 5.4 | 300.0 | 5.6 | 138.9 | 218% |
| Example(85) | compound(2-85) | 4.3 | 7.7 | 300.0 | 3.9 | 136.1 | 214% |
| Example(86) | compound(2-86) | 5.2 | 7.3 | 300.0 | 4.1 | 92.1 | 145% |
| Example(87) | compound(2-87) | 4.5 | 6.7 | 300.0 | 4.5 | 98.6 | 155% |
| Example(88) | compound(2-88) | 5.1 | 6.3 | 300.0 | 4.7 | 122.5 | 193% |
| Example(89) | compound(2-89) | 4.1 | 5.6 | 300.0 | 5.4 | 121.2 | 190% |
| Example(90) | compound(2-90) | 4.0 | 6.1 | 300.0 | 4.9 | 110.7 | 174% |
| Example(91) | compound(2-91) | 5.4 | 6.8 | 300.0 | 4.4 | 119.6 | 188% |
| Example(92) | compound(2-92) | 4.7 | 8.3 | 300.0 | 3.6 | 94.3 | 148% |
| Example(93) | compound(2-93) | 5.0 | 8.3 | 300.0 | 3.6 | 120.1 | 189% |
| Example(94) | compound(2-94) | 4.9 | 5.3 | 300.0 | 5.7 | 13.7 | 179% |
| Example(95) | compound(2-95) | 5.2 | 5.9 | 300.0 | 5.1 | 101.4 | 159% |
| Example(96) | compound(2-96) | 5.3 | 7.1 | 300.0 | 4.2 | 147.3 | 232% |
| Example(97) | compound(2-97) | 4.5 | 7.1 | 300.0 | 4.2 | 141.3 | 222% |
| Example(98) | compound(2-98) | 4.1 | 5.4 | 300.0 | 5.6 | 127.0 | 200% |
| Example(99) | compound(2-99) | 4.8 | 5.9 | 300.0 | 5.1 | 140.9 | 221% |
| Example(100) | compound(2-100) | 4.2 | 7.9 | 300.0 | 3.8 | 103.4 | 162% |
| Example(101) | compound(2-101) | 4.7 | 6.4 | 300.0 | 4.7 | 147.5 | 232% |
| Example(102) | compound(2-102) | 4.6 | 5.6 | 300.0 | 5.4 | 94.4 | 148% |
| Example(103) | compound(2-103) | 5.0 | 5.4 | 300.0 | 5.6 | 119.3 | 188% |
| Example(104) | compound(2-104) | 4.3 | 5.8 | 300.0 | 5.2 | 142.1 | 223% |
| Example(105) | compound(2-105) | 4.4 | 8.3 | 300.0 | 3.6 | 139.3 | 219% |
| Example(106) | compound(2-106) | 5.6 | 6.6 | 300.0 | 4.5 | 118.9 | 187% |
| Example(107) | compound(2-107) | 5.0 | 7.8 | 300.0 | 3.9 | 102.2 | 161% |
| Example(108) | compound(2-108) | 4.7 | 7.3 | 300.0 | 4.1 | 95.5 | 150% |
| Example(109) | compound(2-109) | 4.7 | 6.4 | 300.0 | 4.7 | 117.8 | 185% |
| Example(110) | compound(2-110) | 5.2 | 5.3 | 300.0 | 5.7 | 114.7 | 180% |
| Example(111) | compound(2-111) | 5.7 | 8.6 | 300.0 | 3.5 | 101.4 | 159% |
| Example(112) | compound(2-112) | 5.8 | 6.5 | 300.0 | 4.6 | 111.8 | 176% |
| Example(113) | compound(2-113) | 4.8 | 5.3 | 300.0 | 5.7 | 117.3 | 184% |
| Example(114) | compound(2-114) | 5.4 | 8.0 | 300.0 | 3.8 | 129.1 | 203% |
| Example(115) | compound(2-115) | 4.1 | 8.0 | 300.0 | 3.8 | 98.6 | 155% |
| Example(116) | compound(2-116) | 4.4 | 8.7 | 300.0 | 3.5 | 146.9 | 231% |
| Example(117) | compound(2-117) | 5.2 | 6.2 | 300.0 | 4.8 | 109.3 | 172% |
| Example(118) | compound(2-118) | 4.1 | 6.7 | 300.0 | 4.5 | 114.3 | 180% |
| Example(119) | compound(2-119) | 4.1 | 10.0 | 300.0 | 3.0 | 109.9 | 173% |
| Example(120) | compound(2-120) | 4.9 | 5.9 | 300.0 | 5.1 | 112.2 | 176% |
| Example(121) | compound(2-121) | 5.7 | 5.7 | 300.0 | 5.3 | 115.6 | 182% |
| Example(122) | compound(2-122) | 4.2 | 5.9 | 300.0 | 5.1 | 115.4 | 181% |
| Example(123) | compound(2-123) | 5.0 | 7.4 | 300.0 | 4.1 | 108.4 | 170% |
| Example(124) | compound(2-124) | 4.5 | 6.8 | 300.0 | 4.4 | 91.1 | 143% |
| Example(125) | compound(2-125) | 4.3 | 9.9 | 300.0 | 3.0 | 120.2 | 189% |
| Example(126) | compound(2-126) | 5.7 | 6.8 | 300.0 | 4.4 | 144.5 | 227% |
| Example(127) | compound(2-127) | 5.4 | 9.9 | 300.0 | 3.0 | 144.4 | 227% |
| Example(128) | compound(2-128) | 4.9 | 8.5 | 300.0 | 3.5 | 106.9 | 168% |
| Example(129) | compound(2-129) | 4.1 | 6.7 | 300.0 | 4.5 | 129.9 | 204% |
| Example(130) | compound(2-130) | 4.7 | 8.2 | 300.0 | 3.6 | 141.8 | 223% |
| Example(131) | compound(2-131) | 5.8 | 7.9 | 300.0 | 3.8 | 116.9 | 184% |
| Example(132) | compound(2-132) | 5.7 | 5.7 | 300.0 | 5.3 | 129.5 | 203% |
| Example(133) | compound(2-133) | 5.0 | 7.4 | 300.0 | 4.1 | 92.9 | 146% |
| Example(134) | compound(2-134) | 4.2 | 6.6 | 300.0 | 4.5 | 117.5 | 185% |
| Example(135) | compound(2-135) | 4.4 | 7.7 | 300.0 | 3.9 | 140.1 | 220% |
| Example(136) | compound(2-136) | 4.9 | 7.3 | 300.0 | 4.1 | 99.5 | 156% |
| Example(137) | compound(2-137) | 4.3 | 8.3 | 300.0 | 3.6 | 143.5 | 225% |
| Example(138) | compound(2-138) | 4.2 | 5.8 | 300.0 | 5.2 | 93.8 | 147% |
| Example(139) | compound(2-139) | 5.8 | 6.2 | 300.0 | 4.9 | 95.4 | 150% |
| Example(140) | compound(2-140) | 4.7 | 6.4 | 300.0 | 4.7 | 106.5 | 167% |
| Example(141) | compound(2-141) | 4.5 | 5.5 | 300.0 | 5.5 | 142.9 | 225% |
| Example(142) | compound(2-142) | 5.2 | 7.4 | 300.0 | 4.1 | 90.5 | 142% |
| Example(143) | compound(2-143) | 4.0 | 5.6 | 300.0 | 5.3 | 103.9 | 163% |
| Example(144) | compound(2-144) | 5.8 | 5.7 | 300.0 | 5.3 | 104.7 | 165% |
| Example(145) | compound(2-145) | 5.5 | 9.5 | 300.0 | 3.2 | 134.0 | 211% |
| Example(146) | compound(2-146) | 4.8 | 7.5 | 300.0 | 4.0 | 143.0 | 225% |

TABLE 3-continued

| | Compound | driving voltage | Current (mA/cm$^2$) | Luminance (cd/m$^2$) | Efficiency (cd/A) | T(90) | With respect to NPB (%) |
|---|---|---|---|---|---|---|---|
| Example(147) | compound(2-147) | 5.8 | 9.5 | 300.0 | 3.2 | 146.8 | 231% |
| Example(148) | compound(2-148) | 5.5 | 5.3 | 300.0 | 5.6 | 148.0 | 233% |
| Example(149) | compound(2-149) | 4.2 | 7.0 | 300.0 | 4.3 | 145.2 | 228% |
| Example(150) | compound(2-150) | 5.8 | 5.4 | 300.0 | 5.6 | 143.1 | 225% |
| Example(151) | compound(2-151) | 4.1 | 7.1 | 300.0 | 4.2 | 144.2 | 227% |
| Example(152) | compound(2-152) | 4.4 | 6.7 | 300.0 | 4.5 | 144.9 | 228% |
| Example(153) | compound(2-153) | 4.7 | 5.4 | 300.0 | 5.6 | 118.7 | 187% |
| Example(154) | compound(2-154) | 4.5 | 7.4 | 300.0 | 4.1 | 137.2 | 216% |
| Example(155) | compound(2-155) | 4.6 | 6.8 | 300.0 | 4.4 | 122.3 | 192% |
| Example(156) | compound(2-156) | 5.2 | 5.3 | 300.0 | 5.6 | 133.2 | 209% |
| Example(157) | compound(2-157) | 4.6 | 8.1 | 300.0 | 3.7 | 101.3 | 159% |
| Example(158) | compound(2-158) | 5.3 | 5.7 | 300.0 | 5.3 | 94.4 | 148% |
| Example(159) | compound(2-159) | 5.9 | 6.8 | 300.0 | 4.4 | 114.8 | 180% |
| Example(160) | compound(2-160) | 4.9 | 5.2 | 300.0 | 5.7 | 121.2 | 190% |
| Example(161) | compound(2-161) | 4.6 | 6.5 | 300.0 | 4.6 | 122.8 | 193% |
| Example(162) | compound(2-162) | 5.8 | 5.7 | 300.0 | 5.2 | 122.9 | 193% |
| Example(163) | compound(2-163) | 5.9 | 5.2 | 300.0 | 5.7 | 104.8 | 165% |
| Example(164) | compound(2-164) | 5.3 | 7.9 | 300.0 | 3.8 | 118.7 | 187% |
| Example(165) | compound(2-165) | 5.0 | 5.8 | 300.0 | 5.2 | 120.0 | 189% |
| Example(166) | compound(2-166) | 4.6 | 5.5 | 300.0 | 5.4 | 149.1 | 234% |
| Example(167) | compound(2-167) | 5.6 | 9.3 | 300.0 | 3.2 | 131.2 | 206% |
| Example(168) | compound(2-168) | 5.4 | 6.6 | 300.0 | 4.6 | 131.9 | 207% |
| Example(169) | compound(2-169) | 5.3 | 6.6 | 300.0 | 4.5 | 138.2 | 217% |
| Example(170) | compound(2-170) | 4.5 | 7.9 | 300.0 | 3.8 | 146.8 | 231% |
| Example(171) | compound(2-171) | 4.7 | 5.4 | 300.0 | 5.5 | 147.4 | 232% |
| Example(172) | compound(2-172) | 4.1 | 5.6 | 300.0 | 5.4 | 141.8 | 223% |
| Example(173) | compound(2-173) | 5.3 | 5.4 | 300.0 | 5.6 | 113.3 | 178% |
| Example(174) | compound(2-174) | 5.4 | 5.3 | 300.0 | 5.6 | 99.1 | 156% |
| Example(175) | compound(2-175) | 4.2 | 7.2 | 300.0 | 4.2 | 145.1 | 228% |
| Example(176) | compound(2-176) | 5.6 | 5.7 | 300.0 | 5.3 | 123.1 | 194% |
| Example(177) | compound(2-177) | 4.3 | 6.3 | 300.0 | 4.8 | 137.6 | 216% |
| Example(178) | compound(2-178) | 5.4 | 7.4 | 300.0 | 4.0 | 129.8 | 204% |
| Example(179) | compound(2-179) | 4.3 | 5.4 | 300.0 | 5.6 | 100.4 | 158% |
| Example(180) | compound(2-180) | 4.8 | 6.6 | 300.0 | 4.5 | 101.5 | 159% |
| Example(181) | compound(2-181) | 4.2 | 6.5 | 300.0 | 4.6 | 107.0 | 168% |
| Example(182) | compound(2-182) | 5.6 | 7.8 | 300.0 | 3.9 | 139.6 | 219% |
| Example(183) | compound(2-183) | 4.3 | 7.4 | 300.0 | 4.1 | 96.9 | 152% |
| Example(184) | compound(2-184) | 5.4 | 6.0 | 300.0 | 5.0 | 145.1 | 228% |
| Example(185) | compound(2-185) | 4.5 | 5.5 | 300.0 | 5.4 | 97.8 | 154% |
| Example(186) | compound(2-186) | 4.5 | 5.6 | 300.0 | 5.3 | 104.1 | 164% |
| Example(187) | compound(2-187) | 4.6 | 9.0 | 300.0 | 3.3 | 107.5 | 169% |
| Example(188) | compound(2-188) | 5.8 | 5.4 | 300.0 | 5.5 | 117.3 | 184% |
| Example(189) | compound(2-189) | 5.2 | 8.6 | 300.0 | 3.5 | 96.6 | 152% |
| Example(190) | compound(2-190) | 5.9 | 5.5 | 300.0 | 5.5 | 140.9 | 222% |
| Example(191) | compound(2-191) | 4.3 | 5.9 | 300.0 | 5.1 | 93.5 | 147% |
| Example(192) | compound(2-192) | 5.3 | 6.6 | 300.0 | 4.5 | 108.6 | 171% |
| Example(193) | compound(2-193) | 5.4 | 5.6 | 300.0 | 5.4 | 104.5 | 164% |
| Example(194) | compound(2-194) | 5.2 | 5.6 | 300.0 | 5.4 | 104.1 | 164% |
| Example(195) | compound(2-195) | 4.9 | 6.3 | 300.0 | 4.8 | 108.9 | 171% |
| Example(196) | compound(2-196) | 5.2 | 9.8 | 300.0 | 3.1 | 102.5 | 161% |
| Example(197) | compound(2-197) | 4.9 | 9.1 | 300.0 | 3.3 | 128.1 | 201% |
| Example(198) | compound(2-198) | 4.4 | 6.8 | 300.0 | 4.4 | 144.6 | 227% |
| Example(199) | compound(2-199) | 4.2 | 5.2 | 300.0 | 5.7 | 101.4 | 159% |
| Example(200) | compound(2-200) | 5.1 | 5.6 | 300.0 | 5.4 | 96.2 | 151% |
| Example(201) | compound(2-201) | 4.6 | 6.3 | 300.0 | 4.8 | 139.1 | 219% |
| Example(202) | compound(2-202) | 5.5 | 7.7 | 300.0 | 3.9 | 132.0 | 207% |
| Example(203) | compound(2-203) | 5.6 | 6.9 | 300.0 | 4.4 | 96.6 | 152% |
| Example(204) | compound(2-204) | 5.1 | 6.6 | 300.0 | 4.6 | 107.3 | 169% |
| Example(205) | compound(2-205) | 5.6 | 6.6 | 300.0 | 4.6 | 136.4 | 214% |
| Example(206) | compound(2-206) | 4.2 | 6.5 | 300.0 | 4.6 | 140.0 | 220% |
| Example(207) | compound(2-207) | 4.5 | 9.8 | 300.0 | 3.1 | 92.3 | 145% |
| Example(208) | compound(3-1) | 4.9 | 5.5 | 300.0 | 5.5 | 124.0 | 195% |
| Example(209) | compound(3-2) | 5.7 | 5.5 | 300.0 | 5.5 | 144.4 | 227% |
| Example(210) | compound(3-3) | 5.9 | 6.7 | 300.0 | 4.5 | 96.7 | 152% |
| Example(211) | compound(3-4) | 5.3 | 5.4 | 300.0 | 5.6 | 117.3 | 184% |
| Example(212) | compound(3-5) | 4.9 | 6.7 | 300.0 | 4.5 | 131.9 | 207% |
| Example(213) | compound(3-6) | 5.8 | 7.8 | 300.0 | 3.9 | 97.7 | 154% |
| Example(214) | compound(3-7) | 4.6 | 8.6 | 300.0 | 3.5 | 109.2 | 172% |
| Example(215) | compound(3-8) | 4.2 | 5.7 | 300.0 | 5.3 | 101.0 | 159% |
| Example(216) | compound(3-9) | 5.7 | 6.2 | 300.0 | 4.8 | 145.0 | 228% |
| Example(217) | compound(3-10) | 4.6 | 7.3 | 300.0 | 4.1 | 147.5 | 232% |
| Example(218) | compound(3-11) | 5.8 | 6.2 | 300.0 | 4.9 | 91.0 | 143% |
| Example(219) | compound(3-12) | 5.2 | 6.1 | 300.0 | 4.9 | 149.3 | 235% |
| Example(220) | compound(3-13) | 5.1 | 8.2 | 300.0 | 3.6 | 131.9 | 207% |
| Example(221) | compound(3-14) | 5.2 | 5.5 | 300.0 | 5.4 | 108.5 | 171% |
| Example(222) | compound(3-15) | 5.7 | 5.5 | 300.0 | 5.5 | 103.4 | 162% |
| Example(223) | compound(3-16) | 4.5 | 5.6 | 300.0 | 5.3 | 113.0 | 178% |

TABLE 3-continued

| | Compound | driving voltage | Current (mA/cm$^2$) | Luminance (cd/m$^2$) | Efficiency (cd/A) | T(90) | With respect to NPB (%) |
|---|---|---|---|---|---|---|---|
| Example(224) | compound(3-17) | 5.4 | 8.0 | 300.0 | 3.8 | 121.8 | 191% |
| Example(225) | compound(3-18) | 4.1 | 6.5 | 300.0 | 4.6 | 108.9 | 171% |
| Example(226) | compound(3-19) | 5.4 | 6.3 | 300.0 | 4.8 | 124.0 | 195% |
| Example(227) | compound(3-20) | 5.6 | 5.5 | 300.0 | 5.5 | 142.2 | 223% |
| Example(228) | compound(3-21) | 5.5 | 5.3 | 300.0 | 5.7 | 111.2 | 175% |
| Example(229) | compound(3-22) | 4.4 | 6.3 | 300.0 | 4.7 | 96.5 | 152% |
| Example(230) | compound(3-23) | 4.0 | 5.9 | 300.0 | 5.1 | 131.8 | 207% |
| Example(231) | compound(3-24) | 4.0 | 5.7 | 300.0 | 5.2 | 142.3 | 224% |
| Example(232) | compound(3-25) | 4.3 | 9.5 | 300.0 | 3.1 | 132.1 | 208% |
| Example(233) | compound(3-26) | 4.7 | 5.5 | 300.0 | 5.5 | 96.2 | 151% |
| Example(234) | compound(3-27) | 5.1 | 6.5 | 300.0 | 4.6 | 94.7 | 149% |
| Example(235) | compound(3-28) | 5.9 | 5.8 | 300.0 | 5.2 | 128.4 | 202% |
| Example(236) | compound(3-29) | 5.4 | 5.4 | 300.0 | 5.6 | 120.4 | 189% |
| Example(237) | compound(3-30) | 5.0 | 5.7 | 300.0 | 5.2 | 136.0 | 214% |
| Example(238) | compound(3-31) | 5.5 | 6.3 | 300.0 | 4.8 | 134.6 | 212% |
| Example(239) | compound(3-32) | 4.8 | 6.1 | 300.0 | 4.9 | 116.7 | 183% |
| Example(240) | compound(3-33) | 4.3 | 8.8 | 300.0 | 3.4 | 140.4 | 221% |
| Example(241) | compound(3-34) | 4.7 | 7.5 | 300.0 | 4.0 | 149.4 | 235% |
| Example(242) | compound(3-35) | 5.8 | 9.9 | 300.0 | 3.0 | 129.8 | 204% |
| Example(243) | compound(3-36) | 4.4 | 7.9 | 300.0 | 3.8 | 118.7 | 186% |
| Example(244) | compound(3-37) | 5.3 | 6.0 | 300.0 | 5.0 | 132.3 | 208% |
| Example(245) | compound(3-38) | 5.6 | 8.7 | 300.0 | 3.4 | 140.1 | 220% |
| Example(246) | compound(3-39) | 5.7 | 9.3 | 300.0 | 3.2 | 115.6 | 182% |
| Example(247) | compound(3-40) | 4.8 | 6.4 | 300.0 | 4.7 | 116.0 | 182% |
| Example(248) | compound(3-41) | 5.0 | 7.7 | 300.0 | 3.9 | 133.5 | 210% |
| Example(249) | compound(3-42) | 5.1 | 6.7 | 300.0 | 4.5 | 124.3 | 195% |
| Example(250) | compound(3-43) | 4.2 | 5.4 | 300.0 | 5.6 | 93.4 | 147% |
| Example(251) | compound(3-44) | 5.3 | 5.2 | 300.0 | 5.7 | 109.5 | 172% |
| Example(252) | compound(3-45) | 5.0 | 7.8 | 300.0 | 3.8 | 101.2 | 159% |
| Example(253) | compound(3-46) | 5.3 | 5.3 | 300.0 | 5.7 | 91.6 | 144% |
| Example(254) | compound(3-47) | 5.2 | 6.2 | 300.0 | 4.8 | 136.3 | 214% |
| Example(255) | compound(3-48) | 5.9 | 6.5 | 300.0 | 4.6 | 114.4 | 180% |
| Example(256) | compound(3-49) | 5.3 | 5.6 | 300.0 | 5.4 | 90.9 | 143% |
| Example(257) | compound(3-50) | 5.4 | 6.8 | 300.0 | 4.4 | 143.3 | 225% |
| Example(258) | compound(3-51) | 5.6 | 7.2 | 300.0 | 4.1 | 106.4 | 167% |
| Example(259) | compound(3-52) | 4.9 | 8.6 | 300.0 | 3.5 | 100.6 | 158% |
| Example(260) | compound(3-53) | 5.8 | 7.5 | 300.0 | 4.0 | 90.9 | 143% |
| Example(261) | compound(3-54) | 5.0 | 5.6 | 300.0 | 5.4 | 94.6 | 149% |
| Example(262) | compound(3-55) | 4.6 | 8.3 | 300.0 | 3.6 | 144.4 | 227% |
| Example(263) | compound(3-56) | 4.2 | 5.7 | 300.0 | 5.3 | 99.7 | 157% |
| Example(264) | compound(3-57) | 5.7 | 7.0 | 300.0 | 4.3 | 113.3 | 178% |
| Example(265) | compound(3-58) | 5.7 | 6.0 | 300.0 | 5.0 | 93.5 | 147% |
| Example(266) | compound(3-59) | 4.1 | 6.8 | 300.0 | 4.4 | 145.3 | 228% |
| Example(267) | compound(3-60) | 4.1 | 8.0 | 300.0 | 3.8 | 126.9 | 199% |
| Example(268) | compound(3-61) | 5.2 | 8.0 | 300.0 | 3.8 | 113.2 | 178% |
| Example(269) | compound(3-62) | 4.8 | 8.0 | 300.0 | 3.7 | 108.7 | 171% |
| Example(270) | compound(3-63) | 5.1 | 6.0 | 300.0 | 5.0 | 136.7 | 215% |
| Example(271) | compound(3-64) | 4.3 | 5.3 | 300.0 | 5.7 | 110.6 | 174% |
| Example(272) | compound(3-65) | 4.8 | 9.6 | 300.0 | 3.1 | 92.4 | 145% |
| Example(273) | compound(3-66) | 4.0 | 7.2 | 300.0 | 4.2 | 119.0 | 187% |
| Example(274) | compound(3-67) | 4.6 | 7.5 | 300.0 | 4.0 | 91.9 | 144% |
| Example(275) | compound(3-68) | 5.0 | 6.9 | 300.0 | 4.3 | 138.9 | 218% |
| Example(276) | compound(3-69) | 4.3 | 6.3 | 300.0 | 4.8 | 100.2 | 157% |
| Example(277) | compound(3-70) | 4.5 | 6.0 | 300.0 | 5.0 | 118.8 | 187% |
| Example(278) | compound(3-71) | 5.6 | 6.4 | 300.0 | 4.7 | 109.1 | 171% |
| Example(279) | compound(3-72) | 5.1 | 6.9 | 300.0 | 4.3 | 108.4 | 170% |
| Example(280) | compound(3-73) | 5.9 | 6.8 | 300.0 | 4.4 | 91.1 | 143% |
| Example(281) | compound(3-74) | 4.4 | 6.1 | 300.0 | 4.9 | 91.2 | 143% |
| Example(282) | compound(3-75) | 4.9 | 5.8 | 300.0 | 5.2 | 135.8 | 213% |
| Example(283) | compound(3-76) | 5.6 | 5.3 | 300.0 | 5.7 | 103.3 | 162% |
| Example(284) | compound(3-77) | 5.0 | 7.6 | 300.0 | 4.0 | 138.3 | 217% |
| Example(285) | compound(3-78) | 4.7 | 7.9 | 300.0 | 3.8 | 149.7 | 235% |
| Example(286) | compound(3-79) | 5.2 | 6.9 | 300.0 | 4.3 | 121.8 | 191% |
| Example(287) | compound(3-80) | 5.4 | 5.9 | 300.0 | 5.0 | 94.3 | 148% |
| Example(288) | compound(3-81) | 4.1 | 6.2 | 300.0 | 4.8 | 131.1 | 206% |
| Example(289) | compound(3-82) | 4.7 | 8.1 | 300.0 | 3.7 | 95.7 | 150% |
| Example(290) | compound(3-83) | 5.7 | 6.4 | 300.0 | 4.7 | 122.3 | 192% |
| Example(291) | compound(3-84) | 5.7 | 7.2 | 300.0 | 4.2 | 136.3 | 214% |
| Example(292) | compound(3-85) | 4.6 | 8.9 | 300.0 | 3.4 | 132.5 | 208% |
| Example(293) | compound(3-86) | 5.0 | 9.8 | 300.0 | 3.1 | 112.0 | 176% |
| Example(294) | compound(3-87) | 5.5 | 7.6 | 300.0 | 3.9 | 90.6 | 142% |
| Example(295) | compound(3-88) | 4.5 | 6.0 | 300.0 | 5.0 | 131.9 | 207% |
| Example(296) | compound(3-89) | 4.3 | 9.6 | 300.0 | 3.1 | 113.2 | 178% |
| Example(297) | compound(3-90) | 5.5 | 7.3 | 300.0 | 4.1 | 133.9 | 210% |
| Example(298) | compound(3-91) | 4.3 | 6.8 | 300.0 | 4.4 | 98.5 | 155% |
| Example(299) | compound(3-92) | 5.7 | 5.3 | 300.0 | 5.7 | 100.8 | 158% |
| Example(300) | compound(3-93) | 5.8 | 7.3 | 300.0 | 4.1 | 117.5 | 185% |

TABLE 3-continued

| | Compound | driving voltage | Current ($mA/cm^2$) | Luminance ($cd/m^2$) | Efficiency (cd/A) | T(90) | With respect to NPB (%) |
|---|---|---|---|---|---|---|---|
| Example(301) | compound(3-94) | 4.6 | 8.3 | 300.0 | 3.6 | 95.7 | 150% |
| Example(302) | compound(3-95) | 4.1 | 5.7 | 300.0 | 5.3 | 134.2 | 211% |
| Example(303) | compound(3-96) | 4.6 | 9.1 | 300.0 | 3.3 | 128.1 | 201% |
| Example(304) | compound(3-97) | 4.6 | 6.8 | 300.0 | 4.4 | 148.6 | 234% |
| Example(305) | compound(3-98) | 4.8 | 6.1 | 300.0 | 4.9 | 127.3 | 200% |
| Example(306) | compound(3-99) | 4.1 | 7.2 | 300.0 | 4.2 | 96.4 | 151% |
| Example(307) | compound(3-100) | 5.5 | 7.9 | 300.0 | 3.8 | 90.6 | 142% |
| Example(308) | compound(3-101) | 5.1 | 9.2 | 300.0 | 3.3 | 146.1 | 230% |
| Example(309) | compound(3-102) | 4.0 | 8.1 | 300.0 | 3.7 | 95.9 | 151% |
| Example(310) | compound(3-103) | 4.5 | 5.3 | 300.0 | 5.6 | 126.0 | 198% |
| Example(311) | compound(3-104) | 4.7 | 7.3 | 300.0 | 4.1 | 147.2 | 231% |
| Example(312) | compound(3-105) | 5.8 | 8.9 | 300.0 | 3.4 | 91.5 | 144% |
| Example(313) | compound(3-106) | 5.5 | 6.9 | 300.0 | 4.4 | 104.0 | 163% |
| Example(314) | compound(3-107) | 4.6 | 6.4 | 300.0 | 4.7 | 130.8 | 206% |
| Example(315) | compound(3-108) | 5.3 | 6.6 | 300.0 | 4.5 | 105.7 | 166% |
| Example(316) | compound(3-109) | 4.6 | 9.9 | 300.0 | 3.0 | 96.8 | 152% |
| Example(317) | compound(3-110) | 4.4 | 7.7 | 300.0 | 3.9 | 124.2 | 195% |
| Example(318) | compound(3-111) | 4.9 | 8.0 | 300.0 | 3.8 | 95.7 | 150% |
| Example(319) | compound(3-112) | 5.2 | 5.5 | 300.0 | 5.4 | 126.7 | 199% |
| Example(320) | compound(3-113) | 4.7 | 6.1 | 300.0 | 4.9 | 98.0 | 154% |
| Example(321) | compound(3-114) | 5.8 | 7.9 | 300.0 | 3.8 | 92.8 | 146% |
| Example(322) | compound(3-115) | 5.6 | 8.3 | 300.0 | 3.6 | 102.6 | 161% |
| Example(323) | compound(3-116) | 4.7 | 6.6 | 300.0 | 4.5 | 149.1 | 234% |
| Example(324) | compound(3-117) | 4.9 | 7.3 | 300.0 | 4.1 | 142.4 | 224% |
| Example(325) | compound(3-118) | 4.7 | 7.1 | 300.0 | 4.2 | 131.6 | 207% |
| Example(326) | compound(3-119) | 5.6 | 6.5 | 300.0 | 4.6 | 143.7 | 226% |
| Example(327) | compound(3-120) | 4.7 | 7.9 | 300.0 | 3.8 | 117.3 | 184% |
| Example(328) | compound(3-121) | 5.5 | 8.9 | 300.0 | 3.4 | 98.9 | 155% |
| Example(329) | compound(3-122) | 5.6 | 5.6 | 300.0 | 5.3 | 132.2 | 208% |
| Example(330) | compound(3-123) | 4.4 | 5.8 | 300.0 | 5.2 | 108.4 | 170% |
| Example(331) | compound(3-124) | 5.7 | 5.7 | 300.0 | 5.3 | 140.5 | 221% |
| Example(332) | compound(3-125) | 4.6 | 9.1 | 300.0 | 3.3 | 116.1 | 182% |
| Example(333) | compound(3-126) | 5.1 | 6.2 | 300.0 | 4.8 | 100.4 | 158% |
| Example(334) | compound(3-127) | 4.0 | 9.5 | 300.0 | 3.2 | 143.5 | 225% |
| Example(335) | compound(3-128) | 5.0 | 7.4 | 300.0 | 4.0 | 129.5 | 204% |
| Example(336) | compound(3-129) | 4.7 | 6.0 | 300.0 | 5.0 | 126.1 | 198% |
| Example(337) | compound(3-130) | 5.0 | 7.5 | 300.0 | 4.0 | 146.0 | 229% |
| Example(338) | compound(3-131) | 4.7 | 6.2 | 300.0 | 4.8 | 101.9 | 160% |
| Example(339) | compound(3-132) | 4.4 | 5.3 | 300.0 | 5.6 | 110.8 | 174% |
| Example(340) | compound(3-133) | 4.9 | 6.3 | 300.0 | 4.7 | 128.3 | 202% |
| Example(341) | compound(3-134) | 4.7 | 6.2 | 300.0 | 4.8 | 130.3 | 205% |
| Example(342) | compound(3-135) | 4.4 | 5.8 | 300.0 | 5.2 | 93.3 | 147% |
| Example(343) | compound(3-136) | 4.0 | 7.5 | 300.0 | 4.0 | 93.4 | 147% |
| Example(344) | compound(3-137) | 5.7 | 8.0 | 300.0 | 3.8 | 110.8 | 174% |
| Example(345) | compound(3-138) | 5.4 | 5.3 | 300.0 | 5.6 | 130.0 | 204% |
| Example(346) | compound(3-139) | 5.2 | 9.9 | 300.0 | 3.0 | 128.6 | 202% |
| Example(347) | compound(3-140) | 5.7 | 5.9 | 300.0 | 5.1 | 128.8 | 202% |
| Example(348) | compound(3-141) | 5.2 | 6.8 | 300.0 | 4.4 | 106.4 | 167% |
| Example(349) | compound(3-142) | 4.1 | 6.5 | 300.0 | 4.6 | 100.6 | 158% |
| Example(350) | compound(3-143) | 4.5 | 6.3 | 300.0 | 4.7 | 115.2 | 181% |
| Example(351) | compound(3-144) | 4.8 | 5.6 | 300.0 | 5.4 | 145.5 | 229% |
| Example(352) | compound(3-145) | 5.4 | 6.4 | 300.0 | 4.7 | 144.0 | 226% |
| Example(353) | compound(3-146) | 4.6 | 8.9 | 300.0 | 3.4 | 126.3 | 199% |
| Example(354) | compound(3-147) | 5.1 | 5.5 | 300.0 | 5.5 | 143.9 | 226% |
| Example(355) | compound(3-148) | 4.8 | 7.9 | 300.0 | 3.8 | 138.8 | 218% |
| Example(356) | compound(3-149) | 4.1 | 8.6 | 300.0 | 3.5 | 111.2 | 175% |
| Example(357) | compound(3-150) | 5.7 | 8.9 | 300.0 | 3.4 | 138.1 | 217% |
| Example(358) | compound(3-151) | 5.1 | 7.5 | 300.0 | 4.0 | 142.3 | 224% |
| Example(359) | compound(3-152) | 5.3 | 8.0 | 300.0 | 3.8 | 128.7 | 202% |
| Example(360) | compound(3-153) | 4.8 | 7.7 | 300.0 | 3.9 | 102.5 | 161% |
| Example(361) | compound(3-154) | 5.7 | 9.0 | 300.0 | 3.3 | 122.1 | 192% |
| Example(362) | compound(3-155) | 4.7 | 6.1 | 300.0 | 4.9 | 102.9 | 162% |
| Example(363) | compound(3-156) | 5.6 | 8.7 | 300.0 | 3.4 | 98.6 | 155% |
| Example(364) | compound(3-157) | 5.2 | 8.4 | 300.0 | 3.6 | 101.2 | 159% |
| Example(365) | compound(3-158) | 4.4 | 5.3 | 300.0 | 5.7 | 147.5 | 232% |
| Example(366) | compound(3-159) | 4.5 | 5.9 | 300.0 | 5.1 | 112.6 | 177% |
| Example(367) | compound(3-160) | 5.3 | 7.6 | 300.0 | 3.9 | 95.5 | 150% |
| Example(368) | compound(3-161) | 4.2 | 7.5 | 300.0 | 4.0 | 127.4 | 200% |
| Example(369) | compound(3-162) | 5.9 | 7.2 | 300.0 | 4.2 | 131.3 | 206% |
| Example(370) | compound(3-163) | 5.9 | 7.8 | 300.0 | 3.9 | 131.4 | 206% |
| Example(371) | compound(3-164) | 5.3 | 5.5 | 300.0 | 5.4 | 97.4 | 153% |
| Example(372) | compound(3-165) | 5.3 | 9.5 | 300.0 | 3.2 | 142.9 | 225% |
| Example(373) | compound(3-166) | 4.7 | 7.6 | 300.0 | 3.9 | 121.2 | 190% |
| Example(374) | compound(3-167) | 4.4 | 5.6 | 300.0 | 5.4 | 103.8 | 163% |

TABLE 3-continued

| | Compound | driving voltage | Current ($mA/cm^2$) | Luminance ($cd/m^2$) | Efficiency (cd/A) | T(90) | With respect to NPB (%) |
|---|---|---|---|---|---|---|---|
| Example(375) | compound(3-168) | 5.5 | 7.3 | 300.0 | 4.1 | 99.0 | 156% |
| Example(376) | compound(3-169) | 5.4 | 5.3 | 300.0 | 5.6 | 139.6 | 219% |
| Example(377) | compound(3-170) | 4.3 | 6.6 | 300.0 | 4.5 | 121.9 | 192% |

The organic electro-luminescence elements fabricated according to Examples and Comparative Examples were applied with a forward bias DC voltage while an electro-luminescence (EL) characteristic was measured by PR-650 (photoresearch). As a result, T95 life span was measured by a life span measuring machine (mcscience) at a reference luminance of 300 $cd/m^2$. The measurement results of T95 are noted in Table 3 below. t,?

In a case where Examples are compared to Comparative Examples, compounds substituted with heavy hydrogen showed a reduction in the driving voltage. Also, they showed a life span of twice or more longer than those of Comparative Examples. From these characteristics, it can be found that the compounds from Examples can significantly increase the life span, the driving characteristic, and the manufacturing efficiency of an organic electro-luminescence element.

Specifically, in a case where Examples are compared to Comparative Examples (1) and (2), the compounds from Examples showed a reduction in the driving voltage. Also, they showed a life span of twice or more longer than those of Comparative Examples. Furthermore, in a case where Examples are compared to Comparative Examples (3) to (17), the compounds from Examples showed a reduction in the driving voltage, and showed a life span of twice or more longer than those of Comparative Examples.

From the Tables of Examples and Comparative Examples, it was determined that the inventive compound is significantly excellent in a luminous efficiency, a driving characteristic, and a life span. However, in the compounds in the Tables of Examples and Comparative Examples, the substituents may be substituted by other substitutes. Accordingly, it should be understood that this specification includes Examples and Comparative Examples in which substituents are substituted by other substitutes in the compounds in the Tables of Examples and Comparative Examples.

Although a preferred embodiment of the present invention has been described for illustrative purposes, those skilled in the art will appreciate that various modifications, additions and substitutions are possible, without departing from the scope and spirit of the invention as disclosed in the accompanying claims. Therefore, the embodiments disclosed in the present invention are intended to illustrate the scope of the technical idea of the present invention, and the scope of the present invention is not limited by the embodiment. The scope of the present invention shall be construed on the basis of the accompanying claims in such a manner that all of the technical ideas included within the scope equivalent to the claims belong to the present invention.

The invention claimed is:

1. A compound represented by one of Formulas below:

[Formula 1]

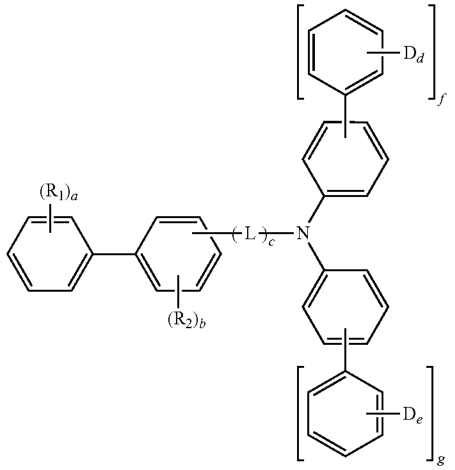

[Formula 2]

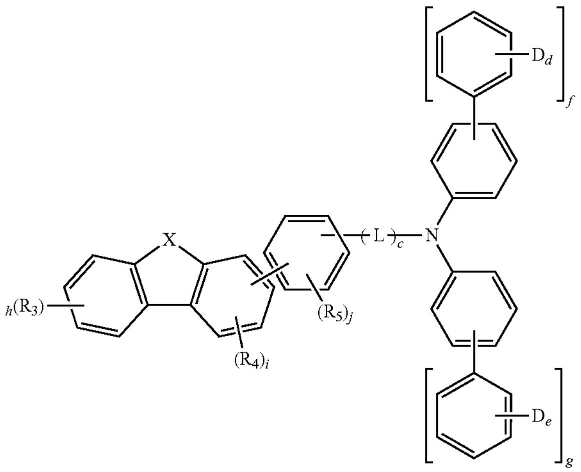

-continued

[Formula 3]

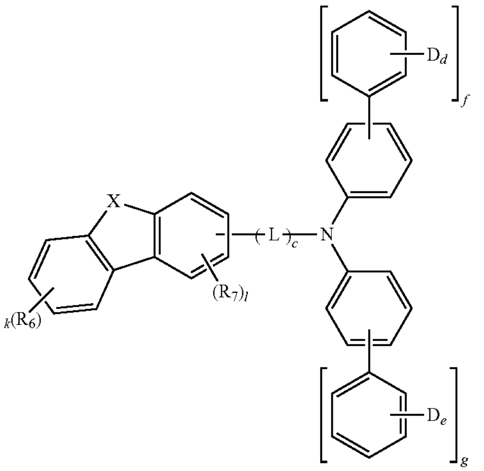

wherein Formulas above, (1) $R_1$~$R_7$ each are independently selected from the group consisting of an hydrogen atom; a $C_6$~$C_{60}$ aryl group substituted or unsubstituted with at least one substituent selected from the group including a halogen group, an amino group, a nitrile group, a nitro group, a $C_1$~$C_{20}$ alkyl group, a $C_1$~$C_{20}$ alkoxy group, a $C_1$~$C_{20}$ alkylamine group, a $C_1$~$C_{20}$ alkylthiophene group, a $C_6$~$C_{20}$ arylthiophene group, a $C_2$~$C_{20}$ alkenyl group, a $C_2$~$C_{20}$ alkynyl group, a $C_3$~$C_{20}$ cycloalkyl group, a $C_6$~$C_{60}$ aryl group, a $C_8$~$C_{20}$arylalkenyl group, a silane group, a boron group, a germanium group, and a $C_2$~$C_{20}$heterocyclic group; a substituted or unsubstituted $C_3$~$C_{60}$ heteroaryl group that is substituted or unsubstituted with at least one substituent selected from the group including a halogen group, a $C_1$~$C_{20}$ alkyl group, a $C_2$~$C_{20}$ alkenyl group, a $C_1$~$C_{20}$ alkoxy group, a $C_6$~$C_{20}$ arylamine group, a $C_6$~$C_{60}$ aryl group, a $C_7$~$C_{20}$ arylalkyl group, a $C_8$~$C_{20}$ arylalkenyl group, a $C_2$~$C_{20}$ heterocyclic group, a nitrile group, and an acetylenic group, and comprises at least one of O, N, and S; a $C_1$~$C_{30}$ alkoxy group substituted or unsubstituted with at least one substituent selected from the group including a halogen group, an amino group, a nitrile group, a nitro group, a $C_1$~$C_{20}$ alkyl group, a $C_2$~$C_{20}$ alkenyl group, a $C_1$~$C_{20}$ alkoxy group, a $C_3$~$C_{30}$ cycloalkyl group, a $C_2$~$C_{30}$ heterocycloalkyl group, a $C_6$~$C_{60}$ aryl group, and a $C_3$~$C_{60}$ heteroaryl group; a $C_6$~$C_{30}$ aryloxy group substituted or unsubstituted with at least one substituent selected from the group including a halogen group, an amino group, a nitrile group, a nitro group, a $C_1$~$C_{20}$ alkyl group, a $C_2$~$C_{20}$ alkenyl group, a $C_1$~$C_{20}$ alkoxy group, a $C_3$~$C_{30}$ cycloalkyl group, a $C_2$~$C_{30}$ heterocycloalkyl group, a $C_6$~$C_{60}$ aryl group, and a $C_3$~$C_{60}$ heteroaryl group; a $C_6$~$C_{60}$ arylamine group substituted or unsubstituted with at least one substituent selected from the group including a halogen group, an amino group, a nitrile group, a nitro group, a $C_1$~$C_{20}$ alkyl group, a $C_2$~$C_{20}$ alkenyl group, a $C_1$~$C_{20}$ alkoxy group, a $C_3$~$C_{30}$ cycloalkyl group, a $C_2$~$C_{30}$ heterocycloalkyl group, a $C_6$~$C_{60}$ aryl group, and a $C_3$~$C_{60}$ hetero aryl group; and a $C_1$~$C_{50}$ alkyl group substituted or unsubstituted with at least one substituent selected from the group including a $C_1$~$C_{20}$ alkyl group, a $C_2$~$C_{20}$ alkenyl group, a $C_1$~$C_{20}$ alkoxy group, a $C_6$~$C_{20}$ aryl group, a $C_7$~$C_{20}$ arylalkyl group, a $C_8$~$C_{20}$ arylalkenyl group, a $C_2$~$C_{20}$ heterocyclic group, a nitrile group, and an acetylenic group, $R_1$ and $R_7$ each may be combined with adjacent groups to form a saturated or unsaturated ring, (2) L is selected from the group consisting of a $C_6$~$C_{60}$ arylene group substituted or unsubstituted with at least one substituent selected from the group including a nitro group, a nitrile group, a halogen group, an alkyl group, an alkoxy group, and an amino group; and a $C_3$~$C_{60}$ hetero arylene group substituted or unsubstituted with at least one substituent selected from the group including a nitro group, a nitrile group, a halogen group, an alkyl group, an alkoxy group, and an amino group, (3) D represents deuterium or tritium, (4) X represents CR'R", NR', O, or S, wherein R' and R" each are independently selected from the group consisting of an hydrogen atom; a $C_1$~$C_{50}$ alkyl group substituted or unsubstituted with at least one substituent selected from the group including a $C_1$~$C_{20}$ alkyl group, a $C_2$~$C_{20}$ alkenyl group, a $C_1$~$C_{20}$ alkoxy group, a $C_6$~$C_{20}$ aryl group, a $C_7$~$C_{20}$ arylalkyl group, a $C_8$~$C_{20}$ arylalkenyl group, a $C_2$~$C_{20}$ heterocyclic group, a nitrile group, and an acetylenic group; a $C_6$~$C_{60}$ aryl group substituted or unsubstituted with at least one substituent selected from the group including a halogen group, an amino group, a nitrile group, a nitro group, a $C_1$~$C_{20}$ alkyl group, a $C_1$~$C_{20}$ alkoxy group, a $C_1$~C20 alkylamine group, a $C_1$~$C_{20}$ alkylthiophene group, a $C_6$~$C_{20}$ arylthiophene group, a $C_2$~$C_{20}$ alkenyl group, a $C_2$~$C_{20}$ alkynyl group, a C3~$C_{20}$ cycloalkyl group, a $C_6$~$C_{60}$ aryl group, a $C_8$~$C_{20}$ arylalkenyl group, a silane group, a boron group, a germanium group, and a $C_2$~$C_{20}$ heterocyclic group; and a substituted or unsubstituted $C_2$~$C_{60}$ heterocyclic group that is substituted or unsubstituted with at least one substituent selected from the group including a halogen group, a $C_1$~$C_{20}$ alkyl group, a $C_2$~$C_{20}$ alkenyl group, a $C_1$~$C_{20}$ alkoxy group, a $C_6$~$C_{20}$ arylamine group, a $C_6$~$C_{60}$ aryl group, a $C_7$~$C_{20}$ arylalkyl group, a $C_8$~$C_{20}$ arylalkenyl group, a $C_2$~$C_{20}$ heterocyclic group, a nitrile group, and an acetylenic group, and comprises at least one of O, N, and S, and (5) "a" represents an integer of 1 to 5, and "b, h, j and k" each represent an integer of 1 to 4, "c" represents an integer of 0 to 2, "d and e" each represent an integer of 0 to 5, "f and g" each represent an integer of 0 to 3, and "i and l" each represent an integer of 1 to 3, with the proviso that d+e≥1, and f+g≥1.

2. The compound as claimed in claim 1, which is one of the compounds below:

2-1
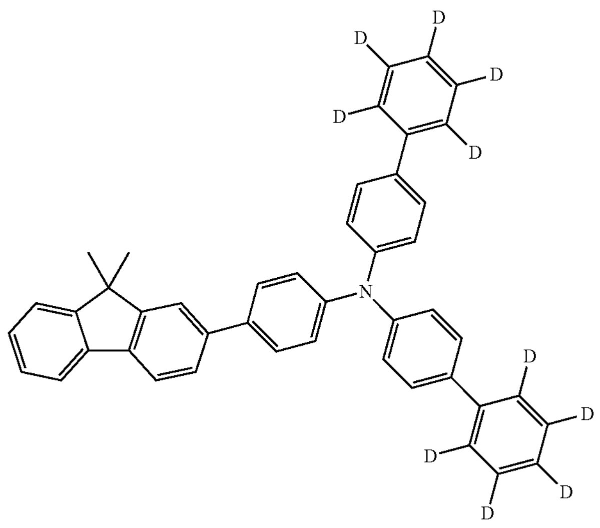
2-2
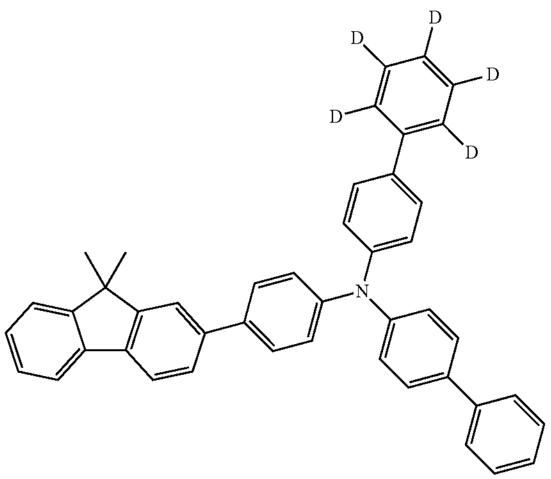
2-3
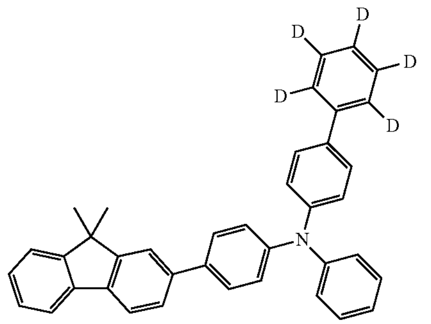
2-4
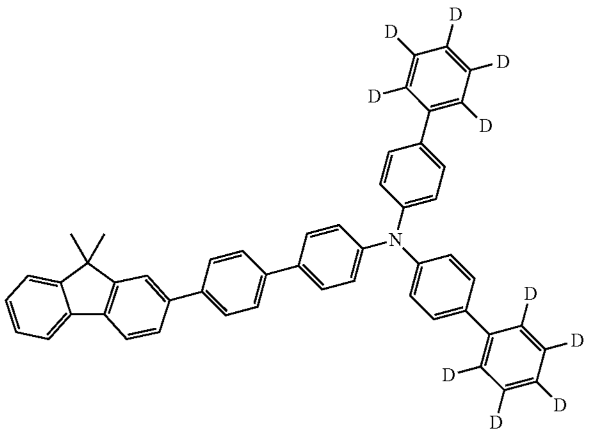
2-5
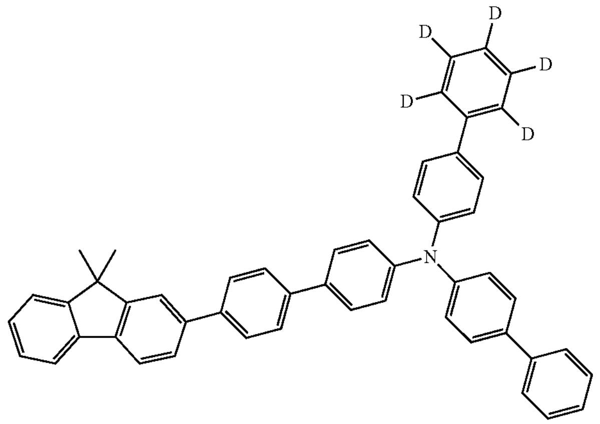
2-6
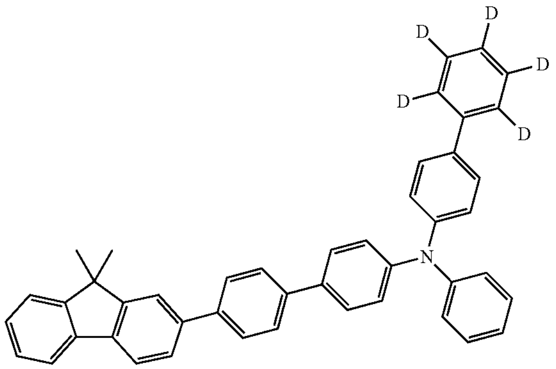

-continued
2-7
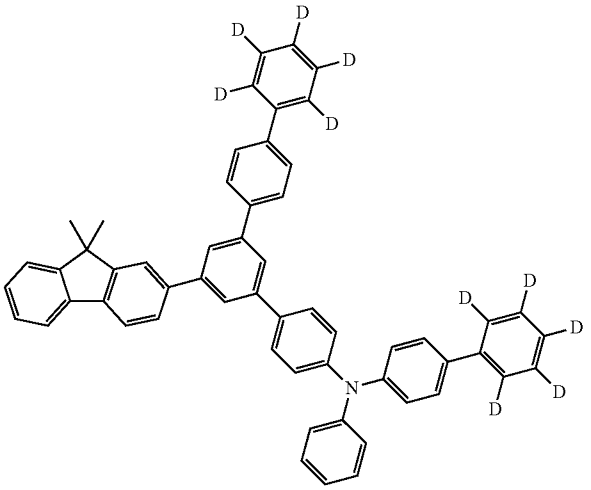
2-8
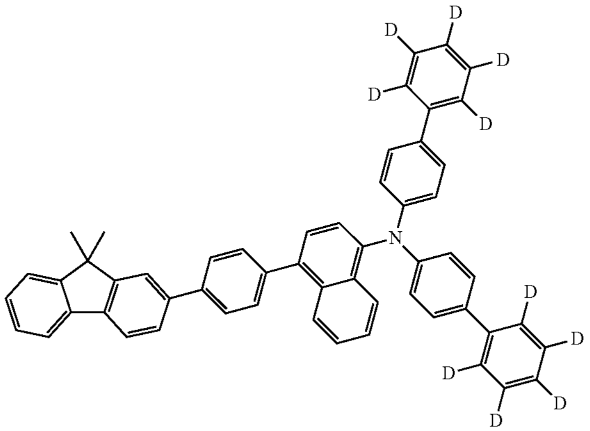
2-9
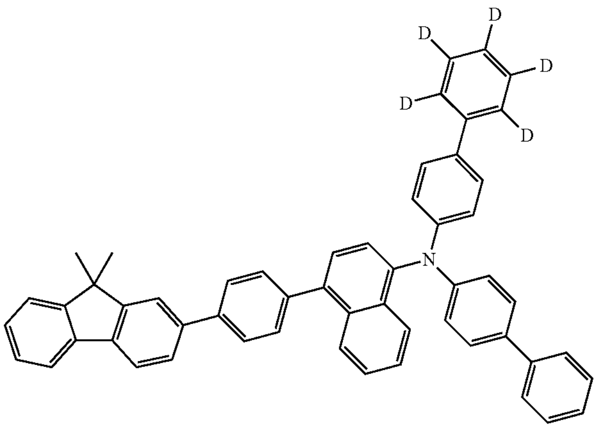
2-10
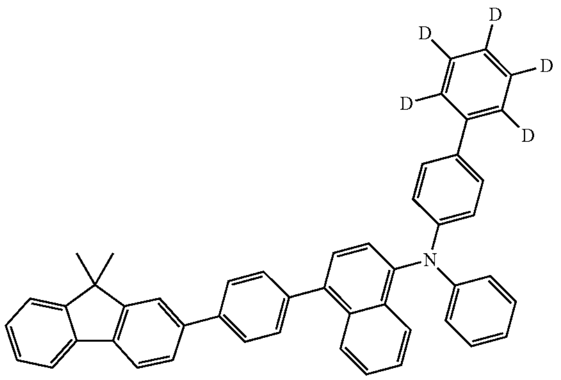
2-11
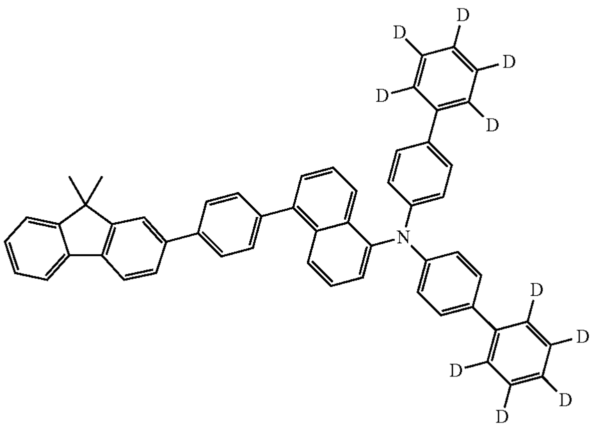
2-12
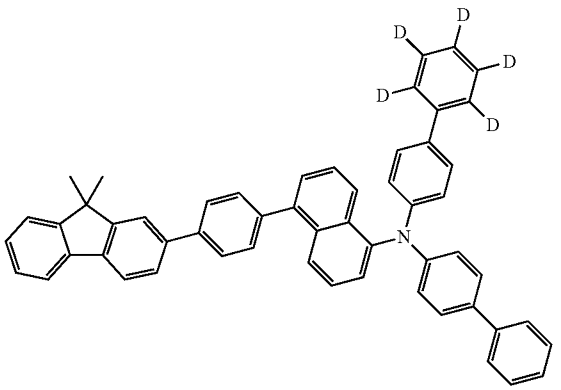

-continued
2-13
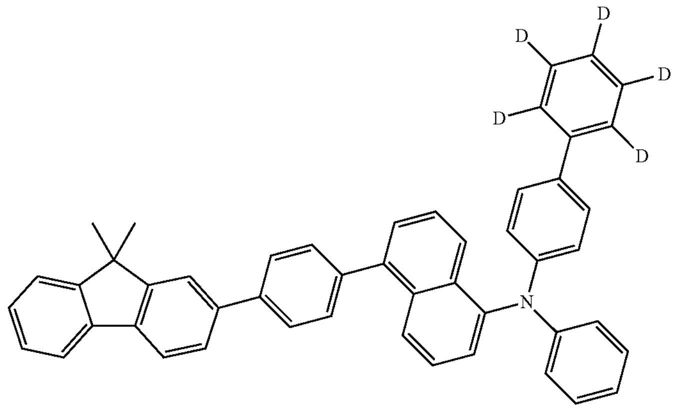
2-14
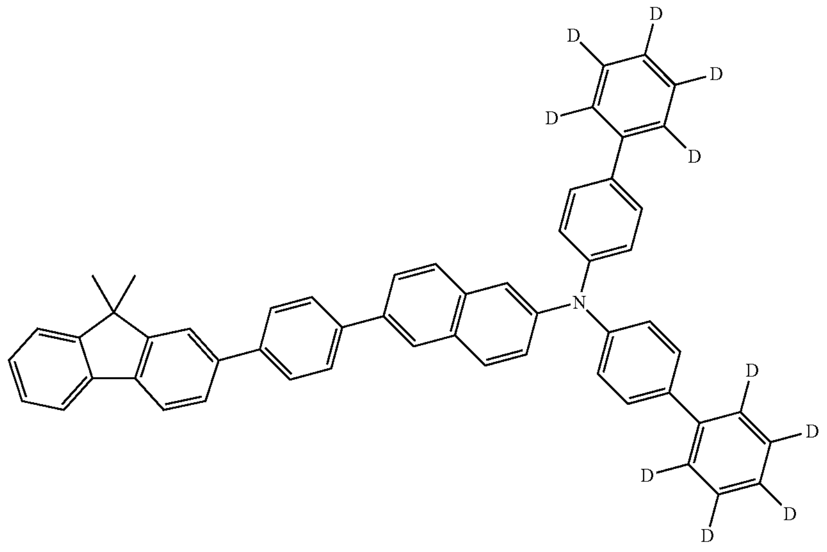
2-15
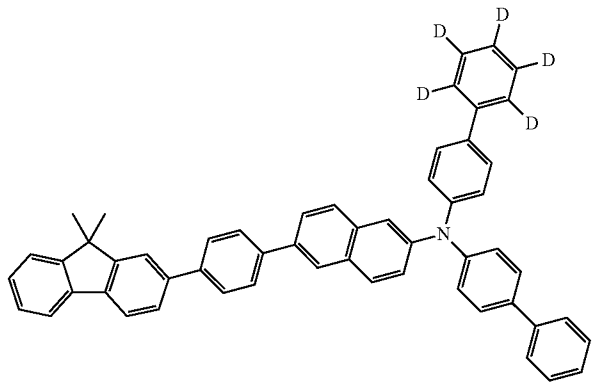
2-16
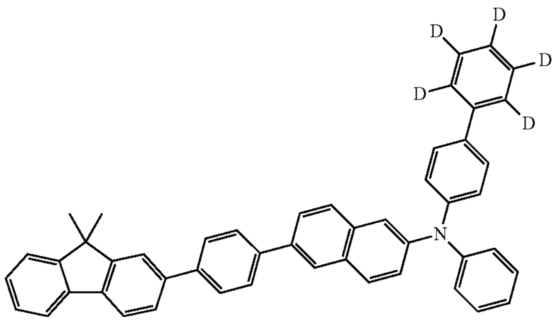

-continued
2-17
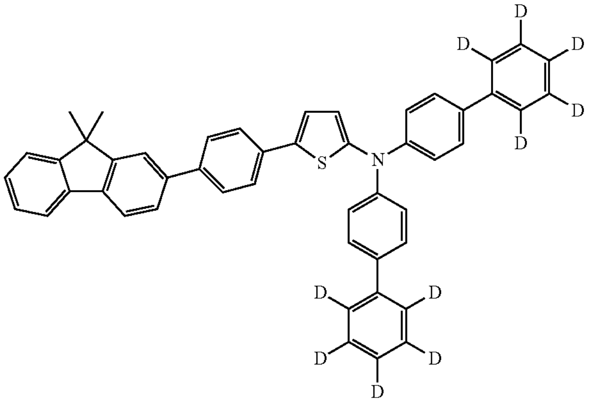
2-18
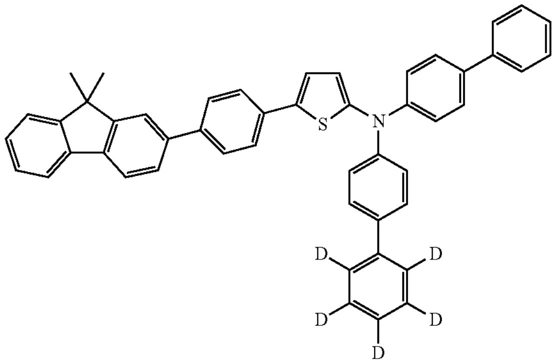
2-19
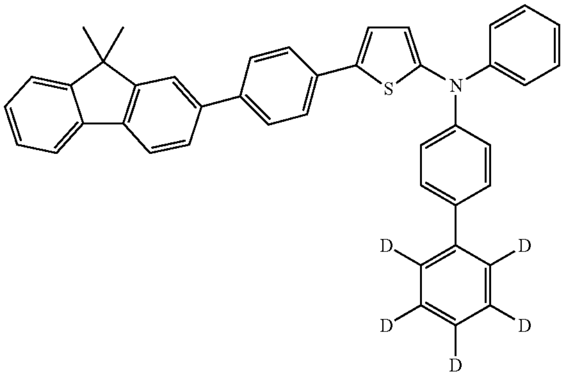
2-20
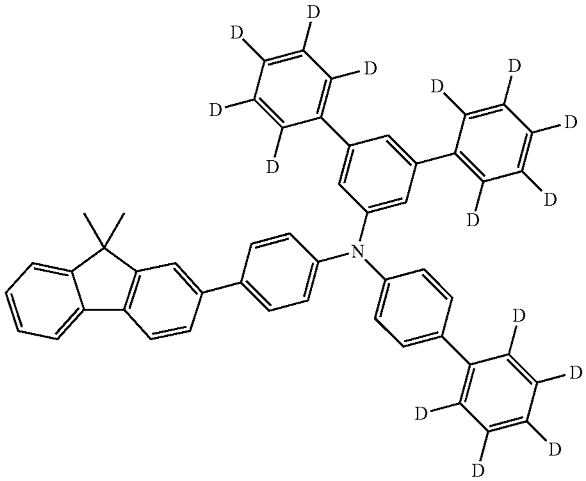
2-21
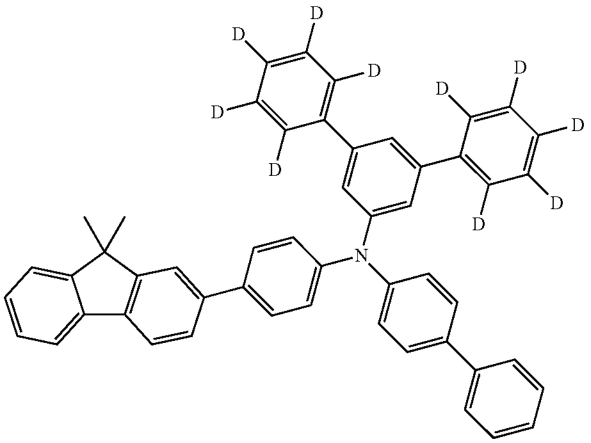
2-22
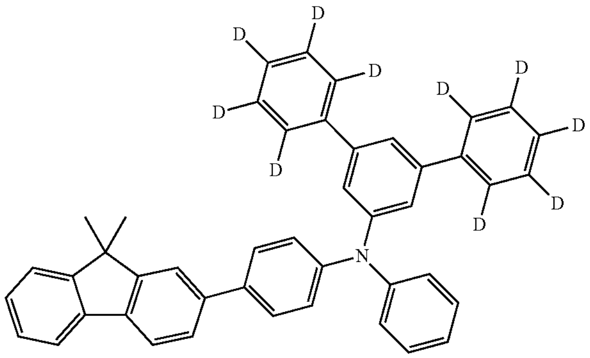

-continued
2-23
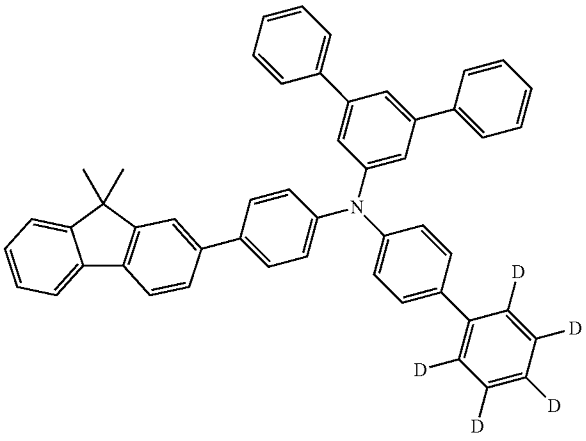
2-24
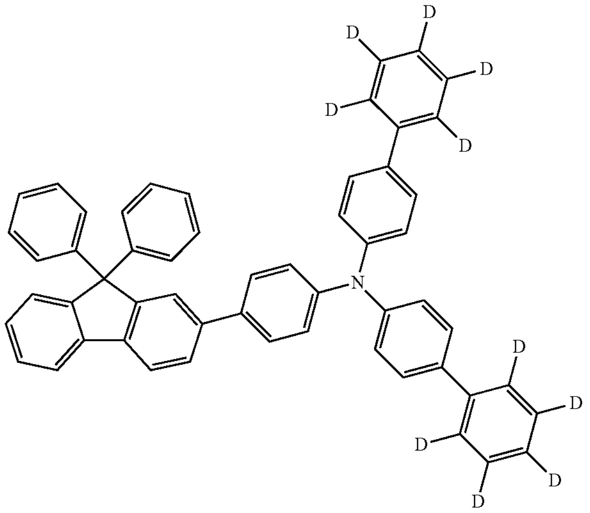
2-25
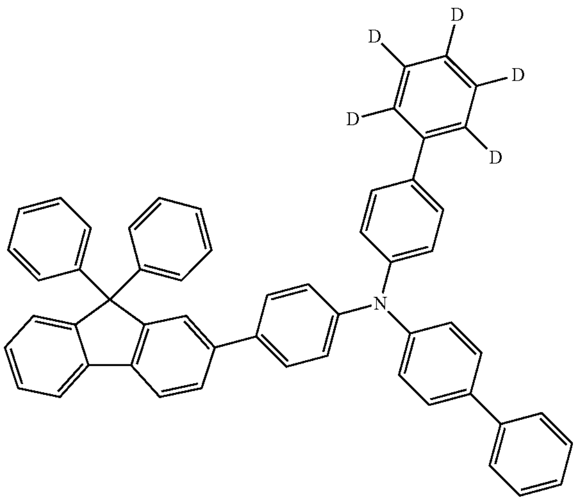
2-26
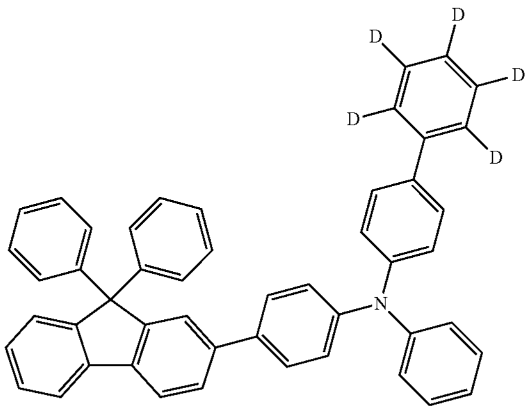
2-27
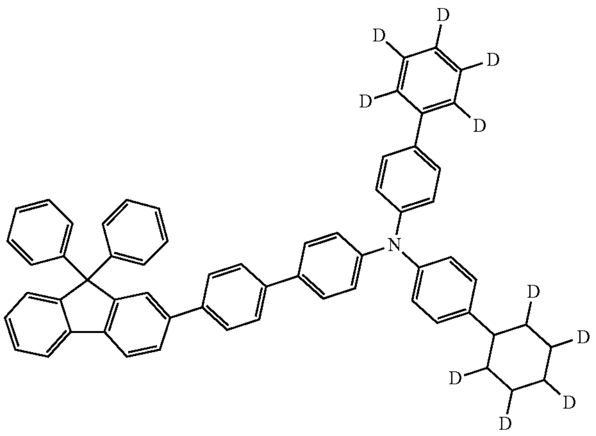
2-28
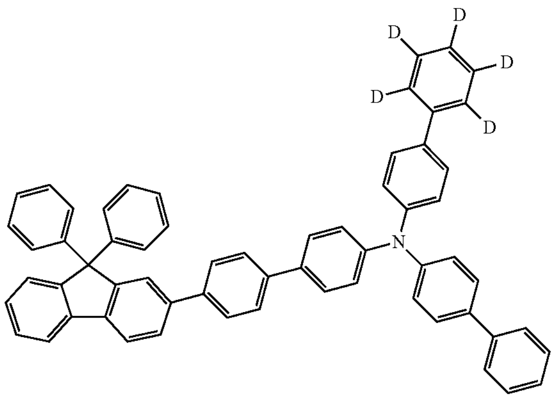

-continued
2-29
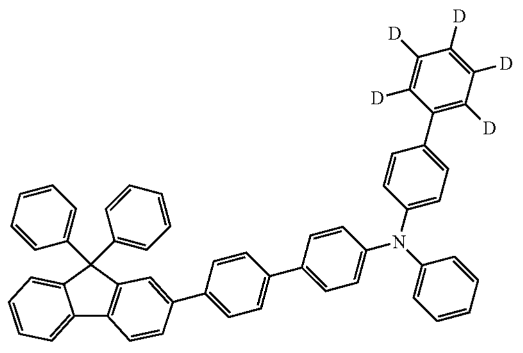
2-30
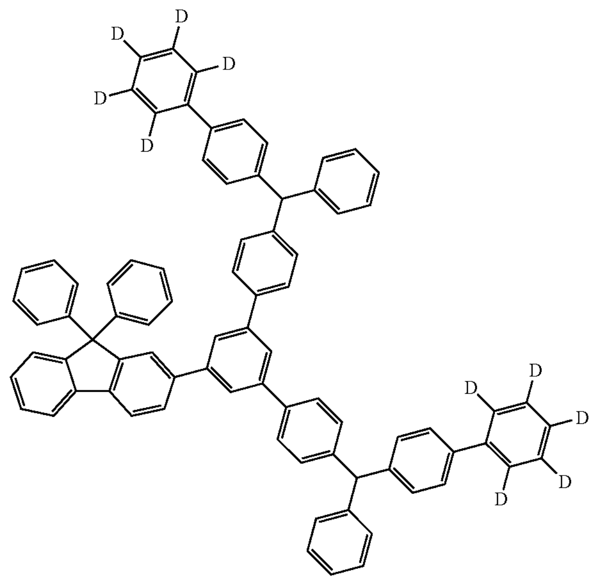
2-31
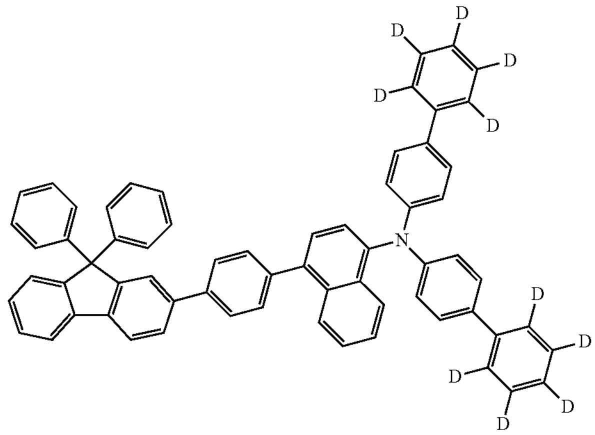
2-32
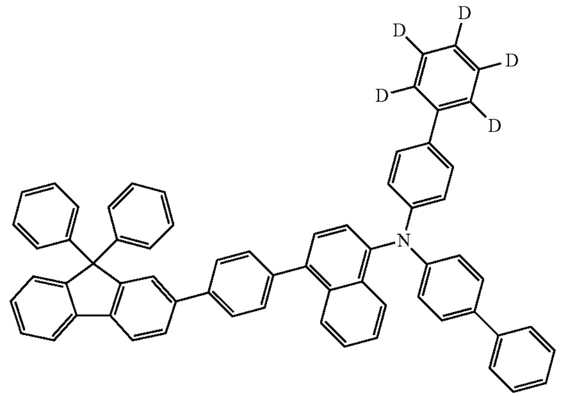
2-33
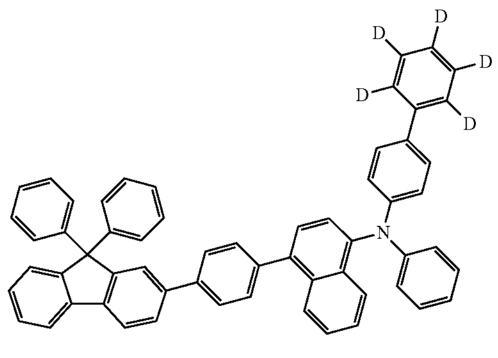
2-34
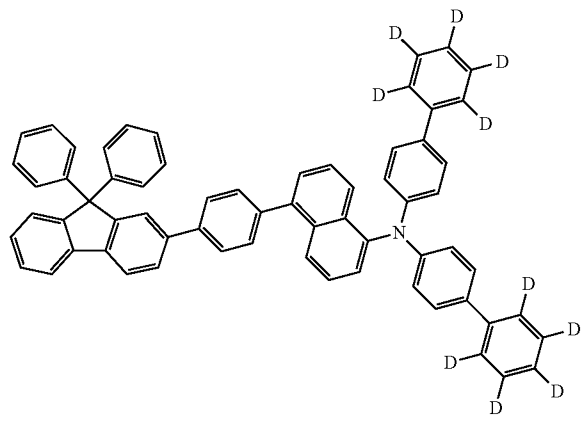

-continued
2-35
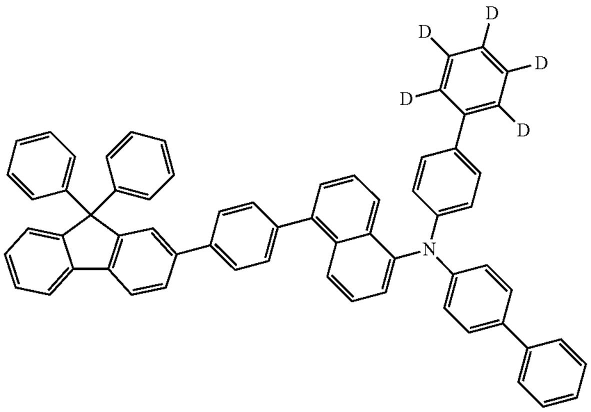
2-36
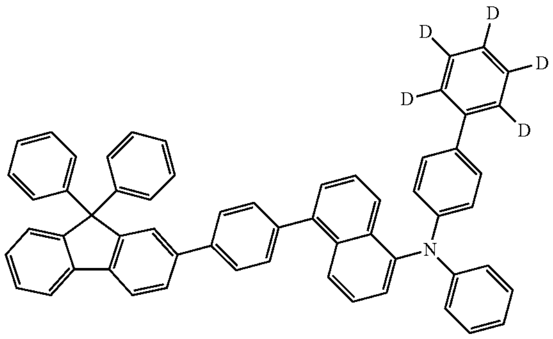
2-37
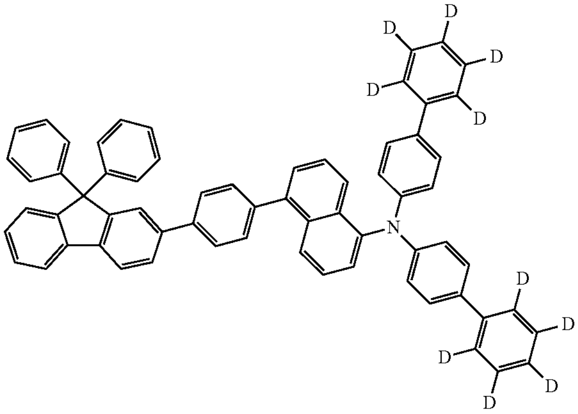
2-38
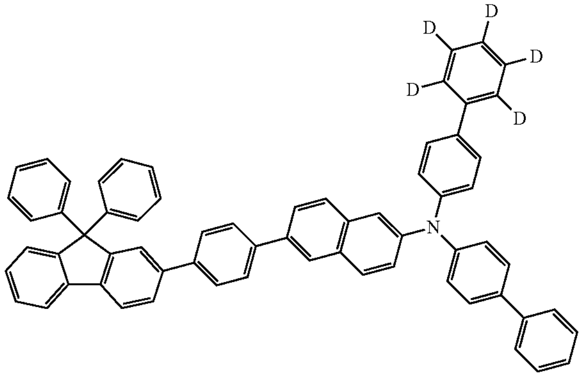
2-39
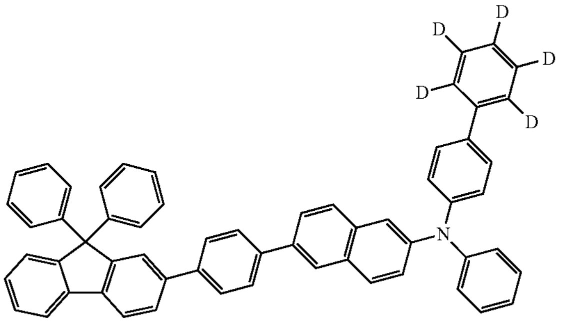
2-40
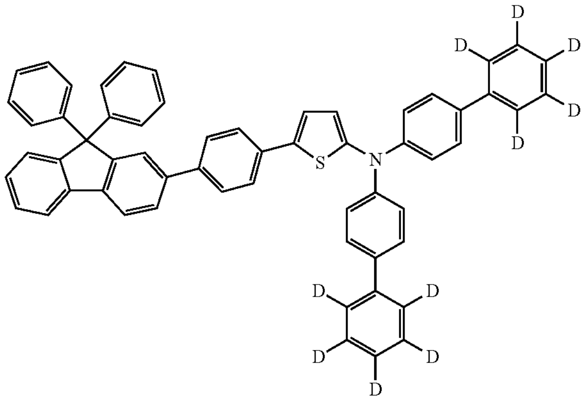

-continued
2-41
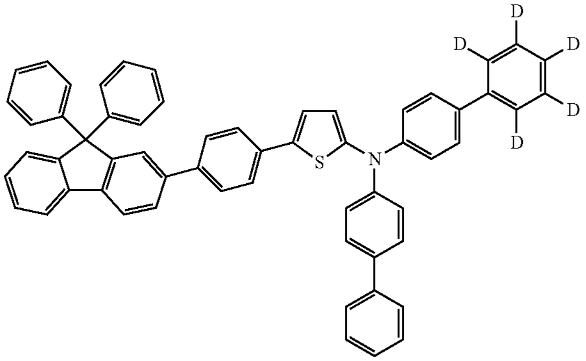
2-42
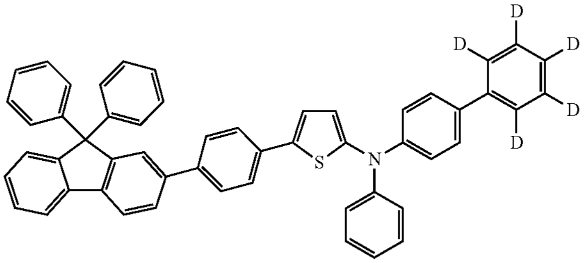
2-43
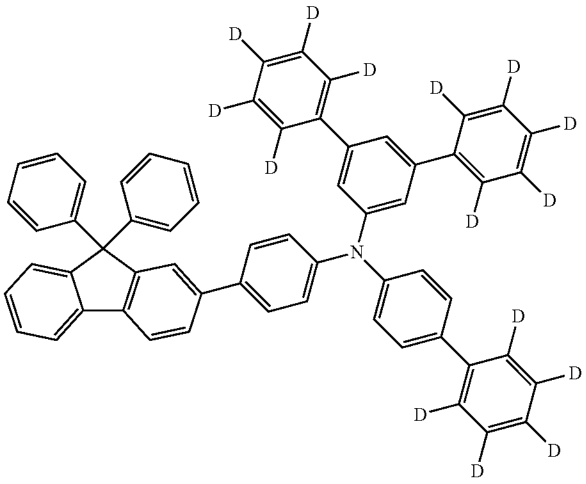
2-44
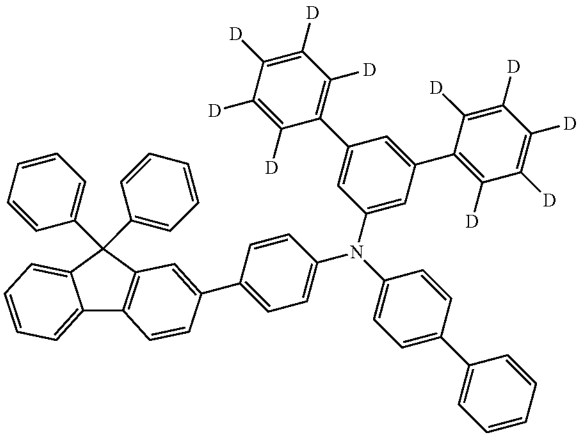
2-45
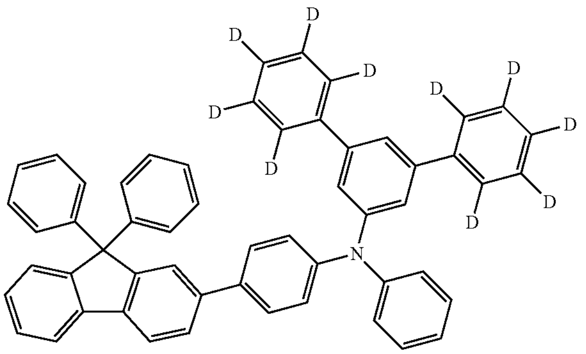
2-46
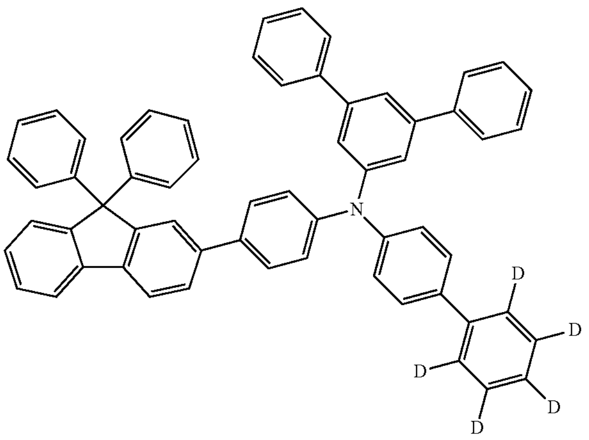

-continued
2-47
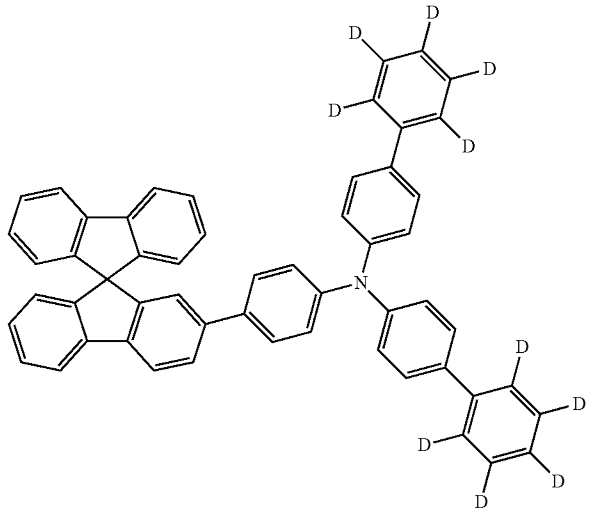
2-48
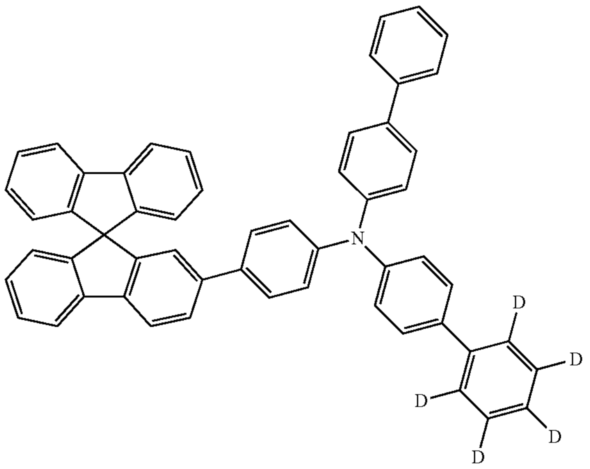
2-49
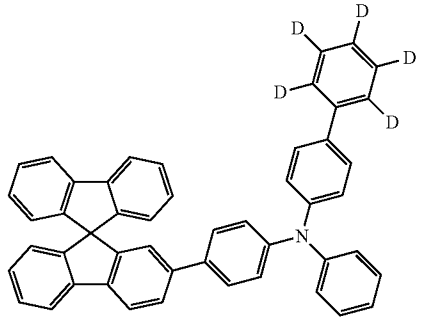
2-50
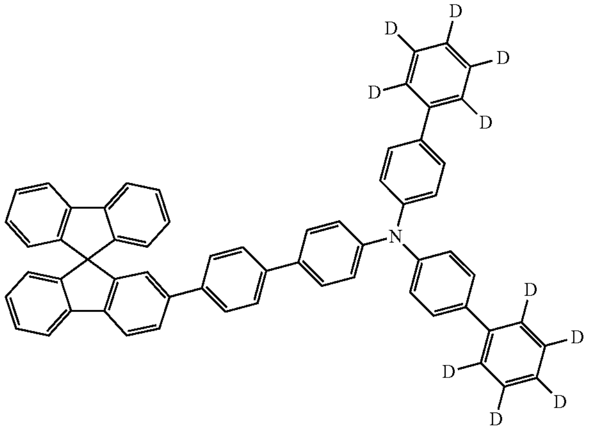
2-51
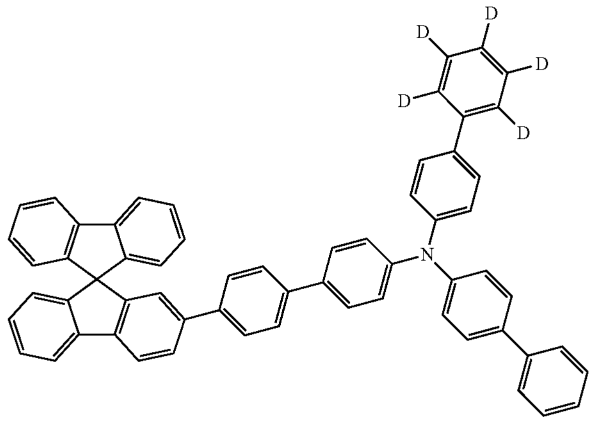
2-52
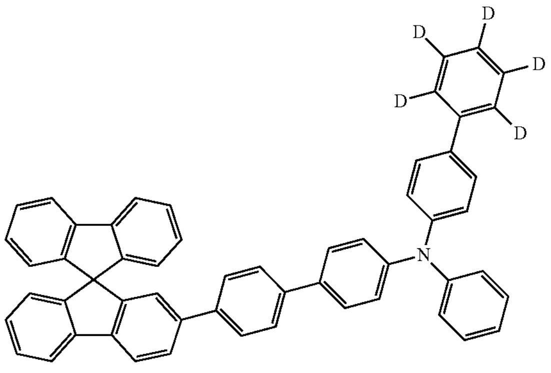

-continued
2-53
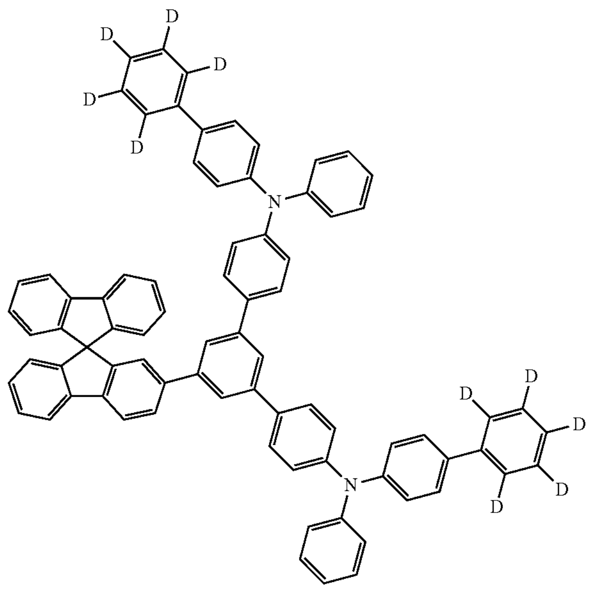
2-54
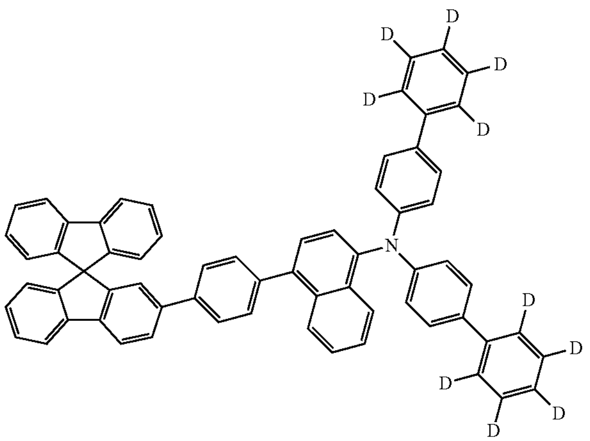
2-55
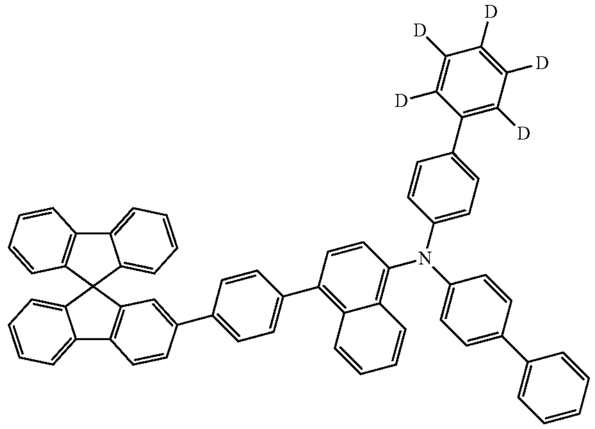
2-56
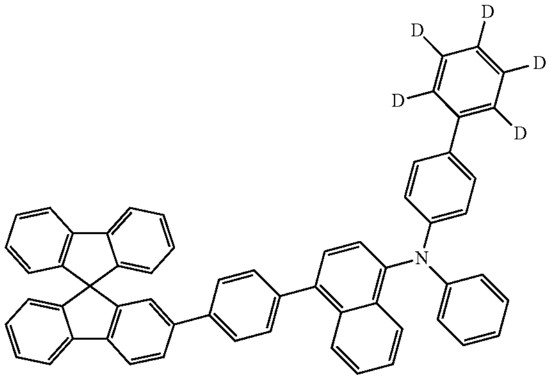
2-57
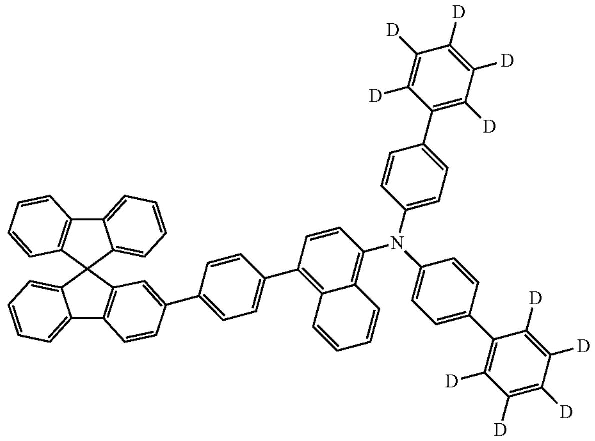
2-58
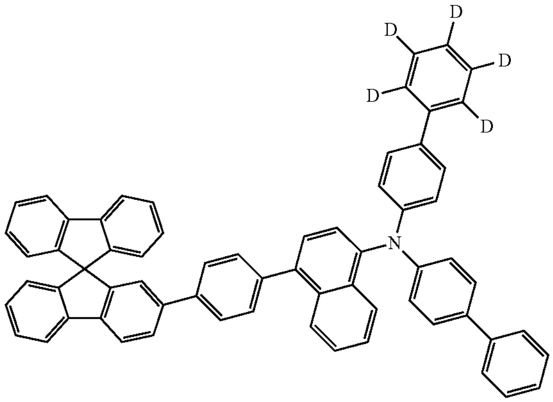

-continued
2-59
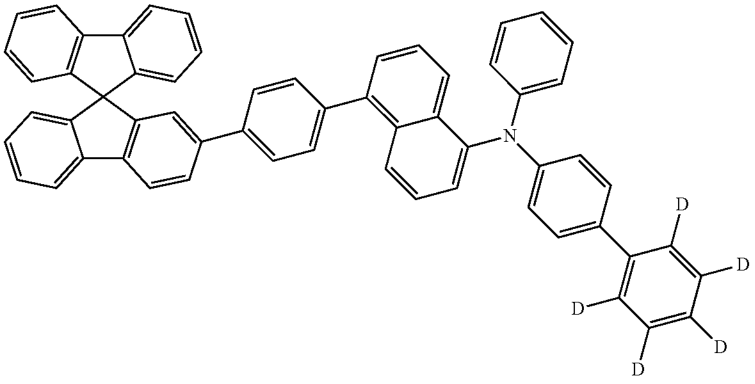
2-60
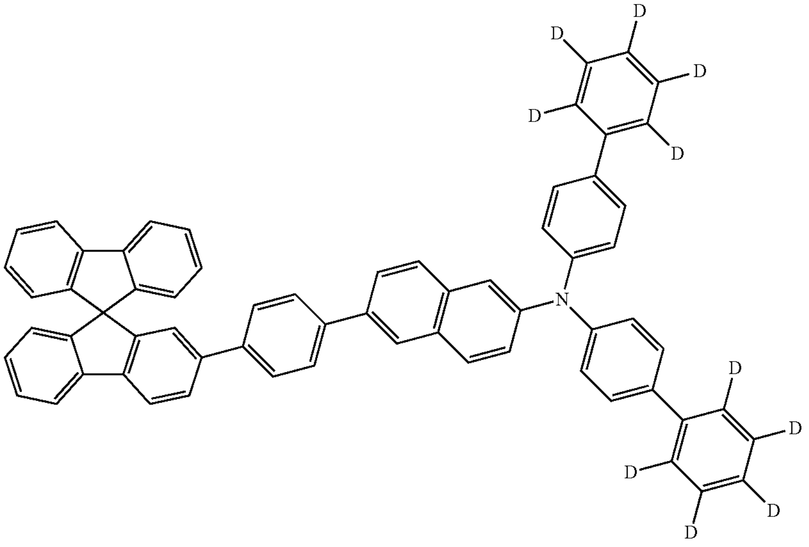
2-61
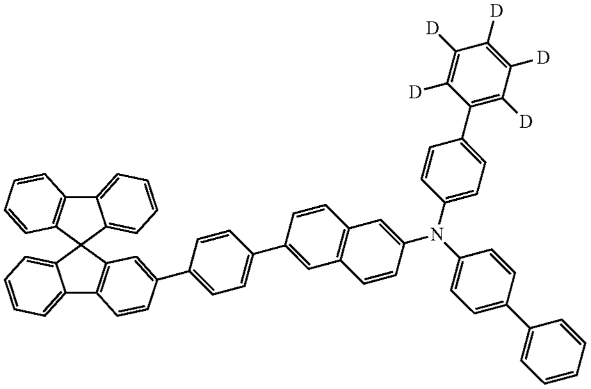
2-62
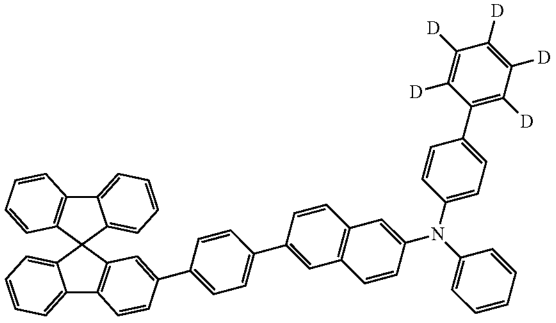

-continued
2-63
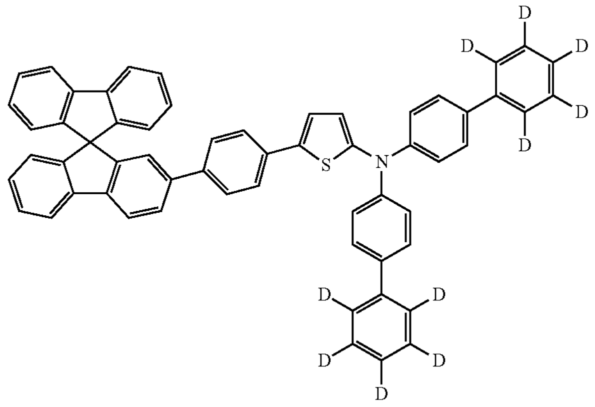
2-64
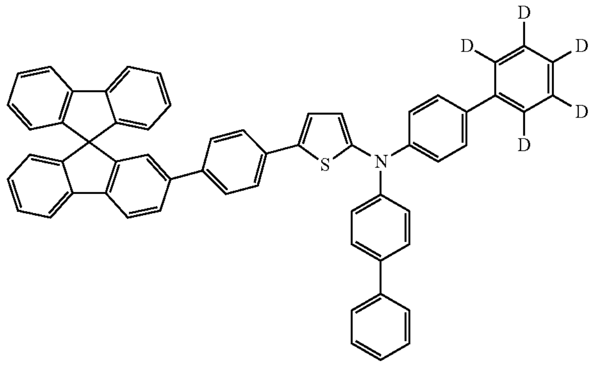
2-65
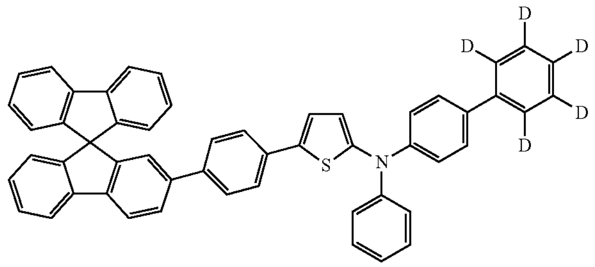
2-66
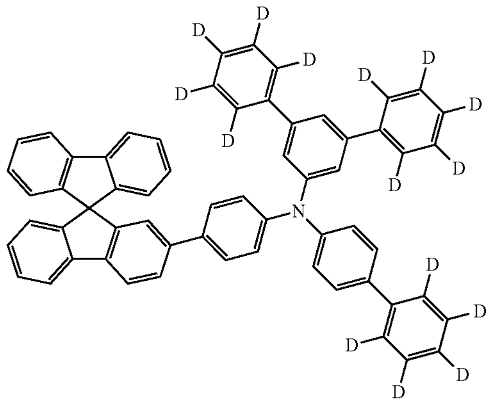
2-67
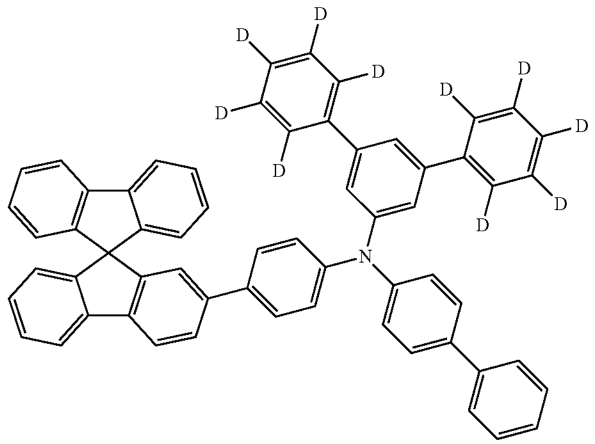
2-68
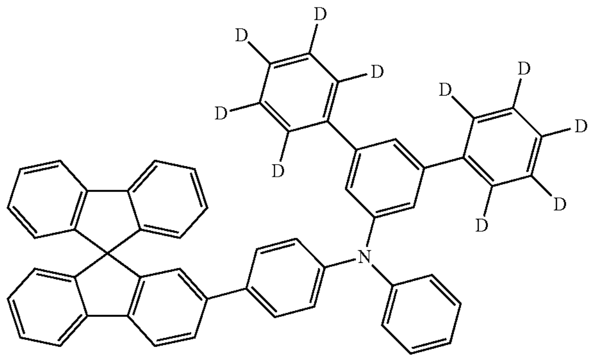

-continued
2-69
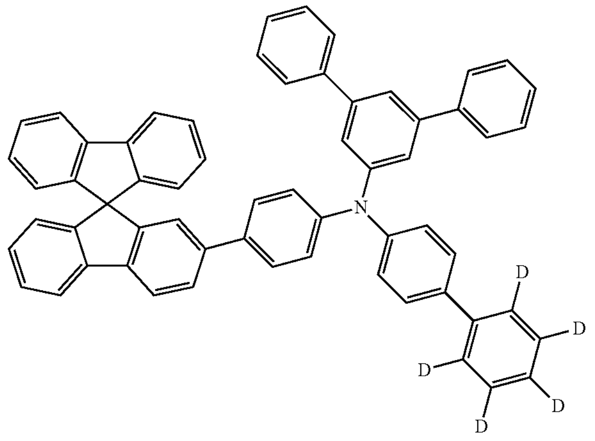
2-70
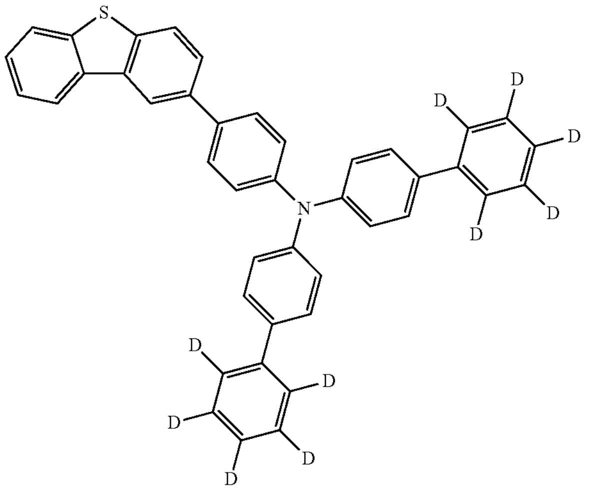
2-71
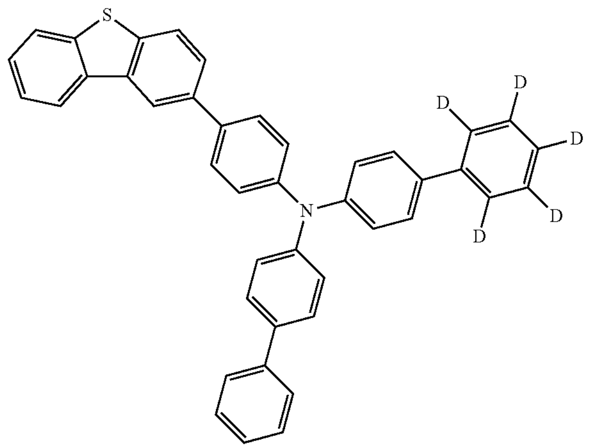
2-72
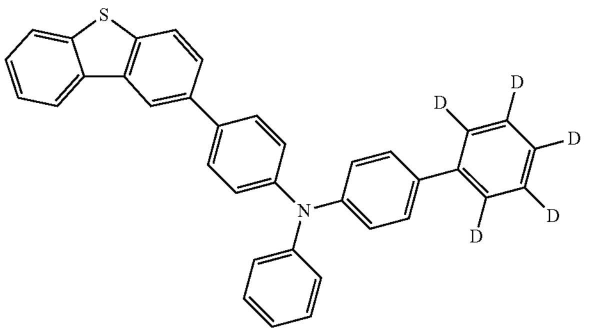
2-73
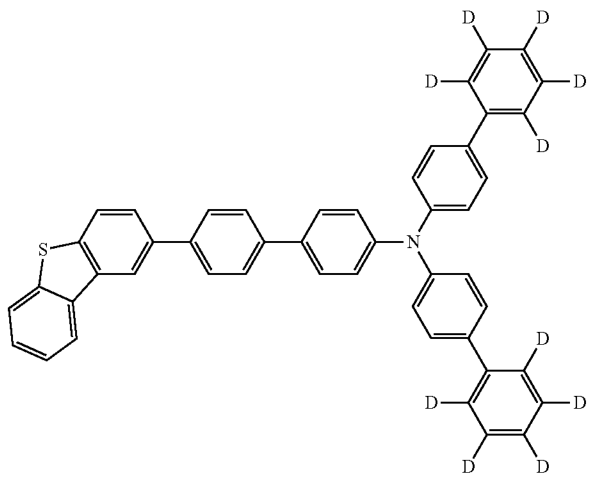
2-74
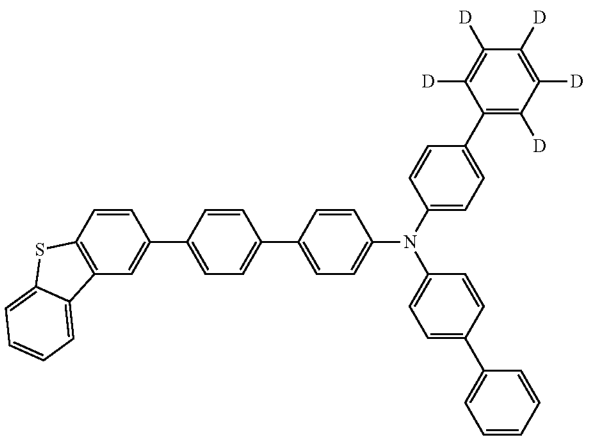

-continued
2-75
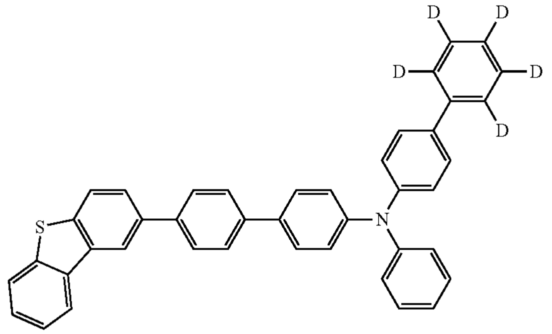
2-76
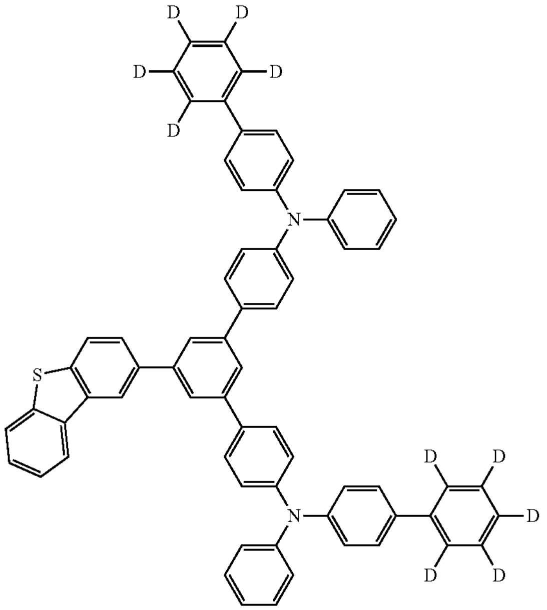
2-77
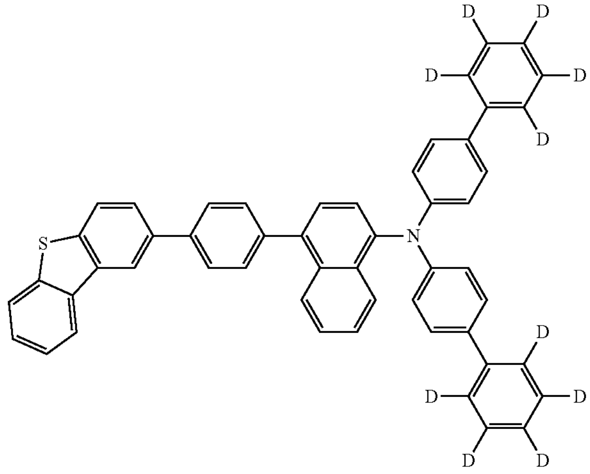
2-78
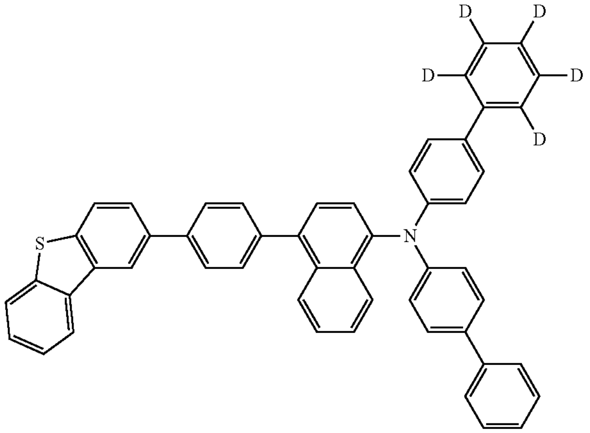
2-79
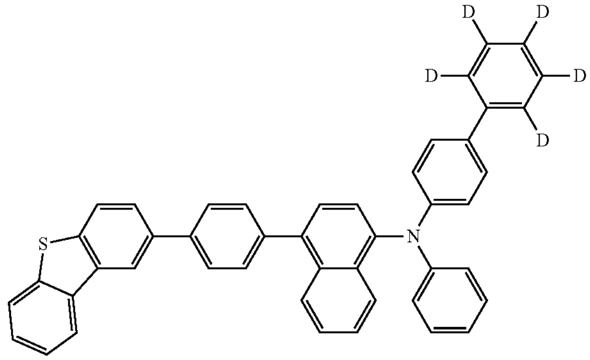
2-80
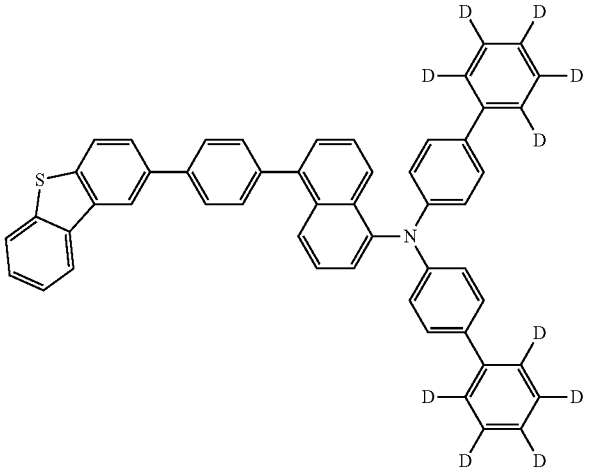

-continued
2-81
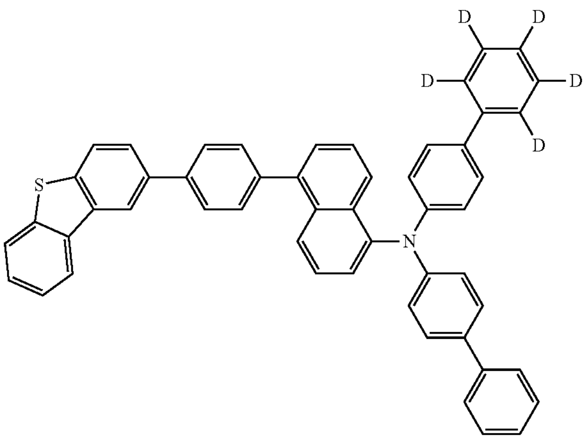
2-82
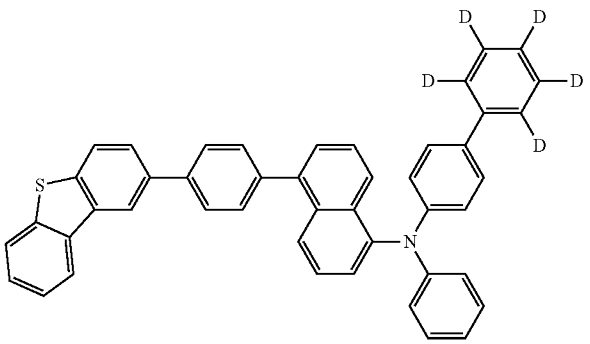
2-83
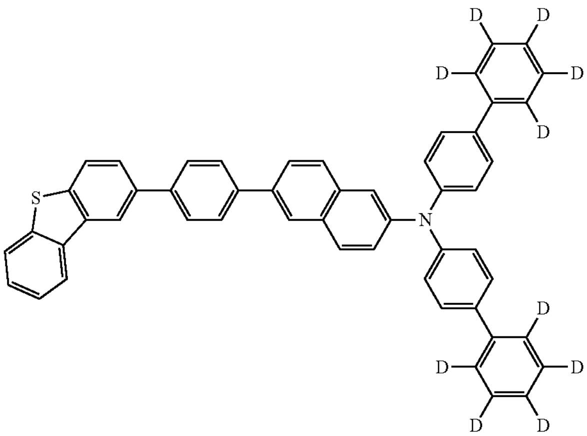
2-84
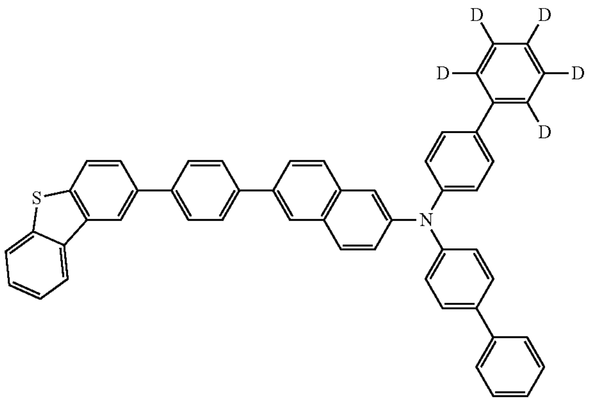
2-85
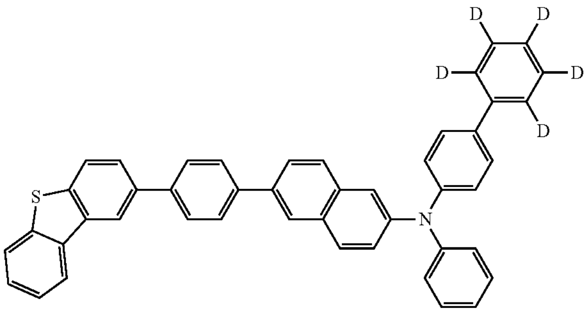
2-86
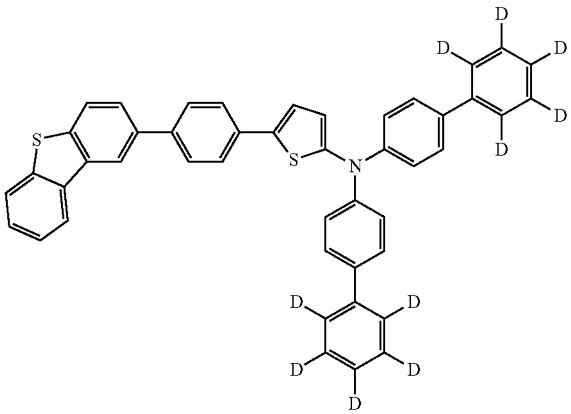

-continued
2-87
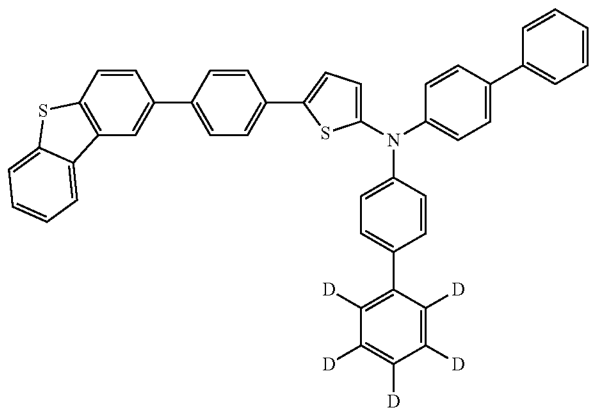
2-88
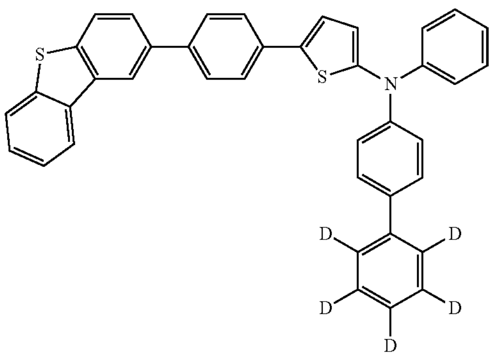
2-89
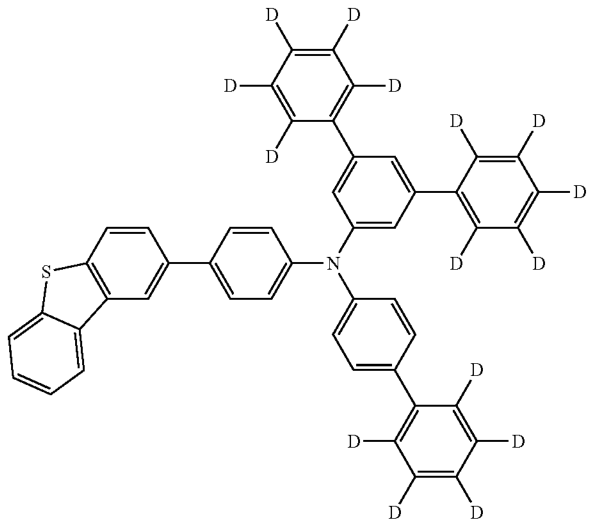
2-90
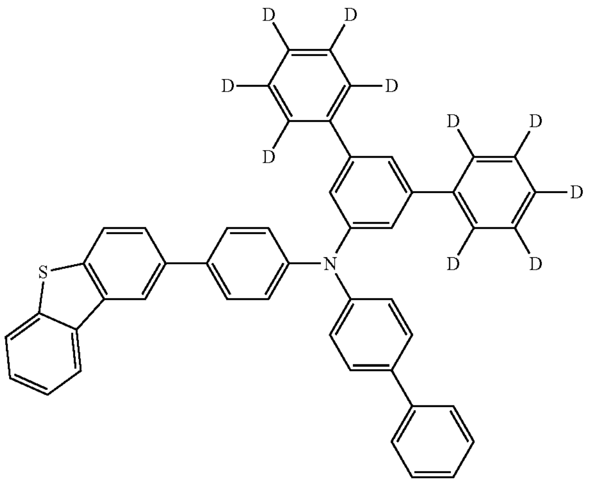
2-91
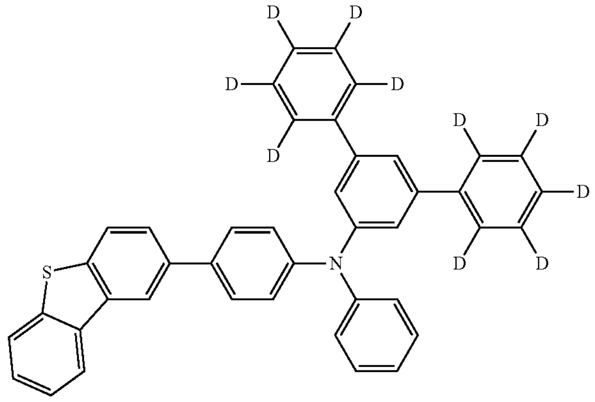
2-92
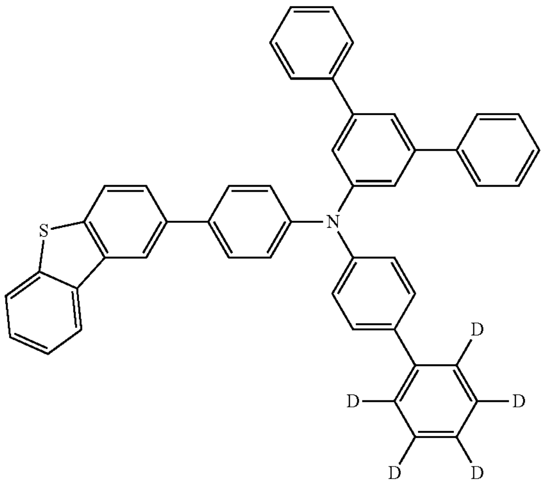

-continued
2-93
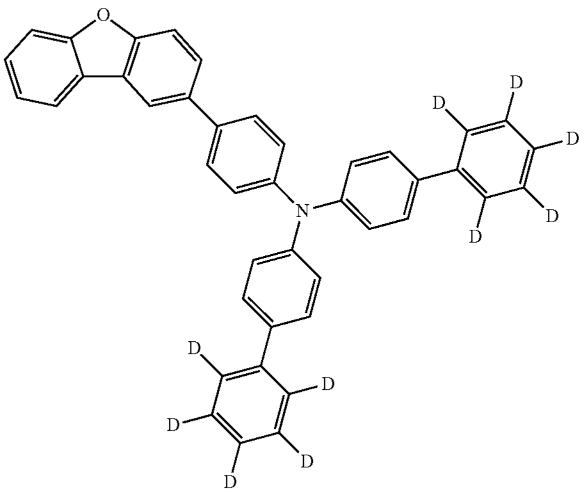
2-94
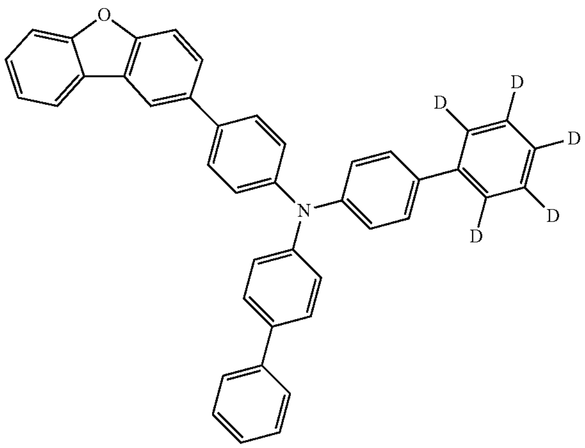
2-95
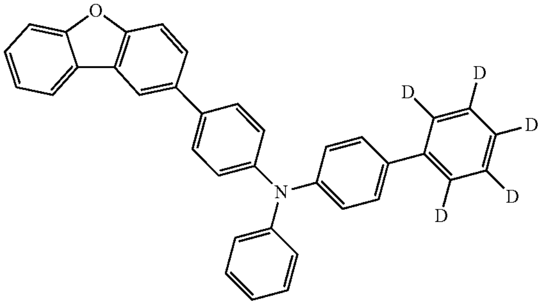
2-96
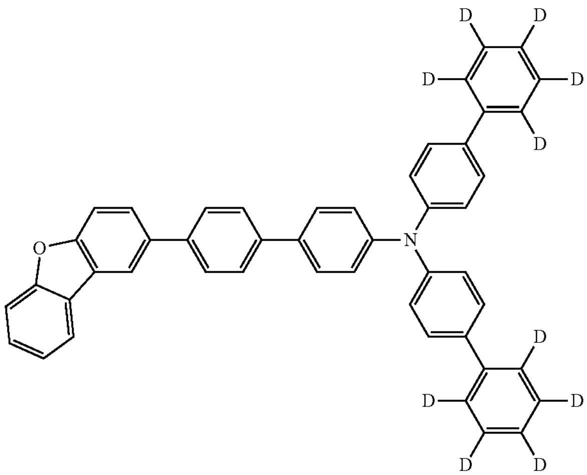
2-97
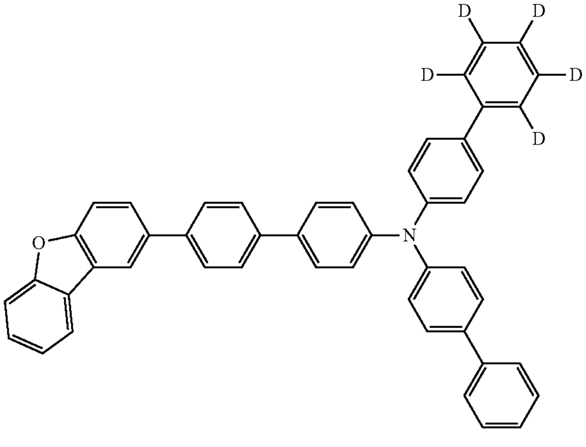
2-98
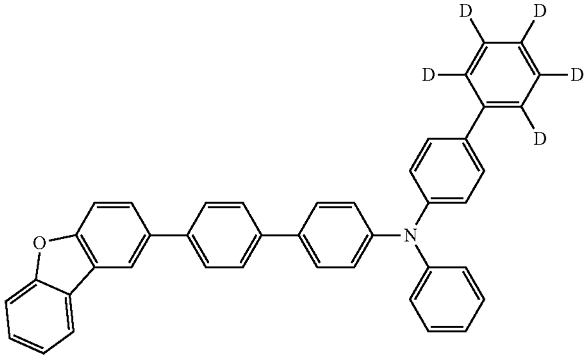

-continued
2-99
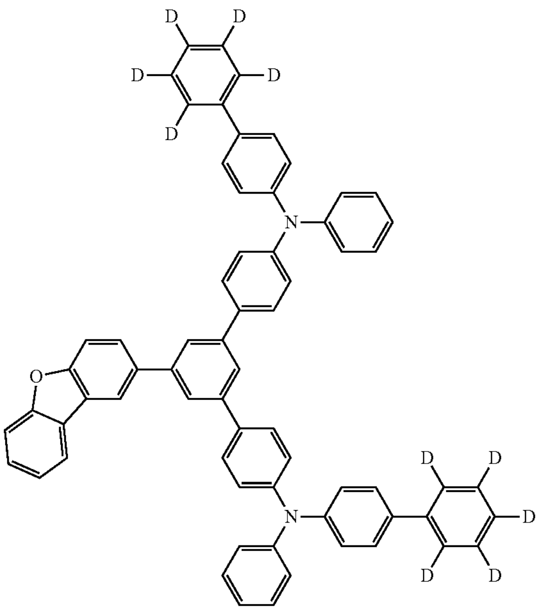
2-100
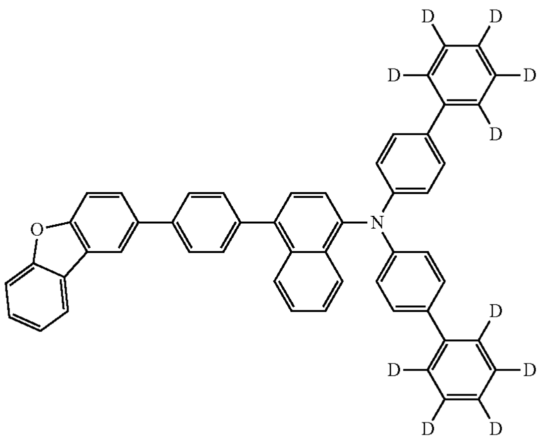
2-101
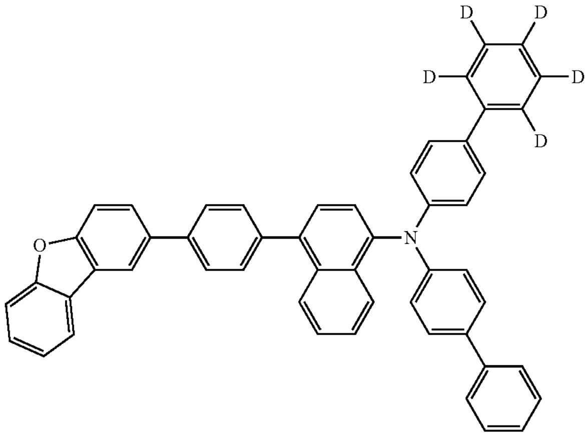
2-102
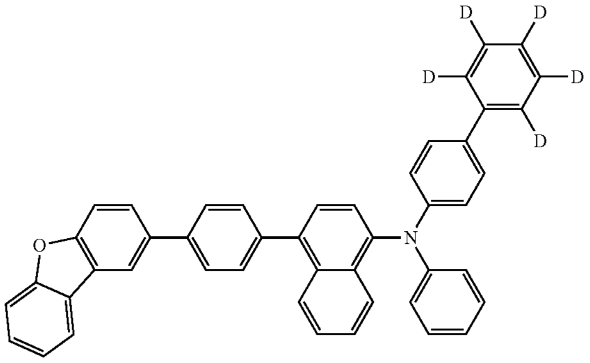
2-103
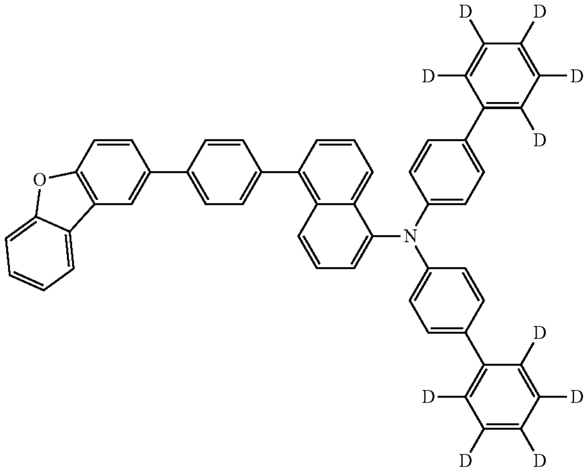
2-104
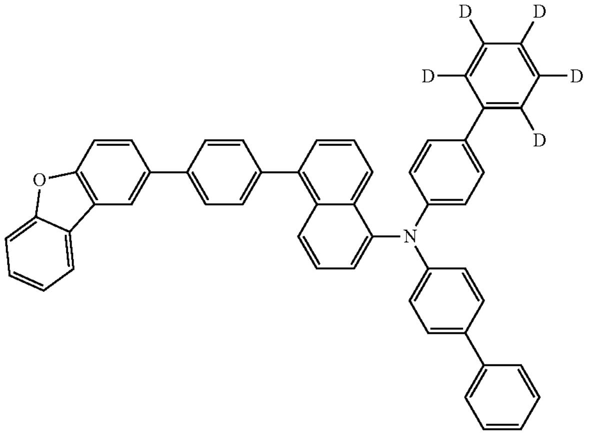

-continued
2-105
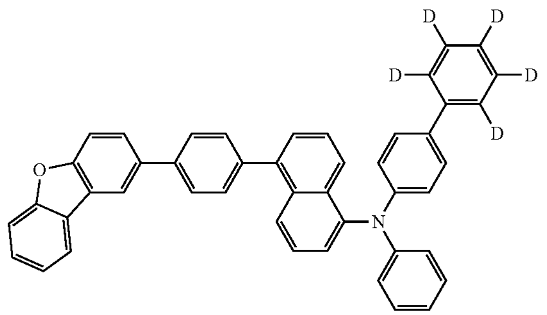
2-106
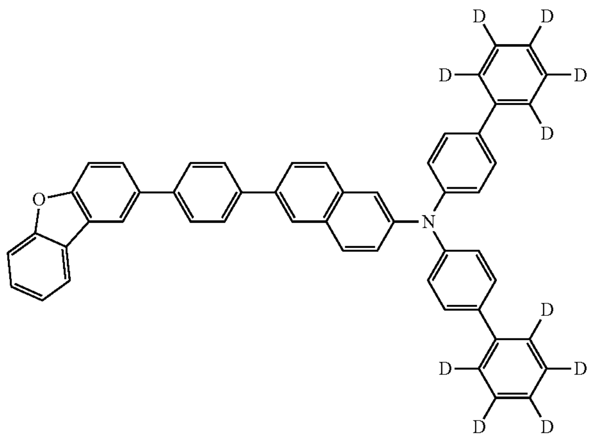
2-107
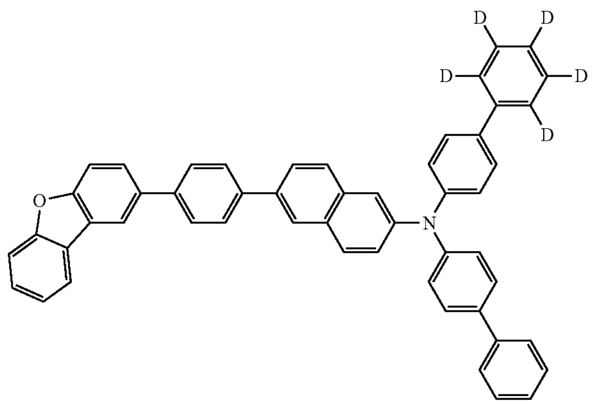
2-108
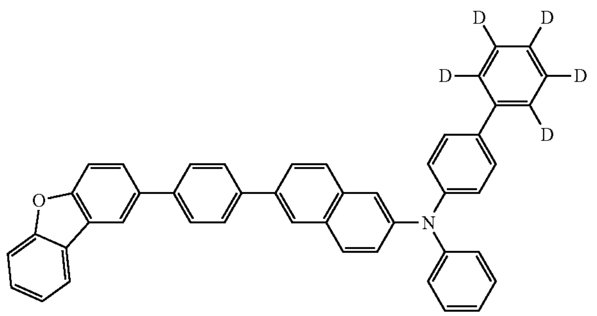
2-109
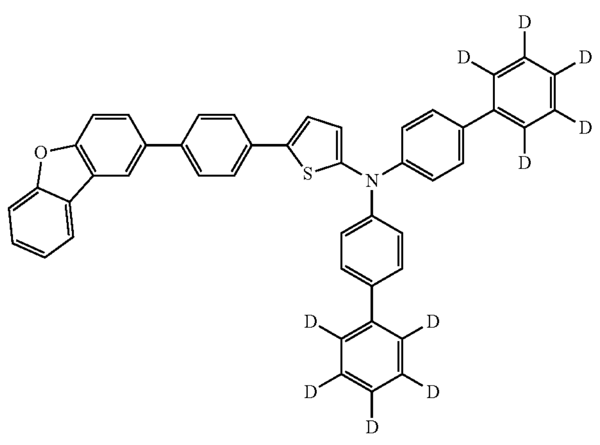
2-110
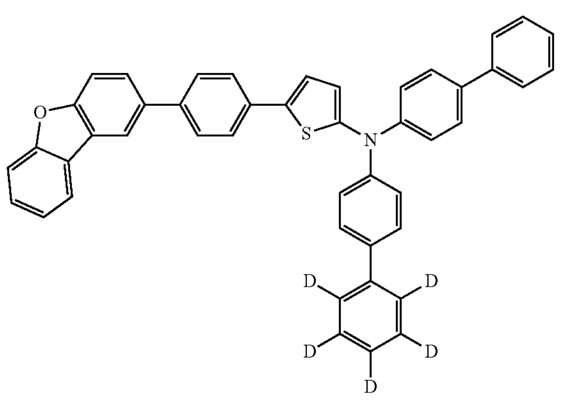

-continued
2-111
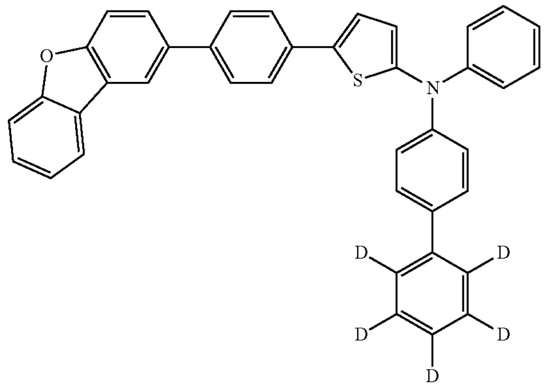
2-112
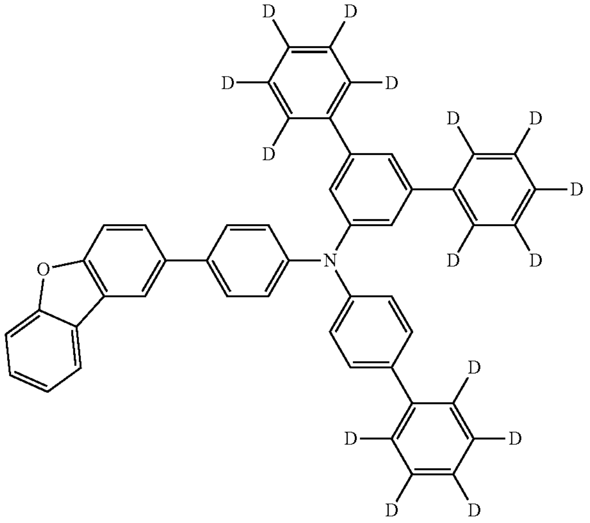
2-113
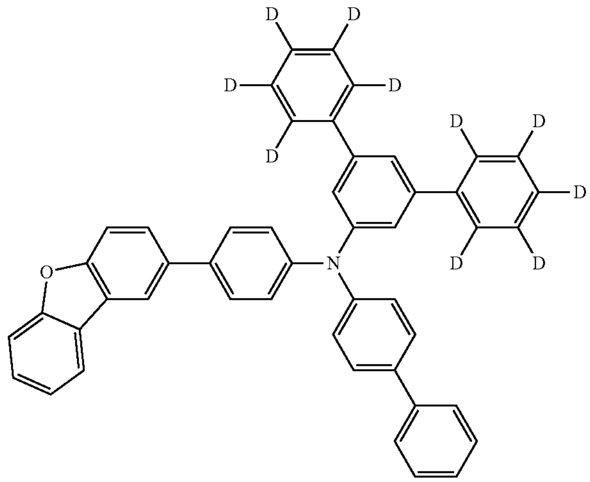
2-114
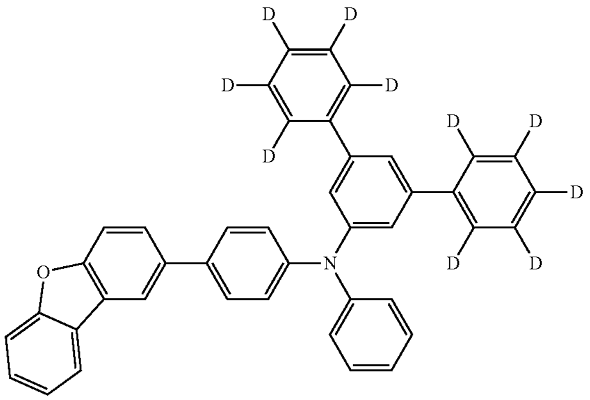
2-115
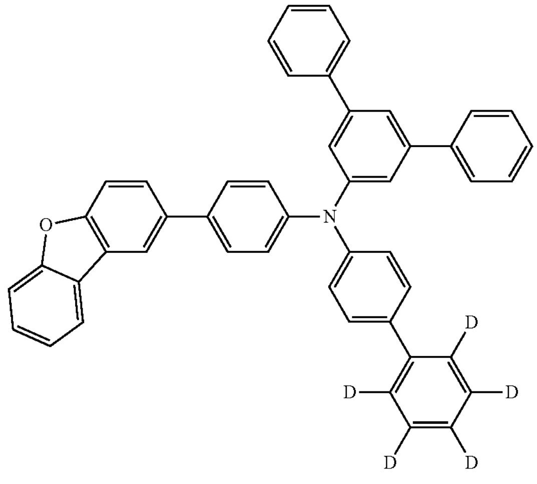
2-116
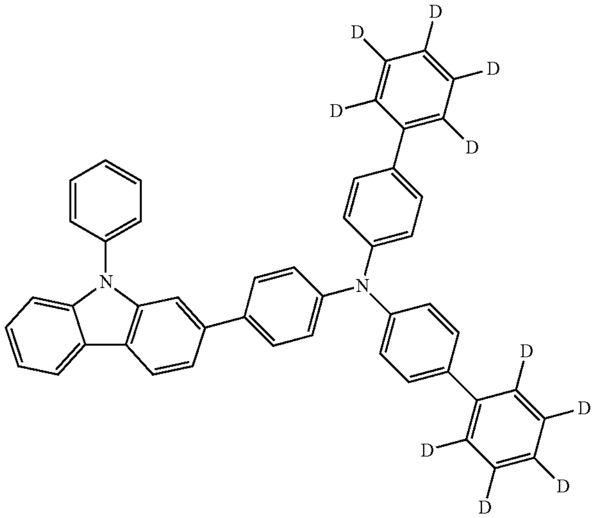

-continued
2-117
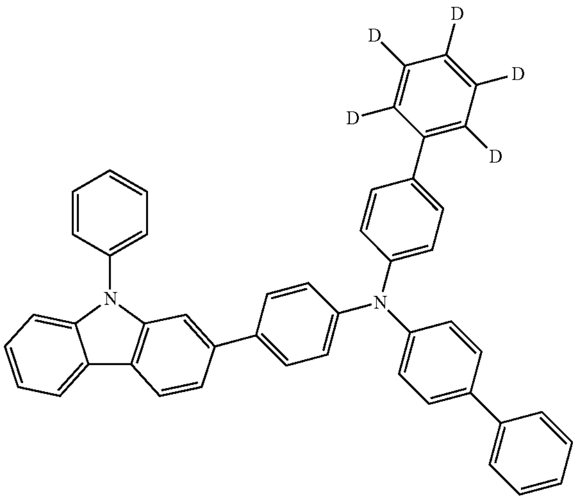
2-118
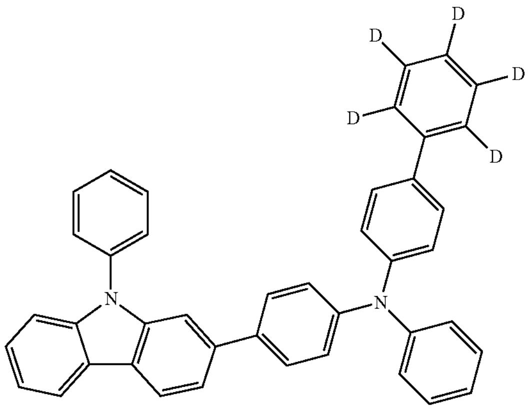
2-119
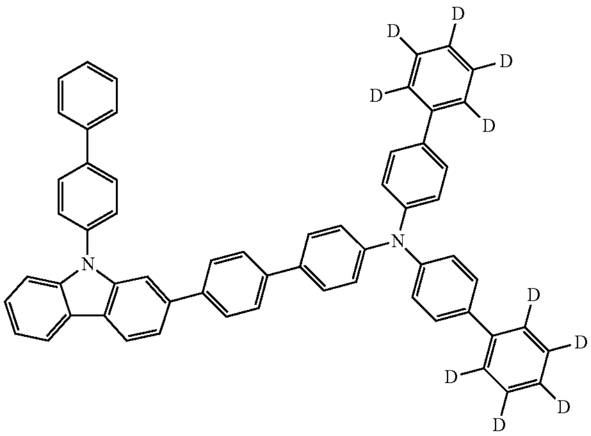
2-120
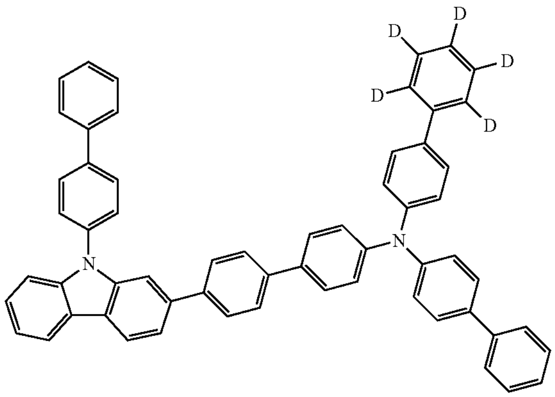
2-121
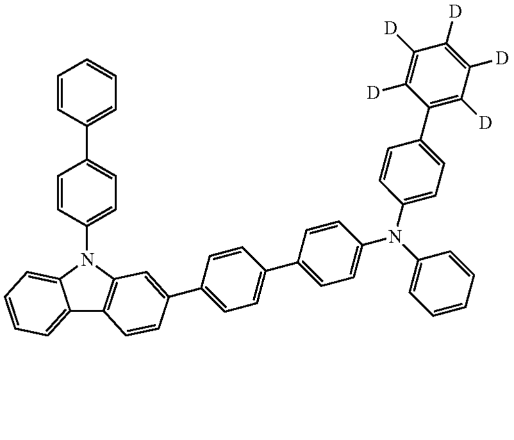
2-122
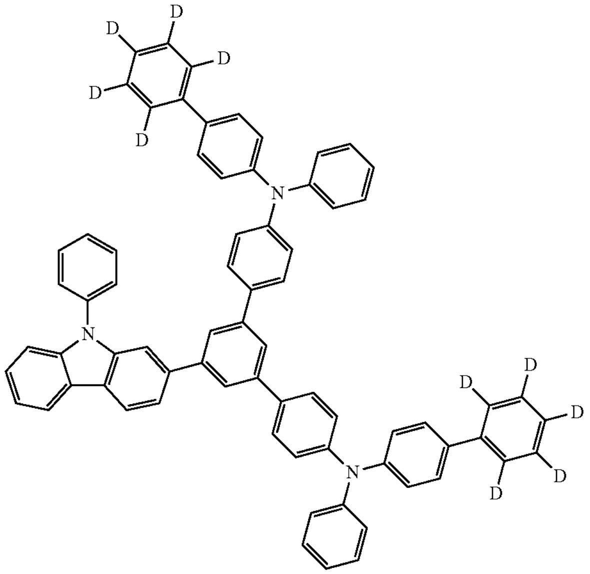

-continued
2-123
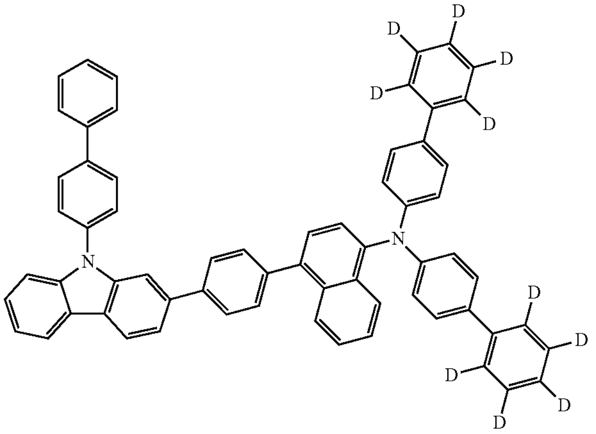
2-124
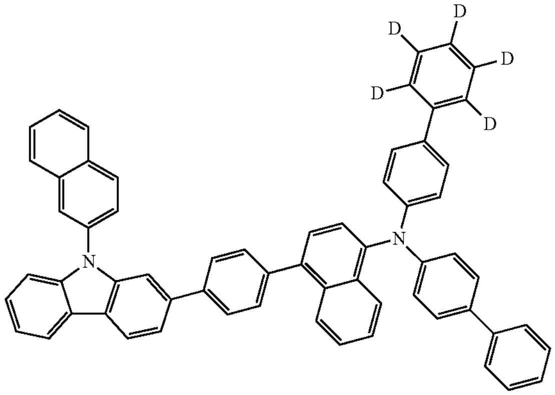
2-125
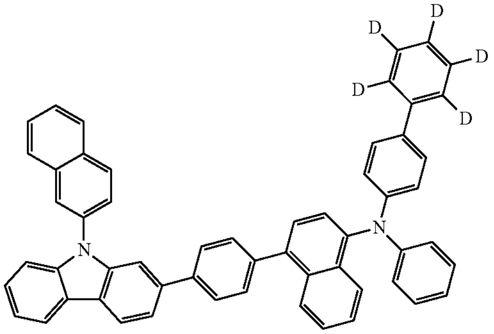
2-126
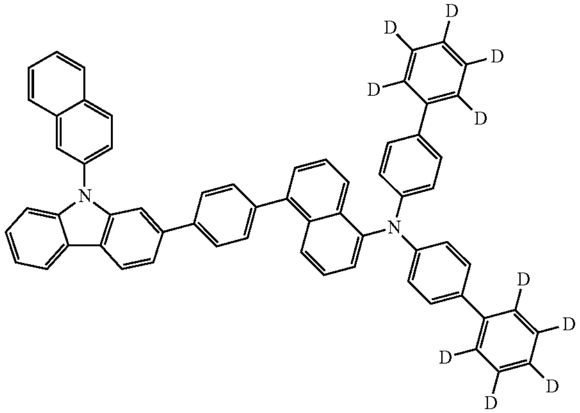
2-127
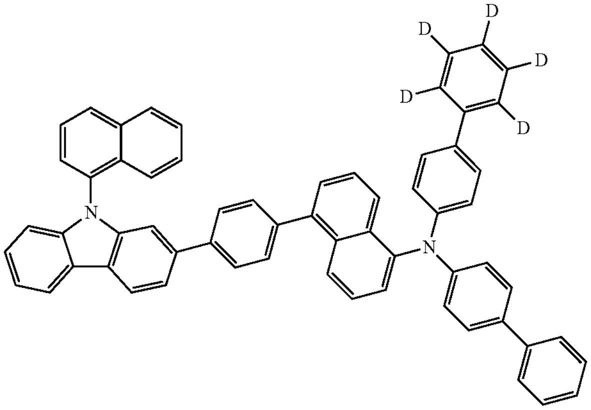
2-128
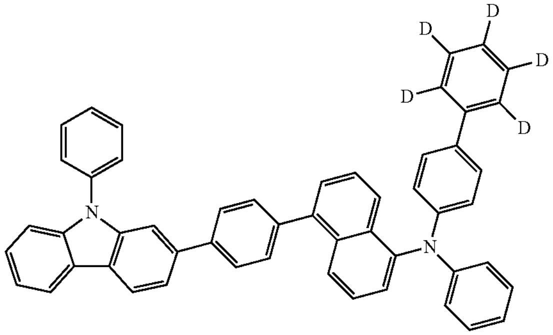

-continued
2-129
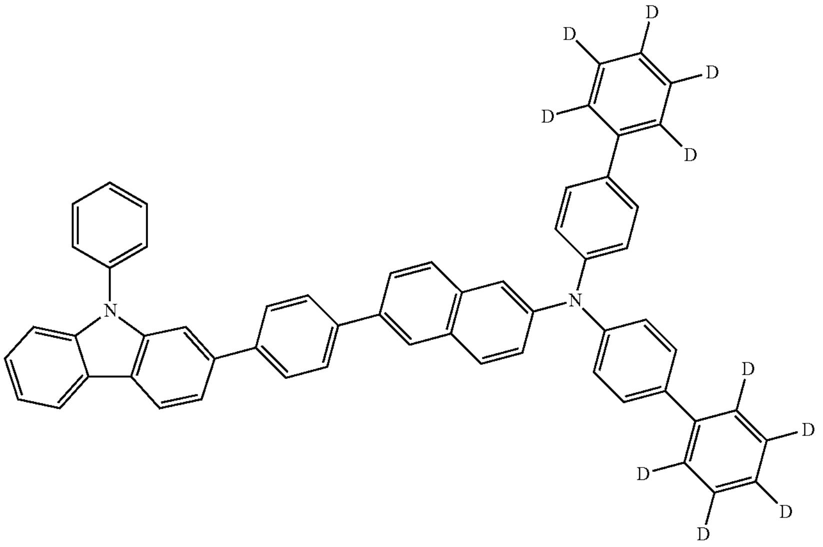
2-130
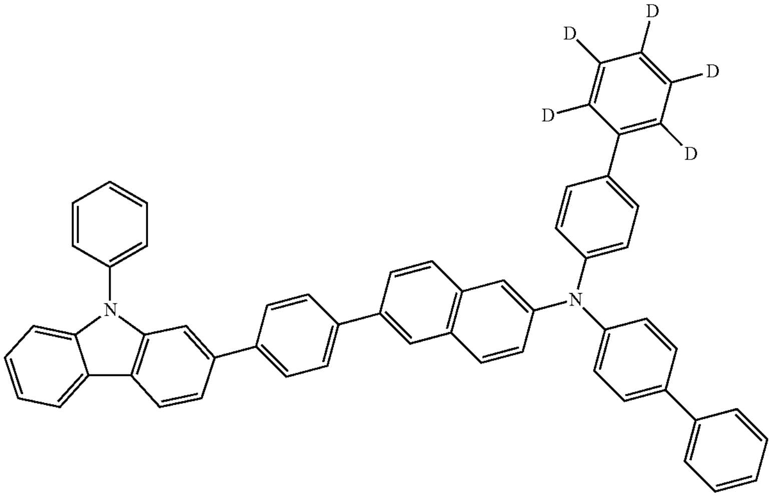
2-131
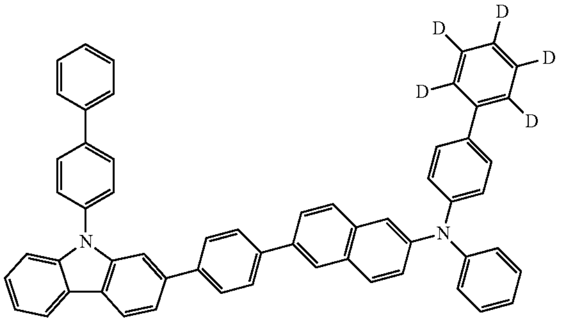
2-132
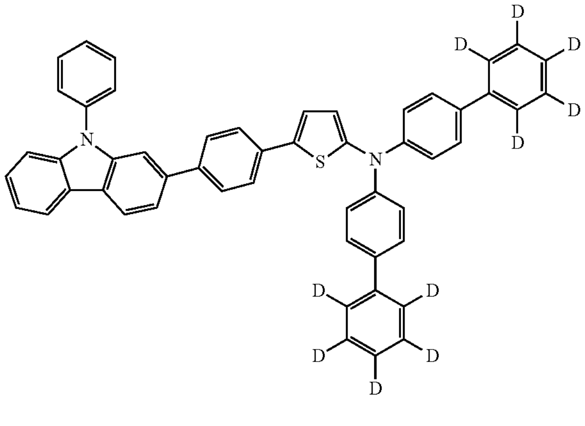

-continued
2-133
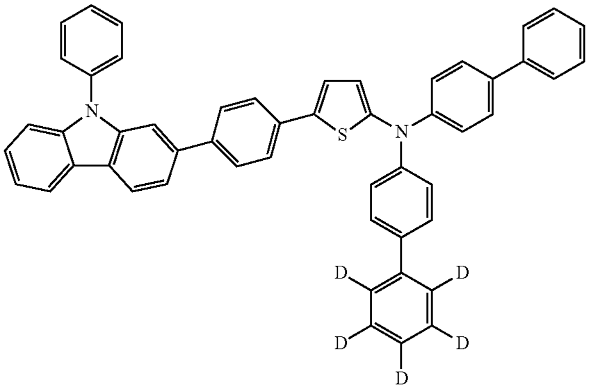
2-134
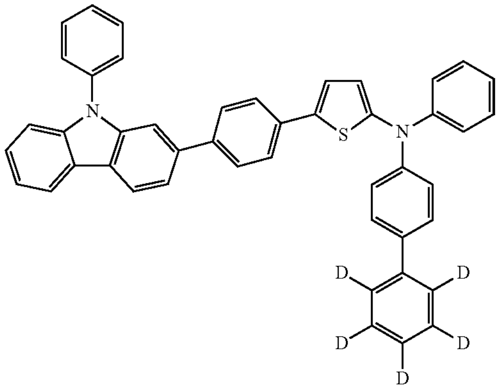
2-135
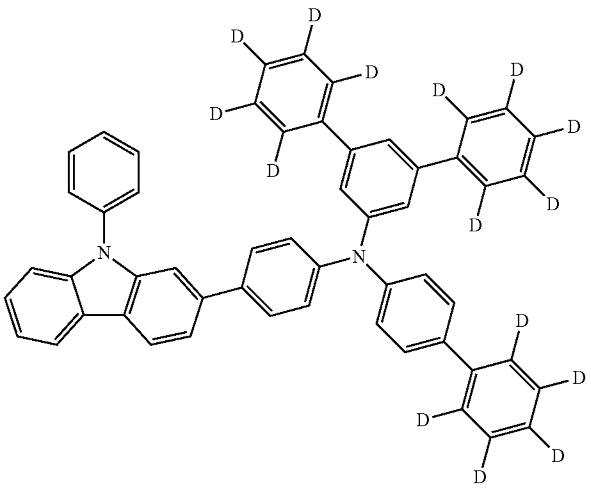
2-136
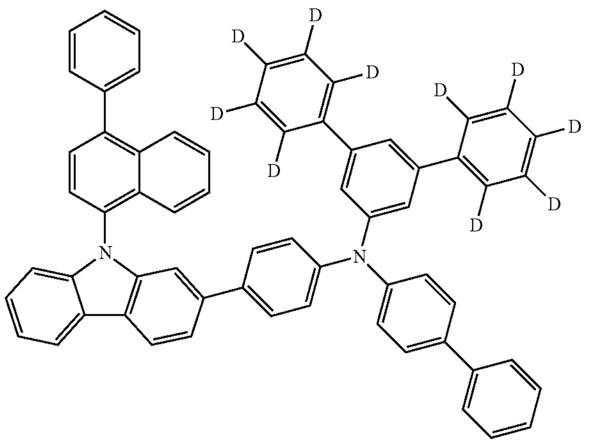
2-137
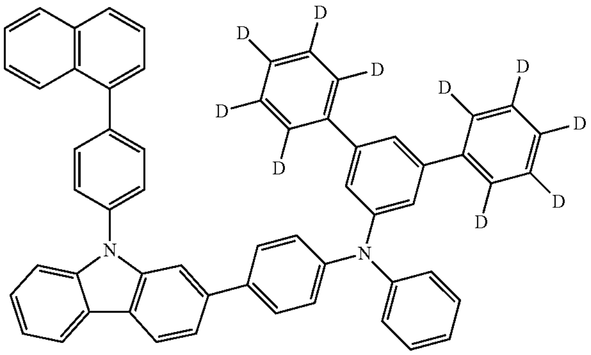
2-138
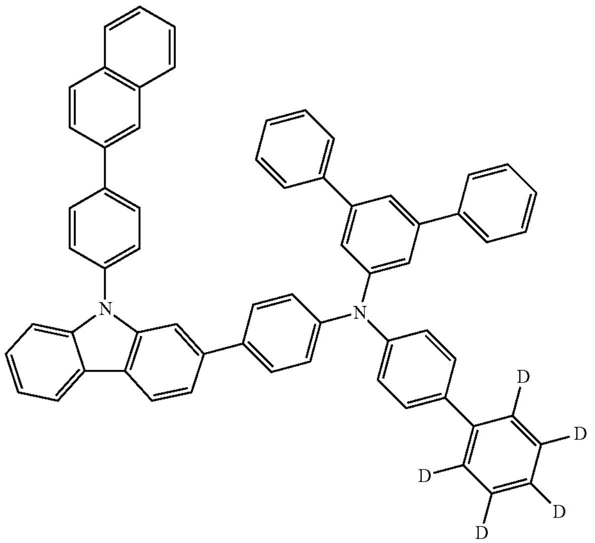

-continued
2-139
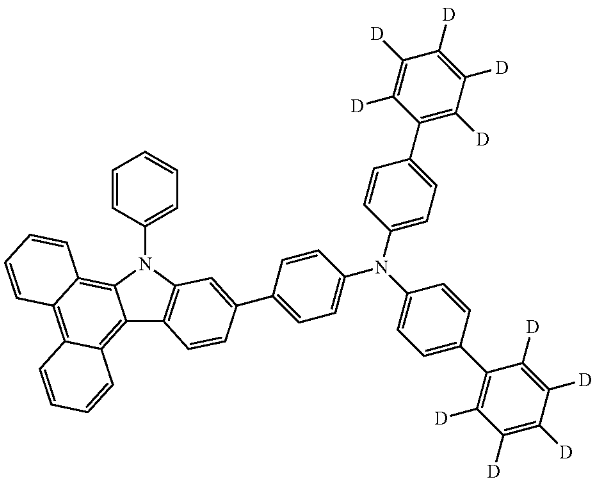
2-140
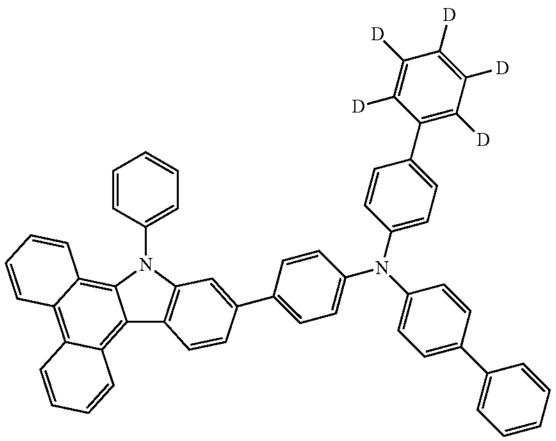
2-141
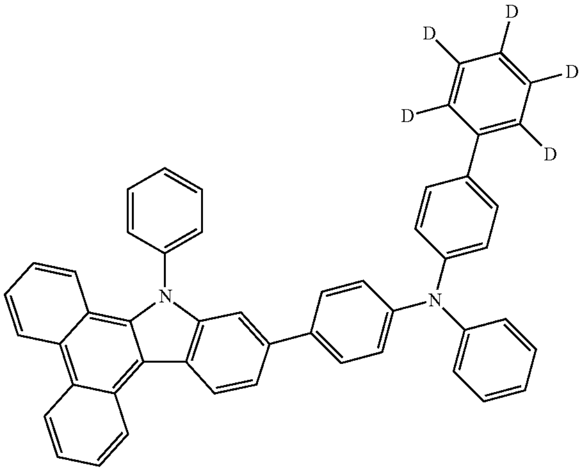
2-142
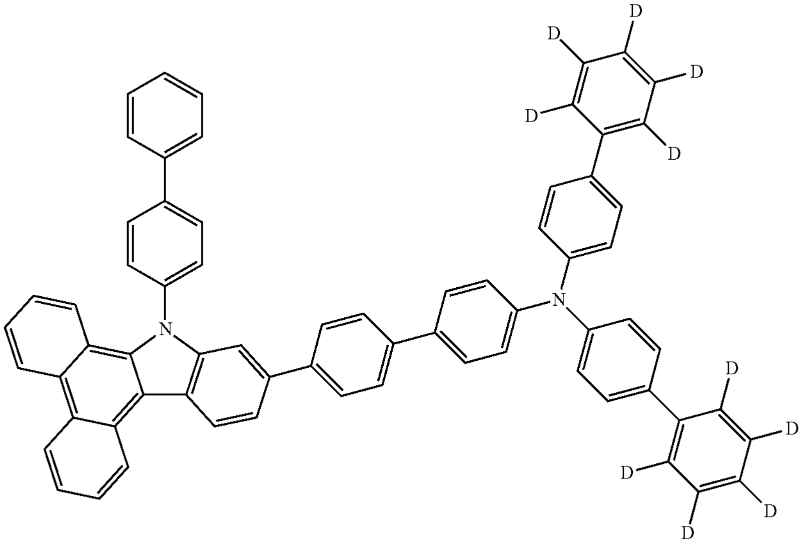

-continued
2-139
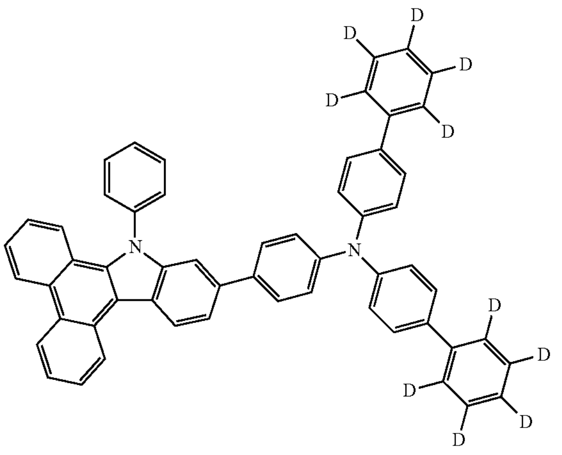
2-140
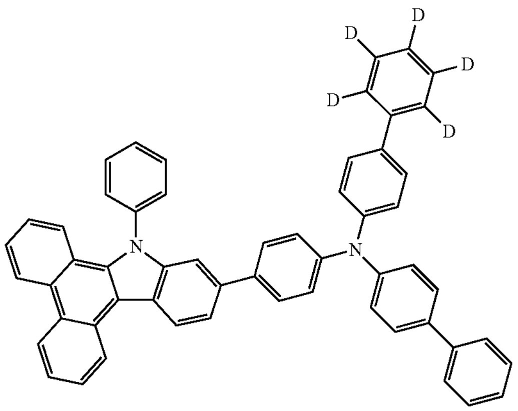
2-141
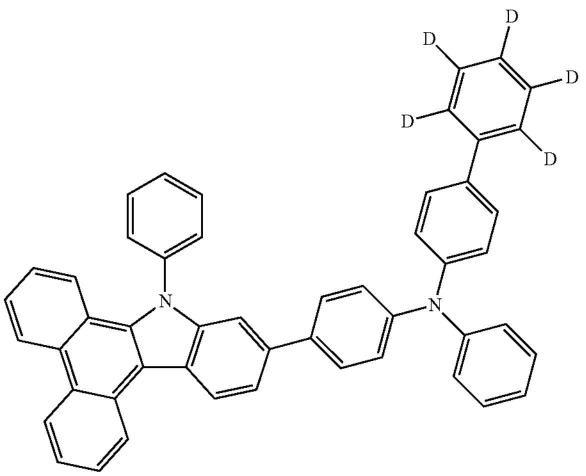
2-142
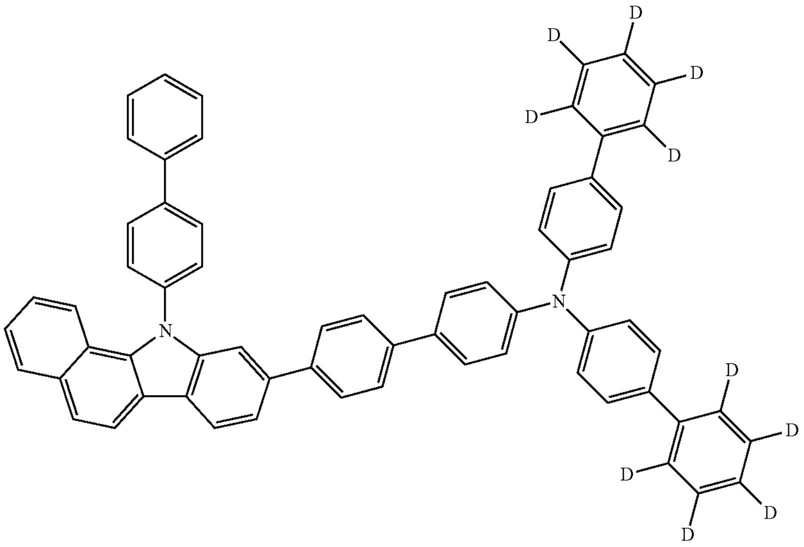

-continued
2-147
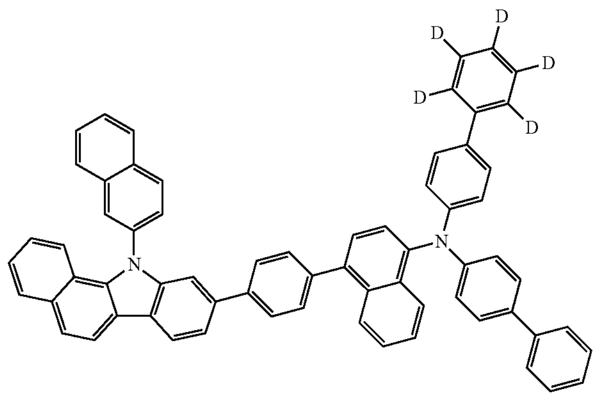
2-148
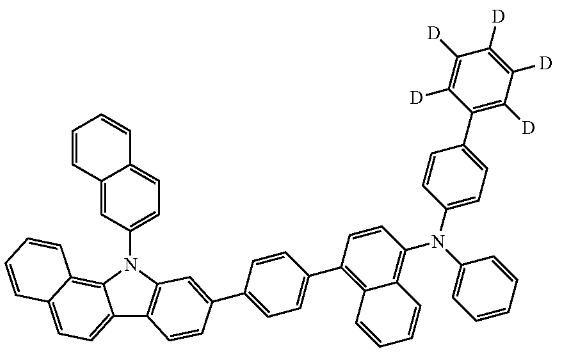
2-149
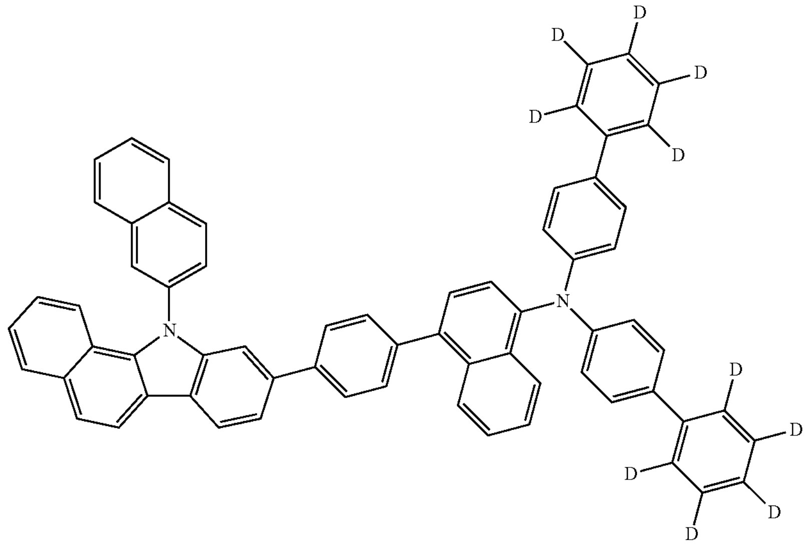
2-150
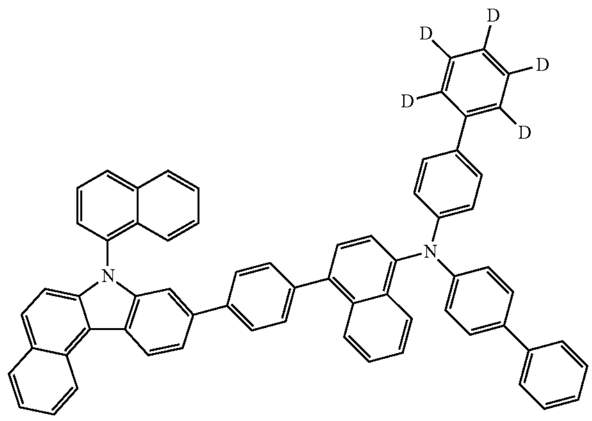
2-151
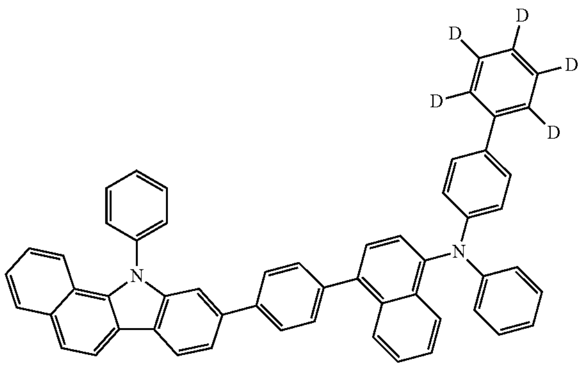

-continued
2-152
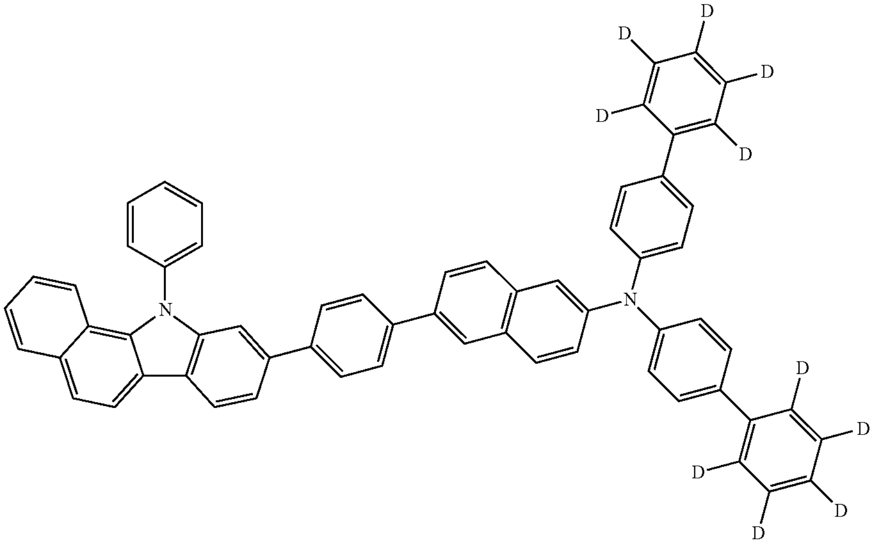
2-153
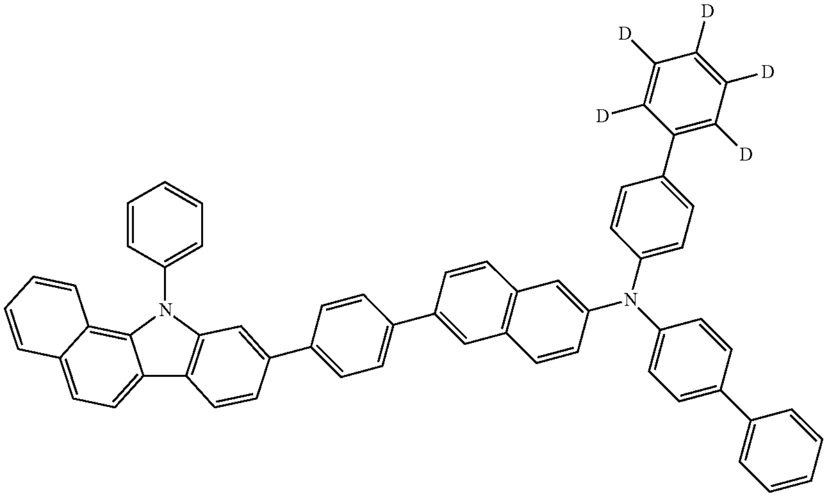
2-154
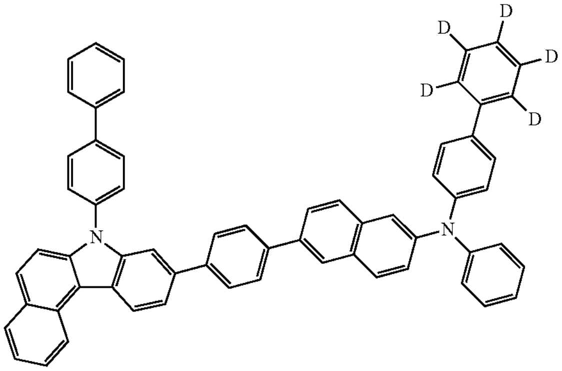
2-155
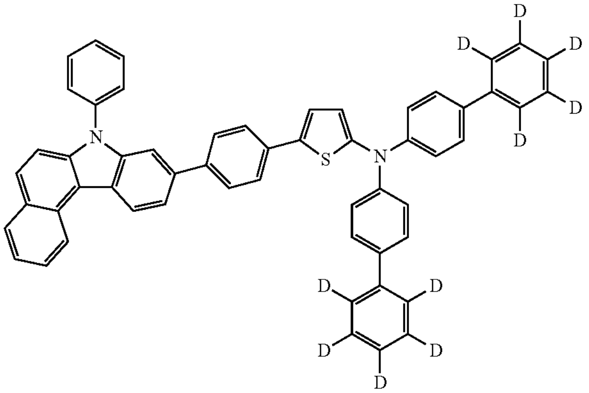

-continued
2-156
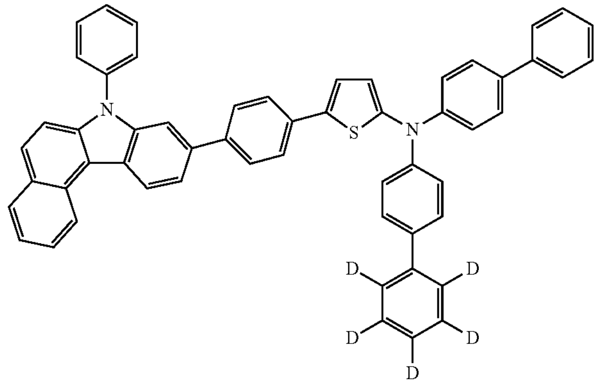
2-157
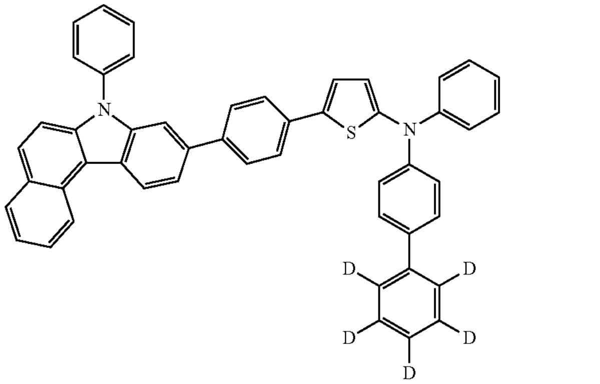
2-158
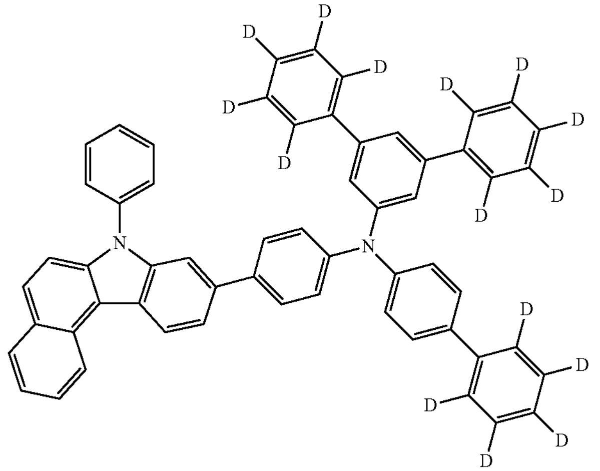
2-159
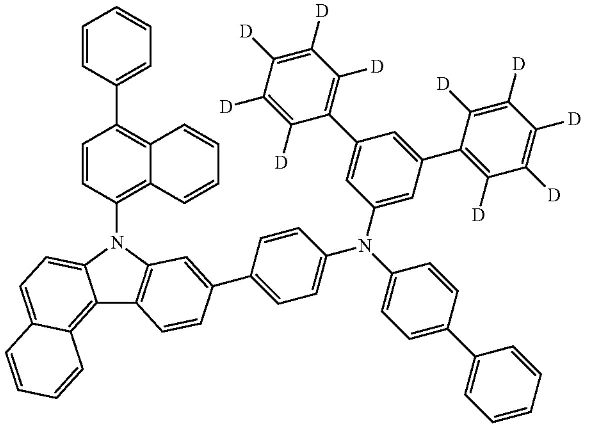
2-160
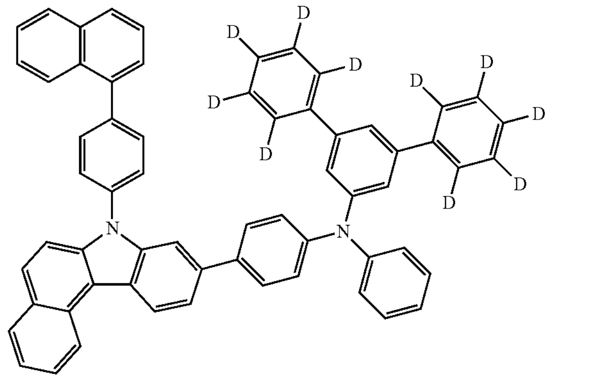
1-161
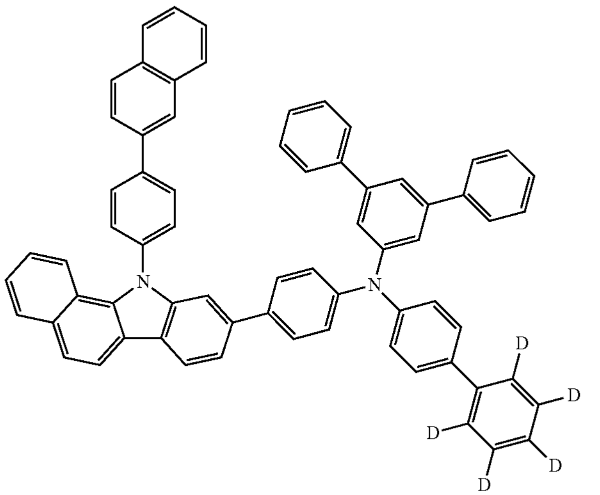

-continued
2-162
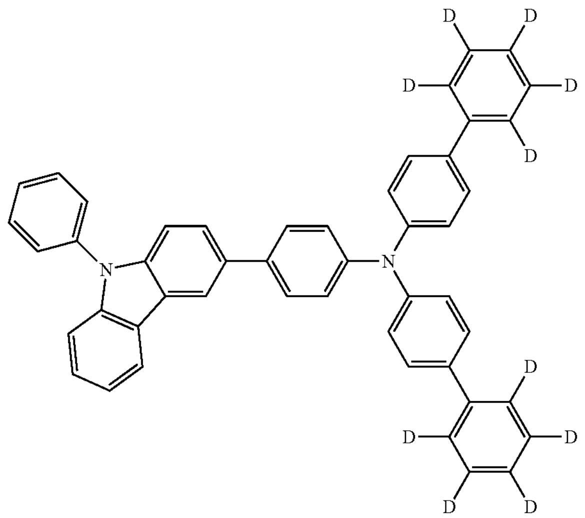
2-163
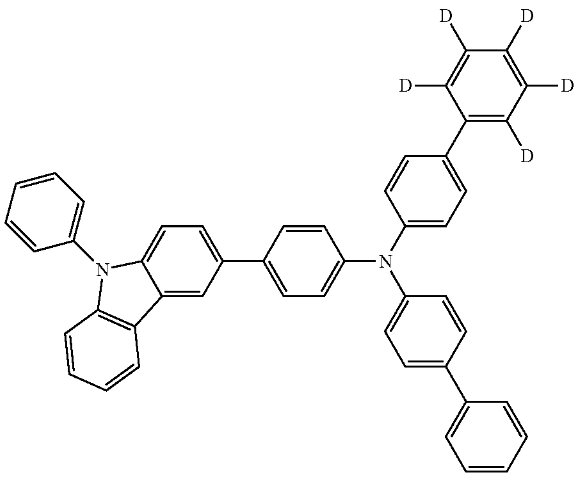
2-164
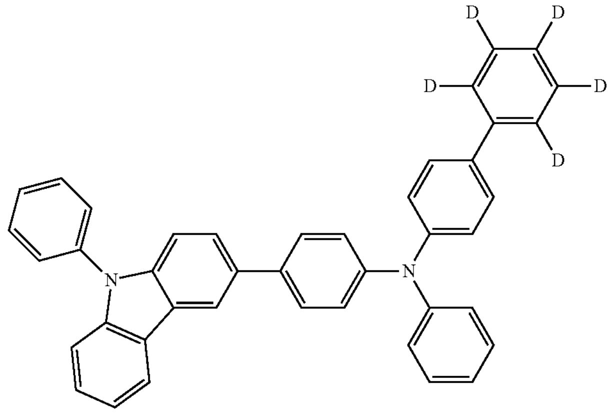
2-165
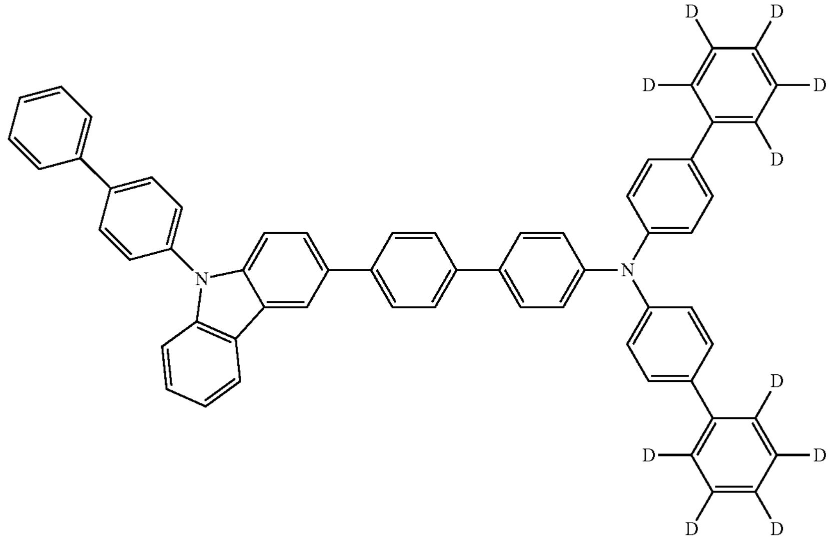

-continued
2-166
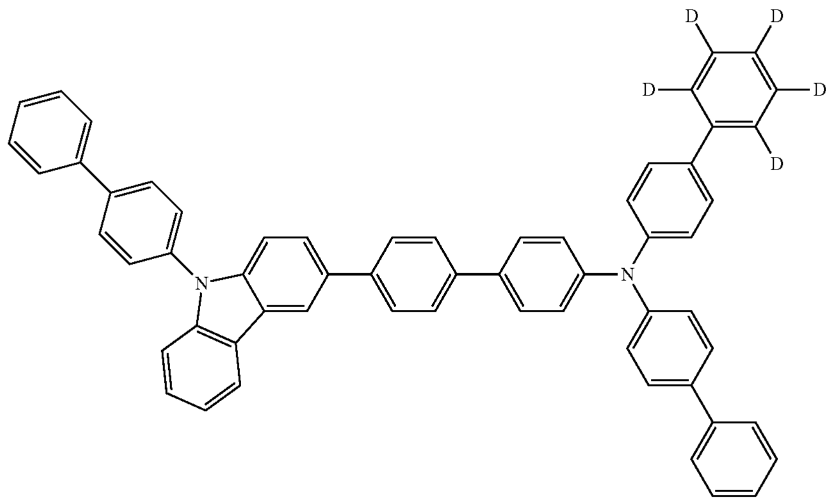
2-167
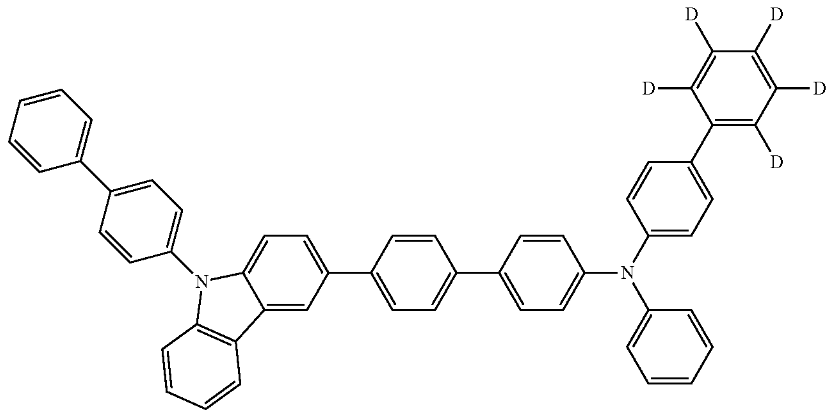
2-168
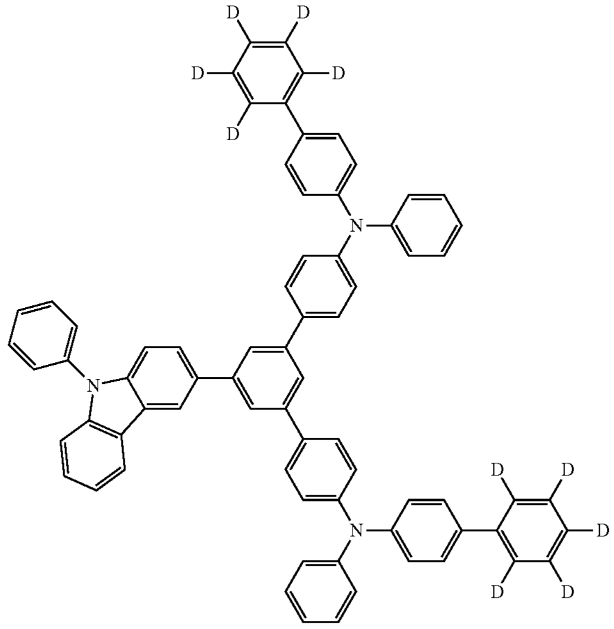

-continued
2-169
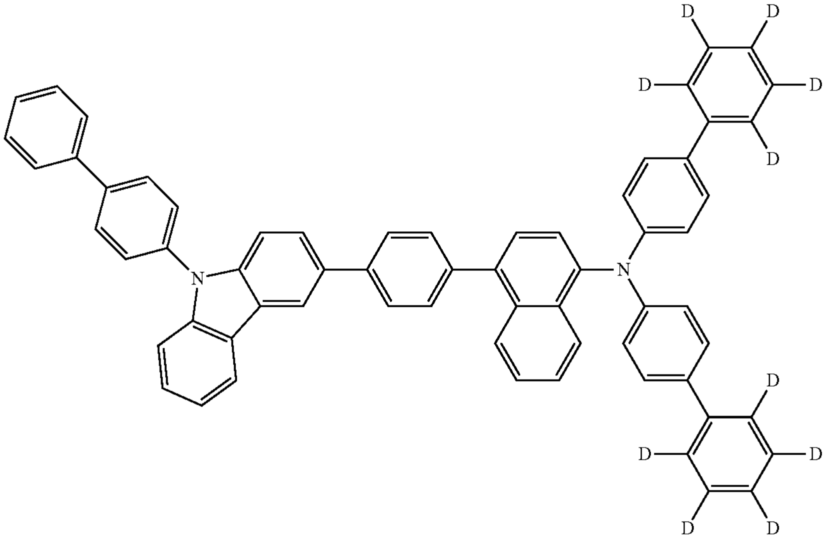
2-170
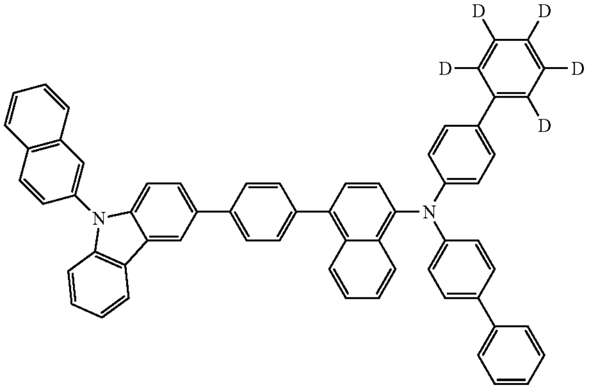
2-171
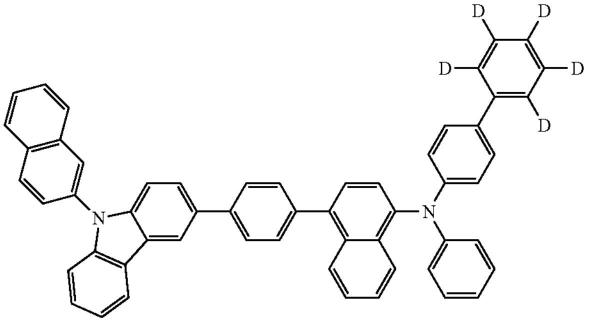
2-172
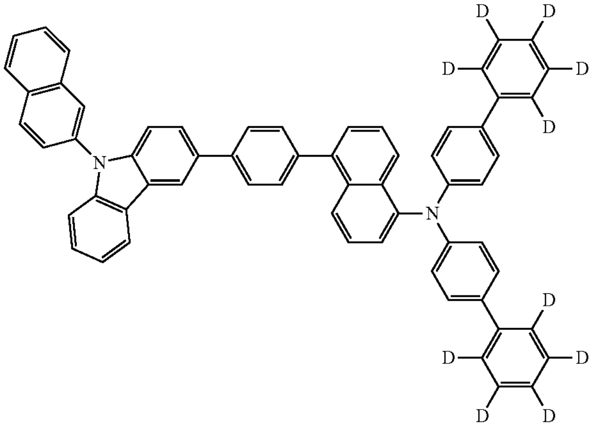
2-173
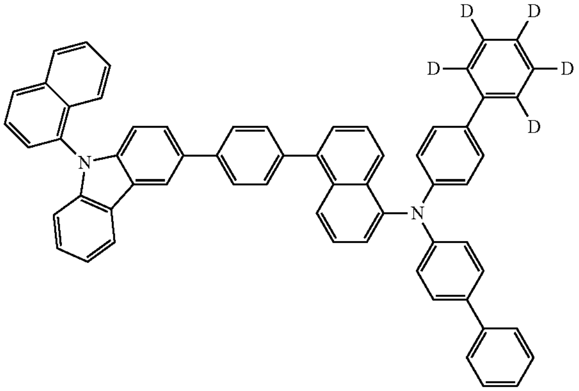

-continued
2-174
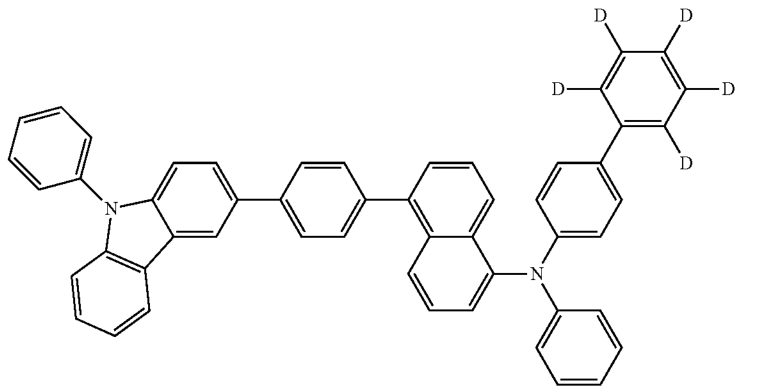
2-175
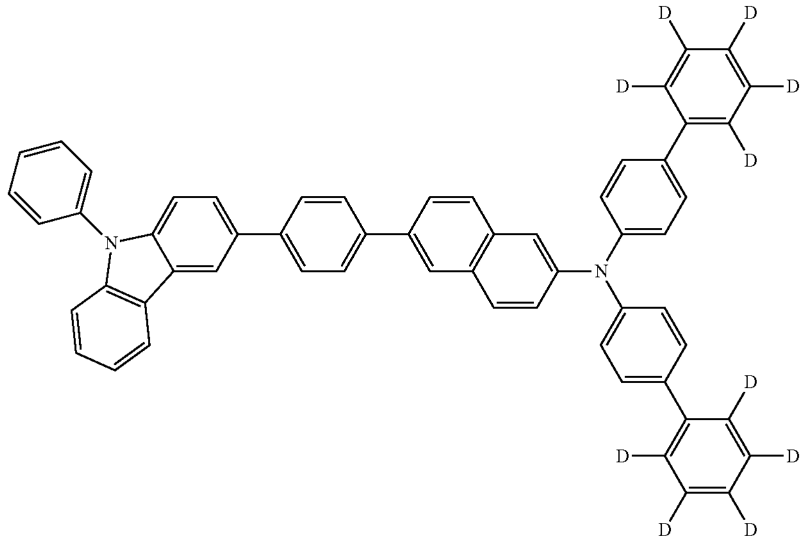
2-176
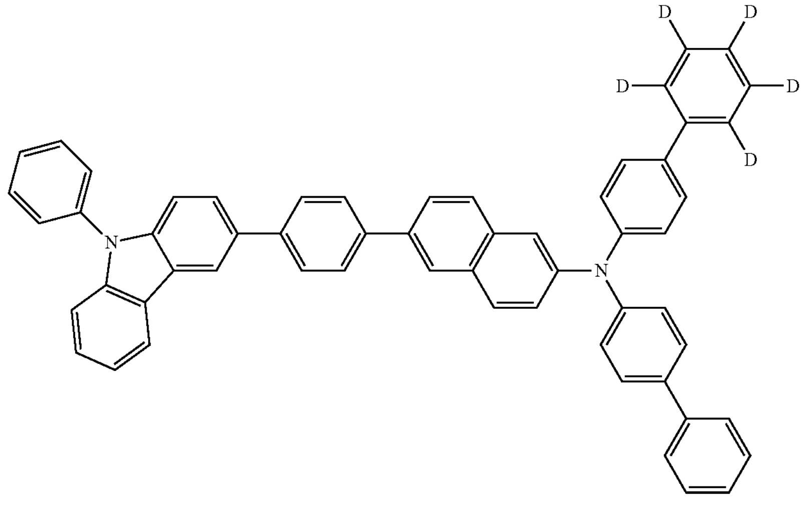

-continued
2-177
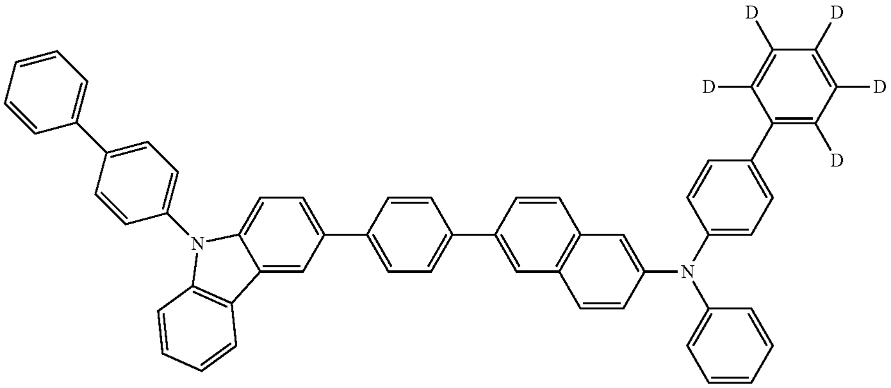
2-178
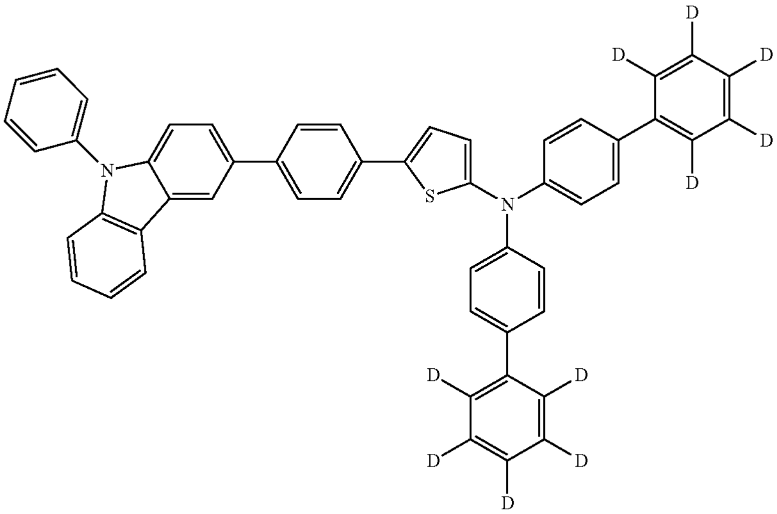
2-179
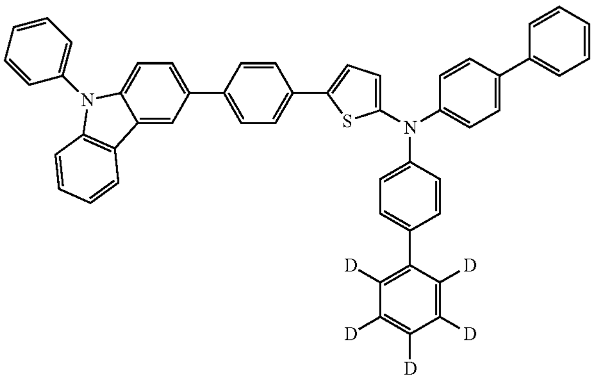
2-180
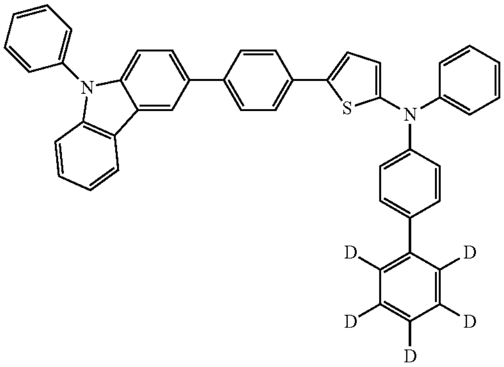

-continued
2-181
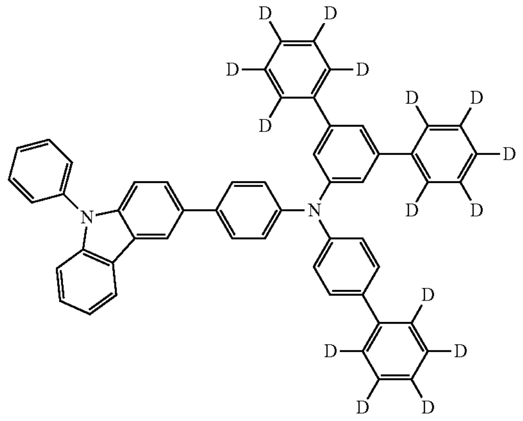
2-182
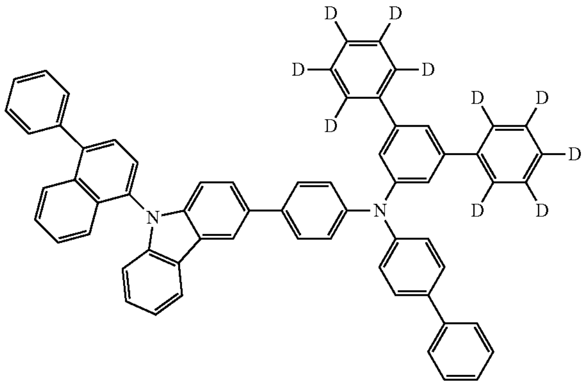
2-183
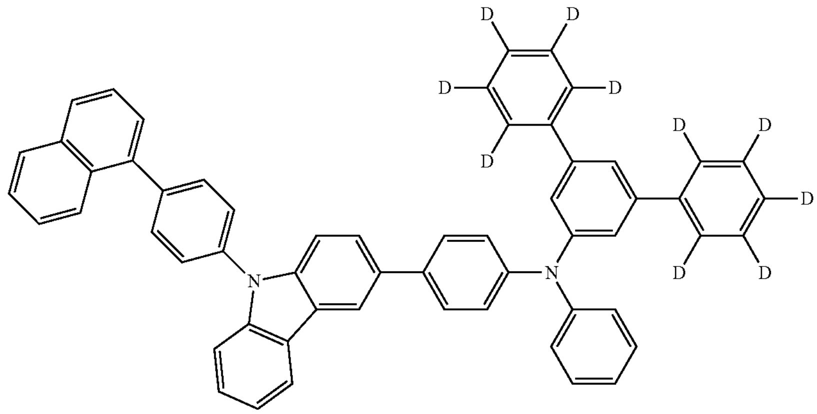
2-184
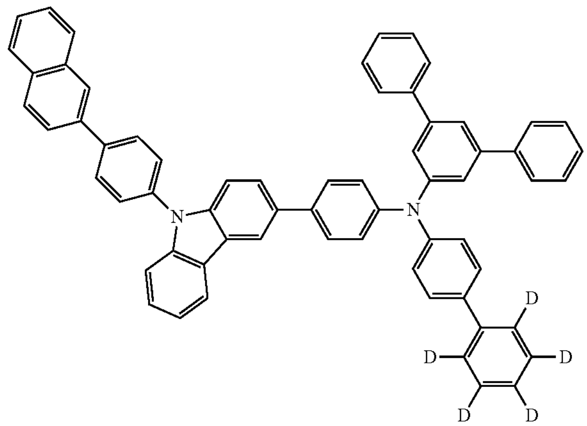
2-185
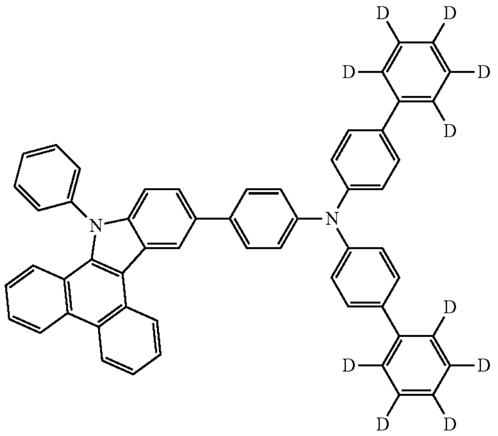

-continued
2-186
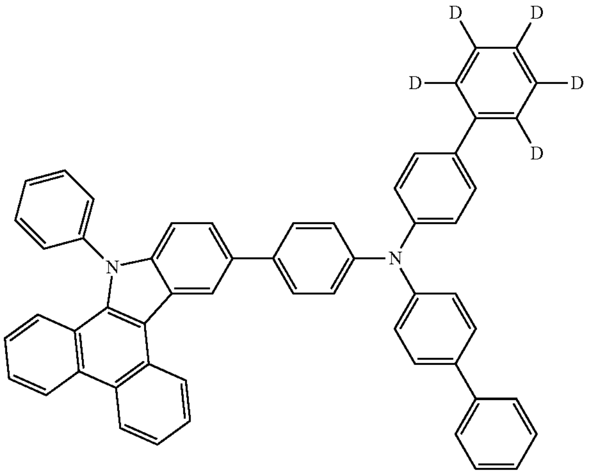
2-187
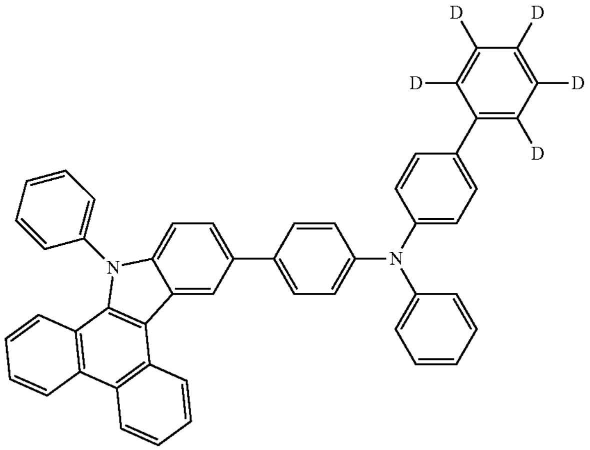
2-188
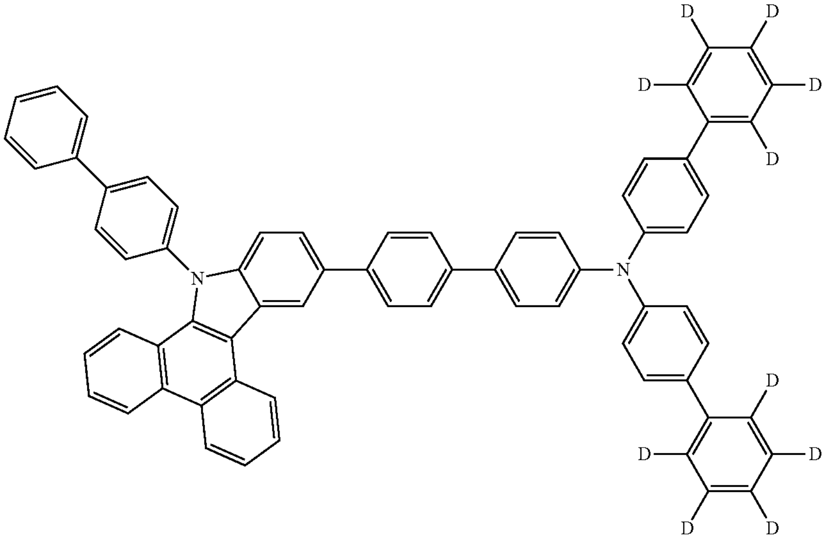
2-189
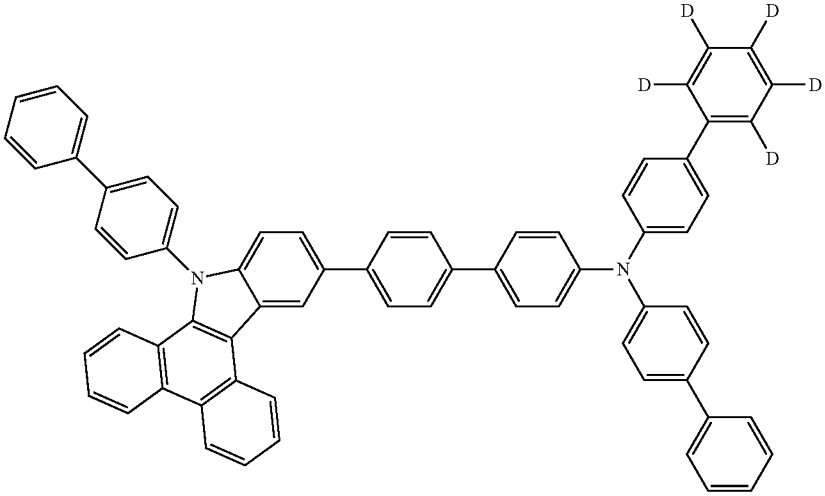

-continued
2-190
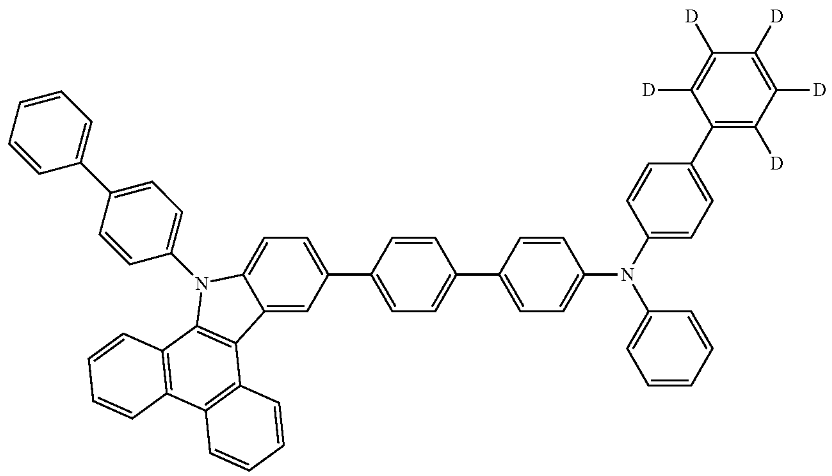
2-191
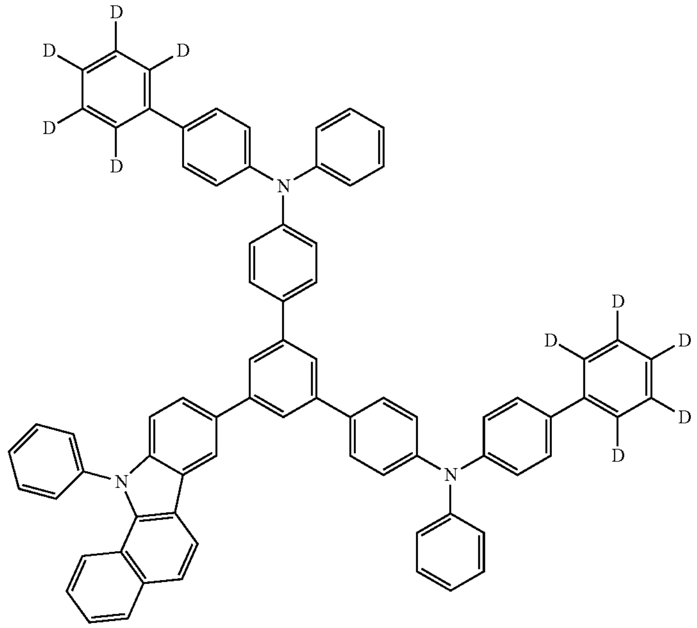
2-192
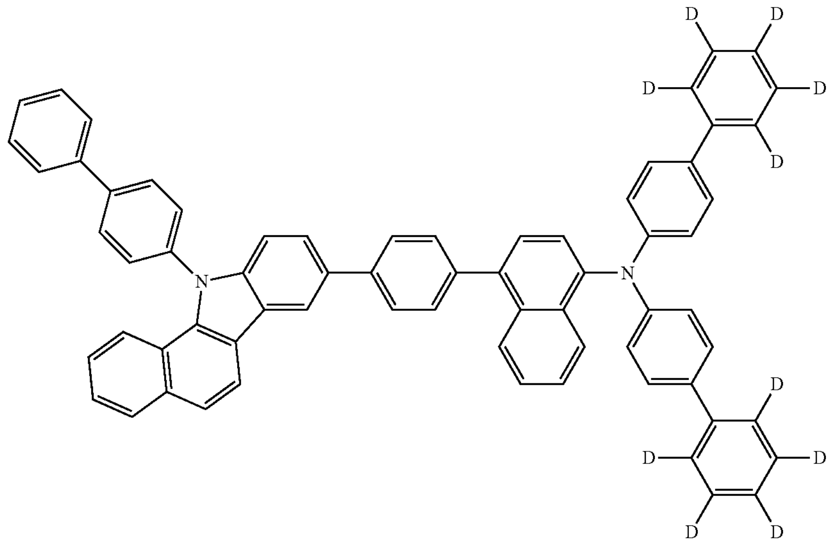

-continued
2-193
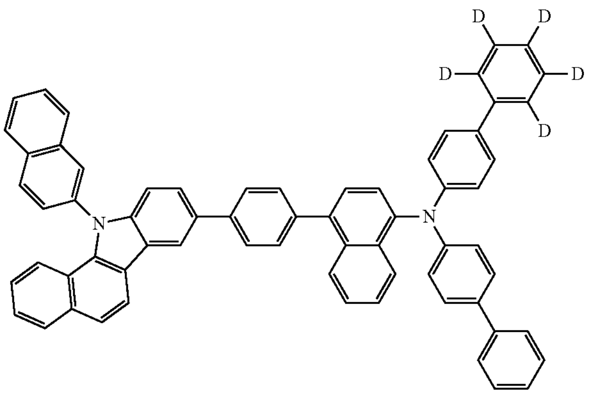
2-194
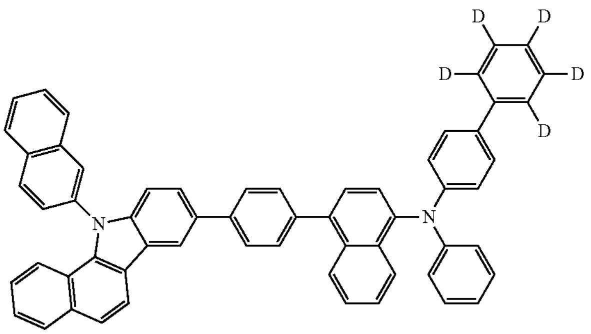
2-195
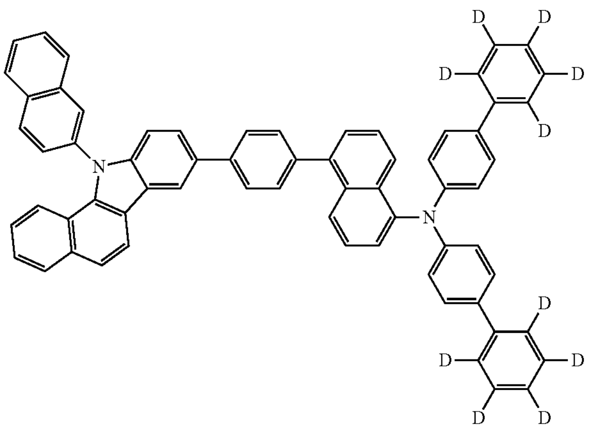
2-196
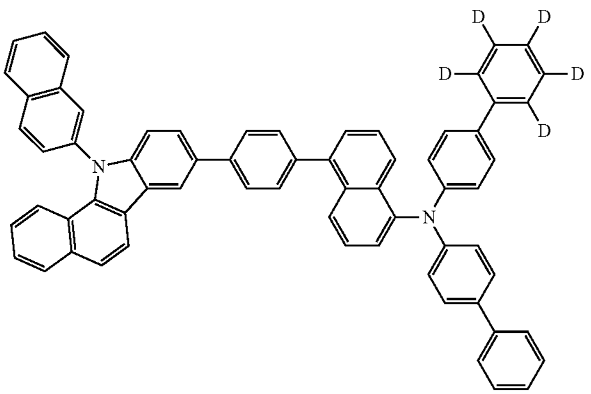
2-197
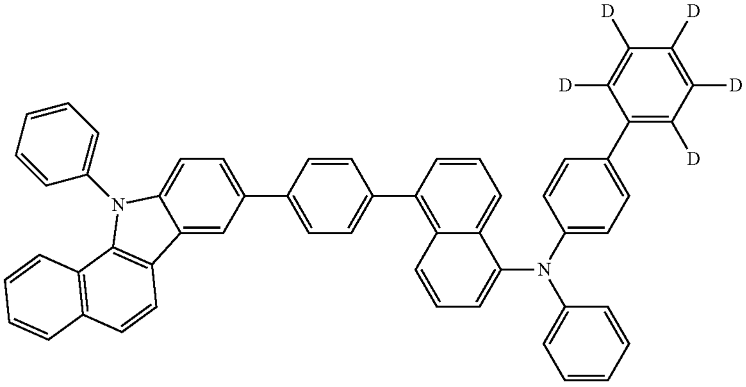

-continued
2-198
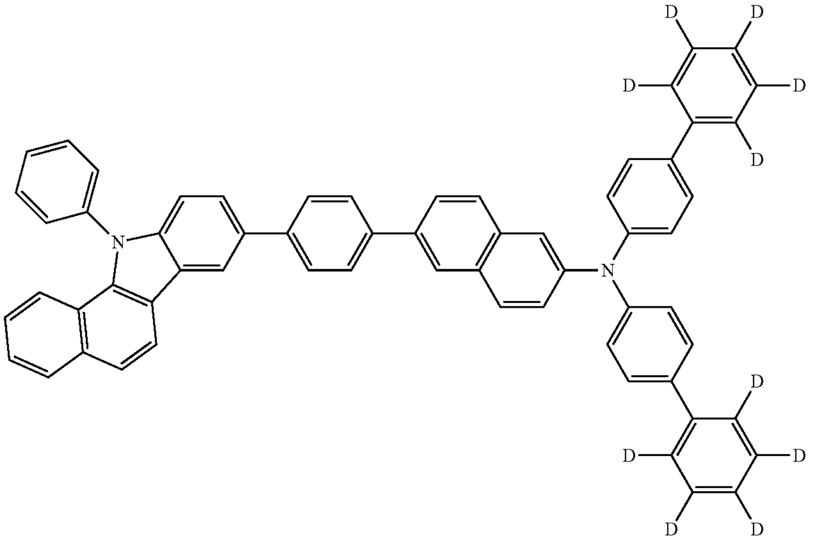
2-199
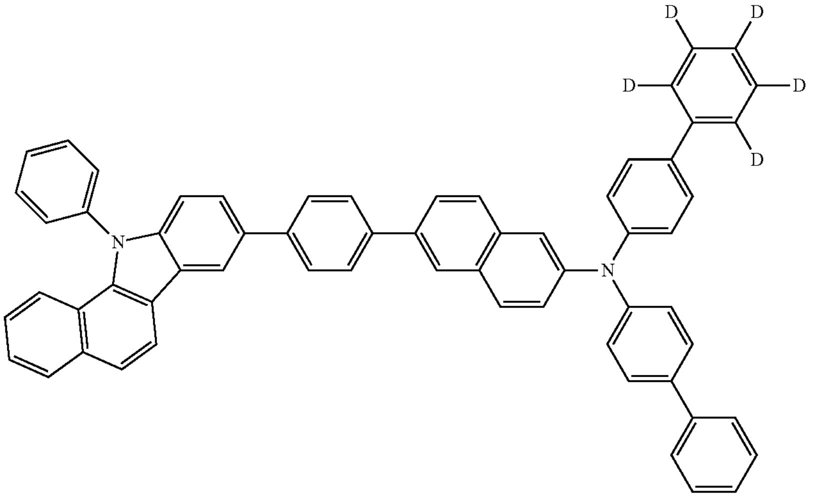
2-200
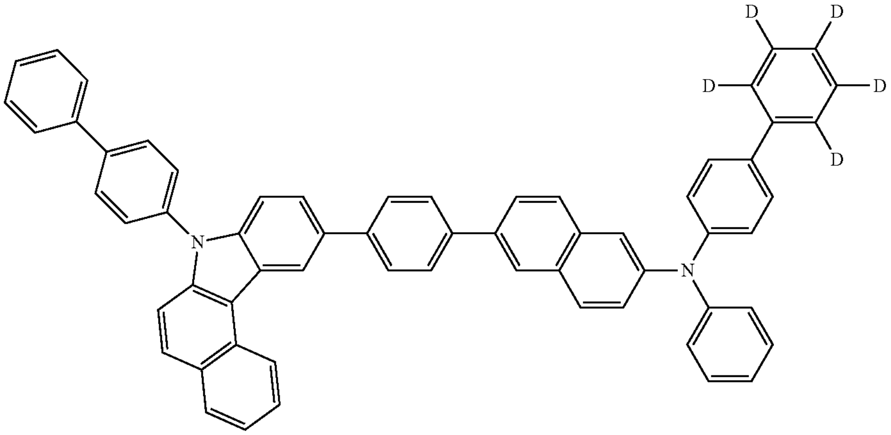

-continued
2-201
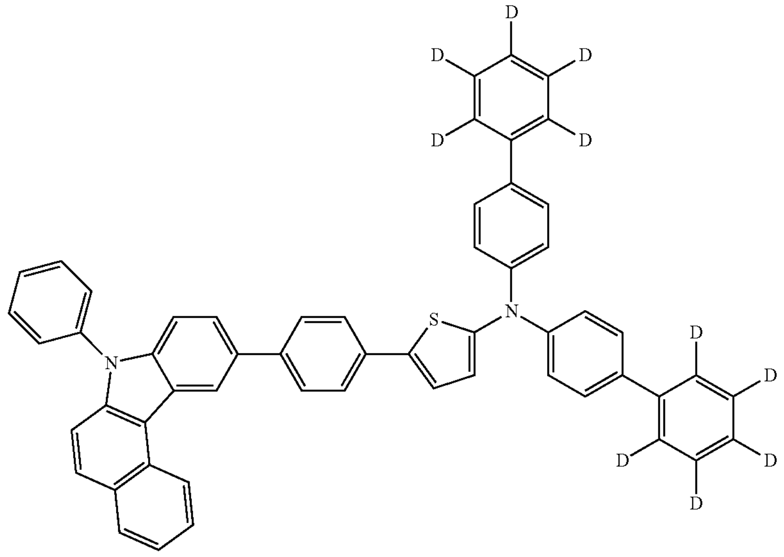
2-202
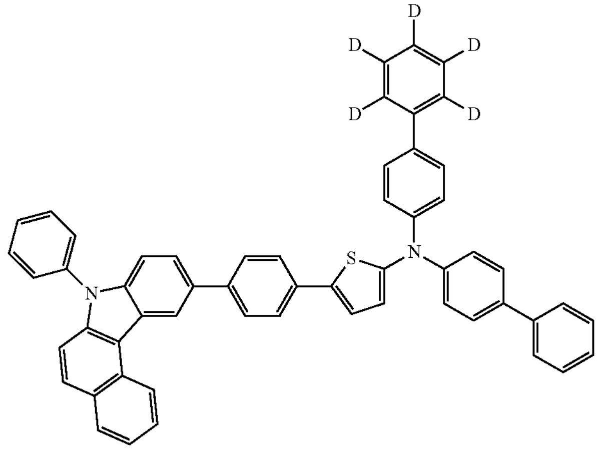
2-203
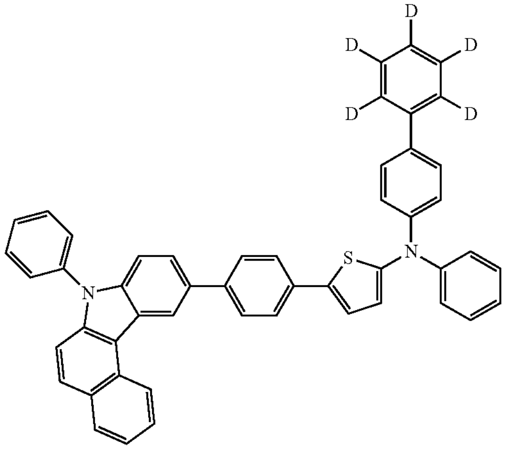
2-204
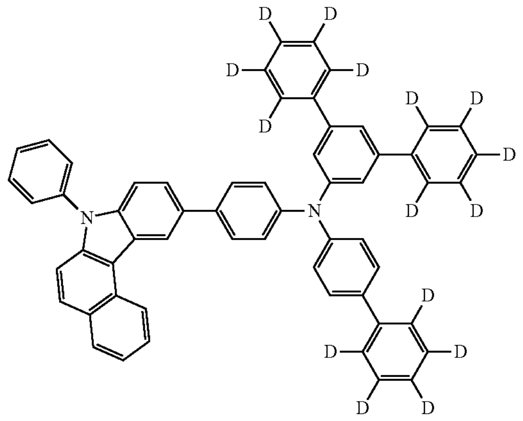
2-205
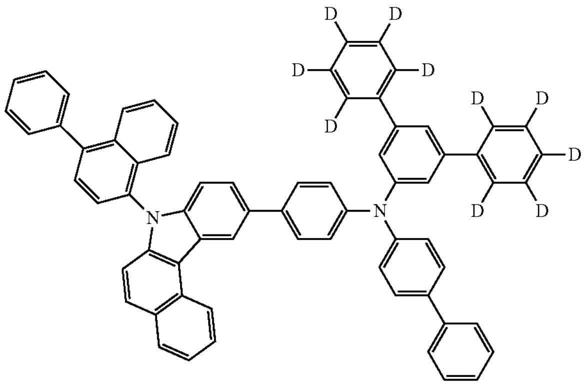

-continued
2-206
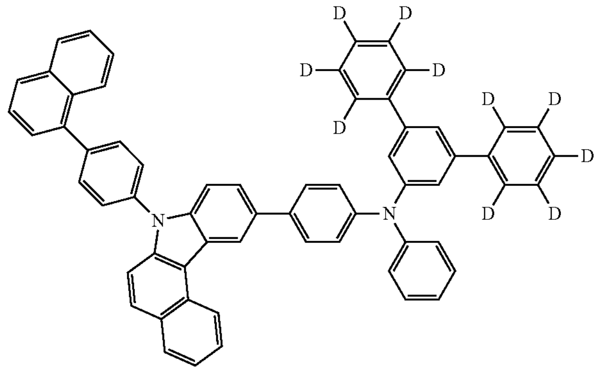
2-207
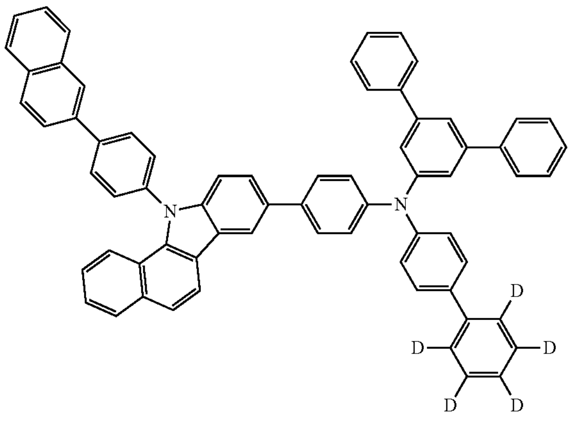
3-1
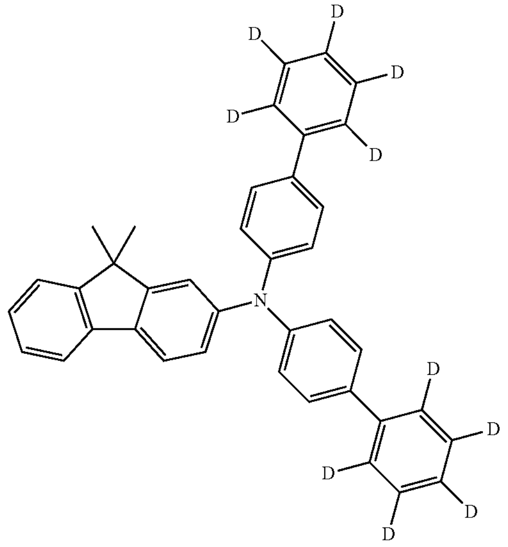
3-2
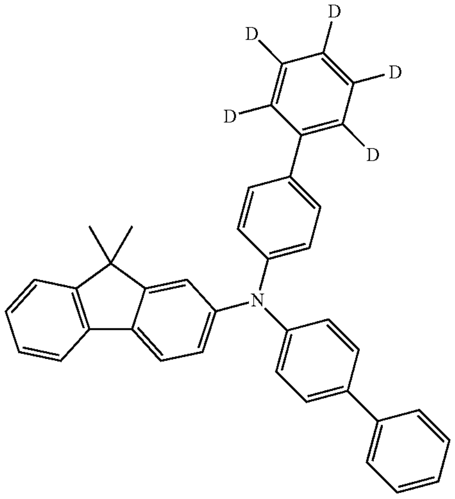
3-3
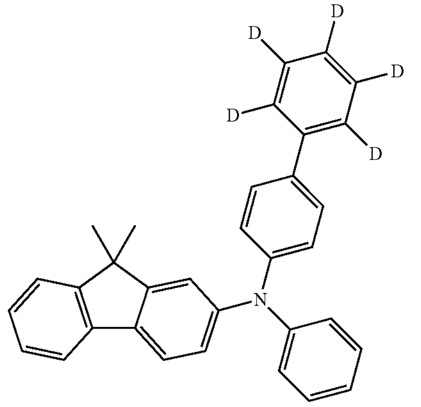
3-4
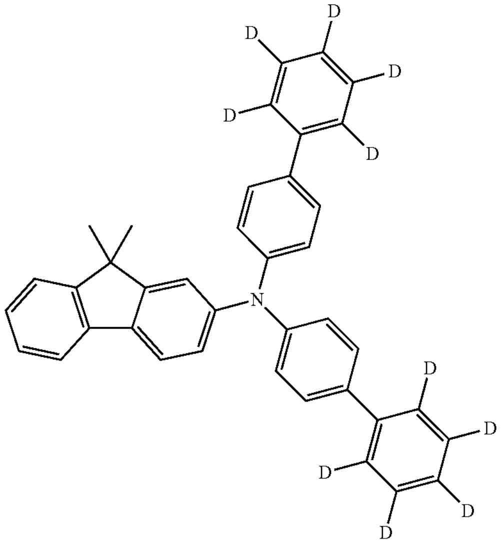

-continued
3-5
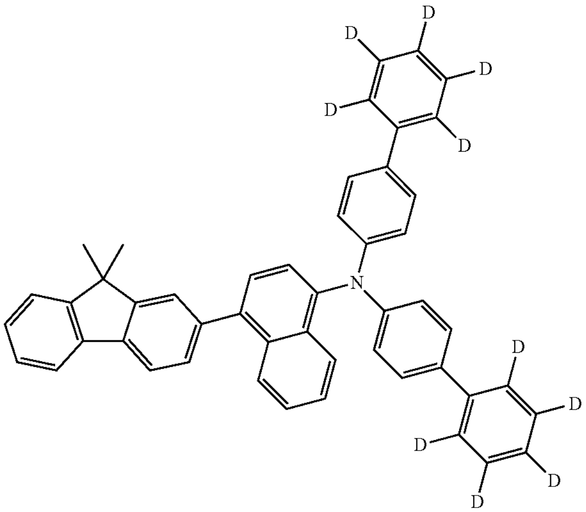
3-6
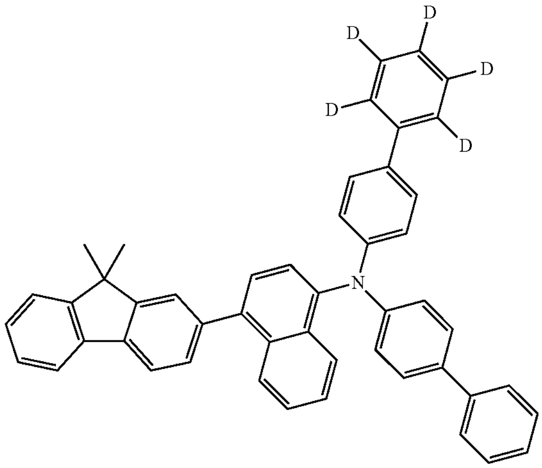
3-7
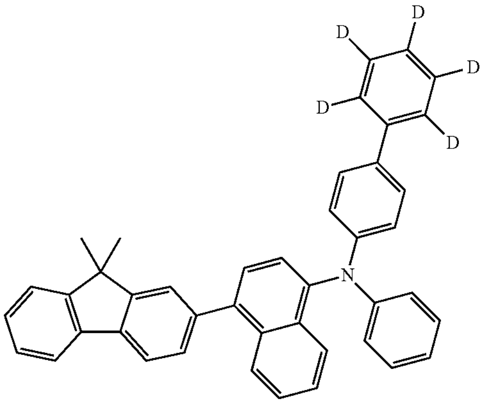
3-8
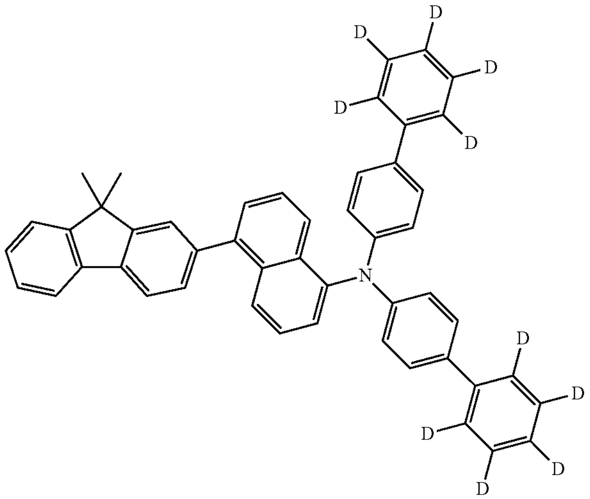
3-9
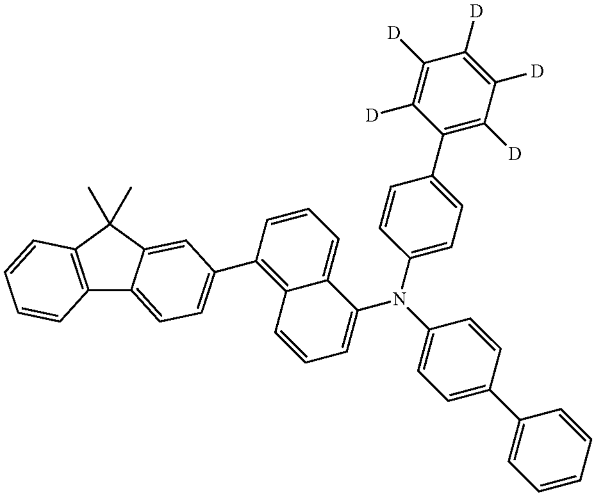
3-10
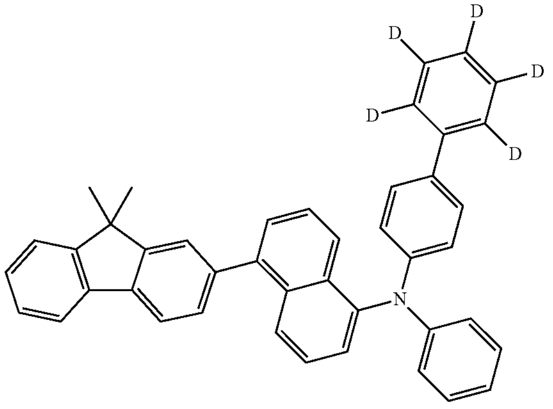

-continued
3-11
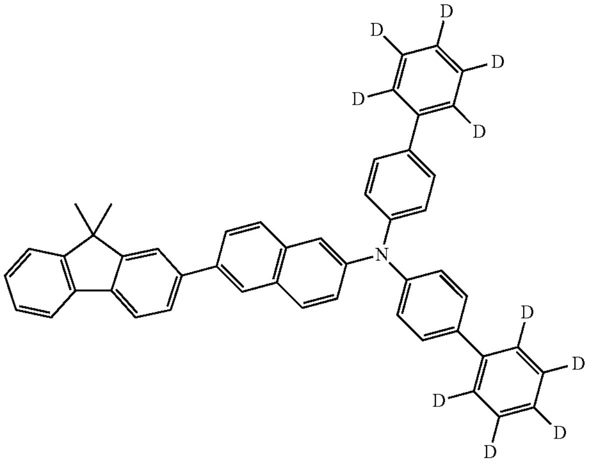
3-12
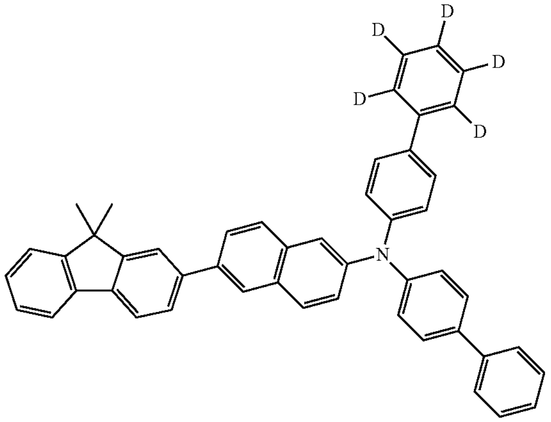
3-13
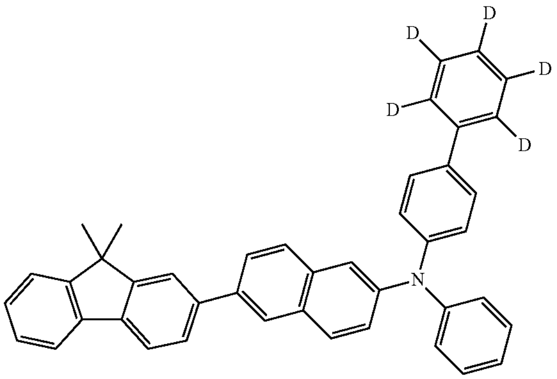
3-14
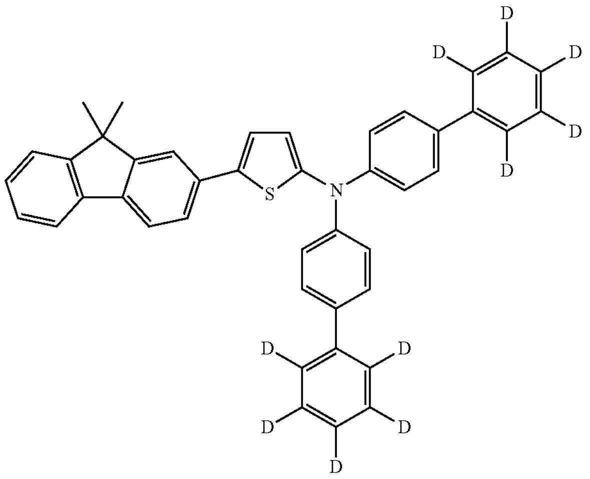
3-15
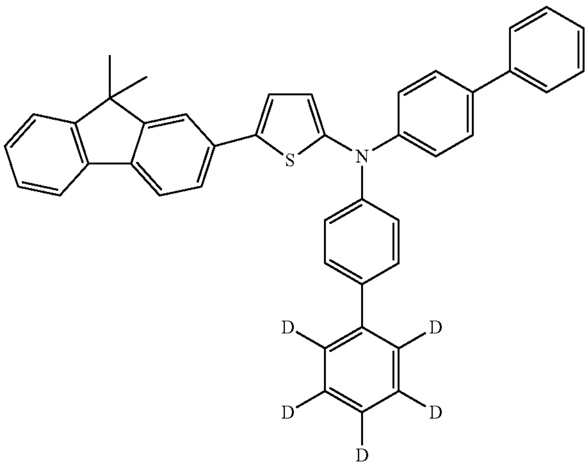
3-16
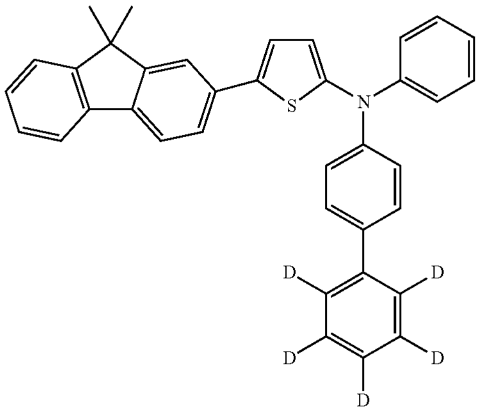

-continued
3-17
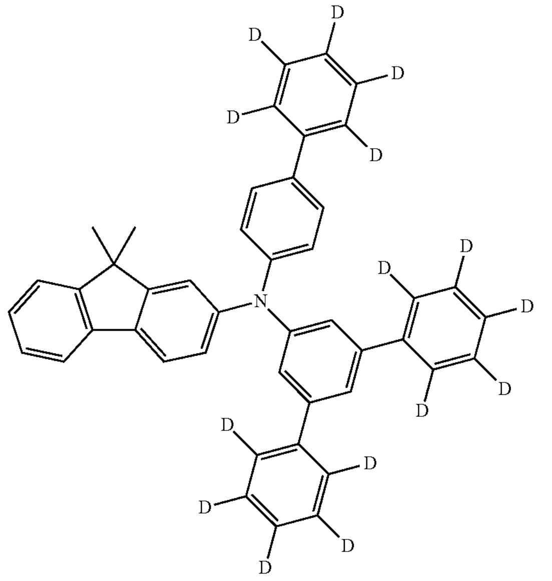
3-18
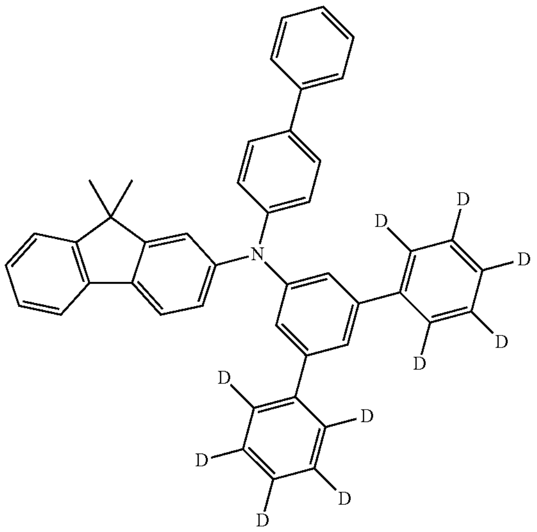
3-19
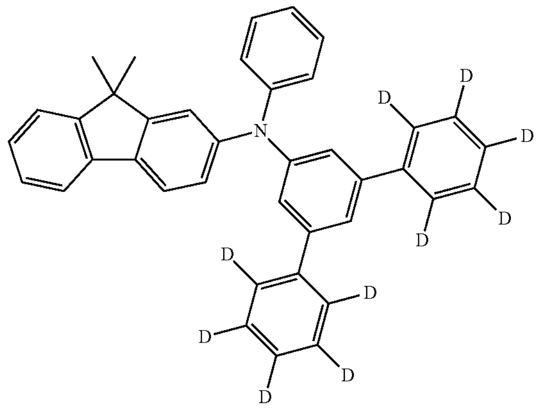
3-20
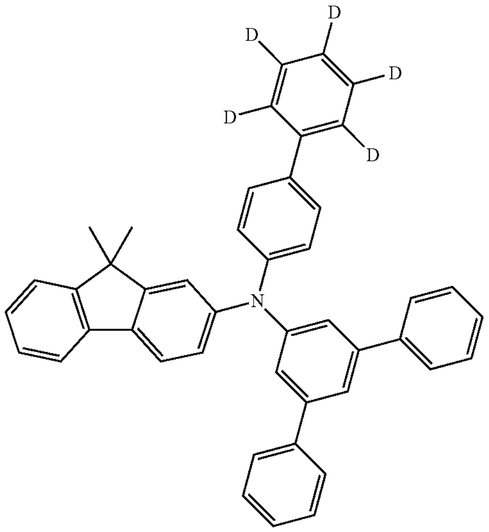
3-21
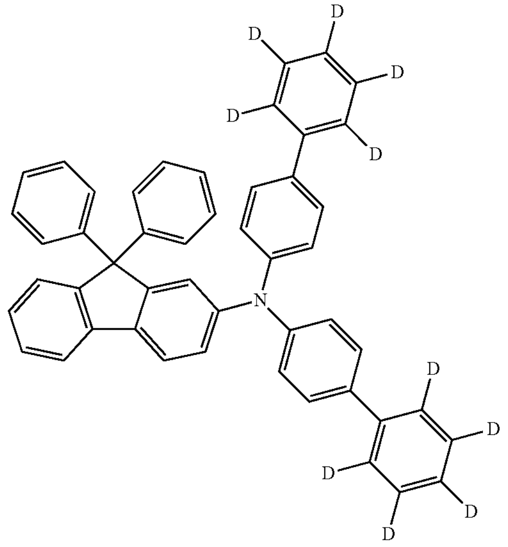
3-22
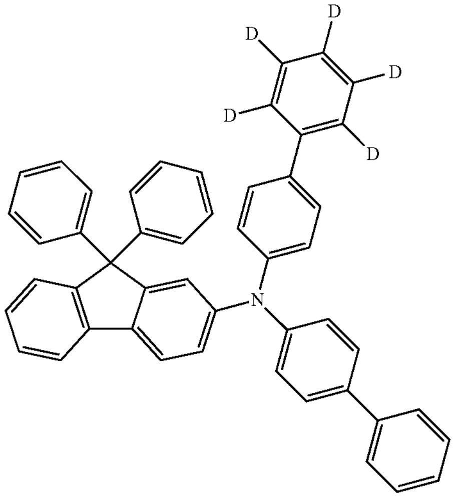

-continued
3-23
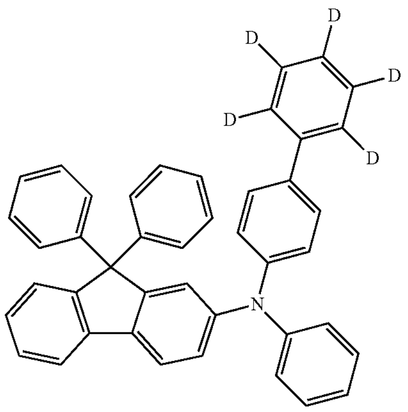
3-24
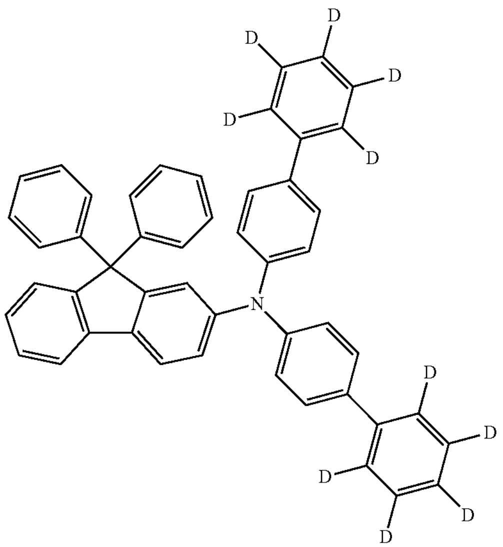
3-25
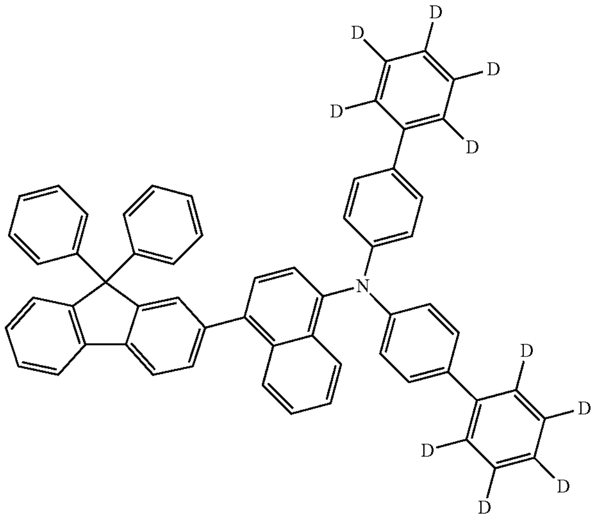
3-26
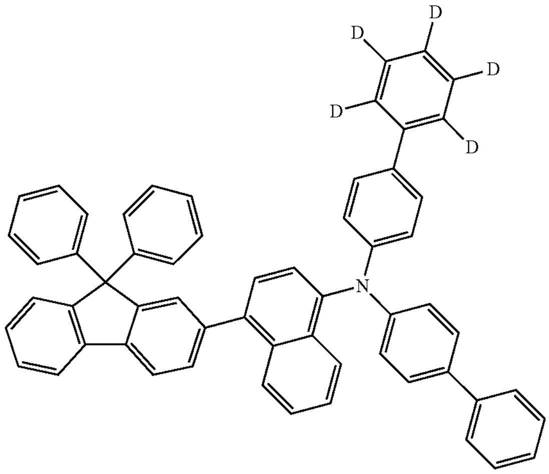
3-27
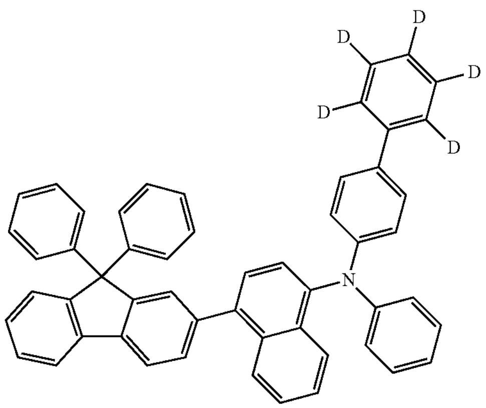
3-28
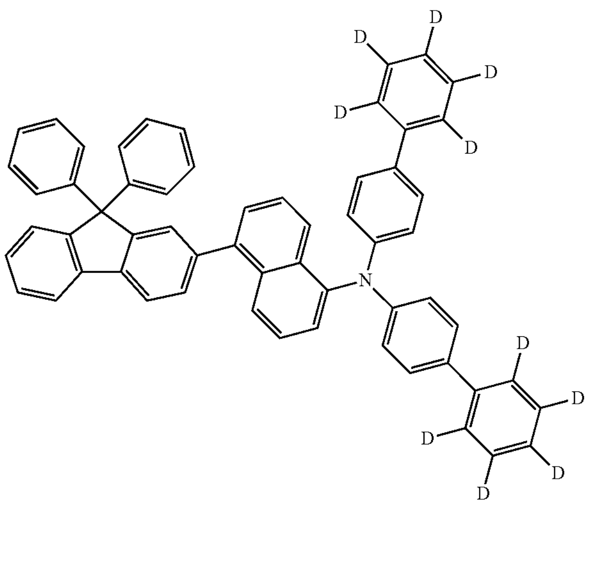

-continued
3-29
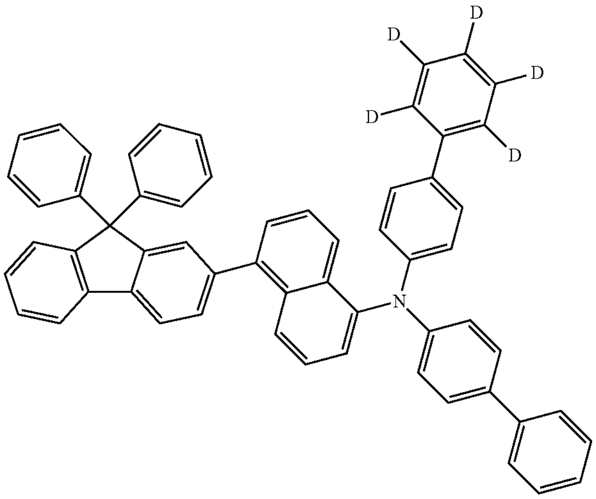
3-30
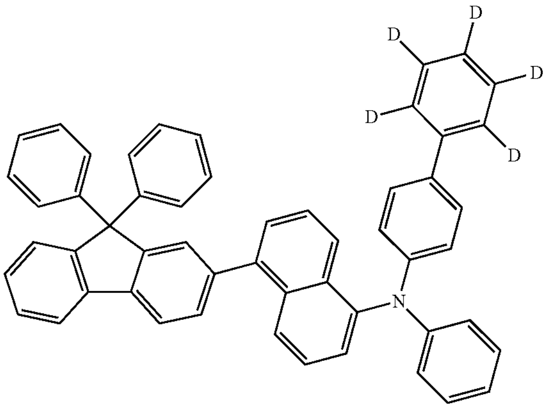
3-31
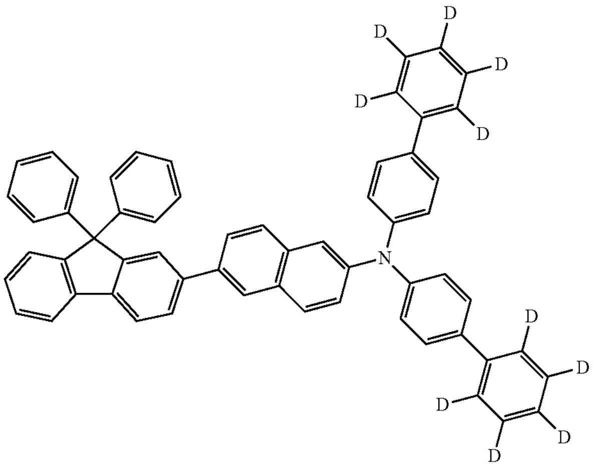
3-32
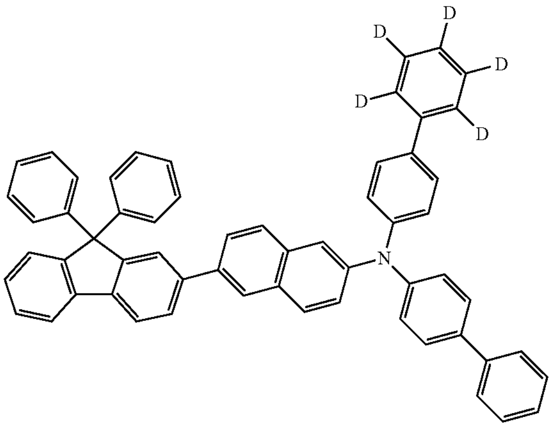
3-33
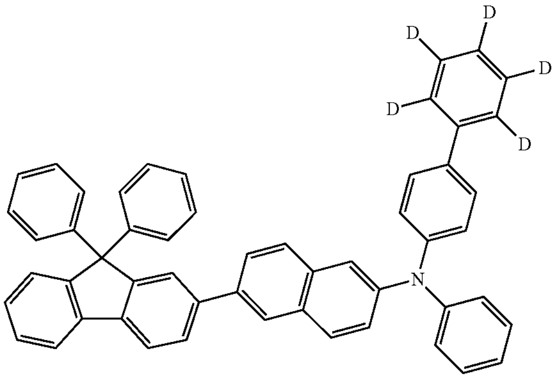
3-34
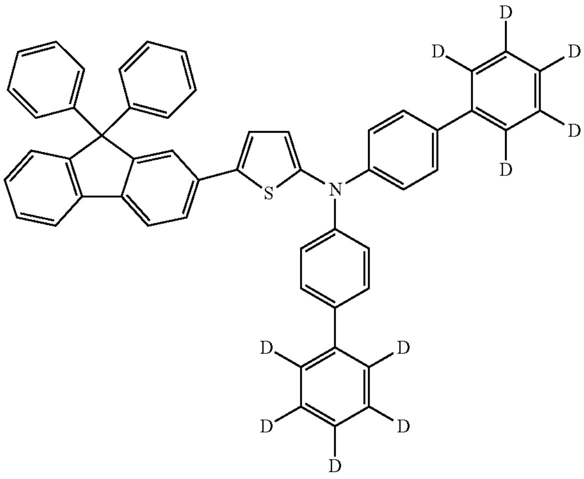

-continued
3-35
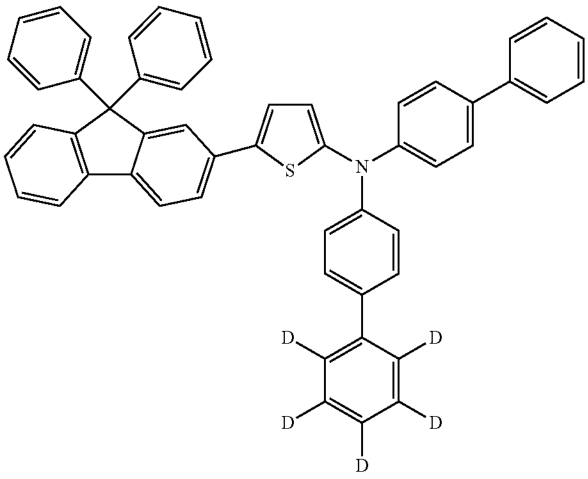
3-36
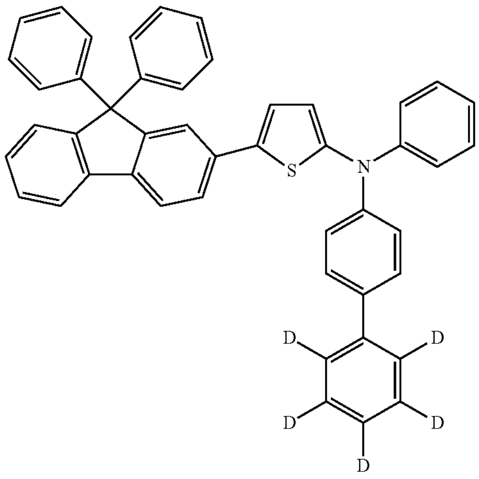
3-37
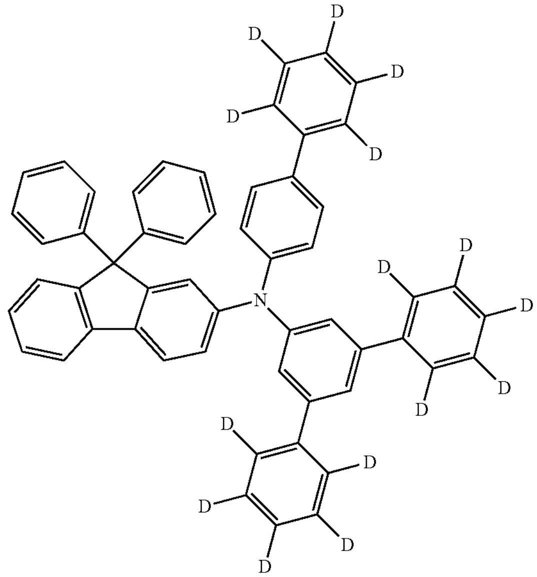
3-38
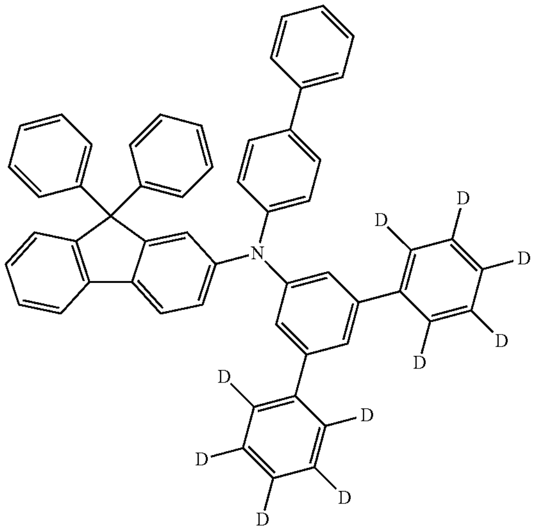
3-39
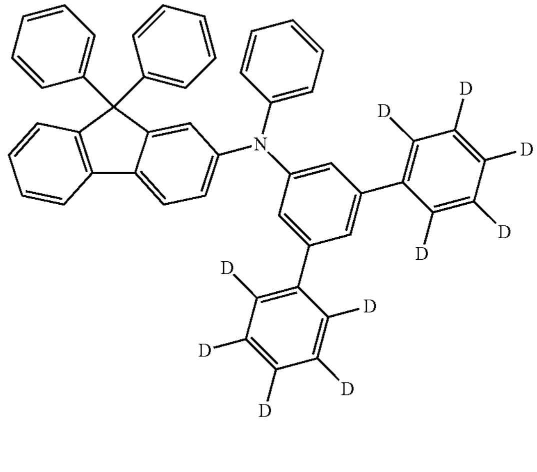
3-40
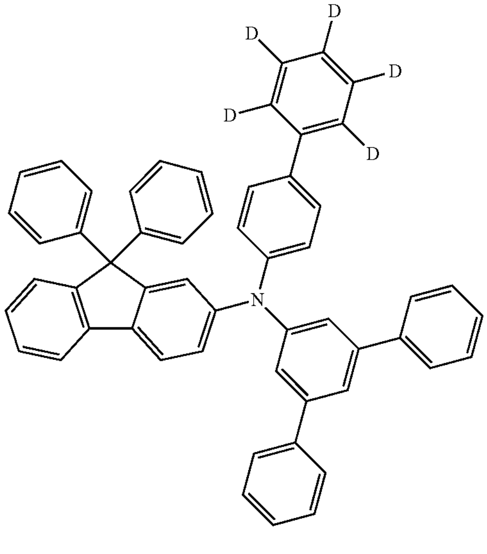

-continued
3-41
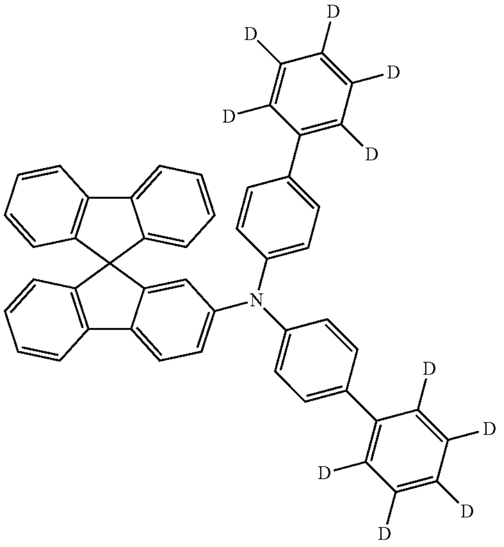
3-42
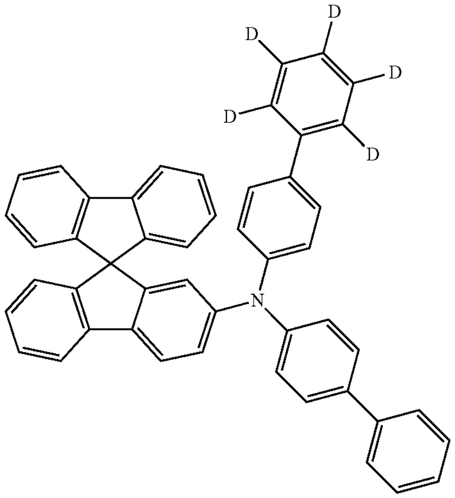
3-43
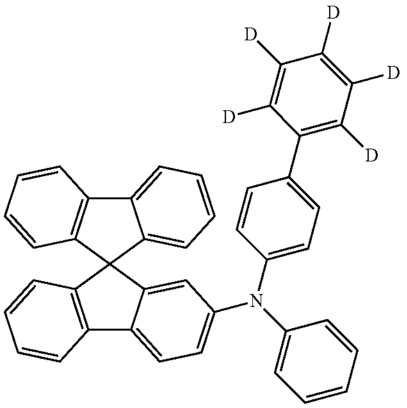
3-44
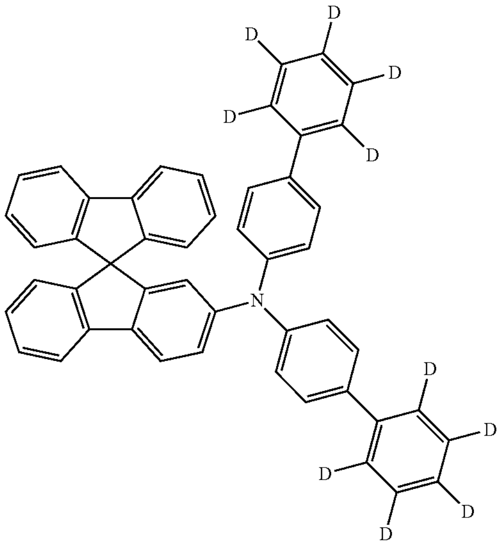
3-45
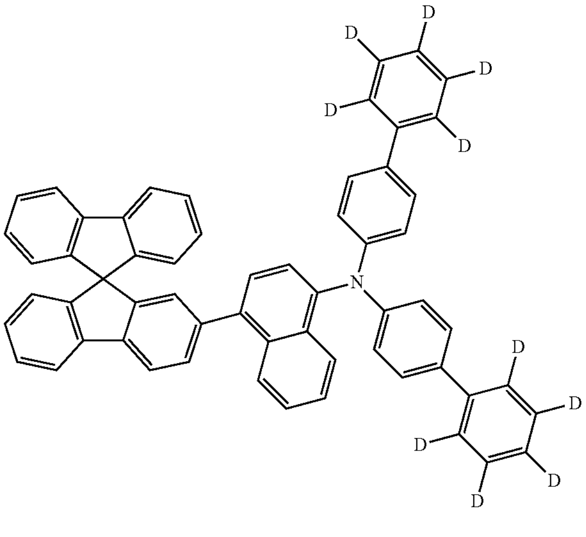
3-46
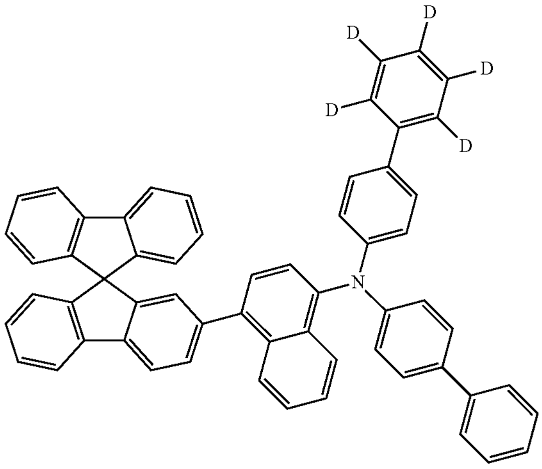

-continued
3-47
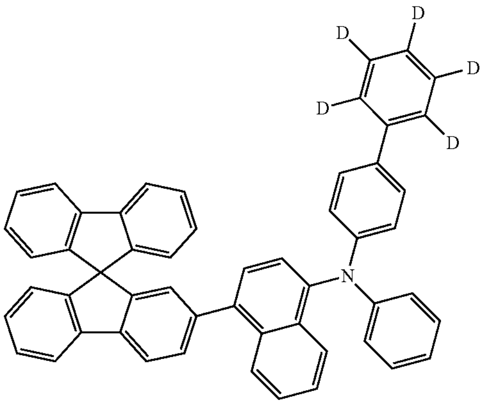
3-48
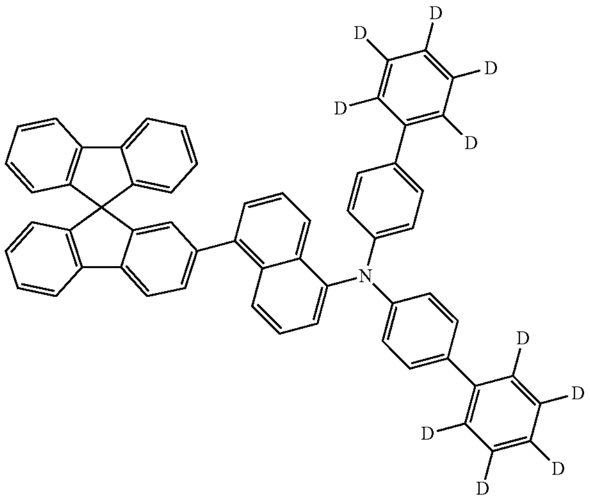
3-49
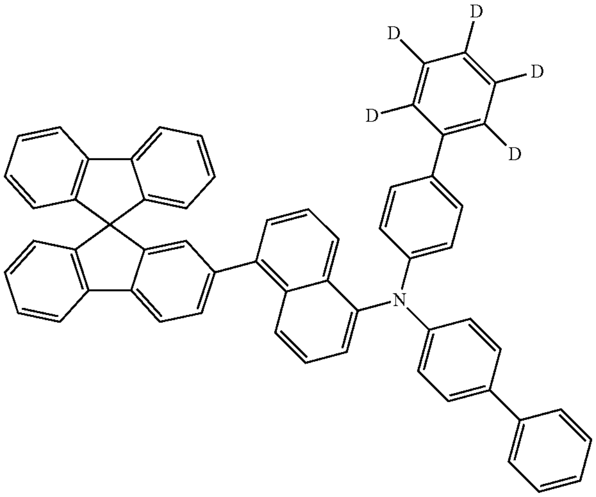
3-50
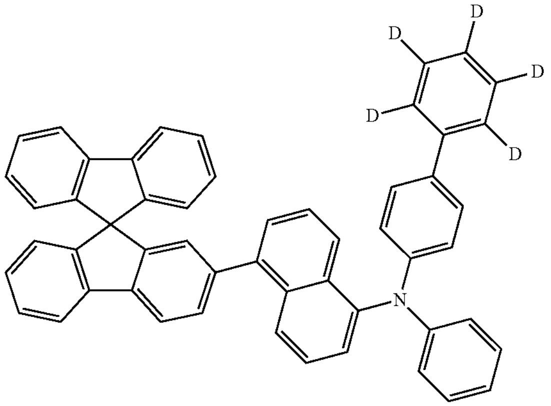
3-51
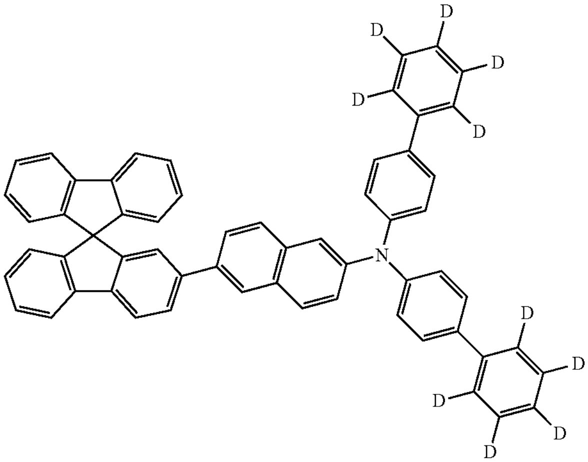
3-52
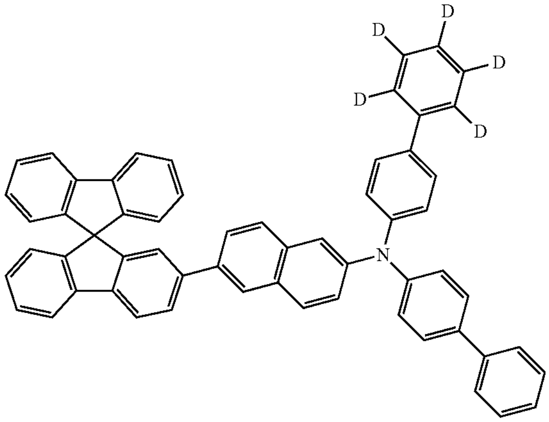

-continued
3-53
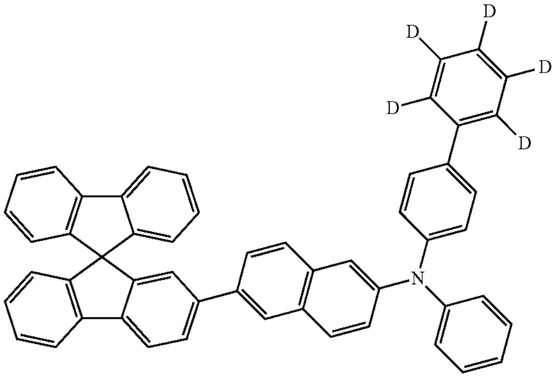
3-54
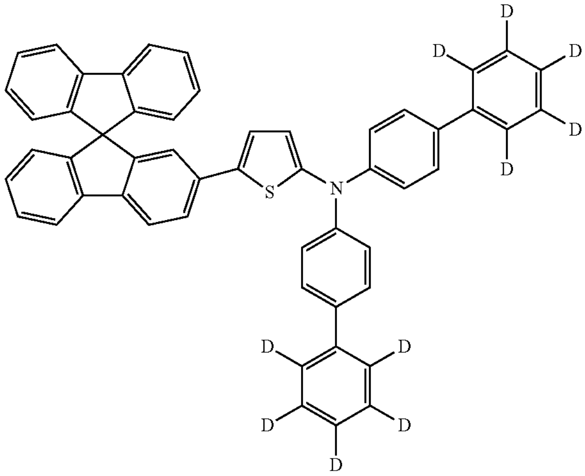
3-55
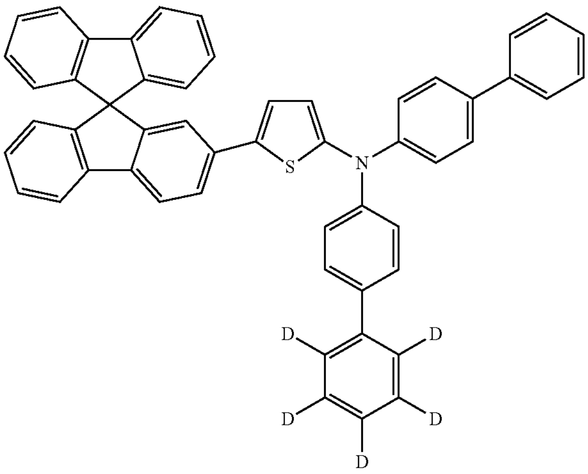
3-56
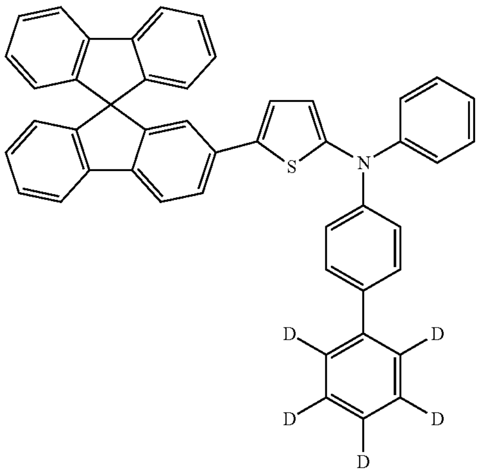
3-57
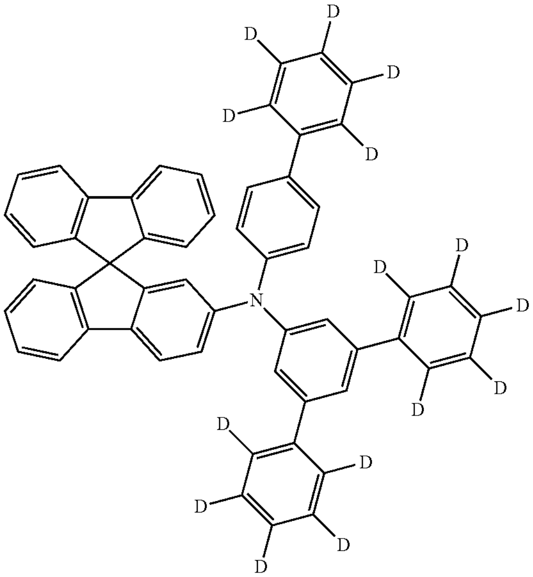
3-58
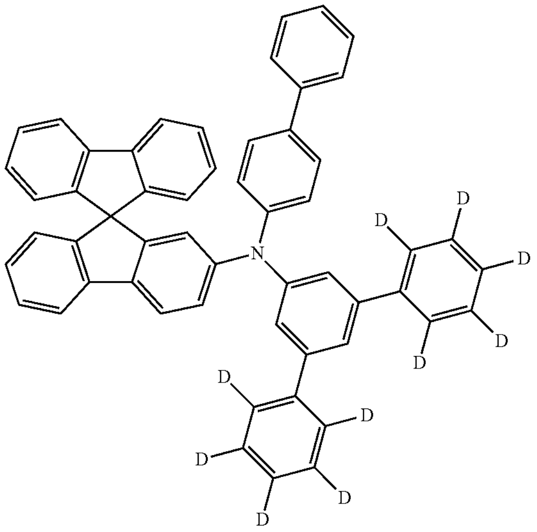

-continued
3-59
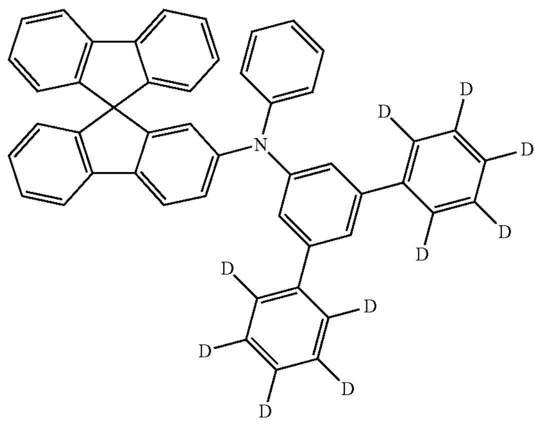
3-60
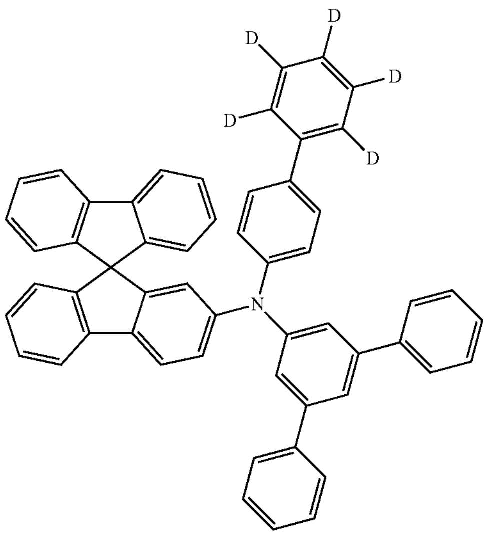
3-61
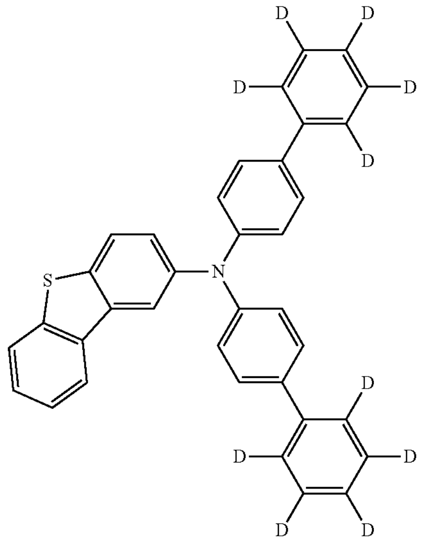
3-62
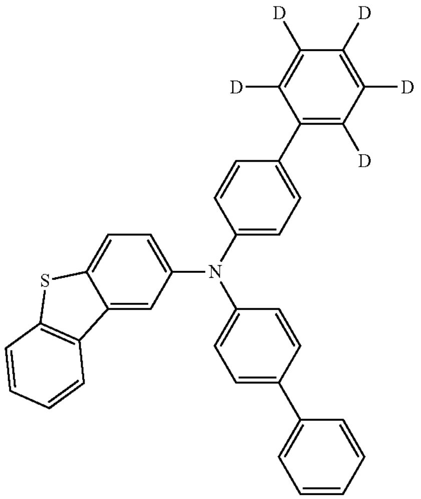
3-63
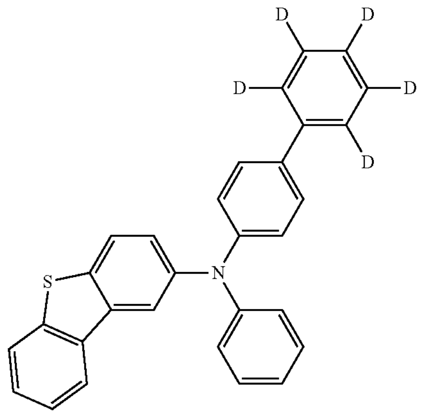
3-64
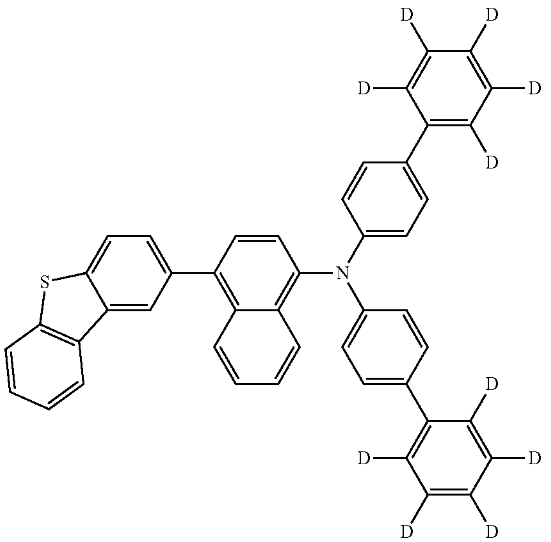

-continued
3-65
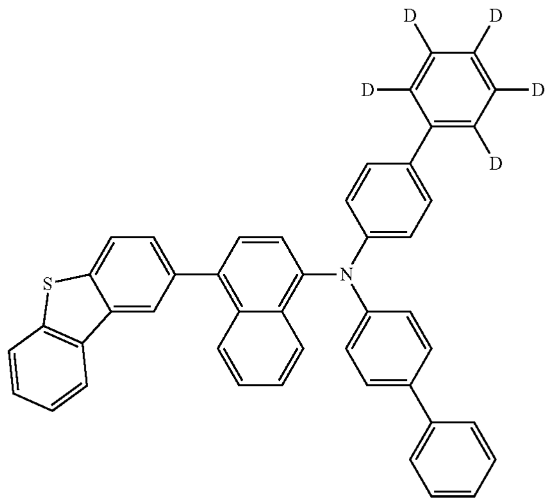
3-66
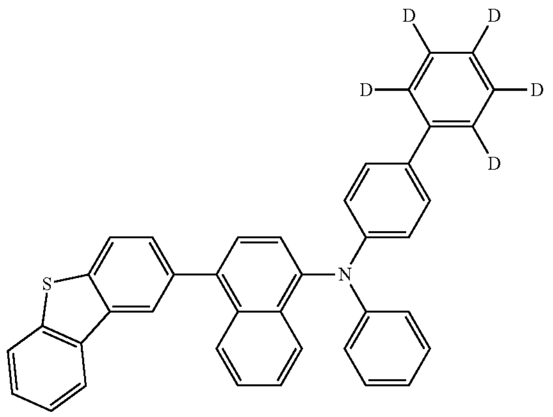
3-67
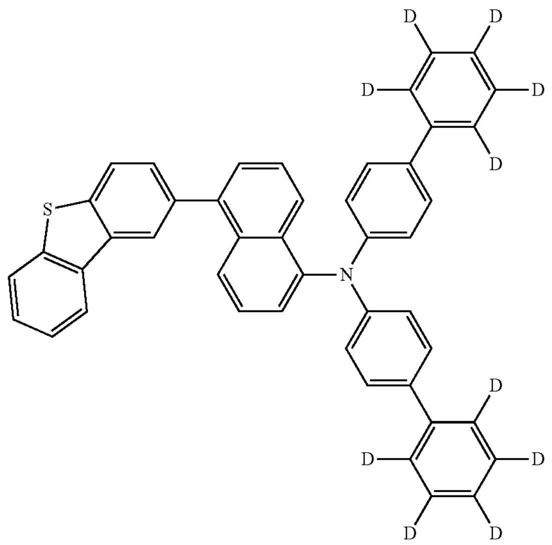
3-68
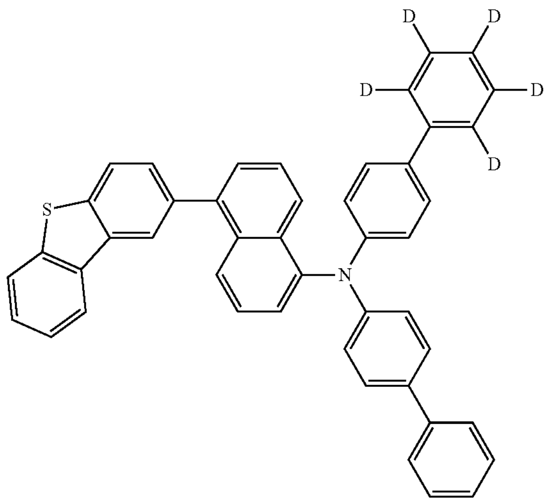
3-69
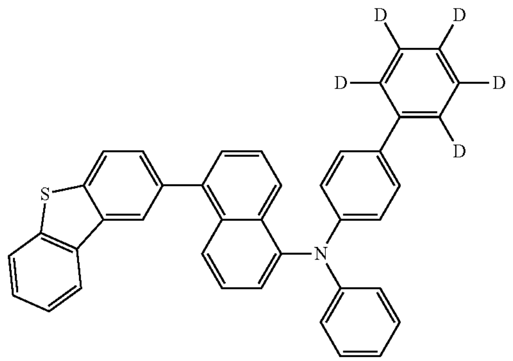
3-70
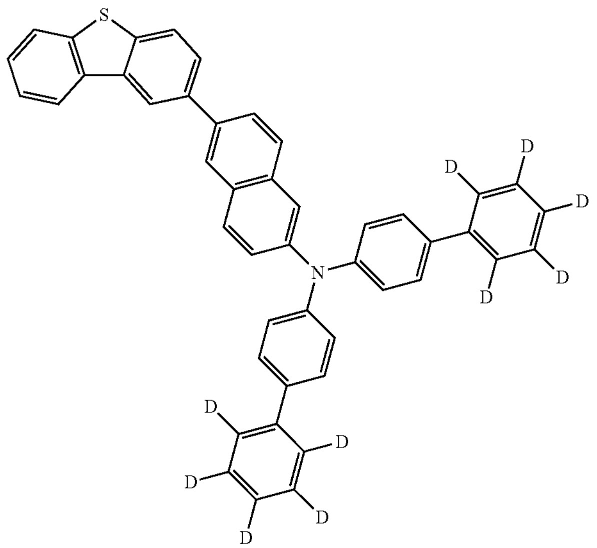

-continued
3-71
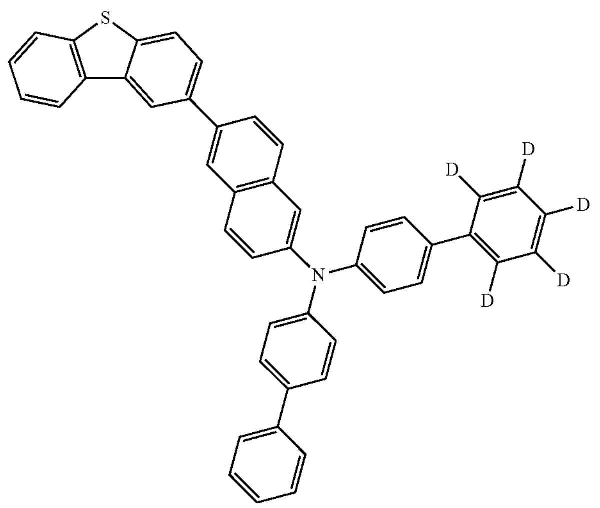
3-72
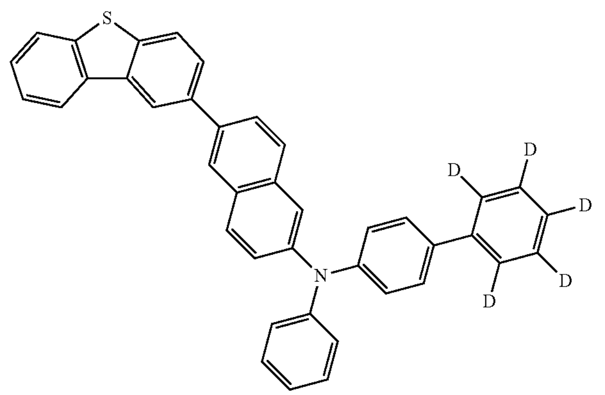
3-73
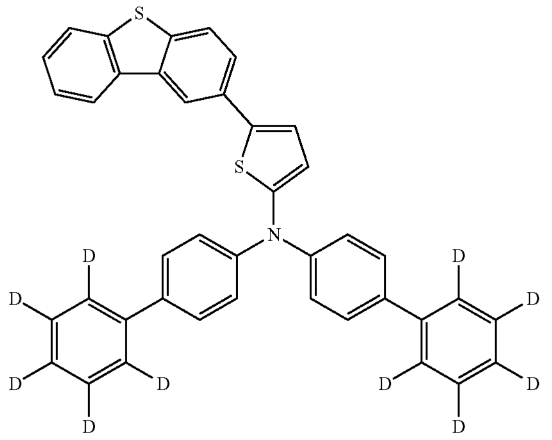
3-74
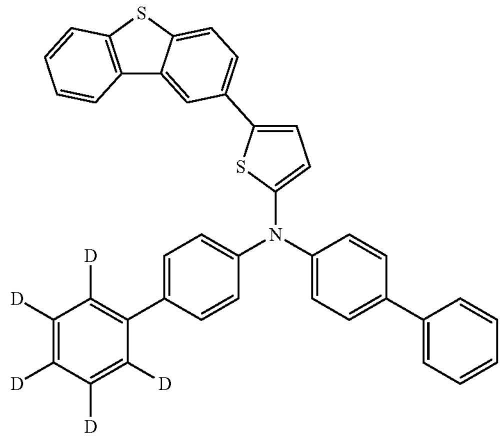
3-75
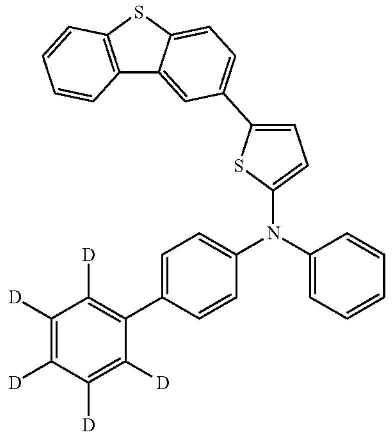
3-76
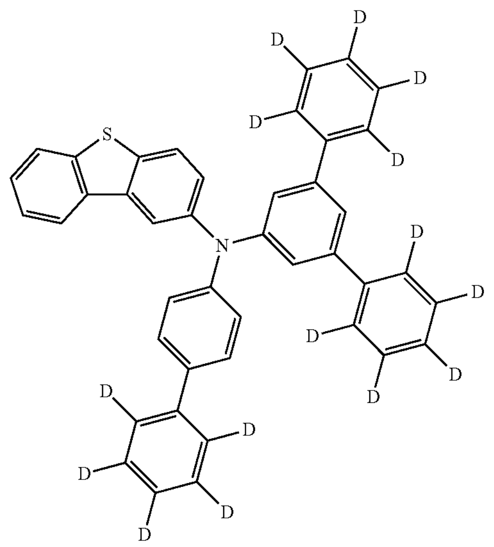

-continued
3-77
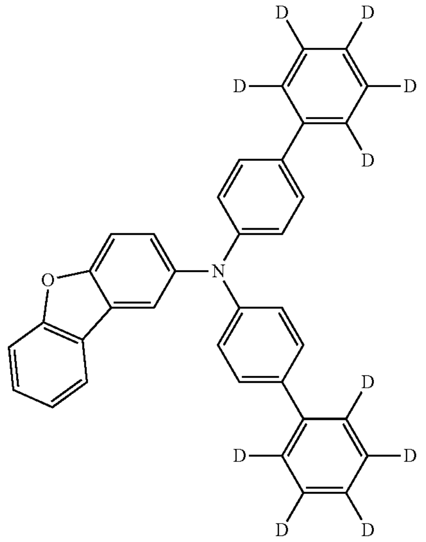
3-78
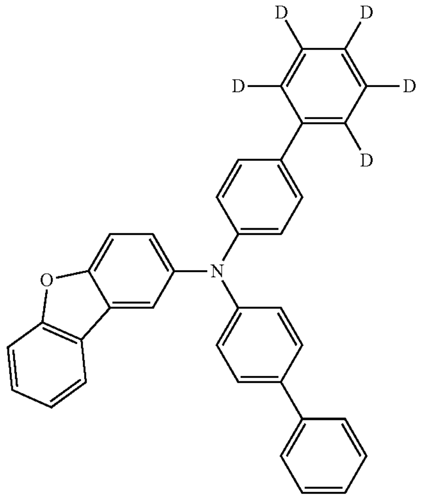
3-79
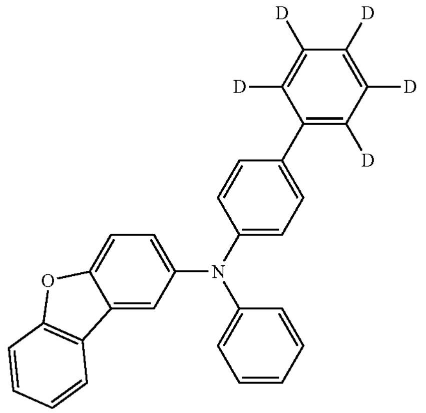
3-80
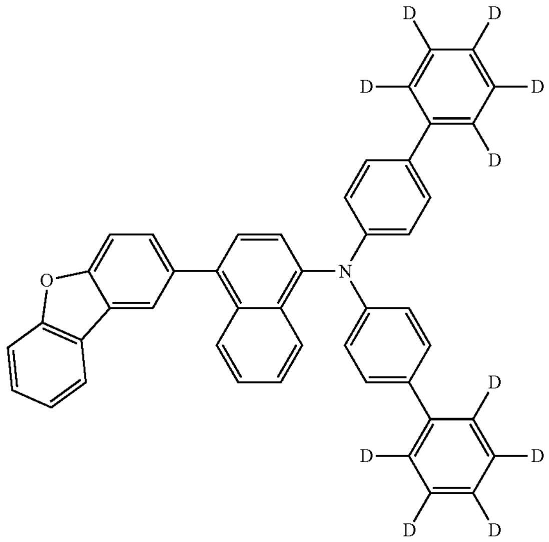
3-81
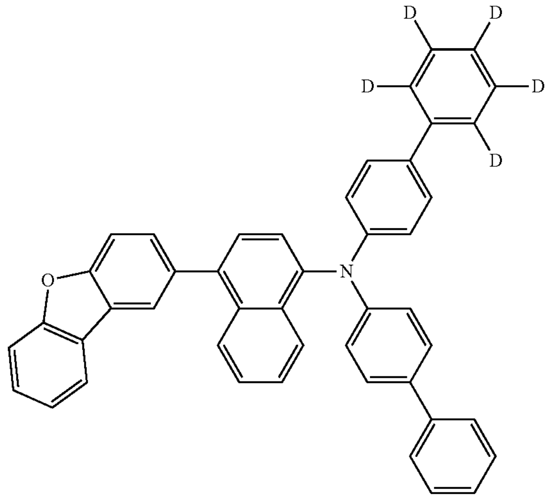
3-82
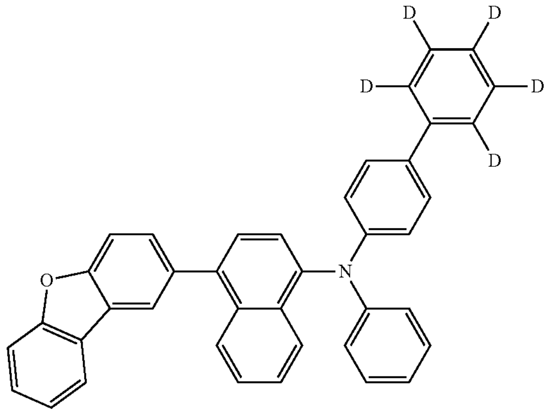

-continued
3-83
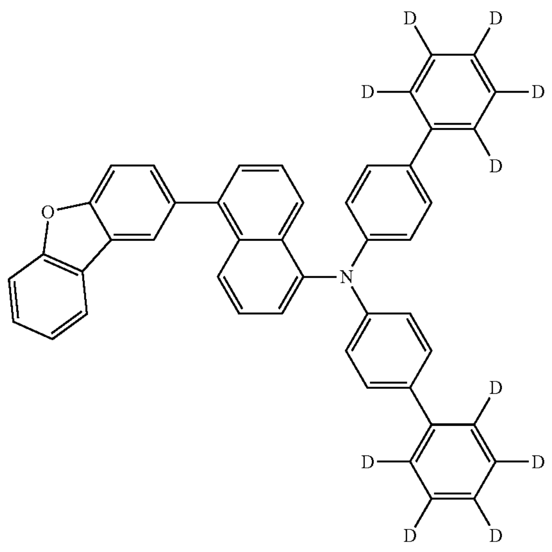
3-84
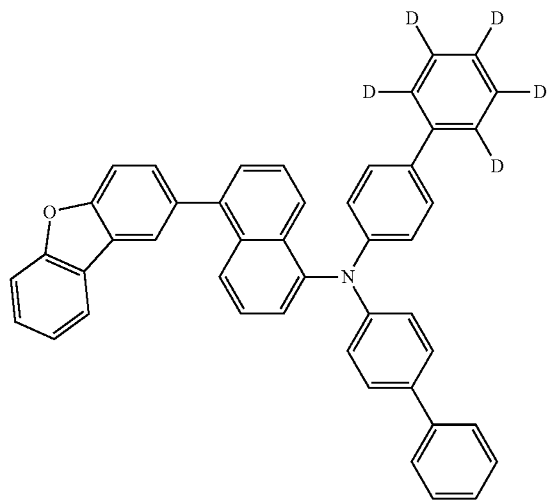
3-85
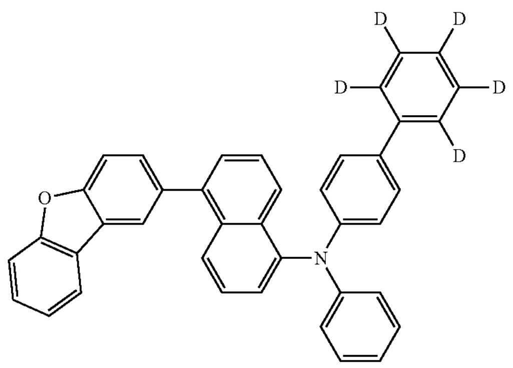
3-86
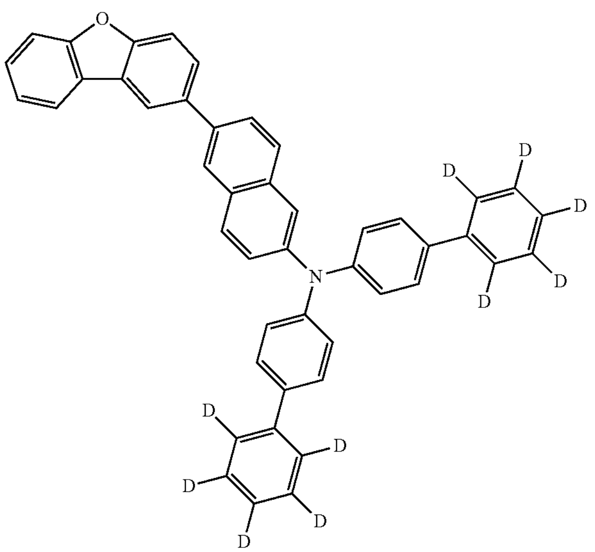
3-87
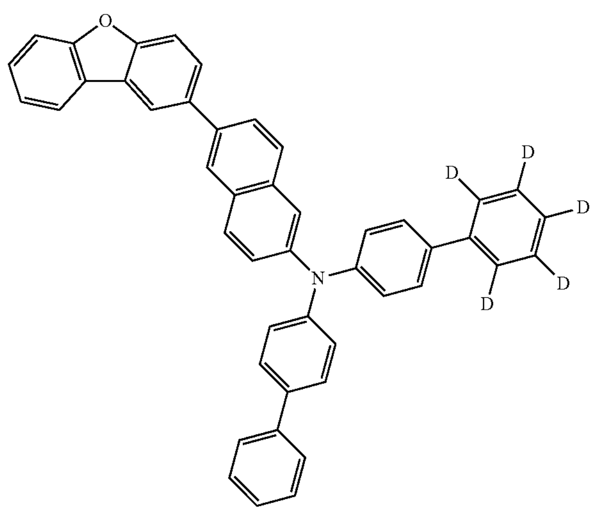
3-88
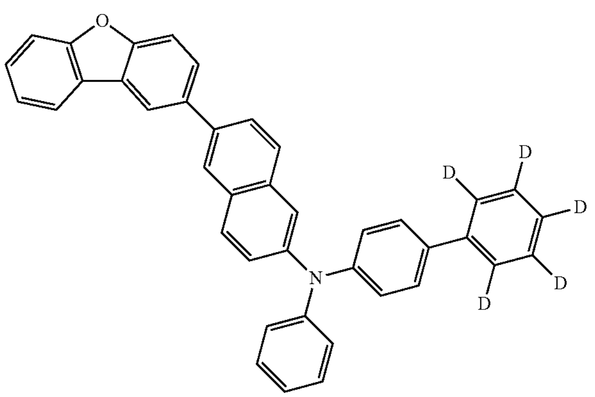

-continued
3-89
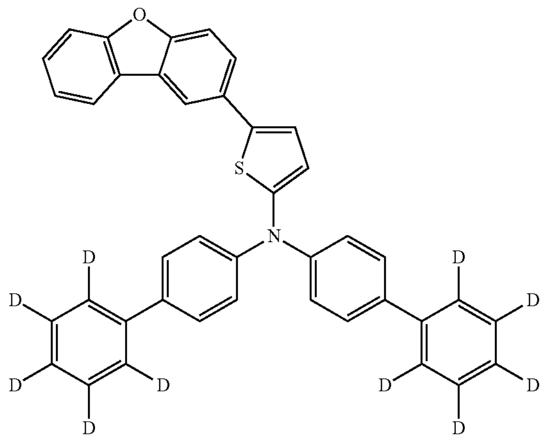
3-90
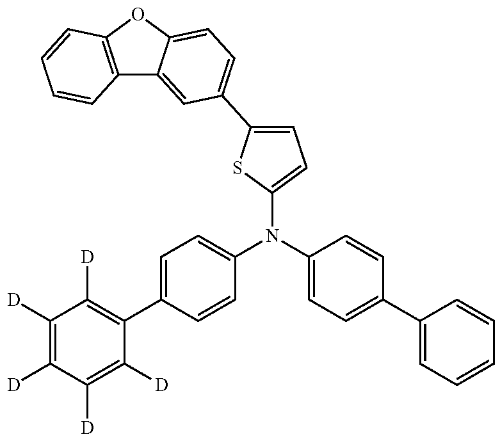
3-91
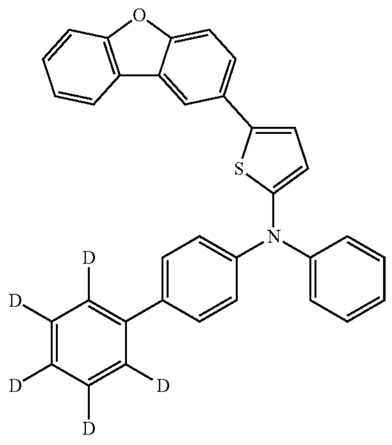
3-92
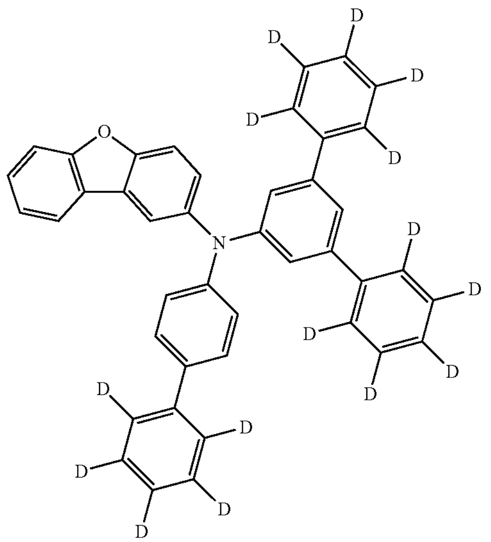
3-93
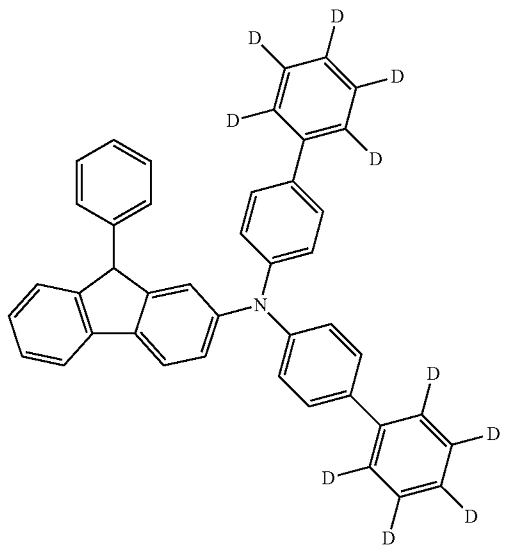
3-94
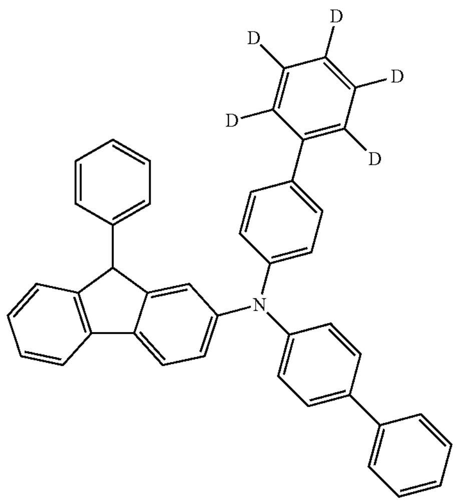

-continued
3-95
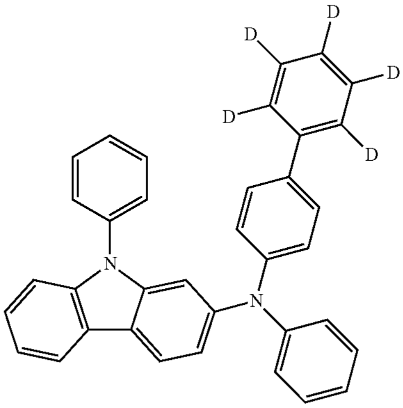
3-96
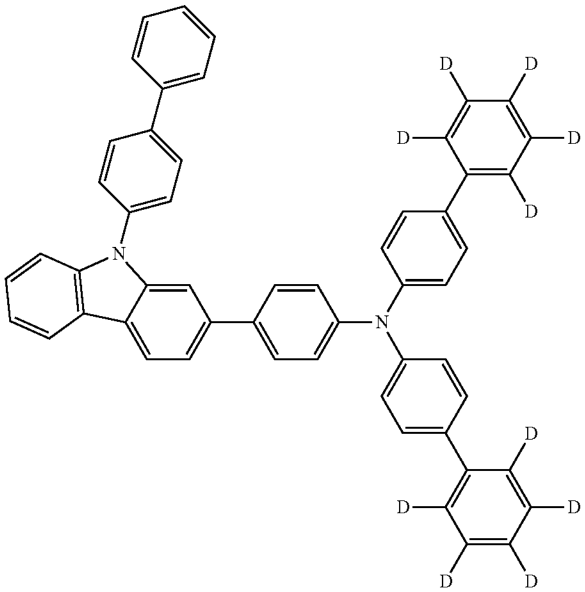
3-97
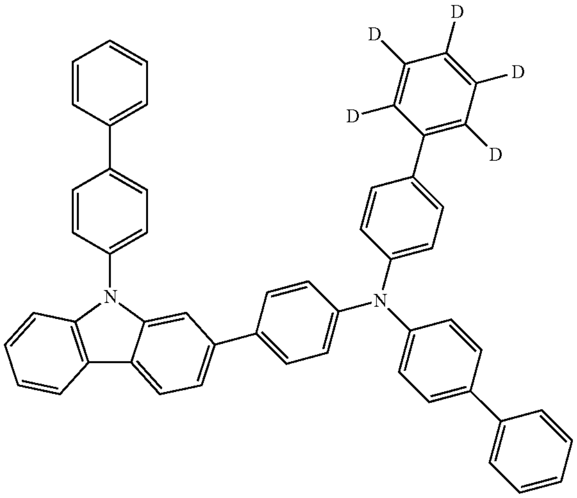
3-98
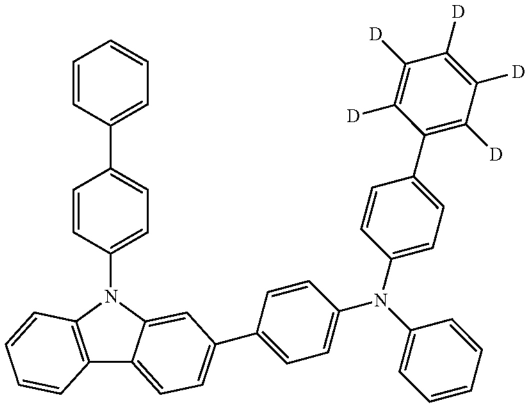
3-99
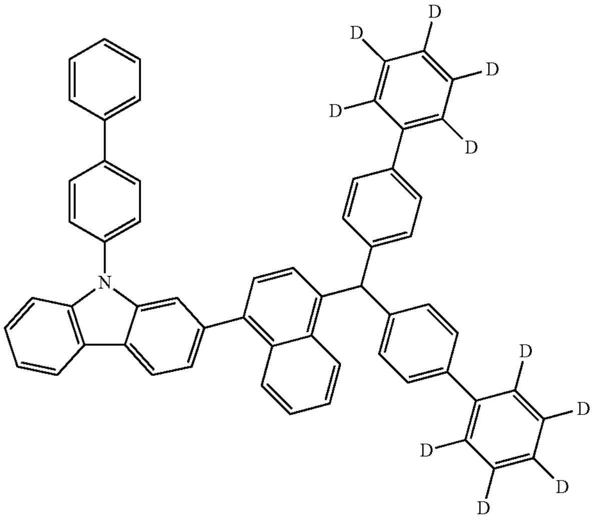
3-100
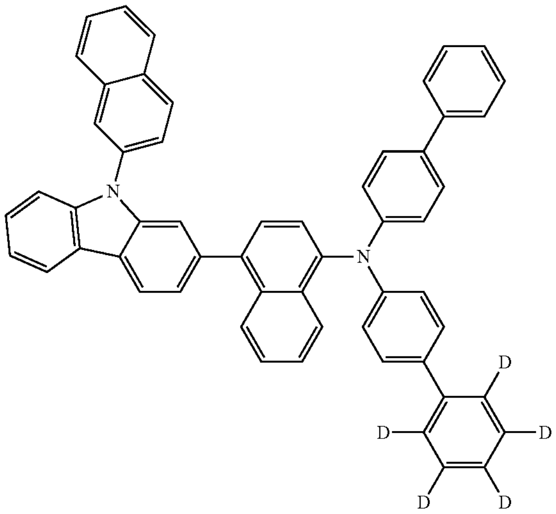

-continued
3-101
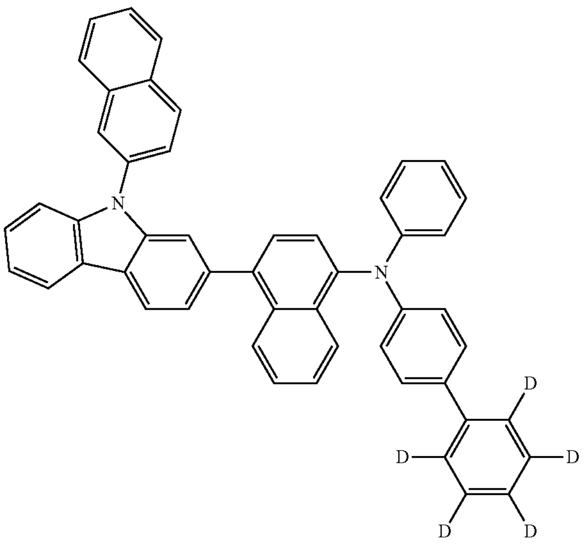
3-102
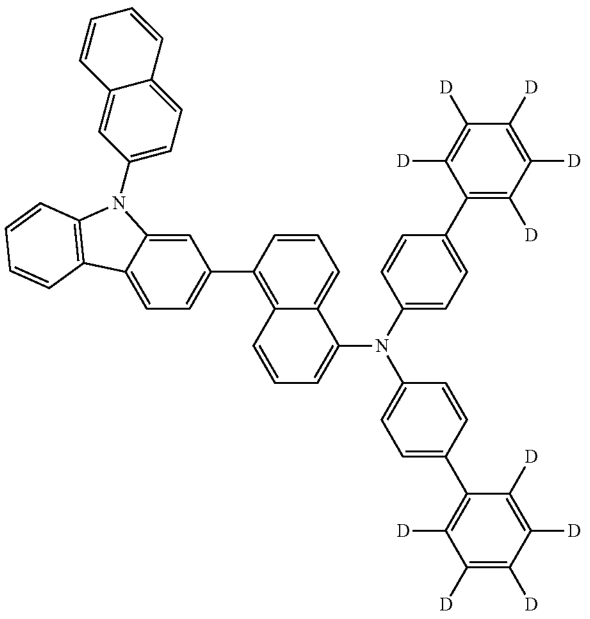
3-103
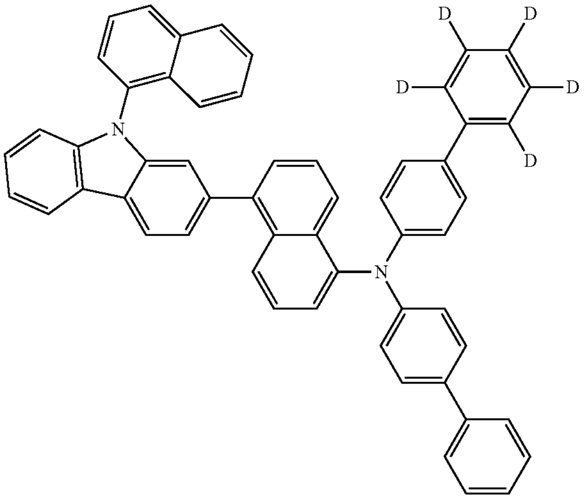
3-104
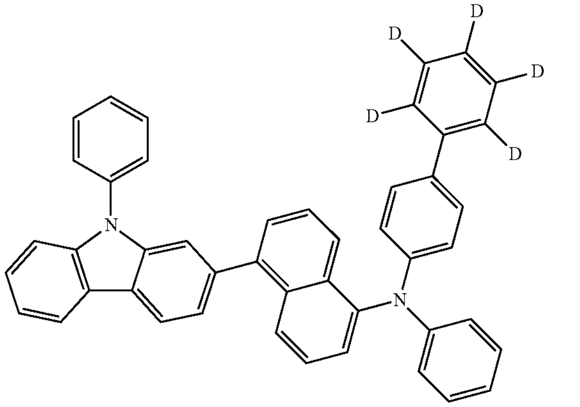
3-105
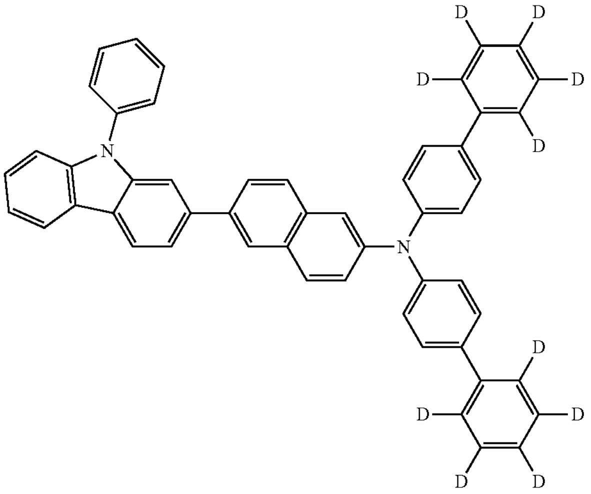
3-106
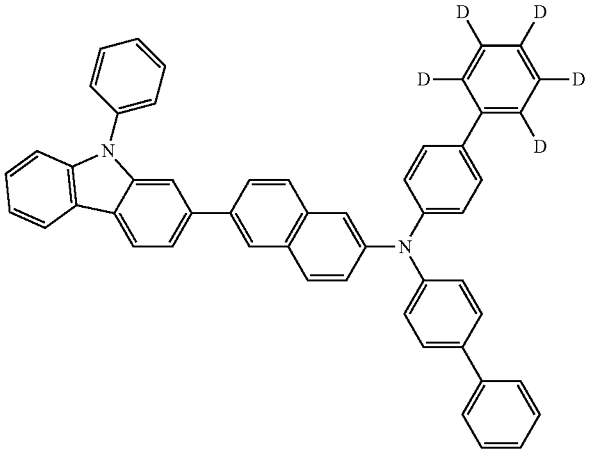

-continued
3-107
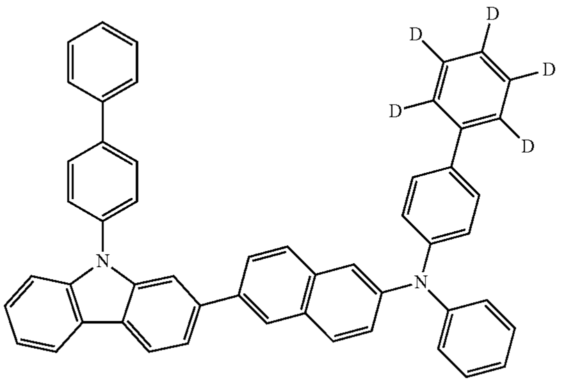
3-108
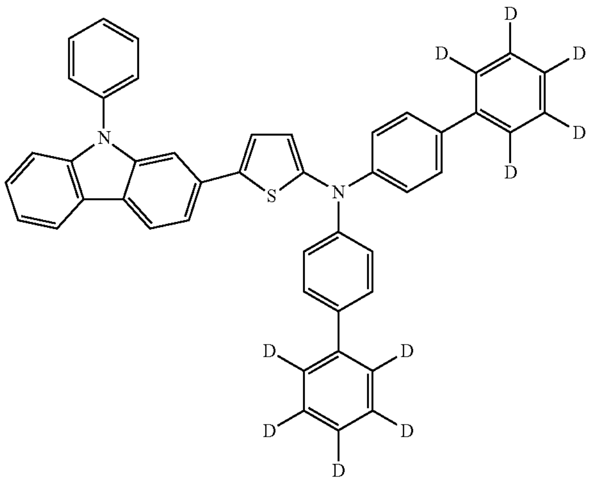
3-109
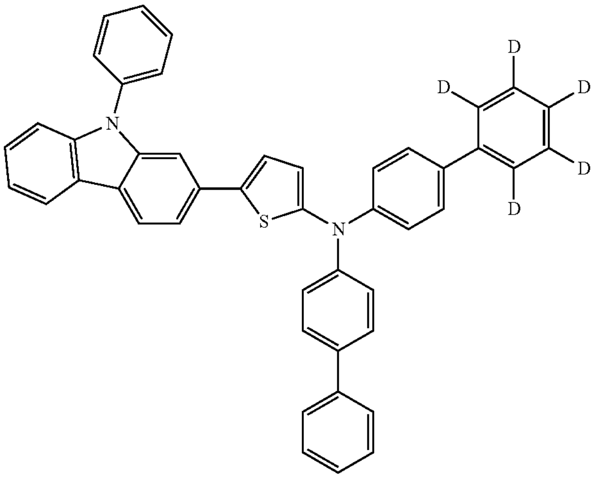
3-110
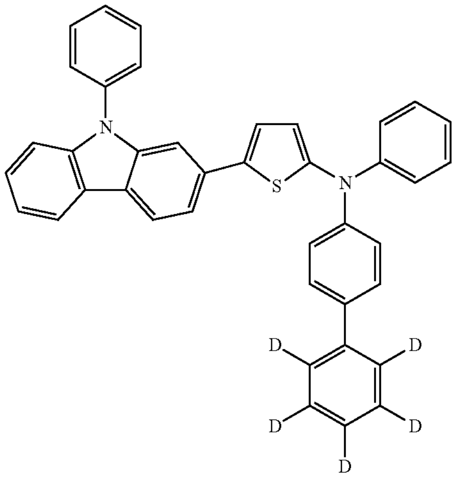
3-111
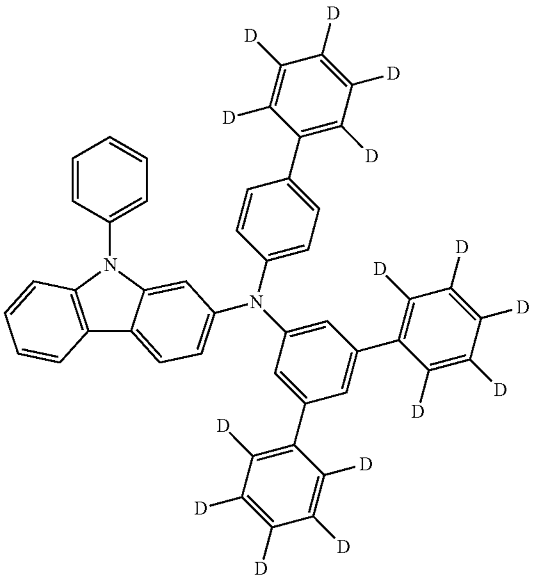
3-112
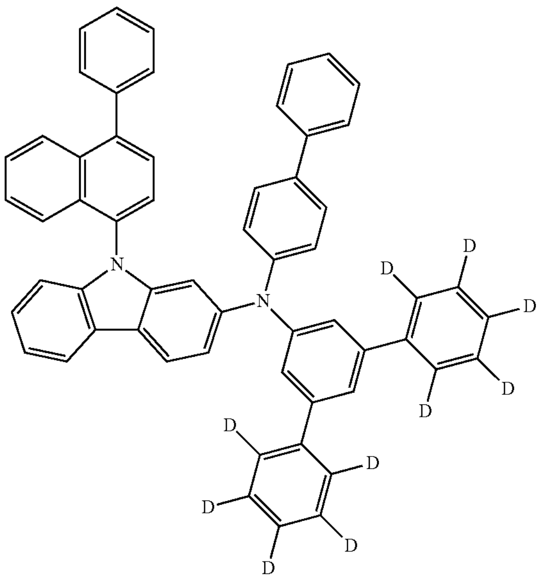

-continued
3-113
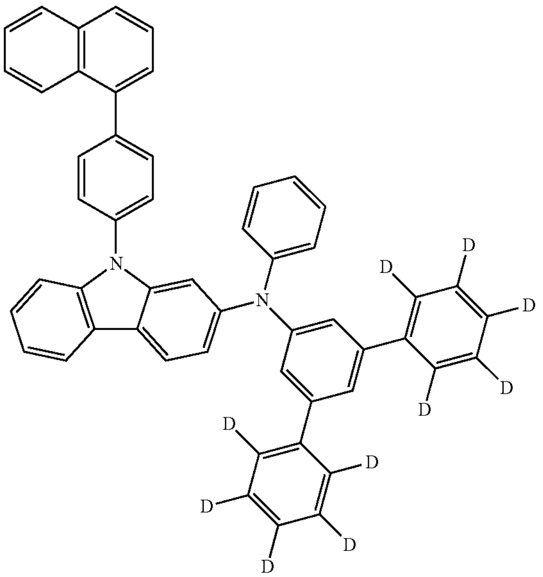
3-114
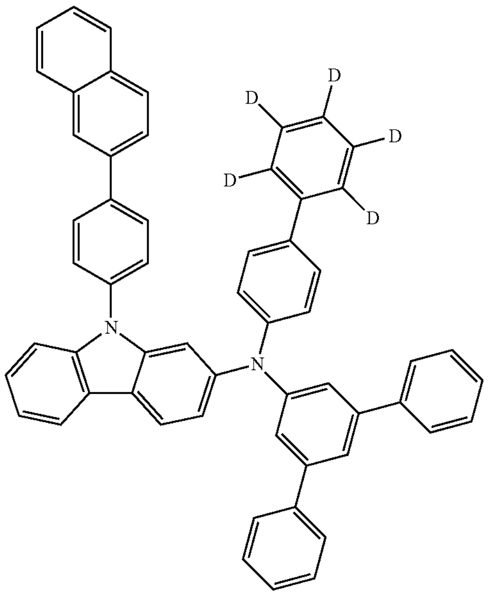
3-115
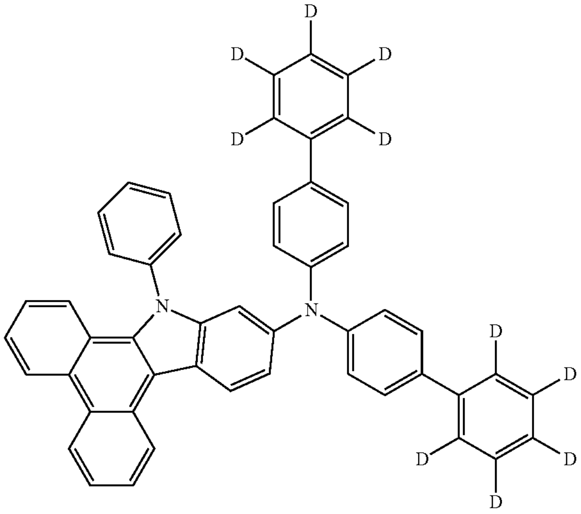
3-116
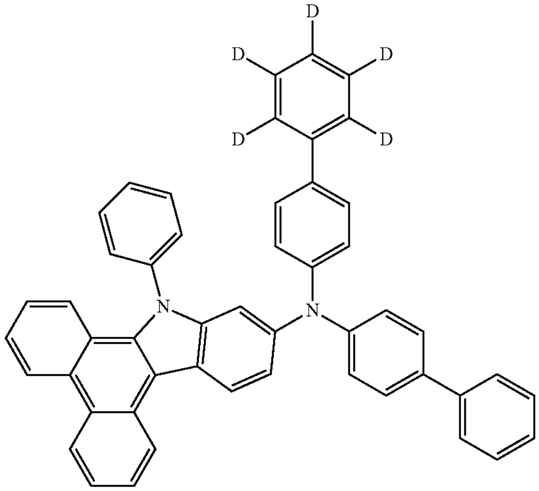
3-117
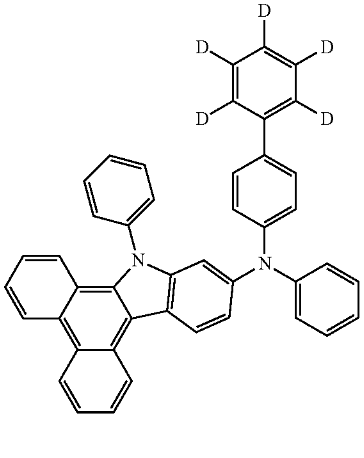
3-118
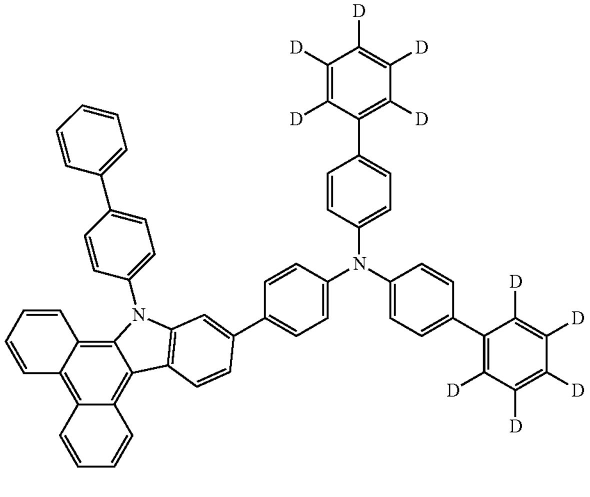

-continued
3-119
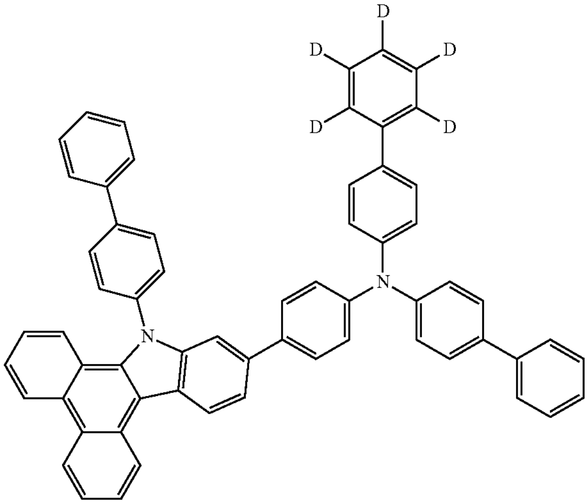
3-120
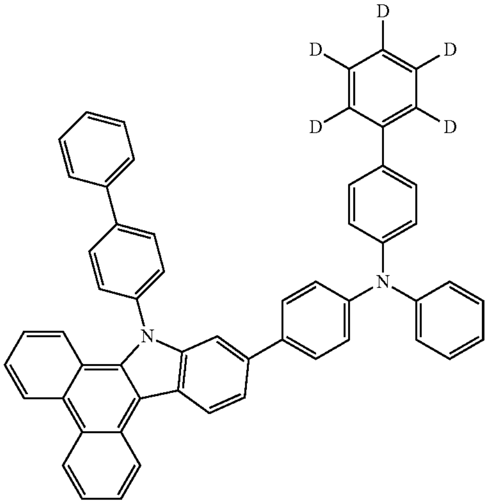
3-121
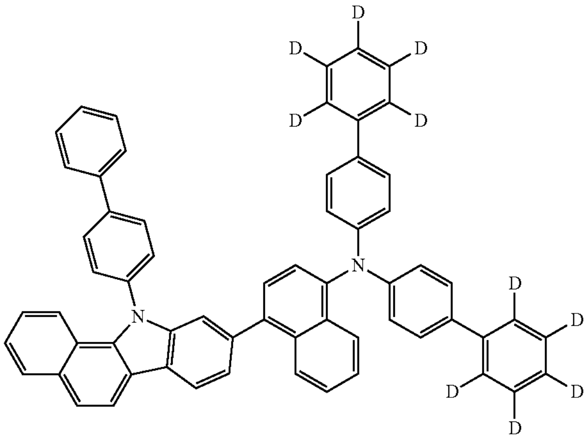
3-122
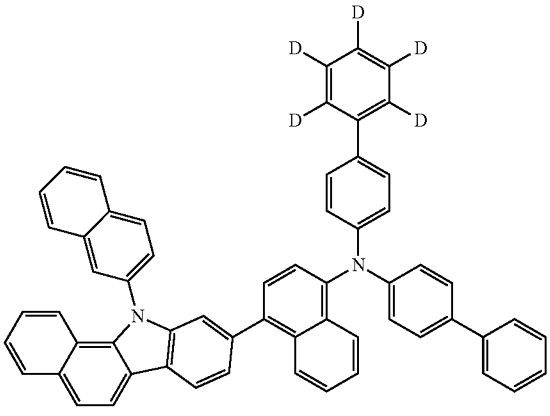
3-123
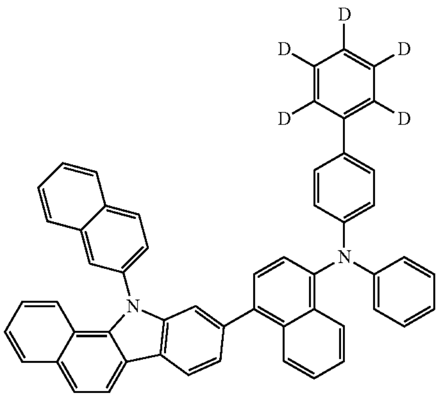
3-124
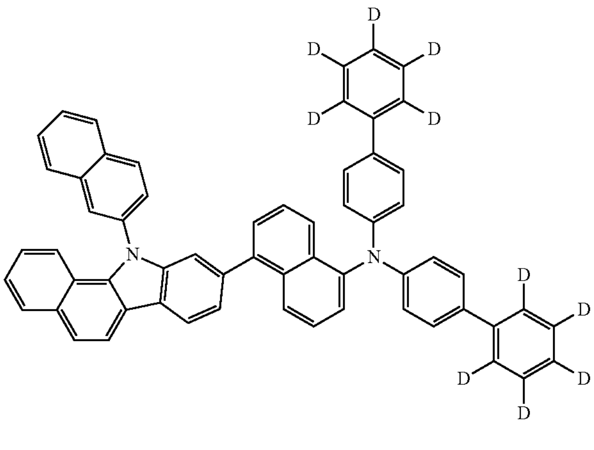

-continued
3-125
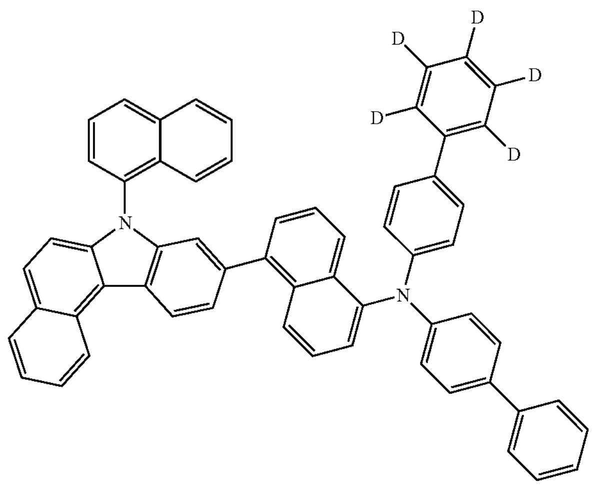
3-126
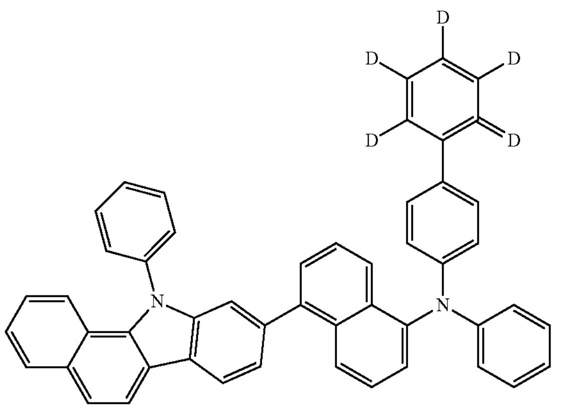
3-127
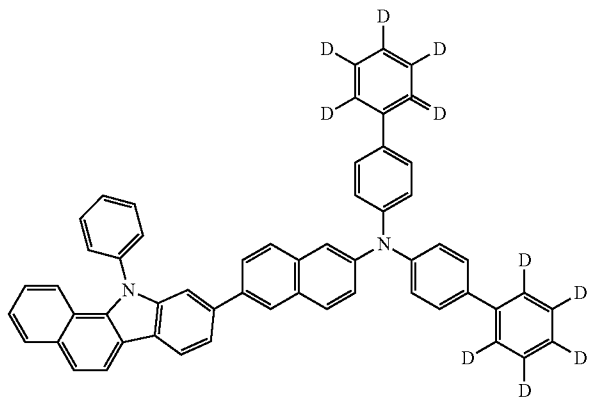
3-128
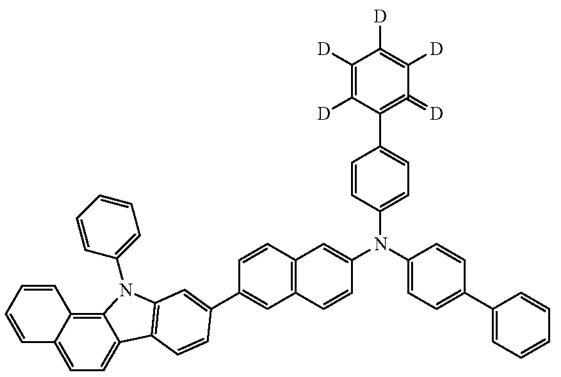
3-129
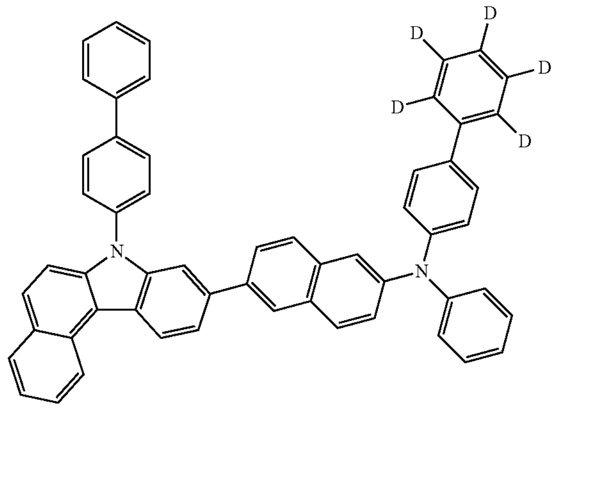
3-130
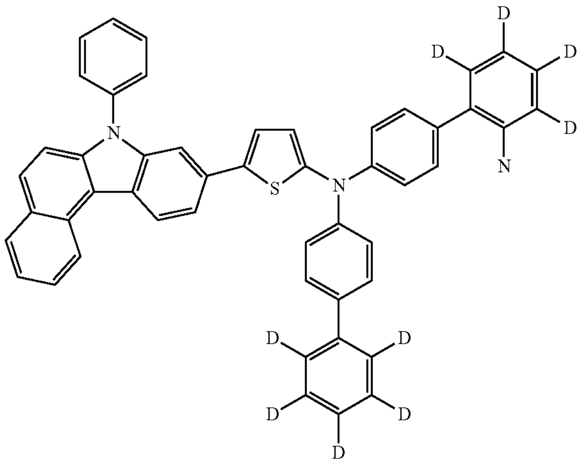

-continued
3-131
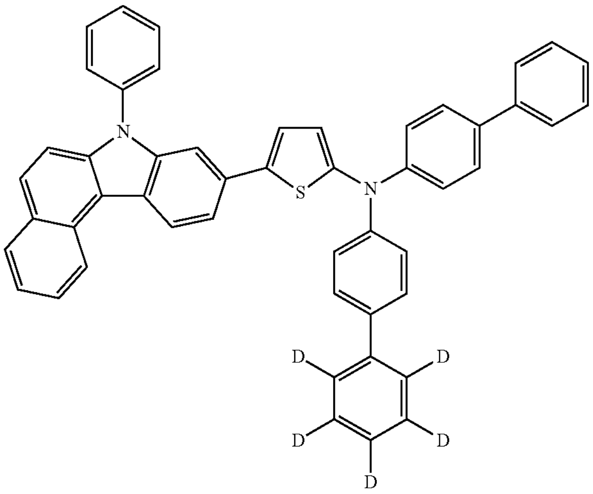
3-132
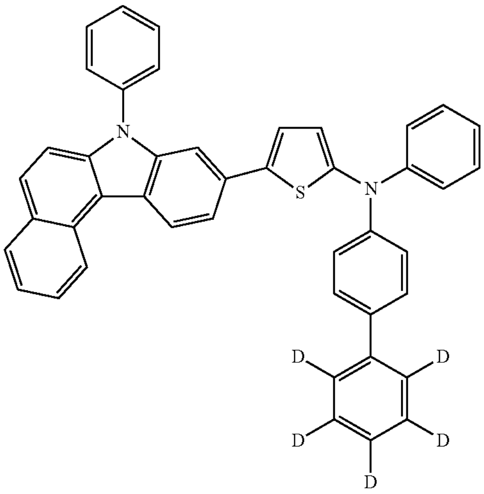
3-133
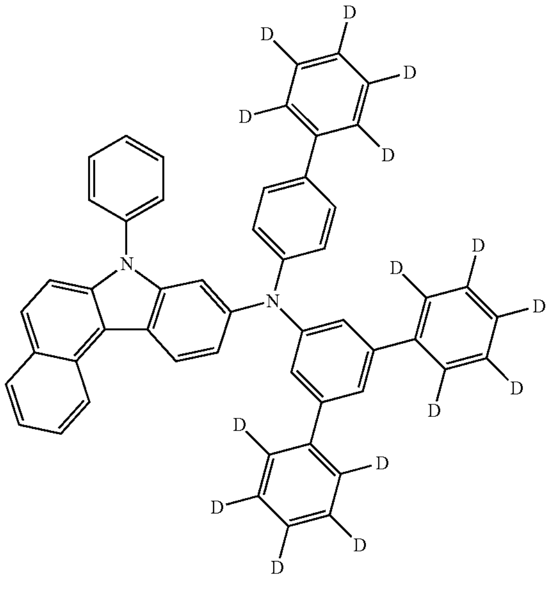
3-134
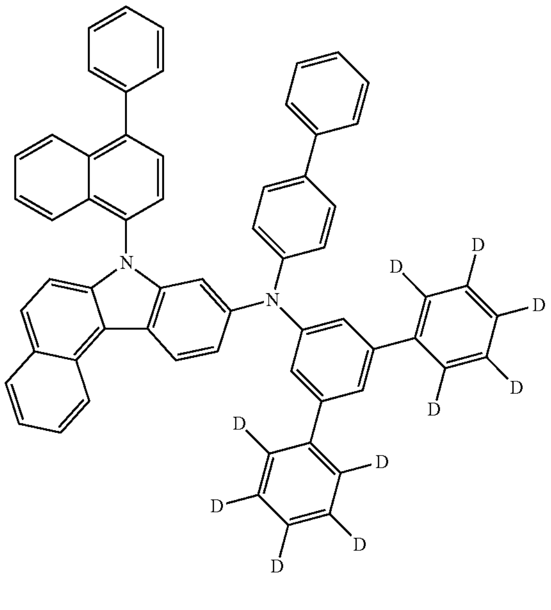

-continued
3-135
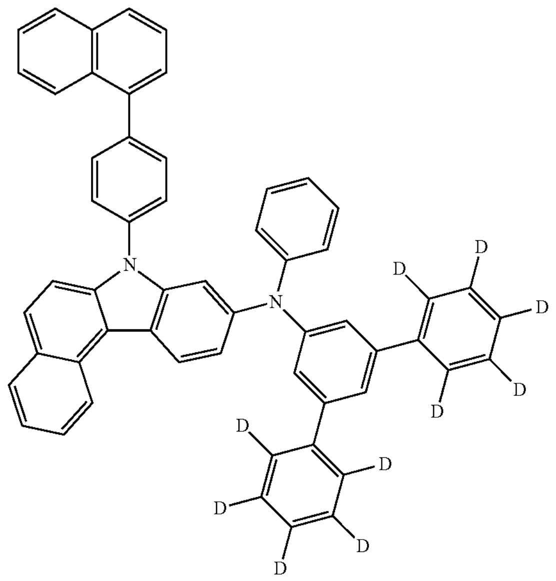
3-136
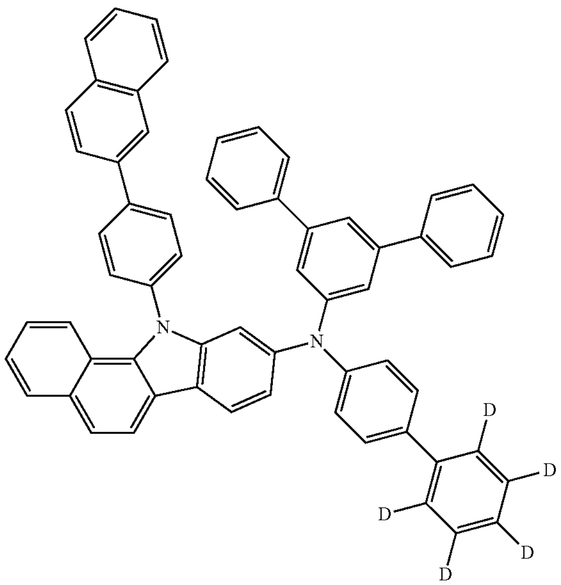
3-137
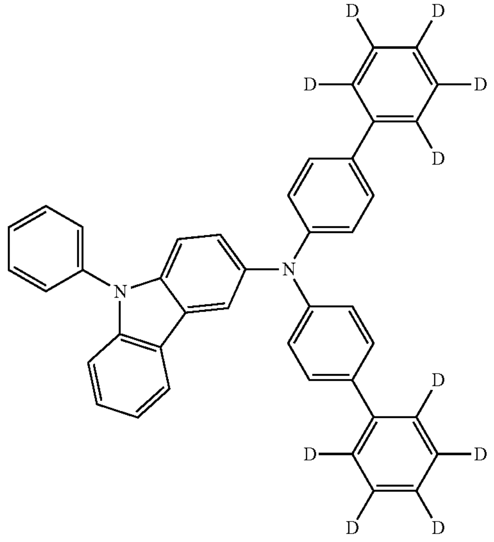
3-138
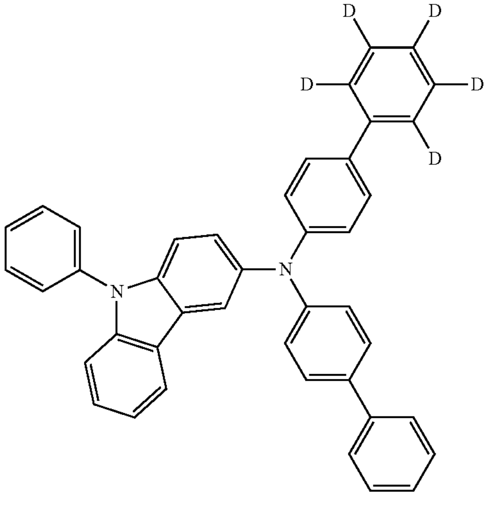
3-139
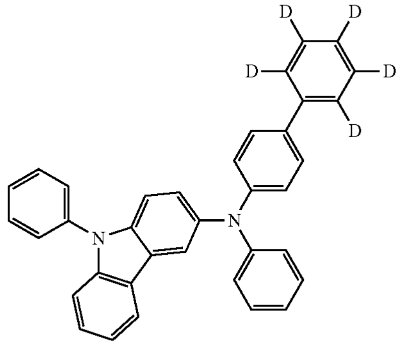
3-140
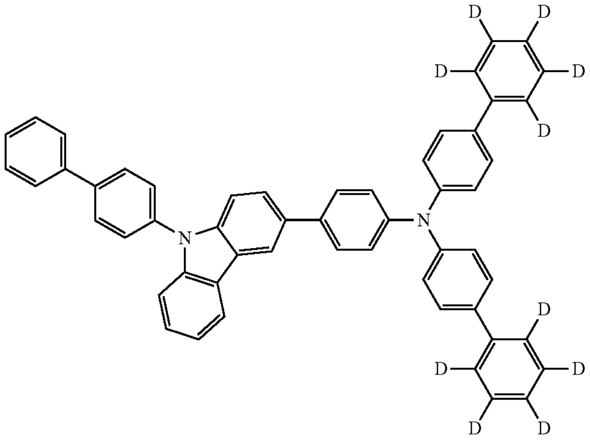

-continued
3-141
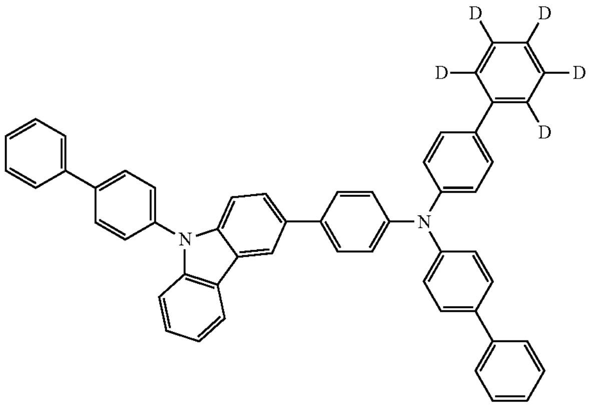
3-142
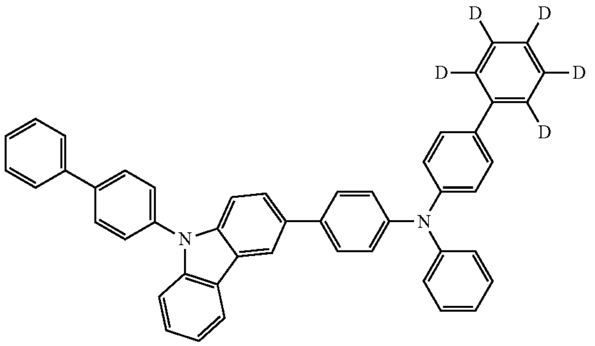
3-143
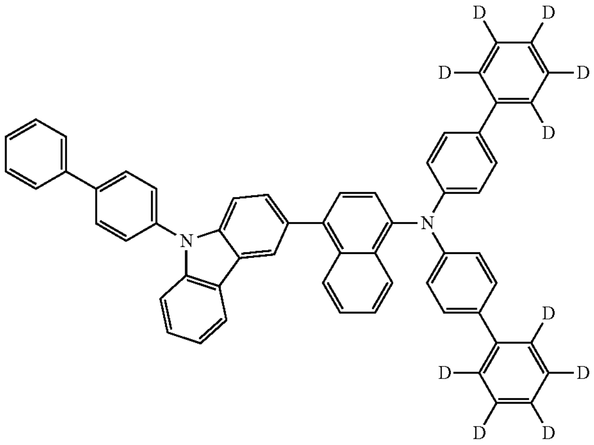
3-144
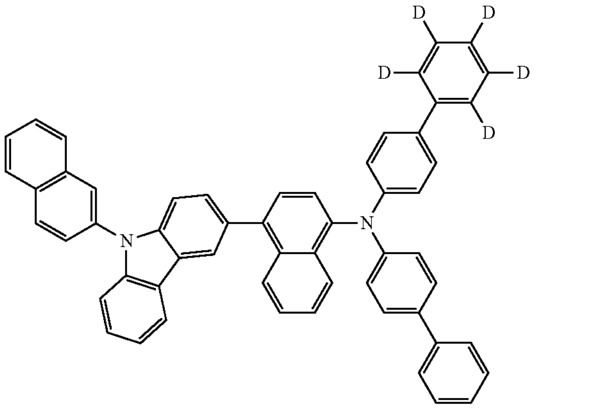
3-145
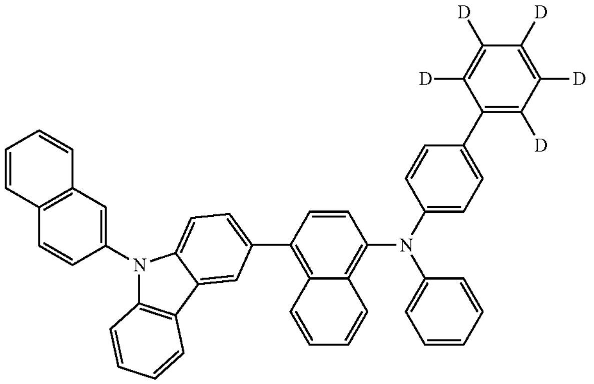
3-146
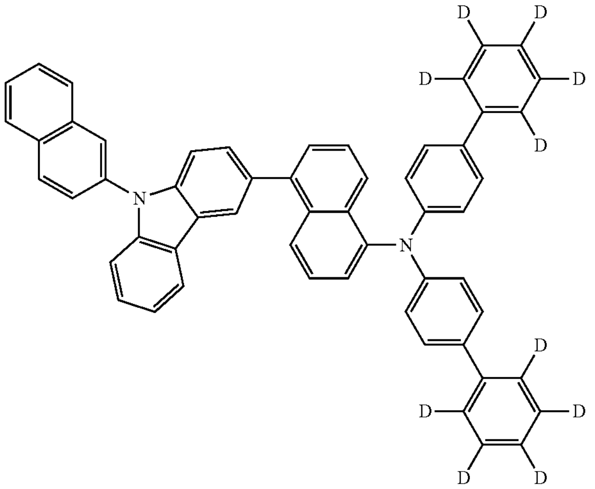

-continued
3-147
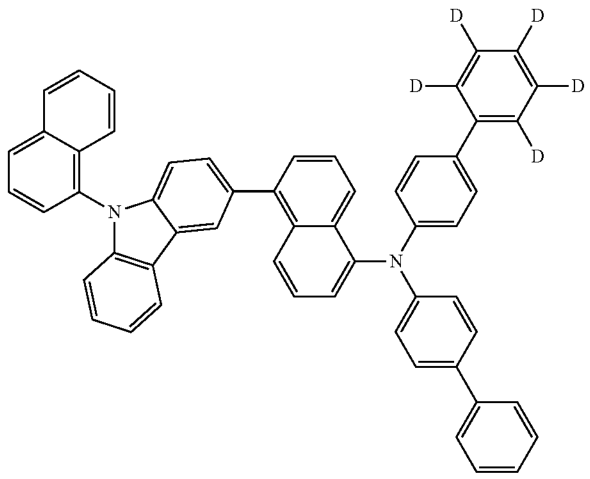
3-148
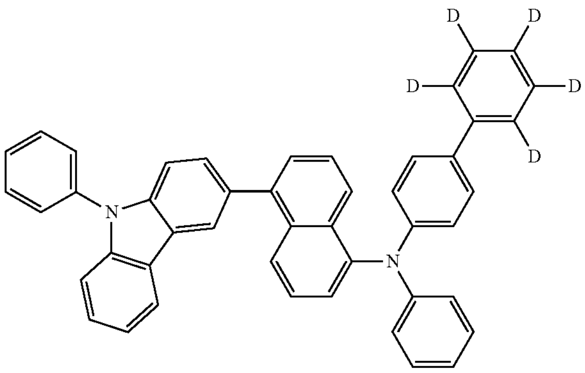
3-149
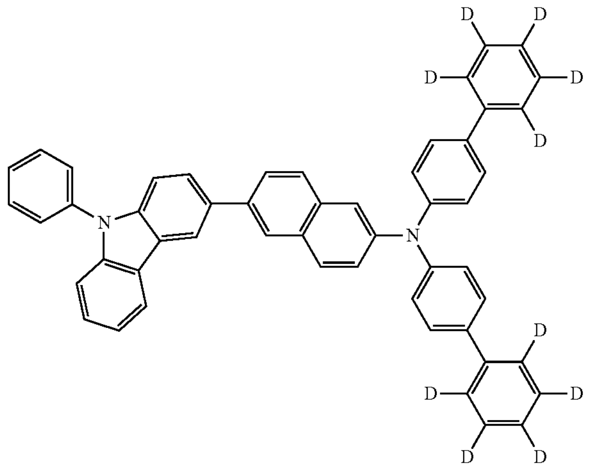
3-150
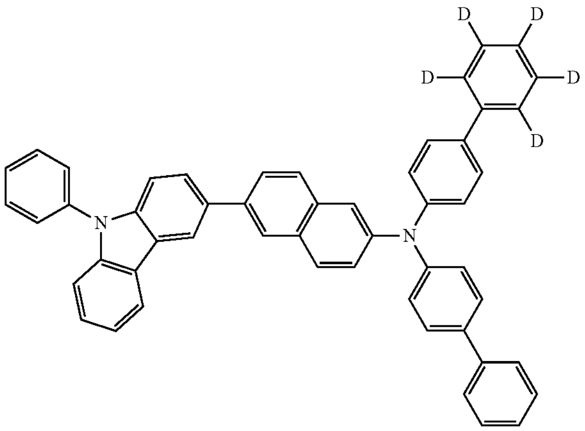
3-151
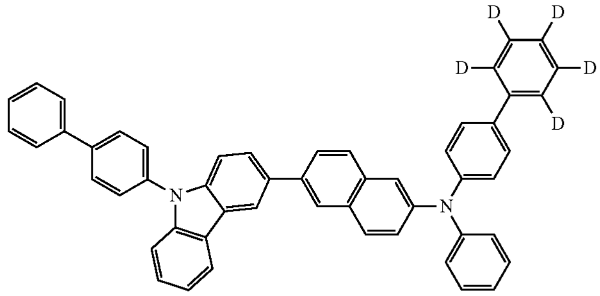
3-152
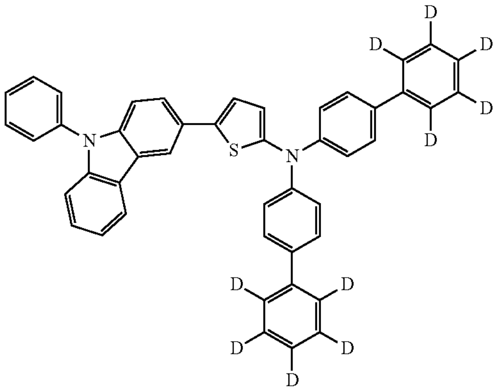

-continued
3-153
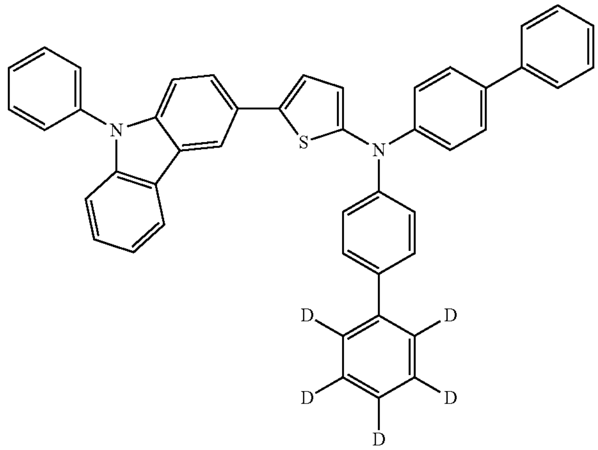
3-154
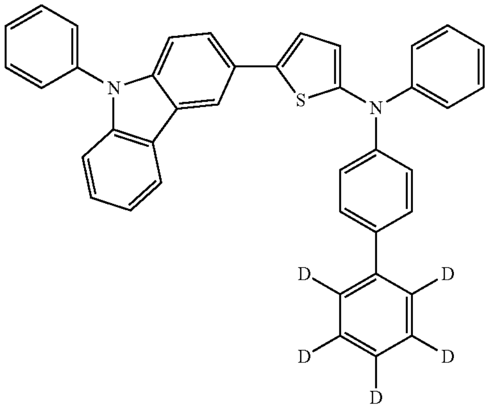
3-155
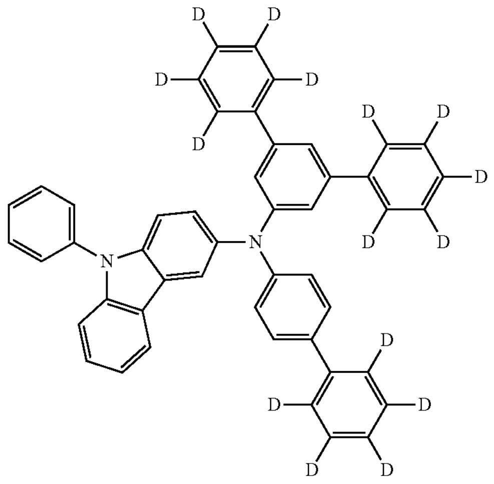
3-156
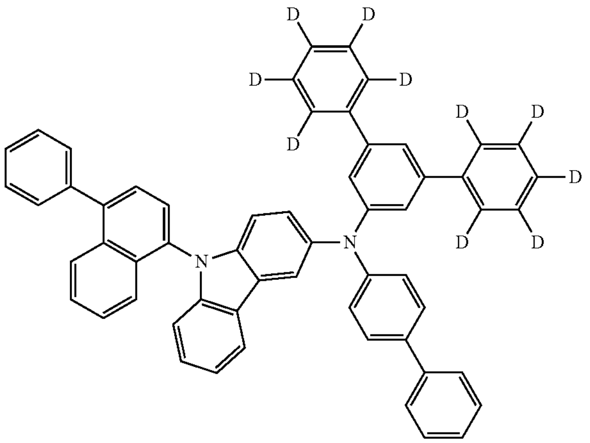
3-157
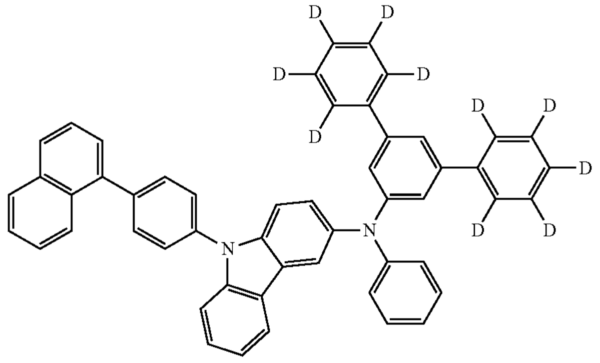
3-158
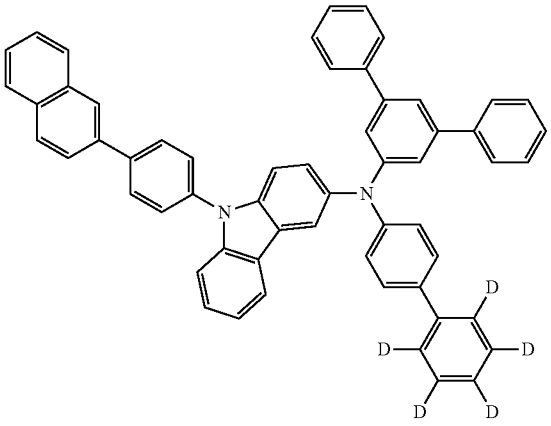

-continued
3-159
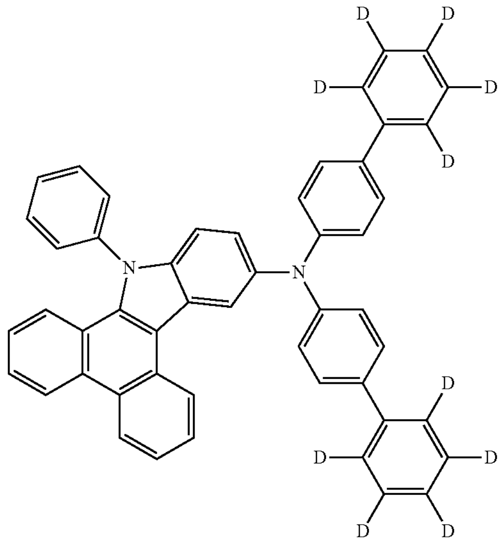
3-160
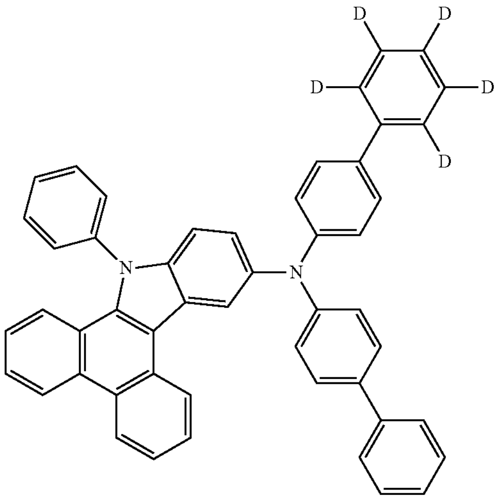
3-161
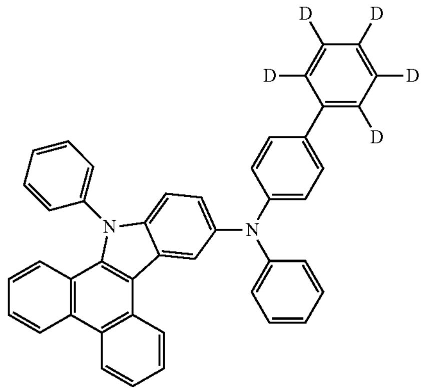
3-162
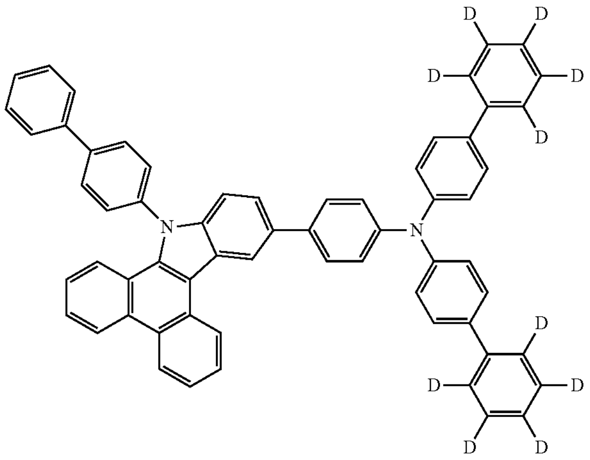
3-163
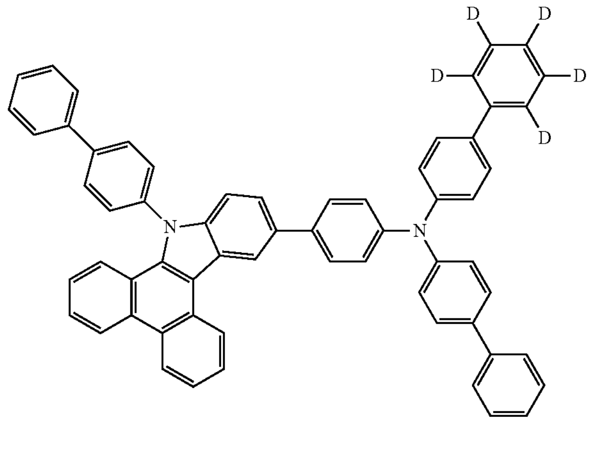
3-164
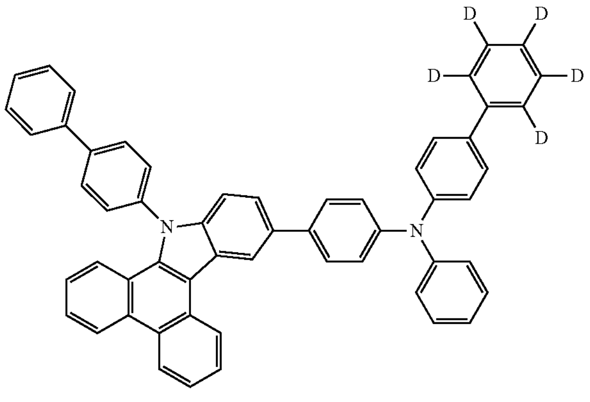

-continued
3-165
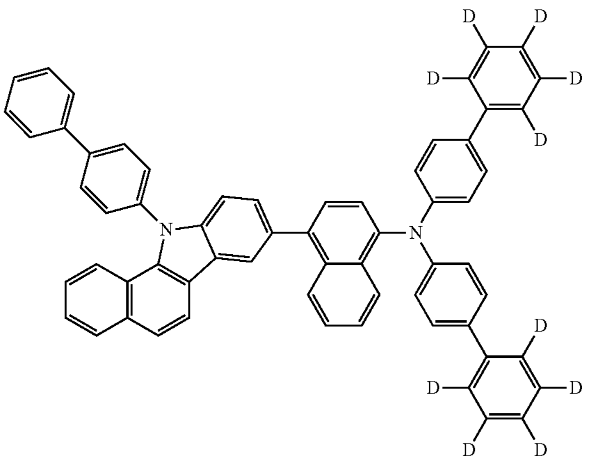
3-166
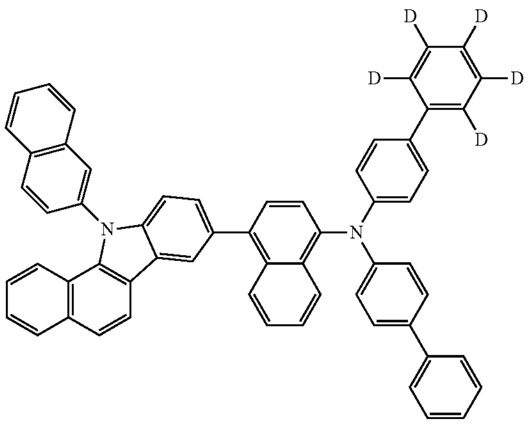
3-167
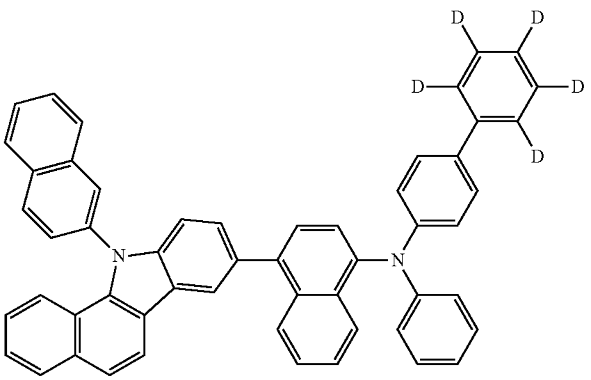
3-168
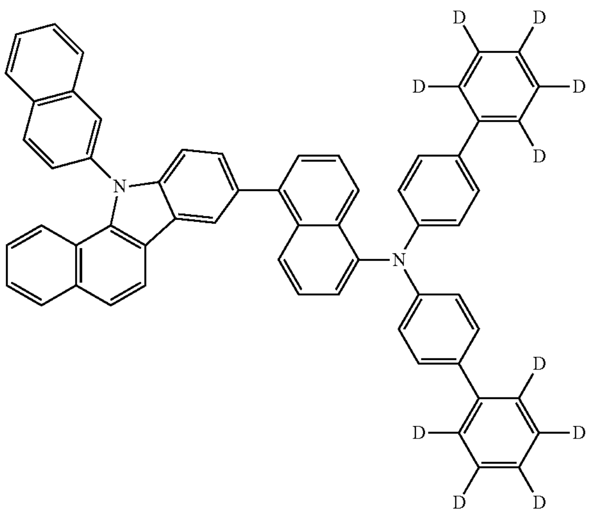
3-169
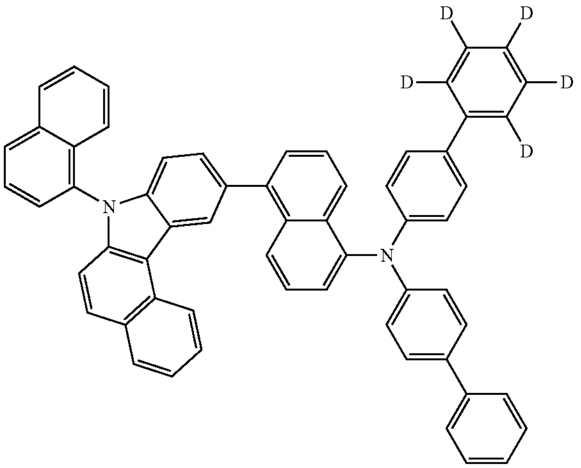
3-170
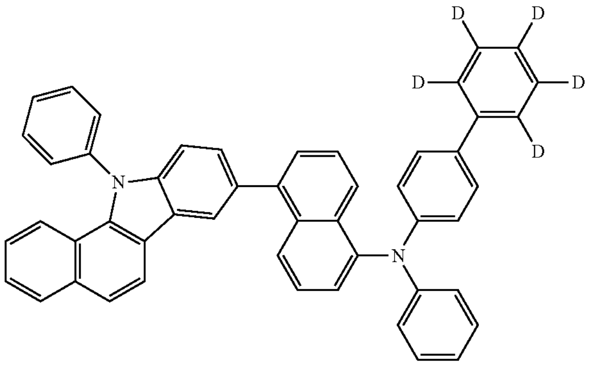

-continued
3-171
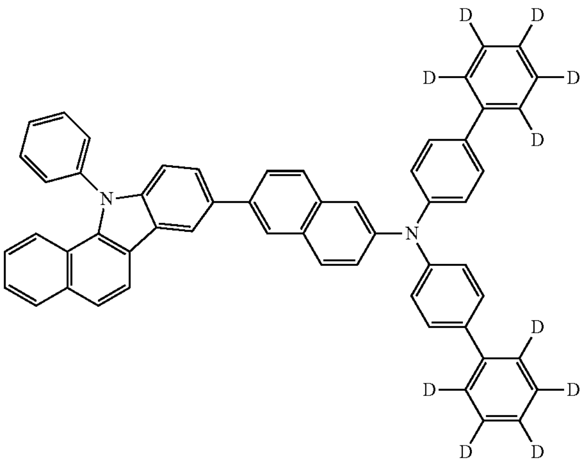
3-172
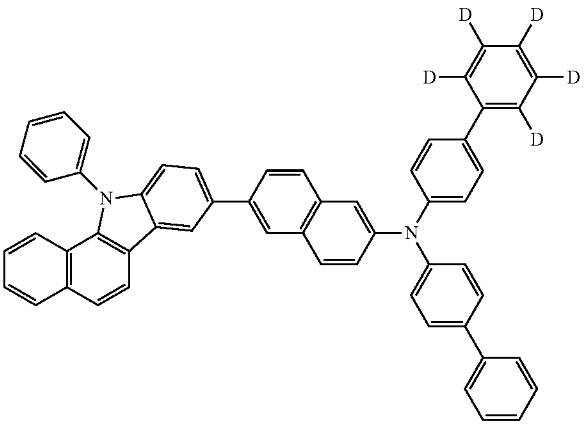
3-173
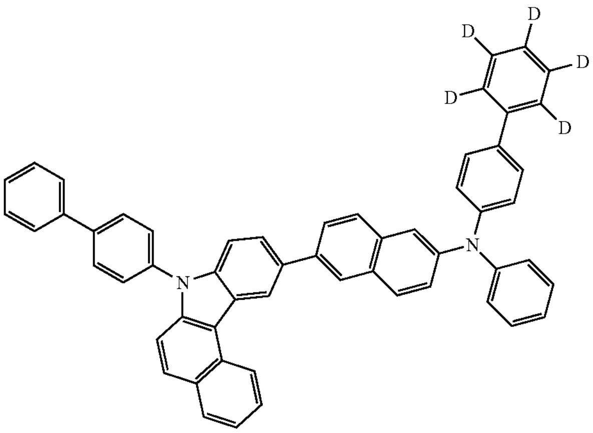
3-174
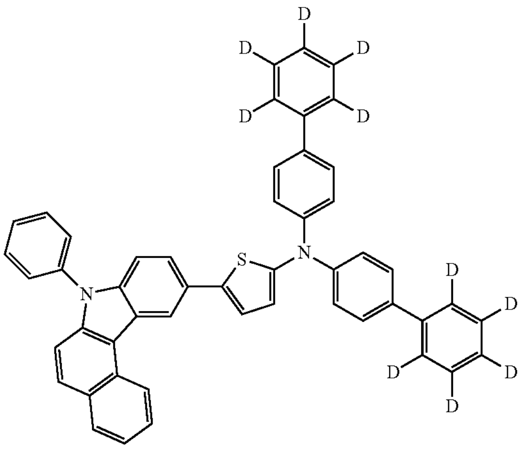
3-175
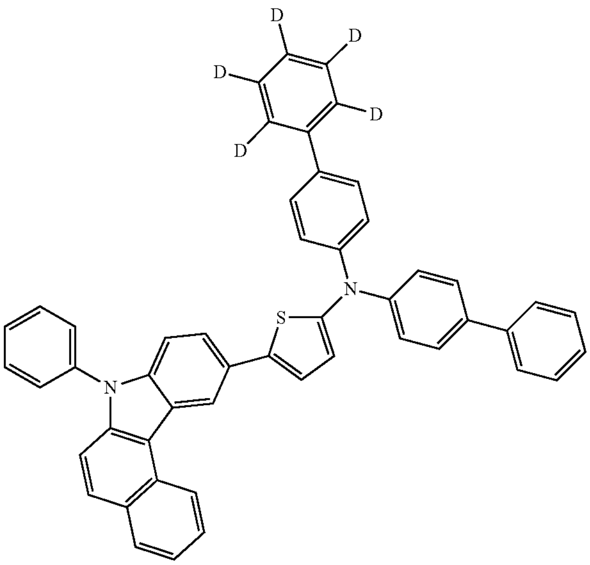
3-176
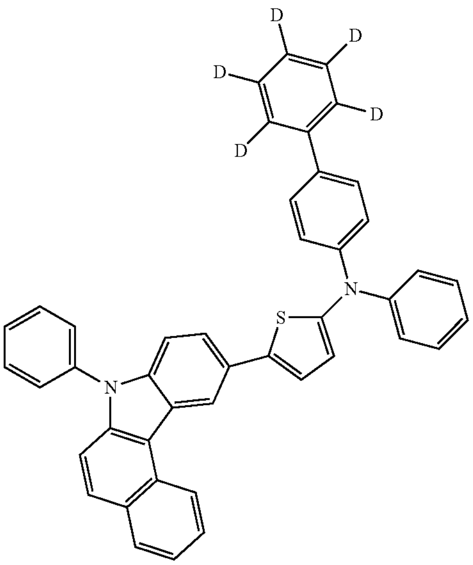

-continued 3-177

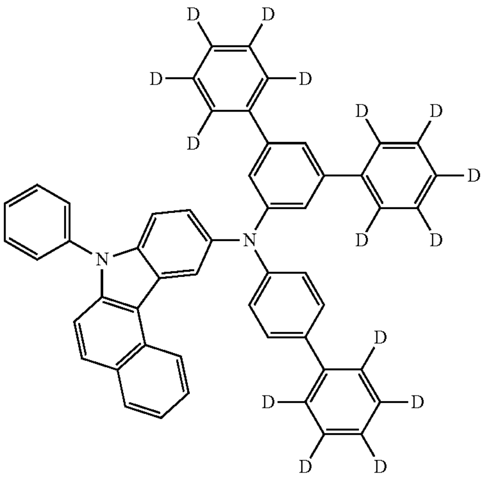

3-178

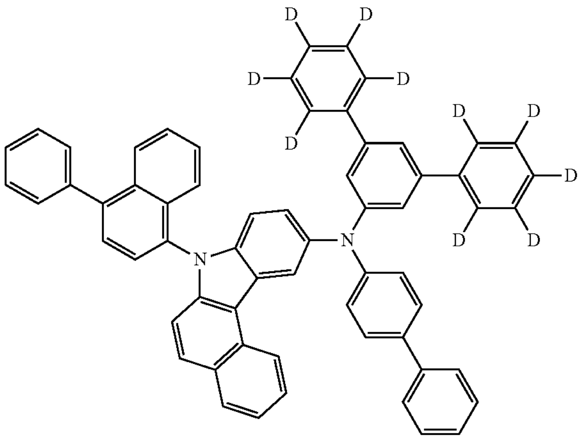

3-179

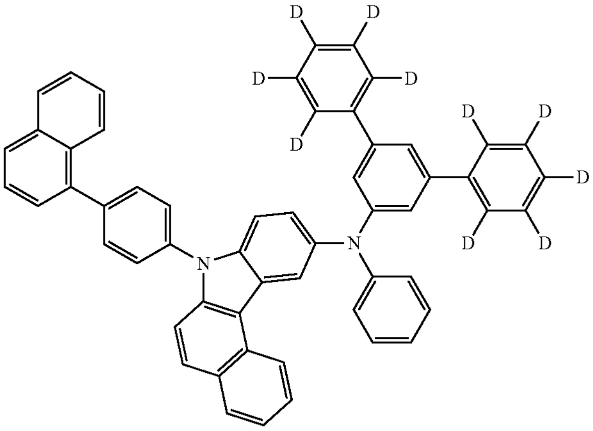

3-180

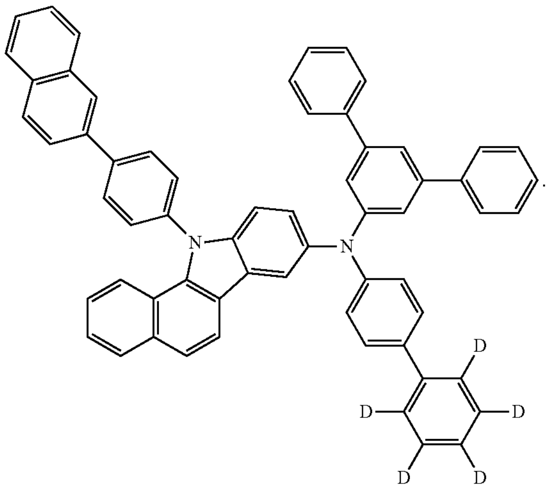

3. An organic electronic element comprising one or more organic material layers comprising the compound as claimed in claim 1.

4. The organic electronic element as claimed in claim 3, wherein the organic material layers are formed by a soluble Process selected from the group consisting of spin coating, dip coating, doctor blading, screen printing, inkjet printing, and thermal transfer.

5. The organic electronic element as claimed in claim 3, wherein the organic electronic element is an organic electroluminescence element in which a first electrode, said one or more organic material layers, and a second electrode are sequentially layered.

6. The organic electronic element as claimed in claim 5, wherein the organic material layers comprise at least one of a hole injection layer, a hole transport layer, an emitting layer, an electron transport layer, and an electron injection layer.

7. An electronic device comprising a display device and a control part for driving the display device, the display device comprising the organic electronic element as claimed in claim 3.

8. The electronic device as claimed in claim 7, wherein the organic electronic element is at least one of an organic light emitting diode (OLED), an organic solar cell, an organic photo conductor (OPC) drum, and an organic transistor (organic TFT).

* * * * *